(12) United States Patent
Krohn et al.

(10) Patent No.: US 7,498,314 B2
(45) Date of Patent: *Mar. 3, 2009

(54) EXPRESSION VECTORS AND USES THEREOF

(75) Inventors: Kai Krohn, Salmentaka (FI); Vesna Blazevic, Tampere (FI); Marja Tähtinen, Tampere (FI); Mart Ustav, Tartu (EE); Urve Toots, Tartu (EE); Andres Männik, Tartu (EE); Annamari Ranki, Helsinki (FI); Ene Ustav, Tartu (EE)

(73) Assignee: Fit Biotech Oyj PLC, Tampere (FI)

( * ) Notice: Subject to any disclaimer, the term of this patent is extended or adjusted under 35 U.S.C. 154(b) by 260 days.

This patent is subject to a terminal disclaimer.

(21) Appl. No.: 10/138,098

(22) Filed: May 3, 2002

(65) Prior Publication Data
US 2003/0129169 A1      Jul. 10, 2003

(30) Foreign Application Priority Data
May 3, 2001    (FI)    ................................. 20010922

(51) Int. Cl.
*A61K 48/00* (2006.01)
*A61K 31/711* (2006.01)
*C07H 21/04* (2006.01)
*C12N 5/10* (2006.01)
*C12N 1/21* (2006.01)
*C12P 21/00* (2006.01)

(52) U.S. Cl. .................. 514/44; 435/320.1; 435/325; 435/366; 435/252.3; 424/93.1; 424/93.2

(58) Field of Classification Search ............... 536/23.1, 536/23.4, 24.5, 24.1, 24.2; 435/320.1, 325
See application file for complete search history.

(56) References Cited

U.S. PATENT DOCUMENTS

| 5,093,246 | A |   | 3/1992 | Cech et al. |
| 5,366,729 | A |   | 11/1994 | Marklund et al. |
| 5,788,961 | A |   | 8/1998 | Marklund et al. |
| 6,130,066 | A | * | 10/2000 | Tartaglia et al. ............ 435/69.1 |
| 6,339,065 | B1 |   | 1/2002 | Cooper |
| 6,479,279 | B2 |   | 11/2002 | Ustav |
| 6,951,928 | B1 | * | 10/2005 | Peltonen et al. ............ 536/23.1 |
| 7,118,751 | B1 | * | 10/2006 | Ledbetter et al. ......... 424/192.1 |
| 2002/0103145 | A1 | * | 8/2002 | Bot et al. ...................... 514/44 |
| 2005/0026137 | A1 |   | 2/2005 | Krohn et al. |

FOREIGN PATENT DOCUMENTS

| EP | 0 918 874 | 3/2001 |
| WO | WO 88/04300 | 6/1988 |
| WO | WO 90/11364 | 10/1990 |
| WO | WO 92/06180 | 4/1992 |
| WO | WO 92/20316 | 11/1992 |
| WO | WO 92/22635 | 12/1992 |
| WO | WO 93/14188 | 7/1993 |
| WO | WO 93/20221 | 10/1993 |
| WO | WO 94/12629 | 6/1994 |
| WO | WO 97/24451 | 7/1997 |
| WO | WO 98/02548 | 1/1998 |
| WO | WO 98/07876 | 2/1998 |
| WO | WO 99/43841 | 9/1999 |

OTHER PUBLICATIONS

Han et al. Infec. Immun. 1997; 65:4100-07.*
Harris et al. Science. 1999; 284: 1673-77.*
Hegde et al. Nature. 1992; 359: 505-12.*
Hung et al. Proc. Natl. Acad. Sci. 2001; 98: 1868-70.*
Johnston et al. Vaccine. 1997; 15:808-9.*
Marechal et al. J. Vir. 1999 ; 73: 4385-92.*
McBride et al. Proc. Natl. Acad. Sci. 1989; 86: 510-14.*
Pierce et al. Nuc. Acids Res. 1998; 26:5093-101.*
Reeves, R. Gene. 2001; 277: 63-81.*
Tu et al. J. Biol. Chem. 2000; 275: 30406-16.*
Warren et al. PNAS. 1990; 87:9823-7.*
Yasir et al. Immun. 2000; 165:7140-9.*
Zheng et al. J. Vir. 2005; 79:1500-09.*
Ayyavoo et al. AIDS. 2000; 14:1-9.*
Berendsen et al. Science. 1998; 282: 1-4.*
Edwards et al. Curr. Opin. Struct. Biol. 1998; 8: 41-53.*
Galperin et al. 2000. Nat. Biotech; 18: 609-13.*
Zheng et al. J. Vir. 2005; 79:1500-09.*
Parker et al. (Virology. 2000; 270: 430-443).*
Grossman et al, 1996, Trends in Microbiology, 4(3); 87-89.*
Bochkarev et al., 1996, Cell, 84: 791-800.*
Doyle et al., 2005, Trends Biotechnology, 23(9) 444-446.*
Abroi et al., 1996, "Transcriptional and replicational activation functions in the bovine papillomavirus type 1 E2 protein are encoded by different structural determinants", J Virol. 70(9):6169-79.
Androphy et al., 1987, "Bovine papillomavirus E2 trans-activating gene product binds to specific sites in papillomavirus DNA", Nature 325(6099):70-3.
Antson et al., 2000, "Structure of the intact transactivation domain of the human papillomavirus E2 protein", Nature 403(6771):805-9.
Bastien et al., 2000, "Interaction of the papillomavirus E2 protein with mitotic chromosomes", Virology 270:124-34.

(Continued)

Primary Examiner—David Guzo
(74) Attorney, Agent, or Firm—Buchanan Ingersoll & Rooney, P.C.

(57) ABSTRACT

The present invention relates to novel vectors, to DNA vaccines and gene therapeutics containing said vectors, to methods for the preparation of the vectors and DNA vaccines and gene therapeutics, and to therapeutic uses of said vectors. More specifically, the present invention relates to novel vectors comprising an expression cassette of a gene of a nuclear-anchoring protein, which contains a DNA binding domain capable of binding to a specific DNA sequence and a functional domain capable of binding to a nuclear component and a multimerized DNA sequence forming a binding site for the nuclear-anchoring protein, and optionally an expression cassette of a gene, genes or a DNA sequence or DNA sequences of interest. The present invention further relates to DNA vaccines and gene therapeutics containing the novel vectors, to methods for the preparation of the novel vectors and the DNA vaccines and gene therapeutics.

64 Claims, 100 Drawing Sheets

OTHER PUBLICATIONS

Boyer et al., 2000, "Vaccination of seronegative volunteers with a human immunodeficiency virus type 1 env/rev DNA vaccine induces antigen-specific proliferation and lymphocyte production of beta-chemokines", J Inject Dis. 181(2):476-83.

Brokaw et al., 1996, "Amino Acids Critical for the Functions of the Bovine Papillomavirus Type 1 E2 Transactivator", J. Virol. 71:23-9.

Dostatni et al., 1988, "A dimer of BPV-1 E2 containing a protease resistant core interacts with its DNA target", EMBO J. 7(12):3807-16.

Ferguson et al., 1996, "Genetic analysis of the activation domain of bovine papillomavirus protein E2: its role in transcription and replication", J Virol. 70(7):4193-9.

Grossel et al., 1996, "Transcriptional activation function is not required for stimulation of DNA replication by bovine papillomavirus type 1 E2", J Virol. 70(10):7264-9.

Harris et al., 1999, "Crystal structure of the human papillomavirus type 18 E2 activation domain", Science. 284(5420):1673-7.

Haugen et al., 1988, "Sequence-specific and general transcriptional activation by the bovine papillomavirus-1 E2 trans-activator require an N-terminal amphipathic helix-containing E2 domain", EMBO J. 7(13):4245-53.

Hegde et al., 1992, "Crystal structure at 1.7 A of the bovine papillomavirus-1 E2 DNA-binding domain bound to its DNA target", Nature. 359(6395):505-12.

Hegde et al., 1995, "Structure of the BPV-1 E2 DNA-binding domain bound to its DNA target", J Nucl Med. 36(6 Suppl):25S-27S.

Holt et al., 1994, "DNA binding specificity of the bovine papillomavirus E1 protein is determined by sequences contained within an 18-base-pair inverted repeat element at the origin of replication", J Virol. 68(2):1094-102.

Holt et al., 1995, "Mutational analysis of the 18-base-pair inverted repeat element at the bovine papillomavirus origin of replication: identification of critical sequences for E1 binding and in vivo replication", J Virol. 69(10):6525-32.

Howley et al., Papillomavirinae: the viruses and their replication, Virology, Fields et al. eds. Phililedphia, Lippincott-Raven Publishers, 1996, p. 2045-2076.

Hung et al., 2001, "Maintenance of Epstein Barr Virus (EBV) oriP based episomes requires EBV-encoded nuclear antigen-1 chromosome binding domains , which can be replaced by high mobility group-1 or histone H1", PNAS 98:1865-70.

Ilves et al., 1999, "Long Term Episomal Maintenance of Bovine Papillomavirus Type I Plasmids Is Determined by Attachement to Host Chromosomes, Which is Mediated by the Viral E2 Protein and Its Blinding Sites", J of Virol. 73:4404-12.

Lambert et al., 1988, "The genetics of bovine papillomavirus type 1", Annu Rev Genet. 22:235-58.

Lusky et al., 1994, "The bovine papillomavirus E2 protein modulates the assembly of but is not stably maintained in a replication-competent multimeric E1-replication origin complex", Proc Natl Acad Sci U S A, 91(19):8895-9.

McBride et al., 1989, E2 polypeptides encoded by bovine papillomavirus type 1 form dimers through the common carboxyl-terminal domain: transactivation is mediated by the conserved amino-terminal domain. Proc Natl Acad Sci U S A. 86(2):510-4.

Mueke et al., 1997, "Suitability of Epstein Barr virus based episomal vectors for expression of cytokine genes in human lymphoma cells", Gene Therapy 4:82-92.

Ohe et al., 1995, "Construction of a Novel Bovine Papillomavirus Vector Without Detectable Transforming Activity Suitable for Gene Transfer", Human Gene Therapy 6:325-333.

Sedman et al., 1997, "Binding of the E1 and E2 proteins to the origin of replication of bovine papillomavirus", J Virol. 71(4):2887-96.

Ulmer et al., 1993, "Heterologous protection against influenza by injection of DNA encoding a viral protein", Science 259(5102):1745-9.

Ustav et al., 1991, "Identification of the origin of replication of bovine papillomavirus and characterization of the viral origin recognition factor", EMBO J. 10(13):4321-9.

Ustav et al., 1993, "The bovine papillomavirus origin of replication requires a binding site for the E2 transcriptional activator", PNAS USA 90:898-902.

Ustav et al., 1991, "Transient replication of BPV-1 requires two viral polypeptides encoded by the E1 and E2 open reading frames", EMBO J. 10(2):449-57.

Collings, et al., 2000, "Humoral and cellular immune responses to HIV-1 Nef in mice DNA-immunised with non-replicating or self-replicating expression vectors", Vaccine 18(2000):460-467.

Van Craenenbroeck, et al., 2000. "Episomal vectors for gene expression in mammalian cells", Eur. J. Biochem. 267:5665-5678.

U.S. Appl. No. 10/476,615, filed Nov. 3, 2003, Kai Krohn.

Krysan et al., "Isolation of Human Sequences that Replicate Autonomously in Human Cells", Molecular ad Cellular Biology, Mar. 1989, vol. 9, No. 3, pp. 1026-1033.

Heinzel et al., "Autonomous DNA Replication in Human Cells is Affected by the Size and the Source of the DNA", Molecular ad Cellular Biology, Apr. 1991, vol. 11, No. 4, pp. 2263-2272.

Haase et al., "Replication Control of Autonomously Replicating Human Sequences", Nucleic Acids Research, vol. 19, No. 18, pp. 5053-5058.

Krysan et al., "Autonomous Replication in Human Cells of Multimers of Specific Human and Bacterial DNA Seqquences", Molecular ad Cellular Biology, May 1993, vol. 13, No. 5, pp. 2688-2696.

Stoll et al., "Epstein-Barr Virus/Human Vector Provides High-Level, Long-Term Expression of $\alpha_1$-Antitrypsin in Mice", Molecular Therapy, Aug. 2001, vol. 4, No. 2, pp. 122-129.

Haase et al., "Transcription Inhibits the Replication of Autonomously Replicating Plasmids in Human Cells", Molecular ad Cellular Biology, Apr. 1994, vol. 14, No. 4, pp. 2516-2524.

Jiang et al., "Coadministration of Interleukin 12 Expression Vector with Antigen 2 cDNA Enhances Induction of Protective Immunity Against *Coccidioides immitis*", Infection and Immunity, Nov. 1999, vol. 67, No. 11, pp. 5848-5853.

Strasser et al., "Herpes Simplex Virus DNA Vaccine Efficacy: Effect of Glycoprotein D Plasmid Constructs", JID, Nov. 2000, vol. 182, pp. 1304-1310.

Farci et al., "Lack of Protective Immunity Against Reinfection with Hepatitis C Virus", Science, Oct. 1992, vol. 258, pp. 135-140.

Liljeqvist et al., "Surface Display of Functional Fibronectin-Binding Domains on *Staphylococcus carnosus*", FEBS Letters, 1999, vol. 446, pp. 299-304.

Kennard et al., "Expression of Cell Surface GPI-Anchored Human p97 Baculovirus-Infected Insect Cells", Biotechnology and Bioengineering, vol. 55, No. 1, pp. 41-53, Jul. 1997.

* cited by examiner

Plasmid pEBO LPP

Plasmid s6E2d1EGFP

SEQUENCE LISTING

<160> NUMBER OF SEQ ID NOS: 52

<210> SEQ ID NO 1

```
<211> LENGTH: 1260
<212> TYPE: DNA
<213> ORGANISM: Artificial Sequence
<220> FEATURE:
<223> OTHER INFORMATION: Hybrid protein comprised of Nef-Tat-Rev (NTR)

<400> SEQUENCE: 1
atggtgggca agtggtcaaa atgtagtgga tggcctactg taagggaaag aatgaaacaa      60
gctgagcctg agccagcagc agatggggtg ggagcagcat ctcgagacct ggaaaaacat     120
ggagcaatca caagtagcaa tacagcaact aataacgctg cttgtgcctg ctagaagca     180 caagaggaag aggaagtggg ttttccagtc agacctcagg tacctttaag accaatgact     240
tacaagggag ctttagatct tagccacttt ttaaaagaaa agggggggact ggaagggtta    300 atttactccc caaaaagaca agagatcctt gatctgtggg tctaccacac acaaggctac     360
ttccctgatt ggcagaacta cacaccaggg ccaggggtca gatatccact gacctttgga     420
tggtgcttca agttagtacc agttgaacca gatgaagaag agaacagcag cctgttacac     480
cctgcgagcc tgcatgggac agaggacacg gagagagaag tgttaaagtg aagtttgac      540 agccatctag catttcatca caaggcccga gagctgcatc cggagtacta caaagactgc     600
actagtgcag gaagaagcgg agacagcgac gaagagctcc tcaagacagt cagactcatc     660
aagtttctct accaaagcaa ccctcctccc agcaacgagg ggacccgaca ggcccgaaga     720
aatcgaagaa gaaggtggag agagacag aggcagatcc gttcgattag tgagcggatt      780
cttagcactt ttctgggacg acctgcggag cctgtgcctc ttcagctacc gccgcttgag    840
agacttactc ttgattgtag cgaagattgt ggaaactctg gacgcagggg ggtgggaagt    900
cctcaagtat tggtggaatc tcctgcagta ttggagccag gaactaaaga aaagcttgag    960
ccagtagatc ctagactaga gcctggaag catccaggaa gtcagcctag gaccccttgt    1020
accaattgct attgtaaaaa gtgttgcctt cattgccaag tttgtttcac aagaaaaggc   1080
ttaggcatct cctatggcag gaagaagcgg agacagcgac gaagagctcc tcaagacagt   1140
cagactcatc aagtttctct accaaagcaa ccctcctccc agcaacgagg ggacccgaca   1200
ggcccgaaga aatcgaagaa gaaggtggag agagacag aggcagatcc gttcgattag    1260

<210> SEQ ID NO 2
<211> LENGTH: 1260
<212> TYPE: DNA
<213> ORGANISM: Artificial Sequence
<220> FEATURE:
<223> OTHER INFORMATION: Hybrid protein comprised of Tat-Rev-Nef (TRN)

<400> SEQUENCE: 2
atggagccag tagatcctag actagagccc tggaagcatc caggaagtca gcctaggacc      60
ccttgtacca attgctattg taaaaagtgt tgccttcatt gccaagtttg tttcacaaga    120
aaaggcttag gcatctccta tggcaggaag aagcggagac agcgacgaag agctcctcaa    180
gacagtcaga ctcatcaagt ttctctacca aagcaaccct cctcccagca acgaggggac     240
ccgacaggcc cgaagaaatc gaagaagaag gtggagagag agacagaggc agatccgttc    300
gatactagtg caggaagaag cggagacagc gacgaagagc tcctcaagac agtcagactc    360
atcaagtttc tctaccaaag caaccctcct cccagcaacg aggggacccg acaggcccga    420
agaaatcgaa gaagaaggtg gagagagaga cagaggcaga tccgttcgat tagtgagcgg    480
attcttagca ctttttctgg gacgacctgc ggagcctgtg ctcttcagct accgccgctt   540
gagagactta ctcttgattg tagcgaagat tgtggaaact ctgggacgca ggggggtggga   600
```

| | | | |
|---|---|---|---|
| agtcctcaag | tattggtgga | atctcctgca gtattggagc caggaactaa agaaaagctt | 660 |
| gtgggcaagt | ggtcaaaatg | tagtggatgg cctactgtaa gggaaagaat gaaacaagct | 720 |
| gagcctgagc | cagcagcaga | tggggtggga gcagcatctc gagacctgga aaaacatgga | 780 |
| gcaatcacaa | gtagcaatac | agcaactaat aacgctgctt gtgcctggct agaagcacaa | 840 |
| gaggaagagg | aagtgggttt | tccagtcaga cctcaggtac cttt aagacc aatgacttac | 900 |
| aagggagctt | tagatcttag | ccactttt ta aagaaaagg ggggactgga agggttaatt | 960 |
| tactccccaa | aaagacaaga | gatccttgat ctgtgggtct accacacaca aggctacttc | 1020 |
| cctgattggc | agaactacac | accagggcca ggggtcagat atccactgac ctttggatgg | 1080 |
| tgcttcaagt | tagtaccagt | tgaaccagat gaagaagaga acagcagcct gttacaccct | 1140 |
| gcgagcctgc | atgggacaga | ggacacggag agagaagtgt taaagtggaa gtttgacagc | 1200 |
| catctagcat | tcatcacaa | ggcccgagag ctgcatccgg agtactacaa agactgctga | 1260 |

<210> SEQ ID NO 3
<211> LENGTH: 1260
<212> TYPE: DNA
<213> ORGANISM: Artificial Sequence
<220> FEATURE:
<223> OTHER INFORMATION: Hybrid protein comprised of Rev-Tat-Nef (RTN)

<400> SEQUENCE: 3

| | | | |
|---|---|---|---|
| atggcaggaa | gaagcggaga | cagcgacgaa gagctcctca agacagtcag actcatcaag | 60 |
| tttctctacc | aaagcaaccc | tcctcccagc aacgagggga cccgacaggc ccgaagaaat | 120 |
| cgaagaagaa | ggtggagaga | gagacagagg cagatccgtt cgattagtga gcggattctt | 180 |
| agcactttc | tgggacgacc | tgcggagcct gtgcctcttc agctaccgcc gcttgagaga | 240 |
| cttactcttg | attgtagcga | agattgtgga aactctggga cgcaggggt gggaagtcct | 300 |
| caagtattgg | tggaatctcc | tgcagtattg gagccaggaa ctaaagaaac tagtgagcca | 360 |
| gtagatccta | gactagagcc | ctggaagcat ccaggaagtc agcctaggac cccttgtacc | 420 |
| aattgctatt | gtaaaaagtg | ttgccttcat tgccaagttt gtttcacaag aaaaggctta | 480 |
| ggcatctcct | atggcaggaa | gaagcggaga cagcgacgaa gagctcctca agacagtcag | 540 |
| actcatcaag | tttctctacc | aaagcaaccc tcctcccagc aacgagggga cccgacaggc | 600 |
| ccgaagaaat | cgaagaagaa | ggtggagaga gagacagagg cagatccgtt cgataagctt | 660 |
| gtgggcaagt | ggtcaaaatg | tagtggatgg cctactgtaa gggaaagaat gaaacaagct | 720 |
| gagcctgagc | cagcagcaga | tggggtggga gcagcatctc gagacctgga aaaacatgga | 780 |
| gcaatcacaa | gtagcaatac | agcaactaat aacgctgctt gtgcctggct agaagcacaa | 840 |
| gaggaagagg | aagtgggttt | tccagtcaga cctcaggtac cttt aagacc aatgacttac | 900 |
| aagggagctt | tagatcttag | ccactttt ta aagaaaagg ggggactgga agggttaatt | 960 |
| tactccccaa | aaagacaaga | gatccttgat ctgtgggtct accacacaca aggctacttc | 1020 |
| cctgattggc | agaactacac | accagggcca ggggtcagat atccactgac ctttggatgg | 1080 |
| tgcttcaagt | tagtaccagt | tgaaccagat gaagaagaga acagcagcct gttacaccct | 1140 |
| gcgagcctgc | atgggacaga | ggacacggag agagaagtgt taaagtggaa gtttgacagc | 1200 |
| catctagcat | tcatcacaa | ggcccgagag ctgcatccgg agtactacaa agactgctga | 1260 |

<210> SEQ ID NO 4
<211> LENGTH: 1260
<212> TYPE: DNA
<213> ORGANISM: Artificial Sequence
<220> FEATURE:

<223> OTHER INFORMATION: Hybrid protein comprised of Tat-Nef-Rev (TNR)

<400> SEQUENCE: 4

```
atggagccag tagatcctag actagagccc tggaagcatc caggaagtca gcctaggacc      60
ccttgtacca attgctattg taaaaagtgt tgccttcatt gccaagtttg tttcacaaga     120
aaaggcttag gcatctccta tggcaggaag aagcggagac agcgacgaag agctcctcaa     180
gacagtcaga ctcatcaagt ttctctacca aagcaaccct cctcccagca acgaggggac     240
ccgacaggcc cgaagaaatc gaagaagaag gtggagagag agacagaggc agatccgttc     300
gatactagtg tgggcaagtg gtcaaaatgt agtggatggc ctactgtaag ggaagaatg     360
aaacaagctg agcctgagcc agcagcagat ggggtgggag cagcatctcg agacctggaa     420
aaacatggag caatcacaag tagcaataca gcaactaata cgctgcttg tgcctggcta     480
gaagcacaag aggaagagga agtgggtttt ccagtcagac ctcaggtacc tttaagacca     540
atgacttaca agggagcttt agatcttagc cactttttaa agaaaaaggg gggactggaa     600
gggttaattt actccccaaa aagacaagag atccttgatc tgtgggtcta ccacacacaa     660
ggctacttcc ctgattggca gaactacaca ccagggccag ggtcagata tccactgacc     720
tttggatggt gcttcaagtt agtaccagtt gaaccagatg aagaagagaa cagcagcctg     780
ttacaccctg cgagcctgca tgggacagag gacacggaga gaagtgtt aaagtggaag     840
tttgacagcc atctagcatt tcatcacaag gcccgagagc tgcatccgga gtactacaaa     900
gactgcaagc ttgcaggaag aagcggagac agcgacgaag agctcctcaa gacagtcaga     960
ctcatcaagt ttctctacca aagcaaccct cctcccagca acgaggggac ccgacaggcc    1020
cgaagaaatc gaagaagaag gtggagagag agacagaggc agatccgttc gattagtgag    1080
cggattctta gcactttttct gggacgacct gcggagcctg tgcctcttca gctaccgccg    1140
cttgagagac ttactcttga ttgtagcgaa gattgtggaa actctgggac gcaggggtg    1200
ggaagtcctc aagtattggt ggaatctcct gcagtattgg agccaggaac taagaatag    1260
```

<210> SEQ ID NO 5
<211> LENGTH: 1260
<212> TYPE: DNA
<213> ORGANISM: Artificial Sequence
<220> FEATURE:
<223> OTHER INFORMATION: Hybrid protein comprised of Rev-Nef-Tat (RNT)

<400> SEQUENCE: 5

```
atggcaggaa gaagcggaga cagcgacgaa gagctcctca gacagtcag actcatcaag      60
tttctctacc aaagcaaccc tcctcccagc aacgagggga cccgacaggc ccgaagaaat     120
cgaagaagaa ggtggagaga gagacagagg cagatccgtt cgattagtga gcggattctt     180
agcactttc tgggacgacc tgcggagcct gtgcctcttc agctaccgcc gcttgagaga     240
cttactcttg attgtagcga agattgtgga actctgggac gcaggggtg gggaagtcct     300
caagtattgg tggaatctcc tgcagtattg gagccaggaa ctaaagaaac tagtgtgggc     360
aagtggtcaa aatgtagtgg atggcctact gtaaggaaa gaatgaaaca agctgagcct     420
gagccagcag cagatggggt gggagcagca tctcgagacc tggaaaaaca tggagcaatc     480
acaagtagca atacagcaac taataacgct gcttgtgcct ggctagaagc acaagaggaa     540
gaggaagtgg gttttccagt cagacctcag gtaccttaa gaccaatgac ttacaaggga     600
gctttagatc ttagccactt tttaaaagaa aagggggggac tggaagggtt aatttactcc     660
ccaaaaagac aagagatcct tgatctgtgg gtctaccaca cacaaggcta cttcctgat     720
```

```
tggcagaact acacaccagg gccagggtc agatatccac tgacctttgg atggtgcttc      780
aagttagtac cagttgaacc agatgaagaa gagaacagca gcctgttaca ccctgcgagc      840
ctgcatggga cagaggacac ggagagagaa gtgttaaagt ggaagtttga cagccatcta      900
gcatttcatc acaaggcccg agagctgcat ccggagtact acaaagactg caagcttgag      960
ccagtagatc ctagactaga gccctggaag catccaggaa gtcagcctag gaccccttgt     1020
accaattgct attgtaaaaa gtgttgcctt cattgccaag tttgtttcac aagaaaaggc     1080
ttaggcatct cctatggcag gaagaagcgg agacagcgac gaagagctcc tcaagacagt     1140
cagactcatc aagtttctct accaaagcaa ccctcctccc agcaacgagg ggaccccgaca    1200 ggcccgaaga aatcgaagaa gaaggtggag agagagacag aggcagatcc gttcgattag    1260
```

<210> SEQ ID NO 6
<211> LENGTH: 1164
<212> TYPE: DNA
<213> ORGANISM: Artificial Sequence
<220> FEATURE:
<223> OTHER INFORMATION: Protein comprised of Immunodominant parts of
      the Nef-Tat-Rev(NTR)

<400> SEQUENCE: 6

```
atgggatggc tactgtaag ggaaagaatg aaacaagctg agcctgagcc agcagcagat       60
ggggtgggag cagcatctcg agacctggaa aacatggagc aatcacaag tagcaataca      120 gcaactaata acgctgcttg tgcctggcta gaagcacaag aggaagagga agtgggtttt     180
ccagtcagac ctcaggtacc tttaagacca atgacttaca agggagcttt agatcttagc     240 cacttttaa aagaaaaggg gggactggaa gggttaattt actccccaaa aagacaagag     300
atccttgatc tgtgggtcta ccacacacaa ggctacttcc ctgattggca gaactacaca     360
ccagggccag gggtcagata tccactgacc tttggatggt gcttcaagtt agtaccagtt     420
gaaccagatg aagaagagaa cagcagcctg ttacaccctg cgagcctgca tgggacagag     480
gacacggaga gagaagtgtt aaagtggaag tttgacagcc atctagcatt tcatcacaag     540
gcccgagagc tgcatccgga gtactacaaa gactgcgctc tggccgccgt tgagccagta     600
gatcctagac tagagccctg gaagcatcca ggaagtcagc ctaggacccc ttgtaccaat     660
tgctattgta aaaagtgttg ccttcattgc caagtttgtt tcacaagaaa aggcttaggc     720
atctcctatg gcaggaagaa gcggagacag cgacgaagag ctcctcaaga cagtcagact     780
catcaagttt ctctaccaaa gcaaccctcc tcccagcaac gaggggaccc gacaggcccg     840
aagaaatccg gactggccat cctgctgagc gacgaagagc tcctcaagac agtcagactc     900
atcaagtttc tctaccaaag caaccctcct cccagcaacg aggggacccg acaggcccga     960
agaaatcgaa gaagaaggtg gagagagaga cagaggcaga tccgttcgat tagtgagcgg    1020
attcttagca cttttctggg acgacctgcg gagcctgtgc ctcttcagct accgccgctt    1080
gagagactta ctcttgattg tagcgaagat tgtggaaact ctgggacgca gggggtggga    1140
agtcctcaag tattggtgga atga                                           1164
```

<210> SEQ ID NO 7
<211> LENGTH: 1173
<212> TYPE: DNA
<213> ORGANISM: Artificial Sequence
<220> FEATURE:
<223> OTHER INFORMATION: Protein comprised of Immunodominant parts of
      the Nef-Tat-Rev separated by protease sites(NTR)

<400> SEQUENCE: 7

| | |
|---|---|
| atgggatggc ctactgtaag ggaaagaatg aaacaagctg agcctgagcc agcagcagat | 60 |
| ggggtgggag cagcatctcg agacctggaa aacatggaca atcacaag tagcaataca | 120 |
| gcaactaata acgctgcttg tgcctggcta aagcacaag aggaagagga agtgggtttt | 180 |
| ccagtcagac ctcaggtacc tttaagacca atgacttaca agggagcttt agatcttagc | 240 |
| cacttttta aagaaaaggg gggactggaa gggttaattt actccccaaa aagacaagag | 300 |
| atccttgatc tgtgggtcta ccacacacaa ggctacttcc ctgattggca gaactacaca | 360 |
| ccagggccag gggtcagata tccactgacc tttggatggt gcttcaagtt agtaccagtt | 420 |
| gaaccagatg aagaagagaa cagcagcctg ttacaccctg cgagcctgca tgggacagag | 480 |
| gacacggaga gagaagtgtt aaagtggaag tttgacagcc atctagcatt tcatcacaag | 540 |
| gcccgagagc tgcatccgga gtactacaaa gactgcgctc tggccttcaa gcgggttgag | 600 |
| ccagtagatc ctagactaga gccctggaag catccaggaa gtcagcctag gaccccttgt | 660 |
| accaattgct attgtaaaaa gtgttgcctt cattgccaag tttgtttcac aagaaaaggc | 720 |
| ttaggcatct cctatggcag gaagaagcgg agacagcgac gaagagctcc tcaagacagt | 780 |
| cagactcatc aagtttctct accaaagcaa ccctcctccc agcaacgagg ggaccccgaca | 840 |
| ggcccgaaga atccgtacg ggagaagcgg ctgctgagcg acgaagagct cctcaagaca | 900 |
| gtcagactca tcaagtttct ctaccaaagc aaccctcctc ccagcaacga ggggacccga | 960 |
| caggcccgaa gaaatcgaag aagaaggtgg agagagagac agaggcagat ccgttcgatt | 1020 |
| agtgagcgga ttcttagcac ttttctggga cgacctgcgg agcctgtgcc tcttcagcta | 1080 |
| ccgccgcttg agagacttac tcttgattgt agcgaagatt gtggaaactc tgggacgcag | 1140 |
| ggggtgggaa gtcctcaagt attggtggaa tga | 1173 |

<210> SEQ ID NO 8
<211> LENGTH: 1161
<212> TYPE: DNA
<213> ORGANISM: Artificial Sequence
<220> FEATURE:
<223> OTHER INFORMATION: Protein comprised of Immunodominant parts of the regulatory proteins Nef-Tat-Rev started from aa1 of Nef (N11TR)

<400> SEQUENCE: 8

| | |
|---|---|
| atgtggccta ctgtaaggga aagaatgaaa caagctgagc ctgagccagc agcagatggg | 60 |
| gtgggagcag catctcgaga cctggaaaaa catggagcaa tcacaagtag caatacagca | 120 |
| actaataacg ctgcttgtgc ctggctagaa gcacaagagg aagaggaagt gggttttcca | 180 |
| gtcagacctc aggtaccttt aagaccaatg acttacaagg gagctttaga tcttagccac | 240 |
| tttttaaaag aaaaggggg actggaaggg ttaatttact ccccaaaaag acaagagatc | 300 |
| cttgatctgt gggtctacca cacacaaggc tacttccctg attggcagaa ctacacacca | 360 |
| gggccagggg tcagatatcc actgaccttt ggatggtgct tcaagttagt accagttgaa | 420 |
| ccagatgaag aagaacagca gcctgttaca ccctgcgagc ctgcatggga cagaggac | 480 |
| acggagagag aagtgttaaa gtggaagttt gacagccatc tagcatttca tcacaaggcc | 540 |
| cgagagctgc atccggagta ctacaaagac tgcgctctgg ccgcgttga gccagtagat | 600 |
| cctagactag agccctggaa gcatccagga agtcagccta ggacccctg taccaattgc | 660 |
| tattgtaaaa agtgttgcct tcattgccaa gtttgtttca agaaaaagg cttaggcatc | 720 |
| tcctatggca ggaagaagcg agacagcga cgaagagctc ctcaagacag tcagactcat | 780 |
| caagtttctc taccaaagca accctcctcc cagcaacgag gggaccccgac aggcccgaag | 840 |

```
aaatccggac tggccatcct gctgagcgac gaagagctcc tcaagacagt cagactcatc    900
aagtttctct accaaagcaa ccctcctccc agcaacgagg ggacccgaca ggcccgaaga    960
aatcgaagaa gaaggtggag agagagacag aggcagatcc gttcgattag tgagcggatt   1020
cttagcactt ttctgggacg acctgcggag cctgtgcctc ttcagctacc gccgcttgag   1080
agacttactc ttgattgtag cgaagattgt ggaaactctg gacgcagggg ggtgggaagt   1140
cctcaagtat tggtggaatg a                                             1161
```

<210> SEQ ID NO 9
<211> LENGTH: 1170
<212> TYPE: DNA
<213> ORGANISM: Artificial Sequence
<220> FEATURE:
<223> OTHER INFORMATION: Protein comprised of Immunodominant parts of
      the regulatory proteins Nef-Tat-Rev started from aa1 of Nef
      separated by protease sites (N11TR)

<400> SEQUENCE: 9

```
atgtggccta ctgtaaggga agaatgaaa caagctgagc ctgagccagc agcagatggg      60
gtgggagcag catctcgaga cctggaaaaa catggagcaa tcacaagtag caatacagca    120
actaataacg ctgcttgtgc ctggctagaa gcacaagagg aagaggaagt gggttttcca    180
gtcagacctc aggtaccttt aagaccaatg acttacaagg gagctttaga tcttagccac    240 ttttaaaag aaaaggggggg actggaaggg ttaatttact ccccaaaaag acaagagatc    300
cttgatctgt gggtctacca cacacaaggc tacttccctg attggcagaa ctacacacca    360
gggccagggg tcagatatcc actgaccttt ggatggtgct tcaagttagt accagttgaa    420
ccagatgaag aagagaacag cagcctgtta caccctgcga gcctgcatgg gacagaggac    480
acggagagag aagtgttaaa gtggaagttt gacagccatc tagcatttca tcacaaggcc    540
cgagagctgc atccggagta ctacaaagac tgcgctctgg ccttcaagcg ggttgagcca    600
gtagatccta gactagagcc ctggaagcat ccaggaagtc agcctaggac cccttgtacc    660
aattgctatt gtaaaaagtg ttgccttcat tgccaagttt gtttcacaag aaaaggctta    720
ggcatctcct atggcaggaa gaagcggaga cagcgacgaa gagctcctca agacagtcag    780
actcatcaag tttctctacc aaagcaaccc tcctcccagc aacgagggga cccgacaggc    840
ccgaagaaat ccgtacggga gaagcggctg ctgagcgacg aagagctcct caagacagtc    900
agactcatca gtttctctac caaagcaacc cctcctccca gcaacgaggg gacccgacag    960
gcccgaagaa atcgaagaag aaggtggaga gagagacaga ggcagatccg ttcgattagt   1020
gagcggattc ttagcacttt tctgggacga cctgcggagc ctgtgcctct tcagctaccg   1080
ccgcttgaga gacttactct tgattgtagc gaagattgtg gaaactctgg acgcagggg   1140 gtgggaagtc ctcaagtatt ggtggaatga                                    1170
```

<210> SEQ ID NO 10
<211> LENGTH: 663
<212> TYPE: DNA
<213> ORGANISM: Artificial Sequence
<220> FEATURE:
<223> OTHER INFORMATION: Protein comprised of Cytotoxic T-cell epitopes
      of Pol and Env genes (CTL)

<400> SEQUENCE: 10

```
atgatcaccc tgtggcagcg ccccctggtg gccctgatcg agatctgcac cgagatggag     60
aaggagggca gatcagcaa gatcggcccc gccggcctga agaagaagaa gagcgtgacc    120
gtgctggacg tgggcgacgc ctacttcagc gtgcccctgg ataaggactt ccgcaagtac    180
```

-continued

```
accgccttca ccatcccag catctggaag ggcagccccg ccatcttcca gagcagcatg    240
accaagaagc agaaccccga catcgtgatc taccagtaca tggacgacct gtacgtgccc    300
atcgtgctgc ccgagaagga cagctggctg gtgggcaagc tgaactgggc cagccagatc    360
tacgccggca tcaaggtgaa gcagctgatc ctgaaggagc ccgtgcacgg cgtgtacgag    420
cccatcgtgg cgccgagac cttctacgtg acggcgccg ccaaccgcgc cggcaacctg     480
tgggtgaccg tgtactacgg cgtgcccgtg tggaaggagg ccaccaccac cctggtggag    540
cgctacctgc cgaccagca gctgctgggc atctggggct gcgcctgcac ccctacgac     600 atcaaccaga tgctgcgcgg ccctggccgc gccttcgtga ccatccgcca gggcagcctg    660
tag                                                                  663

<210> SEQ ID NO 11
<211> LENGTH: 1266
<212> TYPE: DNA
<213> ORGANISM: Artificial Sequence
<220> FEATURE:
<223> OTHER INFORMATION: Truncated Gag protein sequence (dgag)

<400> SEQUENCE: 11
atgttagaca atgggaaaa aattcggtta aggccagggg gaaagaaaaa atatcaatta     60
aaacatatag tatgggcaag cagggagcta gaacgattcg cagttaatcc tggcctgtta   120
gaaacatcag aaggctgtag acagataatg ggacagctac aaccgtccct tcagacagga   180
tcagaagaac ttagatcatt atataataca gtagcaaccc tctattgtgt gcatcaaaag   240
atagaggtaa aagacaccaa ggaagcttta gacaaggtag aggaagagca aaacaacagt   300
aagaaaaagg cacagcaaga agcagctgac gcaggaaaca gaaaccaggt cagccaaaat   360
taccctatag tgcaaaacct acagggacaa atggtacatc aggccatatc acctagaact   420
ttaaatgcat gggtaaaagt agtggaagag aaggcttttca gcccagaagt aatacccatg   480
ttttcagcat tatcagaagg agccacccca caagatttaa acaccatgct aaacacagtg   540
gggggacatc aagcagccat gcaaatgtta aagaaaccca tcaatgagga agctgcagaa   600
tgggatagat tgcacccagt gcatgcaggg cctattgcac caggccagat gagagaacca   660
aggggaagtg acatagcagg aactactagt acccttcagg aacaaatagg atggatgaca   720 ataatccac ctatcccagt aggagaaata tataagagat ggataatcct gggattaaat    780
aaaatagtaa gaatgtatag ccctaccagc attctggata aaaacaagg accaaaagaa    840 ccctttagag attatgtaga ccggttctat aaaaccctaa gagccgagca agctacacag    900
gaagtaaaaa attggatgac agaaaccttg ttggtccaaa atgcgaatcc agattgtaag   960
actattttaa aagcattagg accagcagct acactagaag aaatgatgac agcatgtcag   1020 ggagtgggg gacccggcca taaagcaaga gttttggctg aagcaatgag ccaagtaaca   1080
ggttcagctg ccataatgat gcagagaggc aattttagga ccaaagaaa gactgttaag   1140 tgtttcaatt gtggcaaaga agggcacata gccagaaatt gcagggcccc taggaaaaag   1200
ggctgttgga aatgtggaaa ggaaggacat caaatgaagg attgcacaga agacaggct   1260 aattag                                                              1266

<210> SEQ ID NO 12
<211> LENGTH: 1092
<212> TYPE: DNA
<213> ORGANISM: Artificial Sequence
<220> FEATURE:
<223> OTHER INFORMATION: Synthetic coding sequence for p17/24 protein of
```

Gag gene (syn 17/24)

<400> SEQUENCE: 12

```
atgggcgcaa gagcctccgt gctgagcggc ggagagctgg acaagtggga gaagatccgc      60
ctgcgccccg gcggcaagaa gaagtaccag ctgaagcaca tcgtgtgggc cagccgcgag     120
ctggagcgct tcgccgtgaa ccccggcctg ctcgagacca gcgaaggctg ccgccagatc     180
atgggccagc tccagcccag cctccagacc ggcagcgagg agctgcgcag cctgtacaac     240
accgtggcca ccctgtactg cgtgcaccag aagatcgagg tgaaggacac caaggaggcc     300
ctggacaagg tggaggagga gcagaacaac agcaagaaga aggcccagca ggaggccgcc     360
gacgccggca accgcaacca ggtgagccag aactacccca tcgtgcagaa cctgcagggc     420
cagatggtgc accaggccat cagccccgc accctgaacg cctgggtgaa ggtggtggag     480
gagaaggcct tcagccccga ggtgatcccc atgttcagcg ccctgagcga gggcgctacc     540
ccccaggacc tgaacaccat gctgaacacc gtgggcggcc accaggccgc catgcagatg     600
ctgaaggaga ccatcaacga ggaggccgcc gagtgggacc gcctgcaccc cgtgcacgcc     660
gggcccatcg cccccggcca gatgcgcgag ccccgcggca gcgacatcgc cggcaccacc     720
agcaccctcc aggagcagat cggctggatg accaacaacc ccccatccc cgtgggcgag     780
atctacaagc gctggatcat cctgggcctg aacaagatcg tccgcatgta cagccccacc     840
agcatcctgg acatcaagca gggccccaag gagcccttcc gcgactacgt ggaccgcttc     900
tacaagaccc tgcgcgccga gcaggccacc caggaggtga agaactggat gaccgagacc     960
ctgctggtgc agaacgccaa ccccgactgc aagaccatcc tcaaggccct gggacccgcc    1020
gccacccctgg aggagatgat gaccgcctgc caaggcgtgg gcggccccgg ccacaaggcc    1080
cgcgtgctgt ga                                                        1092
```

<210> SEQ ID NO 13
<211> LENGTH: 1092
<212> TYPE: DNA
<213> ORGANISM: Artificial Sequence
<220> FEATURE:
<223> OTHER INFORMATION: Synthetic coding sequence for p17/24 protein of Gag gene optimized for expression in eukaryotic cells (optp17/24)

<400> SEQUENCE: 13

```
atgggcgcaa gagcctccgt gctgagcggc ggagagctgg acaagtggga gaagatccgc      60
ctgcgccccg gcggcaagaa gaagtaccag ctgaagcaca tcgtgtgggc cagccgcgag     120
ctggagcgct tcgccgtgaa ccccggcctg ctcgagacca gcgaaggctg ccgccagatc     180
atgggccagc tccagcccag cctccagacc ggcagcgagg agctgcgcag cctgtacaac     240
accgtggcca ccctgtactg cgtgcaccag aagatcgagg tgaaggacac caaggaggcc     300
ctggacaagg tggaggagga gcagaacaac agcaagaaga aggcccagca ggaggccgcc     360
gacgccggca accgcaacca agtcagccag aactacccca tcgtgcagaa cctgcagggc     420
cagatggtgc accaggccat cagccccgc accctgaacg cctgggtgaa ggtggtggag     480
gagaaggcct tcagccccga ggtgatcccc atgttcagcg ccctgagcga gggcgctacc     540
ccccaggacc tgaacaccat gctgaacacc gtgggcggcc accaggccgc catgcagatg     600
ctgaaggaga ccatcaacga ggaggccgcc gagtgggacc gcctgcaccc cgtgcacgcc     660
gggcccatcg cccccggcca gatgcgcgag ccccgcggca gcgacatcgc cggcaccacc     720
agcaccctcc aggagcagat cggctggatg accaacaacc ccccatccc cgtgggcgag     780
atctacaagc gctggatcat cctgggcctg aacaagatcg tccgcatgta cagccccacc     840
```

```
agcatcctgg acatcaagca gggcccaag gagcccttcc gcgactacgt ggaccgcttc     900
tacaagaccc tgcgcgccga gcaggccacc caggaggtga agaactggat gaccgagacc     960
ctgctggtgc agaacgccaa ccccgactgc aagaccatcc tcaaggccct gggacccgcc    1020
gccaccctgg aggagatgat gaccgcctgc caaggcgtgg gcggcccgg ccacaaggcc    1080 cgcgtgctgt ga                                                         1092
```

<210> SEQ ID NO 14
<211> LENGTH: 1926
<212> TYPE: DNA
<213> ORGANISM: Artificial Sequence
<220> FEATURE:
<223> OTHER INFORMATION: Hybrid protein cds comprised of Tat-Rev-Nef and CTL (TRN-CTL)

<400> SEQUENCE: 14

```
atggagccag tagatcctag actagagccc tggaagcatc caggaagtca gcctaggacc      60
ccttgtacca attgctattg taaaaagtgt tgccttcatt gccaagtttg tttcacaaga     120
aaaggcttag gcatctccta tggcaggaag aagcggagac agcgacgaag agctcctcaa     180
gacagtcaga ctcatcaagt ttctctacca agcaacccct cctcccagca acgaggggac     240
ccgacaggcc cgaagaaatc gaagaagaag gtggagagag agacagaggc agatccgttc     300
gatactagtg caggaagaag cggagacagc gacgaagagc tcctcaagac agtcagactc     360
atcaagtttc tctaccaaag caacccctcc tcccagcaac ggggacccg acaggcccga     420 agaaatcgaa gaagaaggtg gagagagaga cagaggcaga tccgttcgat tagtgagcgg     480
attcttagca cttttctggg acgacctgcg gagcctgtgc ctcttcagct accgccgctt     540
gagagactta ctcttgattg tagcgaagat tgtggaaact ctgggacgca ggggtggga     600 agtcctcaag tattggtgga atctcctgca gtattggagc caggaactaa gaaaagctt     660 gtgggcaagt ggtcaaaatg tagtggatgg cctactgtaa gggaaagaat gaaacaagct     720
gagcctgagc cagcagcaga tggggtggga gcagcatctc gagacctgga aaaacatgga     780
gcaatcacaa gtagcaatac agcaactaat aacgctgctt gtgcctggct agaagcacaa     840
gaggaagagg aagtgggttt tccagtcaga cctcaggtac cttttaagacc aatgacttac     900 aagggagctt tagatcttag ccacttttta aagaaaagg ggggactgga agggttaatt     960
tactccccaa aaagacaaga gatccttgat ctgtgggtct accacacaca aggctacttc    1020
cctgattggc agaactacac accagggcca ggggtcagat atccactgac ctttggatgg    1080
tgcttcaagt tagtaccagt tgaaccagat gaagaagaga acagcagcct gttacaccct    1140
gcgagcctgc atgggacaga ggacacggag agagaagtgt taagtggaa gtttgacagc    1200 catctagcat ttcatcacaa ggcccgagag ctgcatccgg agtactacaa agactgcgcg    1260
gccgtcatca ccctgtggca gcgccccctg gtgccctga tcgagatctg caccgagatg    1320
gagaaggagg gcaagatcag caagatcggc cccgccggcc tgaagaagaa gaagagcgtg    1380
accgtgctgg acgtgggcga cgcctacttc agcgtgcccc tggataagga cttccgcaag    1440
tacaccgcct tcaccatccc cagcatctgg aagggcagcc ccgccatctt ccagagcagc    1500
atgaccaaga gcagaaccc cgacatcgtg atctaccagt acatggacga cctgtacgtg    1560
cccatcgtgc tgcccgagaa ggacagctgg ctggtgggca agctgaactg gccagccag    1620 atctacgccg gcatcaaggt gaagcagctg atcctgaagg agcccgtgca cggcgtgtac    1680
gagcccatcg tgggcgccga gaccttctac gtggacggcg ccgccaaccg cgccggcaac    1740
```

```
ctgtgggtga ccgtgtacta cggcgtgccc gtgtggaagg aggccaccac caccctggtg      1800
gagcgctacc tgcgcgacca gcagctgctg ggcatctggg gctgcgcctg cacccccctac      1860 gacatcaacc agatgctgcg cggccctggc cgcgccttcg tgaccatccg ccagggcagc      1920
ctgtag                                                                 1926
```

<210> SEQ ID NO 15
<211> LENGTH: 1926
<212> TYPE: DNA
<213> ORGANISM: Artificial Sequence
<220> FEATURE:
<223> OTHER INFORMATION: Hybrid protein cds comprised of Rev-Nef-Tat and CTL (RNT-CTL)

<400> SEQUENCE: 15

```
atggcaggaa gaagcggaga cagcgacgaa gagctcctca agacagtcag actcatcaag       60
tttctctacc aaagcaaccc tcctcccagc aacgagggga cccgacaggc ccgaagaaat      120
cgaagaagag gtggagagag agacagagg cagatccgtt cgattagtga gcggattctt      180 agcactttc tgggacgacc tgcggagcct gtgcctcttc agctaccgcc gcttgagaga      240
cttactcttg attgtagcga agattgtgga aactctggga cgcagggggt gggaagtcct      300
caagtattgg tggaatctcc tgcagtattg gagccaggaa ctaaagaaac tagtgtgggc      360
aagtggtcaa atgtagtgg atggcctact gtaaggaaa gaatgaaaca agctgagcct      420
gagccagcag cagatggggt gggagcagca tctcgagacc tggaaaaaca tggagcaatc      480
acaagtagca atacagcaac taataacgct gcttgtgcct ggctagaagc acaagaggaa      540
gaggaagtgg gttttccagt cagacctcag gtacctttaa gaccaatgac ttacaaggga      600
gctttagatc ttagccactt tttaaaagaa aagggggga ctggaagggt taatttactcc      660 ccaaaaagac aagagatcct tgatctgtgg gtctaccaca caaggcta cttccctgat      720 tggcagaact acaccaggg ccagggggtc agatatccac tgacctttgg atggtgcttc      780
aagttagtac cagttgaacc agatgaagaa gagaacagca gcctgttaca ccctgcgagc      840
ctgcatggga cagaggacac ggagagagaa gtgttaaagt ggaagtttga cagccatcta      900
gcatttcatc acaaggcccg agagctgcat ccggagtact acaaagactg caagcttgag      960
ccagtagatc ctagactaga gccctggaag catccaggaa gtcagcctag gaccccttgt     1020
accaattgct attgtaaaaa gtgttgcctt cattgccaag tttgtttcac aagaaaaggc     1080
ttaggcatct cctatggcag gaagaagcgg agacagcgac gaagagctcc tcaagacagt     1140
cagactcatc aagtttctct accaaagcaa ccctcctccc agcaacgagg ggaccccgaca    1200 ggcccgaaga atcgaagaa gaaggtggag agagagacag aggcagatcc gttcgatgcg     1260
gccgtcatca ccctgtggca gcgcccctg gtgggcctga tcgagatctg caccgagatg     1320
gagaaggagg gcaagatcag caagatcggc ccgccggcc tgaagaagaa gaagagcgtg     1380
accgtgctgg acgtgggcga cgcctactc agcgtgcccc tggataagga cttccgcaag     1440
tacaccgcct tcaccatccc cagcatctgg aagggcagcc ccgccatctt ccagagcagc     1500
atgaccaaga agcagaaccc cgacatcgtg atctaccagt acatggacga cctgtacgtg     1560
cccatcgtgc tgcccgagaa ggacagctgg ctggtgggca agctgaactg ggccagccag     1620
atctacgccg gcatcaaggt gaagcagctg atcctgaagg agcccgtgca cggcgtgtac     1680
gagcccatcg tgggcgccga ccttctac gtggacggcg ccgccaaccg cgccggcaac     1740
ctgtgggtga ccgtgtacta cggcgtgccc gtgtggaagg aggccaccac caccctggtg     1800
gagcgctacc tgcgcgacca gcagctgctg ggcatctggg gctgcgcctg cacccccctac     1860
```

```
gacatcaacc agatgctgcg cggccctggc cgcgccttcg tgaccatccg ccagggcagc    1920
ctgtag                                                                1926

<210> SEQ ID NO 16
<211> LENGTH: 2529
<212> TYPE: DNA
<213> ORGANISM: Artificial Sequence
<220> FEATURE:
<223> OTHER INFORMATION: Hybrid protein cds comprised of Tat-Rev-Nef
      and truncated Gag protein (TRN-dgag)

<400> SEQUENCE: 16
atggagccag tagatcctag actagagccc tggaagcatc caggaagtca gcctaggacc      60
ccttgtacca attgctattg taaaaagtgt tgccttcatt gccaagtttg tttcacaaga     120
aaaggcttag gcatctccta tggcaggaag aagcggagac agcgacgaag agctcctcaa     180
gacagtcaga ctcatcaagt ttctctacca aagcaaccct cctcccagca acgaggggac     240
ccgacaggcc cgaagaaatc gaagaagaag gtggagagag acagaggc agatccgttc       300 gatactagtg caggaagaag cggagacagc gacgaagagc tcctcaagac agtcagactc     360
atcaagtttc tctaccaaag caaccctcct cccagcaacg ggggacccg acaggcccga      420 agaaatcgaa gaaggtg gagagagaga cagaggcaga tccgttcgat tagtgagcgg        480
attcttagca ctttctggg acgacctgcg gagcctgtgc ctcttcagct accgccgctt      540
gagagactta ctcttgattg tagcgaagat tgtggaaact ctgggacgca ggggtggga      600 agtcctcaag tattggtgga atctcctgca gtattggagc caggaactaa agaaaagctt     660
gtgggcaagt ggtcaaaatg tagtggatgg cctactgtaa gggaaagaat gaaacaagct     720
gagcctgagc cagcagcaga tggggtggga gcagcatctc gagacctgga aaaacatgga     780
gcaatcacaa gtagcaatac agcaactaat aacgctgctt gtgcctggct agaagcacaa     840
gaggaagagg aagtgggttt tccagtcaga cctcaggtac ctttaagacc aatgacttac     900
aagggagctt tagatcttag ccactttta aaagaaaagg ggggactgga agggttaatt     960
tactccccaa aaagacaaga gatccttgat ctgtgggtct accacacaca aggctacttc    1020
cctgattggc agaactacac accagggcca ggggtcagat atccactgac ctttggatgg    1080
tgcttcaagt tagtaccagt tgaaccagat gaagaagaga cagcagcct gttacaccct     1140 gcgagcctgc atgggacaga ggacacggag agagaagtgt aaagtggaa gtttgacagc     1200 catctagcat ttcatcacaa ggcccagag ctgcatccgg agtactacaa agactgcgcg     1260
gccgtgttag acaaatggga aaaaattcgg ttaaggccag ggggaaagaa aaatatcaa     1320 ttaaaacata tagtatgggc aagcaggag ctagaacgat tcgcagttaa tcctggcctg    1380
ttagaaacat cagaaggctg tagacagata atgggacagc tacaaccgtc ccttcagaca    1440
ggatcagaag aacttagatc attatataat acagtagcaa ccctctattg tgtgcatcaa    1500
aagatagagg taaagacac caaggaagct ttagacaagg tagaggaaga gcaaaacaac    1560
agtaagaaaa aggcacagca agaagcagct gacgcaggaa acagaaacca ggtcagccaa    1620
aattacccta tagtgcaaaa cctacaggga caaatggtac atcaggccat atcacctaga    1680
actttaaatg catgggtaaa agtagtgaa gagaaggctt tcagcccaga gtaatacccc    1740
atgttttcag cattatcaga aggagccacc ccacaagatt taaacaccat gctaaacaca    1800
gtggggggac atcaagcagc catgcaaatg ttaaaagaaa ccatcaatga ggaagctgca    1860
gaatgggata gattgcaccc agtgcatgca gggcctattg caccaggcca gatgagagaa    1920
```

-continued

| | |
|---|---|
| ccaagggaa gtgacatagc aggaactact agtacccttc aggaacaaat aggatggatg | 1980 |
| acaaataatc cacctatccc agtaggagaa atatataaga gatggataat cctgggatta | 2040 |
| aataaaatag taagaatgta tagccctacc agcattctgg atataaaaca aggaccaaaa | 2100 |
| gaacccttta gagattatgt agaccggttc tataaaaccc taagagccga gcaagctaca | 2160 |
| caggaagtaa aaaattggat gacagaaacc ttgttggtcc aaaatgcgaa tccagattgt | 2220 |
| aagactattt taaaagcatt aggaccagca gctacactag aagaaatgat gacagcatgt | 2280 |
| cagggagtgg ggggacccgg ccataaagca agagttttgg ctgaagcaat gagccaagta | 2340 |
| acaggttcag ctgccataat gatgcagaga ggcaatttta ggaaccaaag aaagactgtt | 2400 |
| aagtgtttca attgtggcaa agaagggcac atagccagaa attgcagggc ccctaggaaa | 2460 |
| aagggctgtt ggaaatgtgg aaaggaagga catcaaatga aggattgcac agaaagacag | 2520 |
| gctaattag | 2529 |

<210> SEQ ID NO 17
<211> LENGTH: 3195
<212> TYPE: DNA
<213> ORGANISM: Artificial Sequence
<220> FEATURE:
<223> OTHER INFORMATION: Hybrid protein cds comprised of Tat-Rev-Nef,
      CTL and truncated Gag protein (TRN-CTL-dgag)

<400> SEQUENCE: 17

| | |
|---|---|
| atggagccag tagatcctag actagagccc tggaagcatc caggaagtca gcctaggacc | 60 |
| ccttgtacca attgctattg taaaaagtgt tgccttcatt gccaagtttg tttcacaaga | 120 |
| aaaggcttag gcatctccta tggcaggaag aagcggagac agcgacgaag agctcctcaa | 180 |
| gacagtcaga ctcatcaagt ttctctacca aagcaaccct cctcccagca acgaggggac | 240 |
| ccgacaggcc cgaagaaatc gaagaagaag gtggagagag agacagaggc agatccgttc | 300 |
| gatactagtg caggaagaag cggagacagc gacgaagagc ctcaagac agtcagactc | 360 |
| atcaagtttc tctaccaaag caaccctcct cccagcaacg aggggacccg acaggcccga | 420 |
| agaaatcgaa gaagaaggtg gagagagaga cagaggcaga tccgttcgat tagtgagcgg | 480 |
| attcttagca cttttctggg acgacctgcg gagcctgtgc ctcttcagct accgccgctt | 540 |
| gagagactta ctcttgattg tagcgaagat tgtggaaact ctgggacgca ggggtgggaa | 600 |
| agtcctcaag tattggtgga atctcctgca gtattggagc caggaactaa agaaaagctt | 660 |
| gtgggcaagt ggtcaaaatg tagtggatgg cctactgtaa gggaaagaat gaaacaagct | 720 |
| gagcctgagc cagcagcaga tggggtggga gcagcatctc gagacctgga aaaacatgga | 780 |
| gcaatcacaa gtagcaatac agcaactaat aacgctgctt gtgcctggct agaagcacaa | 840 |
| gaggaagagg aagtgggttt tccagtcaga cctcaggtac ctttaagacc aatgacttac | 900 |
| aagggagctt tagatcttag ccactttta aaagaaaagg ggggactgga agggttaatt | 960 |
| tactccccaa aaagacaaga gatccttgat ctgtgggtct accacacaca aggctacttc | 1020 |
| cctgattggc agaactacac accagggcca ggggtcagat atccactgac ctttggatgg | 1080 |
| tgcttcaagt tagtaccagt tgaaccagat gaagaagaga cagcagcct gttacaccct | 1140 |
| gcgagcctgc atgggacaga ggacacggag agaagtgtgt aaagtggaa gtttgacagc | 1200 |
| catctagcat ttcatcacaa ggcccgagag ctgcatccgg agtactacaa agactgcgcg | 1260 |
| gccgtcatca ccctgtggca gcgcccctg gtggcccctga tcgagatctg caccgagatg | 1320 |
| gagaaggagg gcaagatcag caagatcggc ccgccggcc tgaagaagaa gaagagcgtg | 1380 |
| accgtgctgg acgtgggcga cgcctacttc agcgtgcccc tggataagga cttccgcaag | 1440 |

```
tacaccgcct tcaccatccc cagcatctgg aagggcagcc ccgccatctt ccagagcagc    1500
atgaccaaga agcagaaccc cgacatcgtg atctaccagt acatggacga cctgtacgtg    1560
cccatcgtgc tgcccgagaa ggacagctgg ctggtgggca agctgaactg ggccagccag    1620
atctacgccg gcatcaaggt gaagcagctg atcctgaagg agcccgtgca cggcgtgtac    1680
gagcccatcg tgggcgccga gaccttctac gtggacggcg ccgccaaccg cgccggcaac    1740
ctgtgggtga ccgtgtacta cggcgtgccc gtgtggaagg aggccaccac caccctggtg    1800
gagcgctacc tgcgcgacca gcagctgctg ggcatctggg gctgcgcctg cacccccta c   1860 gacatcaacc agatgctgcg cggccctggc cgcgccttcg tgaccatccg ccagggcagc    1920
ctggcggccg tgttagacaa atgggaaaaa attcggttaa ggccaggggg aaagaaaaaa    1980
tatcaattaa aacatatagt atgggcaagc agggagctag aacgattcgc agttaatcct    2040
ggcctgttag aaacatcaga aggctgtaga cagataatgg gacagctaca accgtccctt    2100
cagacaggat cagaagaact tagatcatta tataatacag tagcaaccct ctattgtgtg    2160
catcaaaaga tagaggtaaa agacaccaag gaagctttag acaaggtaga ggaagagcaa    2220
aacaacagta agaaaaaggc acagcaagaa gcagctgacg caggaaacag aaaccaggtc    2280
agccaaaatt accctatagt gcaaaaccta caggggacaaa tggtacatca ggccatatca    2340
cctagaactt taaatgcatg ggtaaaagta gtggaagaga aggctttcag cccagaagta    2400
atacccatgt tttcagcatt atcagaagga gccaccccac aagatttaaa caccatgcta    2460
aacacagtgg ggggacatca agcagccatg caaatgttaa agaaaccat caatgaggaa     2520 gctgcagaat gggatagatt gcacccagtg catgcagggc ctattgcacc aggccagatg    2580
agagaaccaa ggggaagtga catagcagga actactagta cccttcagga acaaatagga    2640
tggatgacaa ataatccacc tatcccagta ggagaaatat ataagagatg gataatcctg    2700
ggattaaata aaatagtaag aatgtatagc cctaccagca ttctggatat aaaacaagga    2760
ccaaaagaac cctttagaga ttatgtagac cggttctata aaaccctaag agccgagcaa    2820
gctacacagg aagtaaaaaa ttggatgaca gaaaccttgt tggtccaaaa tgcgaatcca    2880
gattgtaaga ctattttaaa agcattagga ccagcagcta cactagaaga aatgatgaca    2940
gcatgtcagg gagtgggggg acccggccat aaagcaagag ttttggctga agcaatgagc    3000
caagtaacag gttcagctgc cataatgatg cagagaggca attttaggaa ccaaagaaag    3060
actgttaagt gtttcaattg tggcaaagaa gggcacatag ccagaaattg cagggcccct    3120
aggaaaaagg gctgttggaa atgtggaaag gaaggacatc aaatgaagga ttgcacagaa    3180
agacaggcta attag                                                    3195
```

<210> SEQ ID NO 18
<211> LENGTH: 3195
<212> TYPE: DNA
<213> ORGANISM: Artificial Sequence
<220> FEATURE:
<223> OTHER INFORMATION: Hybrid protein cds comprised of Rev-Nef-Tat,
      CTL and truncated Gag protein (RNT-CTL-dgag)

<400> SEQUENCE: 18

```
atggcaggaa gaagcggaga cagcgacgaa gagctcctca agacagtcag actcatcaag      60
tttctctacc aaagcaaccc tcctcccagc aacgagggga cccgacaggc ccgaagaaat     120
cgaagaagaa ggtggagaga gagacagagg cagatccgtt cgattagtga gcggattctt     180 agcactttc tgggacgacc tgcggagcct gtgcctcttc agctaccgcc gcttgagaga     240
```

```
cttactcttg attgtagcga agattgtgga aactctggga cgcagggggt gggaagtcct    300
caagtattgg tggaatctcc tgcagtattg gagccaggaa ctaaagaaac tagtgtgggc    360
aagtggtcaa aatgtagtgg atggcctact gtaagggaaa gaatgaaaca agctgagcct    420
gagccagcag cagatgggt gggagcagca tctcgagacc tggaaaaaca tggagcaatc    480
acaagtagca atacagcaac taataacgct gcttgtgcct ggctagaagc acaagaggaa    540
gaggaagtgg gttttccagt cagacctcag gtacctttaa gaccaatgac ttacaaggga    600
gctttagatc ttagccactt ttttaaaagaa aaggggggac tggaagggtt aatttactcc    660
ccaaaaagac aagagatcct tgatctgtgg gtctaccaca cacaaggcta cttccctgat    720
tggcagaact acacaccagg gccaggggtc agatatccac tgacctttgg atggtgcttc    780
aagttagtac cagttgaacc agatgaagaa gagaacagca gcctgttaca ccctgcgagc    840
ctgcatggga cagaggacac ggagagagaa gtgttaaagt ggaagtttga cagccatcta    900
gcatttcatc acaaggcccg agagctgcat ccggagtact acaaagactg caagcttgag    960
ccagtagatc ctagactaga gccctggaag catccaggaa gtcagcctag gaccccttgt   1020
accaattgct attgtaaaaa gtgttgcctt cattgccaag tttgtttcac aagaaaaggc   1080
ttaggcatct cctatggcag gaagaagcgg agacagcgac gaagagctcc tcaagacagt   1140
cagactcatc aagtttctct accaaagcaa ccctcctccc agcaacgagg ggacccgaca   1200
ggcccgaaga atcgaagaa gaaggtggag agagagacag aggcagatcc gttcgatgcg   1260
gccgtcatca ccctgtggca gcgcccctg gtggccctga tcgagatctg caccgagatg   1320
gagaaggagg gcaagatcag caagatcggc cccgccggcc tgaagaagaa gaagagcgtg   1380
accgtgctgg acgtgggcga cgcctacttc agcgtgcccc tggataagga cttccgcaag   1440
tacaccgcct tcaccatccc cagcatctgg aagggcagcc ccgccatctt ccagagcagc   1500
atgaccaaga agcagaaccc cgacatcgtg atctaccagt acatggacga cctgtacgtg   1560
cccatcgtgc tgcccgagaa ggacagctgg ctggtgggca agctgaactg gccagccag   1620 atctacgccg gcatcaaggt gaagcagctg atcctgaagg agcccgtgca cggcgtgtac   1680
gagcccatcg tgggcgccga gaccttctac gtggacggcg ccgccaaccg cgccggcaac   1740
ctgtgggtga ccgtgtacta cggcgtgccc gtgtggaagg aggccaccac caccctggtg   1800
gagcgctacc tgcgcgacca gcagctgctg ggcatctggg gctgcgcctg caccccctac   1860
gacatcaacc agatgctgcg cggccctggc cgcgccttcg tgaccatccg ccagggcagc   1920
ctggcggccg tgttagacaa atgggaaaaa attcggttaa ggccaggggg aaagaaaaaa   1980
tatcaattaa aacatatagt atgggcaagc agggagctag aacgattcgc agttaatcct   2040
ggcctgttag aaacatcaga aggctgtaga cagataatgg gacagctaca accgtccctt   2100
cagacaggat cagaagaact tagatcatta tataatacag tagcaaccct ctattgtgtg   2160
catcaaaaga tagaggtaaa agacaccaag gaagctttag acaagtagga ggagagcaa   2220 aacaacagta agaaaaggc acagcaagaa gcagctgacg caggaaacag aaaccaggtc   2280
agccaaaatt accctatagt gcaaaaccta cagggacaaa tggtacatca ggccatatca   2340
cctagaactt taaatgcatg ggtaaaagta gtggaagaga aggctttcag cccagaagta   2400
atacccatgt tttcagcatt atcagaagga gccaccccac aagatttaaa caccatgcta   2460
aacacagtgg ggggacatca agcagccatg caaatgttaa aagaaaccat caatgaggaa   2520
gctgcagaat gggatagatt gcacccagtg catgcagggc ctattgcacc aggccagatg   2580
agagaaccaa gggga agtga catagcagga actactagta cccttcagga acaaatagga   2640
```

| | |
|---|---|
| tggatgacaa ataatccacc tatcccagta ggagaaatat aaagagatg gataatcctg | 2700 |
| ggattaaata aaatagtaag aatgtatagc cctaccagca ttctggatat aaaacaagga | 2760 |
| ccaaaagaac cctttagaga ttatgtagac cggttctata aaaccctaag agccgagcaa | 2820 |
| gctacacagg aagtaaaaaa ttggatgaca gaaaccttgt tggtccaaaa tgcgaatcca | 2880 |
| gattgtaaga ctattttaaa agcattagga ccagcagcta cactagaaga aatgatgaca | 2940 |
| gcatgtcagg gagtggggggg acccggccat aaagcaagag ttttggctga agcaatgagc | 3000 |
| caagtaacag gttcagctgc cataatgatg cagagaggca attttaggaa ccaaagaaag | 3060 |
| actgttaagt gtttcaattg tggcaaagaa gggcacatag ccagaaattg cagggcccct | 3120 |
| aggaaaaagg gctgttggaa atgtggaaag gaaggacatc aaatgaagga ttgcacagaa | 3180 |
| agacaggcta attag | 3195 |

<210> SEQ ID NO 19
<211> LENGTH: 3195
<212> TYPE: DNA
<213> ORGANISM: Artificial Sequence
<220> FEATURE:
<223> OTHER INFORMATION: Hybrid protein cds comprised of Tat-Rev-Nef, truncated Gag protein and CTL (TRN-dgag-CTL)

<400> SEQUENCE: 19

| | |
|---|---|
| atggagccag tagatcctag actagagccc tggaagcatc caggaagtca gcctaggacc | 60 |
| ccttgtacca attgctattg taaaaagtgt tgccttcatt gccaagtttg tttcacaaga | 120 |
| aaaggcttag gcatctccta tggcaggaag aagcggagac agcgacgaag agctcctcaa | 180 |
| gacagtcaga ctcatcaagt ttctctacca aagcaaccct cctcccagca acgaggggac | 240 |
| ccgacaggcc cgaagaaatc gaagaagaag gtggagagag agacagaggc agatccgttc | 300 |
| gatactagtg caggaagaag cggagacagc gacgaagagc tcctcaagac agtcagactc | 360 |
| atcaagtttc tctaccaaag caaccctcct cccagcaacg aggggacccg acaggcccga | 420 |
| agaaatcgaa gaagaaggtg gagagagaga cagaggcaga tccgttcgat tagtgagcgg | 480 |
| attcttagca ctttctctggg acgacctgcg gagcctgtgc ctcttcagct accgccgctt | 540 |
| gagagactta ctcttgattg tagcgaagat tgtggaaact ctgggacgca gggggtggga | 600 |
| agtcctcaag tattggtgga atctcctgca gtattggagc caggaactaa gaaaagctt | 660 |
| gtgggcaagt ggtcaaaatg tagtggatgg cctactgtaa gggaaagaat gaaacaagct | 720 |
| gagcctgagc cagcagcaga tggggtggga gcagcatctc gagacctgga aaaacatgga | 780 |
| gcaatcacaa gtagcaatac agcaactaat aacgctgctt gtgcctggct agaagcacaa | 840 |
| gaggaagagg aagtgggttt tccagtcaga cctcaggtac cttaagacc aatgacttac | 900 |
| aagggagctt tagatcttag ccactttta aaagaaaagg ggggactgga agggttaatt | 960 |
| tactccccaa aaagacaaga gatccttgat ctgtgggtct accacacaca aggctacttc | 1020 |
| cctgattggc agaactacac accagggcca ggggtcagat atccactgac ctttggatgg | 1080 |
| tgcttcaagt tagtaccagt tgaaccagat gaagaagaga cagcagcct gttacaccct | 1140 |
| gcgagcctgc atgggacaga ggacacggag agagaagtgt taaagtggaa gtttgacagc | 1200 |
| catctagcat tcatcacaa ggcccgagag ctgcatccgg agtactacaa agactgcgcg | 1260 |
| gccgtgttag acaaatggga aaaaattcgg ttaaggccag ggggaaagaa aaaatatcaa | 1320 |
| ttaaaacata tagtatgggc aagcagggag ctagaacgat tcgcagttaa tcctggcctg | 1380 |
| ttagaaacat cagaaggctg tagacagata atgggacagc tacaaccgtc ccttcagaca | 1440 |
| ggatcagaag aacttagatc attatataat acagtagcaa ccctctattg tgtgcatcaa | 1500 |

```
aagatagagg taaaagacac caaggaagct ttagacaagg tagaggaaga gcaaaacaac    1560
agtaagaaaa aggcacagca agaagcagct gacgcaggaa acagaaacca ggtcagccaa    1620
aattacccta tagtgcaaaa cctacaggga caaatggtac atcaggccat atcacctaga    1680
actttaaatg catgggtaaa agtagtggaa gagaaggctt tcagcccaga agtaataccc    1740
atgttttcag cattatcaga aggagccacc ccacaagatt taaacaccat gctaaacaca    1800 gtgggggggac atcaagcagc catgcaaatg ttaaaagaaa ccatcaatga ggaagctgca    1860
gaatgggata gattgcaccc agtgcatgca gggcctattg caccaggcca gatgagagaa    1920
ccaaggggaa gtgacatagc aggaactact agtacccttc aggaacaaat aggatggatg    1980
acaaataatc cacctatccc agtaggagaa atatataaga gatggataat cctgggatta    2040
aataaaatag taagaatgta tagccctacc agcattctgg atataaaaca aggaccaaaa    2100
gaacccttta gagattatgt agaccggttc tataaaaccc taagagccga gcaagctaca    2160
caggaagtaa aaaattggat gacagaaacc ttgttggtcc aaaatgcgaa tccagattgt    2220
aagactattt taaaagcatt aggaccagca gctacactag aagaaatgat gacagcatgt    2280
cagggagtgg ggggacccgg ccataaagca agagttttgg ctgaagcaat gagccaagta    2340
acaggttcag ctgccataat gatgcagaga ggcaatttta ggaaccaaag aaagactgtt    2400
aagtgtttca attgtggcaa agaagggcac atagccagaa attgcagggc ccctaggaaa    2460
aagggctgtt ggaaatgtgg aaaggaagga catcaaatga aggattgcac agaaagacag    2520
gctaatgcgg ccgtcatcac cctgtggcag cgcccctgg tggccctgat cgagatctgc     2580
accgagatgg agaaggaggg caagatcagc aagatcggcc ccgccggcct gaagaagaag    2640
aagagcgtga ccgtgctgga cgtgggcgac gcctacttca gcgtgcccct ggataaggac    2700
ttccgcaagt acaccgcctt caccatcccc agcatctgga agggcagccc cgccatcttc    2760
cagagcagca tgaccaagaa gcagaacccc gacatcgtga tctaccagta catggacgac    2820
ctgtacgtgc ccatcgtgct gcccgagaag acagctggc tggtgggcaa gctgaactgg     2880
gccagccaga tctacgccgg catcaaggtg aagcagctga tcctgaagga gcccgtgcac    2940
ggcgtgtacg agcccatcgt gggcgccgag accttctacg tggacggcgc cgccaaccgc    3000
gccggcaacc tgtgggtgac cgtgtactac ggcgtgcccg tgtggaagga ggccaccacc    3060
accctggtgg agcgctacct gcgcgaccag cagctgctgg gcatctgggg ctgcgcctgc    3120
accccctacg acatcaacca gatgctgcgc ggccctggcc gcgccttcgt gaccatccgc    3180
cagggcagcc tgtag                                                     3195

<210> SEQ ID NO 20
<211> LENGTH: 3195
<212> TYPE: DNA
<213> ORGANISM: Artificial Sequence
<220> FEATURE:
<223> OTHER INFORMATION: Hybrid protein cds comprised of Rev-Nef-Tat,
      truncated Gag protein and CTL (RNT-dgag-CTL)

<400> SEQUENCE: 20
atggcaggaa gaagcggaga cagcgacgaa gagctcctca agacagtcag actcatcaag    60
tttctctacc aaagcaaccc tcctcccagc aacgagggga cccgacaggc ccgaagaaat    120
cgaagaagaa ggtggagaga gagacagagg cagatccgtt cgattagtga gcggattctt    180 agcactttc tgggacgacc tgcggagcct gtgcctcttc agctaccgcc gcttgagaga     240
cttactcttg attgtagcga agattgtgga aactctggga cgcaggggt gggaagtcct     300
```

```
caagtattgg tggaatctcc tgcagtattg gagccaggaa ctaaagaaac tagtgtgggc    360
aagtggtcaa aatgtagtgg atggcctact gtaaggaaa gaatgaaaca agctgagcct    420
gagccagcag cagatggggt gggagcagca tctcgagacc tggaaaaaca tggagcaatc    480
acaagtagca atacagcaac taataacgct gcttgtgcct ggctagaagc acaagaggaa    540
gaggaagtgg gttttccagt cagacctcag gtacctttaa gaccaatgac ttacaaggga    600
gctttagatc ttagccactt tttaaaagaa aagggggac tggaagggtt aatttactcc    660
ccaaaaagac aagagatcct tgatctgtgg gtctaccaca cacaaggcta cttccctgat    720
tggcagaact acacaccagg gccagggtc agatatccac tgacctttgg atggtgcttc    780
aagttagtac cagttgaacc agatgaagaa gagaacagca gcctgttaca ccctgcgagc    840
ctgcatggga cagaggacac ggagagaaa gtgttaaagt ggaagtttga cagccatcta    900
gcatttcatc acaaggcccg agagctgcat ccggagtact acaaagactg caagcttgag    960
ccagtagatc ctagactaga gccctggaag catccaggaa gtcagcctag gacccctgt    1020
accaattgct attgtaaaaa gtgttgcctt cattgccaag tttgtttcac aagaaaaggc    1080
ttaggcatct cctatggcag gaagaagcgg agacagcgac gaagagctcc tcaagacagt    1140
cagactcatc aagtttctct accaaagcaa ccctcctccc agcaacgagg ggacccgaca    1200
ggccccgaaga aatcgaagaa gaaggtggag agagagacag aggcagatcc gttcgatgcg    1260
gccgtgttag acaaatggga aaaaattcgg ttaaggccag ggggaaagaa aaatatcaa    1320
ttaaaacata tagtatgggc aagcaggag ctagaacgat tcgcagttaa tcctggcctg    1380
ttagaaacat cagaaggctg tagacagata atgggacagc tacaaccgtc ccttcagaca    1440
ggatcagaag aacttagatc attatataat acagtagcaa ccctctattg tgtgcatcaa    1500
aagatagagg taaaagacac caaggaagct ttagacaagg tagaggaaga gcaaaacaac    1560
agtaagaaaa aggcacagca agaagcagct gacgcaggaa acagaaacca ggtcagccaa    1620
aattacccta tagtgcaaaa cctacaggga caaatggtac atcaggccat atcacctaga    1680
actttaaatg catgggtaaa agtagtggaa gagaaggctt tcagcccaga agtaataccc    1740
atgttttcag cattatcaga aggagccacc ccacaagatt taaacaccat gctaaacaca    1800
gtggggggac atcaagcagc catgcaaatg ttaaaagaaa ccatcaatga ggaagctgca    1860
gaatgggata gattgcaccc agtgcatgca gggcctattg caccaggcca gatgagagaa    1920
ccaaggggaa gtgacatagc aggaactact agtaccttc aggaacaaat aggatggatg    1980
acaaataatc cacctatccc agtaggagaa atatataaga gatggataat cctgggatta    2040
aataaaatag taagaatgta tagccctacc agcattctgg atataaaaca aggaccaaaa    2100
gaaccctta gagattatgt agaccggttc tataaaaccc taagagccga gcaagctaca    2160
caggaagtaa aaaattggat gacagaaacc ttgttggtcc aaaatgcgaa tccagattgt    2220
aagactattt taaaagcatt aggaccagca gctacactag aagaaatgat gacagcatgt    2280
cagggagtgg ggggacccgg ccataaagca agagttttgg ctgaagcaat gagccaagta    2340
acaggttcag ctgccataat gatgcagaga ggcaattta ggaaccaaag aaagactgtt    2400
aagtgtttca attgtggcaa agaagggcac atagccagaa attgcagggc ccctaggaaa    2460
aagggctgtt ggaaatgtgg aaaggaagga catcaaatga aggattgcac agaaagacag    2520
gctaatgcgg ccgtcatcac cctgtggcag cgccccctgg tggccctgat cgagatctgc    2580
accgagatgg agaaggaggg caagatcagc aagatcggcc ccgccggcct gaagaagaag    2640
aagagcgtga ccgtgctgga cgtgggcgac gcctacttca gcgtgccct ggataaggac    2700
```

-continued

```
ttccgcaagt acaccgcctt caccatcccc agcatctgga agggcagccc cgccatcttc    2760
cagagcagca tgaccaagaa gcagaacccc gacatcgtga tctaccagta catggacgac    2820
ctgtacgtgc ccatcgtgct gcccgagaag acagctggc tggtgggcaa gctgaactgg    2880
gccagccaga tctacgccgg catcaaggtg aagcagctga tcctgaagga gcccgtgcac    2940
ggcgtgtacg agcccatcgt gggcgccgag accttctacg tggacggcgc cgccaaccgc    3000
gccggcaacc tgtgggtgac cgtgtactac ggcgtgcccg tgtggaagga ggccaccacc    3060
accctggtgg agcgctacct cgcgaccag cagctgctgg gcatctgggg ctgcgcctgc    3120 acccccctacg acatcaacca gatgctgcgc ggccctggcc gcgccttcgt gaccatccgc    3180
cagggcagcc tgtag    3195
```

<210> SEQ ID NO 21
<211> LENGTH: 3020
<212> TYPE: DNA
<213> ORGANISM: Artificial Sequence
<220> FEATURE:
<223> OTHER INFORMATION: Hybrid protein cds comprised of Tat-Rev-Nef,
      truncated Gag protein and CTL (TRN-optp17/24-CTL)

<400> SEQUENCE: 21

```
atggagccag tagatcctag actagagccc tggaagcatc caggaagtca gcctaggacc      60
ccttgtacca attgctattg taaaaagtgt tgccttcatt gccaagtttg tttcacaaga     120
aaaggcttag gcatctccta tggcaggaag aagcggagac agcgacgaag agctcctcaa     180
gacagtcaga ctcatcaagt ttctctacca aagcaaccct cctcccagca acgaggggac     240
ccgacaggcc cgaagaaatc gaagaagaag gtggagagag agacagaggc agatccgttc     300
gatactagtg caggaagaag cggagacagc gacgaagagc tcctcaagac agtcagactc     360
atcaagtttc tctaccaaag caaccctcct cccagcaacg agggaccccg acaggcccga     420
agaaatcgaa gaaggtg agagagagaga cagaggcaga tccgttcgat tagtgagcgg     480
attcttagca cttttctggg acgacctgcg gagcctgtgc ctcttcagct accgccgctt     540
gagagactta ctcttgattg tagcgaagat tgtggaaact ctgggacgca ggggtgggga     600
agtcctcaag tattggtgga atctcctgca gtattggagc caggaactaa gaaaagctt     660 gttggcaagt ggtcaaaatg tagtggatgg cctactgtaa gggaaagaat gaaacaagct     720
gagcctgagc cagcagcaga tggggtggga gcagcatctc gagacctgga aaaacatgga     780
gcaatcacaa gtagcaatac agcaactaat aacgctgctt gtgcctggct agaagcacaa     840
gaggaagagg aagtgggttt tccagtcaga cctcaggtac ctttaagacc aatgacttac     900
aagggagctt tagatcttag ccactttta aaagaaaagg ggggactgga agggttaatt     960
tactccccaa aaagacaaga gatccttgat ctgtgggtct accacacaca aggctacttc    1020
cctgattggc agaactacac accagggcca ggggtcagat atccactgac ctttggatgg    1080
tgcttcaagt tagtaccagt tgaaccagat gaagaagaga cagcagcct gttacaccct    1140 gcgagcctgc atgggacaga ggacacggag agagaagtgt taagtggaa gtttgacagc    1200 catctagcat ttcatcacaa ggcccgagag ctgcatccgg agtactacaa agactgcgcg    1260
gccgtgggcg caagagcctc cgtgctgagc ggcggagagc tggacaagtg ggagaagatc    1320
cgcctgcgcc ccggcggcaa gaagaagtac cagctgaagc acatcgtgtg gccagccgc    1380 gagctggagc gcttcgccgt gaaccccggc ctgctcgaga ccagcgaagg ctgccgccag    1440
atcatgggca gctccagcc cagcctccag accggcagcg aggagctgcg cagcctgtac    1500
aacaccgtgg ccacccctgta ctgcgtgcac cagaagatcg aggtgaagga caccaaggag    1560
```

```
gccctggaca aggtggagga ggagcagaac aacagcaaga agaaggccca gcaggaggcc   1620
gccgacgccg gcaaccgcaa ccaagtcagc cagaactacc ccatcgtgca gaacctgcag   1680
ggccagatgg tgcaccaggc catcagcccc cgcaccctga cgcctgggt gaaggtggtg    1740 gaggagaagg ccttcagccc cgaggtgatc cccatgttca gcgccctaag cgagggcgct   1800
accccccagg acctgaacac catgctgaac accgtgggcg ccaccaggc cgccatgcag    1860 atgctgaagg agaccatcaa cgaggaggcc gccgagtggg accgcctgca ccccgtgcac   1920
gccgggccca tcgcccccgg ccagatgcgc gagccccgcg cagcgacat cgccggcacc    1980 accagcaccc tccaggagca gatcggctgg atgaccaaca ccccccat ccccgtgggc     2040 gagatctaca gcgctggat catcctgggc ctgaacaaga tcgtccgcat gtacagcccc    2100
accagcatcc tggacatcaa gcagggcccc aaggagccct tccgcgacta cgtggaccgc   2160
ttctacaaga ccctgcgcgc cgagcaggcc acccaggagg tgaagaactg gatgaccgag   2220
accctgctgg tgcagaacgc caaccccgac tgcaagacca cctcaaggc cctgggaccc   2280 gccgccaccc tggaggagat gatgaccgcc tgccaaggcg tgggcggccc cggccacaag   2340
gcccgcgtgc tggcggccgt catcacctg tggcagcgcc cctggtggc cctgatcgag     2400 atctgcaccg agatggagaa ggagggcaag atcagcaaga tcggccccgc cggcctgaag   2460
aagaagaaga gcgtgaccgt gctggacgtg ggcgacgcct acttcagcgt gcccctggat   2520
aaggacttcc gcaagtacac cgccttcacc atccccagca tctggaaggg cagccccgcc   2580
atcttccaga gcagcatgac caagaagcag aaccccgaca tcgtgatcta ccagtacatg   2640
gacgacctgt acgtgcccat cgtgctgccc gagaaggaca gctggctggt gggcaagctg   2700
aactgggcca gccagatcta cgccggcatc aaggtgaagc agctgatcct gaaggagccc   2760
gtgcacggcg tgtacgagcc catcgtgggc gccgagacct tctacgtgga cggcgccgcc   2820
aaccgcgccg gcaacctgtg ggtgaccgtg tactacggcg tgcccgtgtg gaaggaggcc   2880
accaccaccc tggtggagcg ctacctgcgc gaccagcagc tgctgggcat ctggggctgc   2940
gcctgcaccc cctacgacat caaccagatg ctgcgcggcc ctggccgcgc ctcgtgacca   3000
tccgccaggg cagcctgtag                                              3020
```

<210> SEQ ID NO 22
<211> LENGTH: 3021
<212> TYPE: DNA
<213> ORGANISM: Artificial Sequence
<220> FEATURE:
<223> OTHER INFORMATION: Hybrid protein cdscomprised of Tat-Rev-Nef, CTL and truncated Gag protein (TRN-CTL-optp17/24)

<400> SEQUENCE: 22

```
atggagccag tagatcctag actagagccc tggaagcatc caggaagtca gcctaggacc    60
ccttgtacca attgctattg taaaaagtgt tgccttcatt gccaagtttg tttcacaaga    120
aaaggcttag gcatctccta tggcaggaag aagcggagac agcgacgaag agctcctcaa    180
gacagtcaga ctcatcaagt ttctctacca aagcaaccct cctcccagca acgaggggac    240
ccgacaggcc cgaagaaatc gaagaagaag gtggagagag agacagaggc agatccgttc    300
gatactagtg caggaagaag cggagacagc gacgaagagc tcctcaagac agtcagactc    360
atcaagtttc tctaccaaag caaccctcct cccagcaacg aggggacccg acaggcccga    420
agaaatcgaa gaagaaggtg gagagagaga cagaggcaga tccgttcgat tagtgagcgg    480
attcttagca cttttctggg acgacctgcg gagcctgtgc ctcttcagct accgccgctt    540
```

```
gagagactta ctcttgattg tagcgaagat tgtggaaact ctgggacgca ggggggtggga    600 agtcctcaag tattggtgga atctcctgca gtattggagc caggaactaa agaaaagctt    660
gtgggcaagt ggtcaaaatg tagtggatgg cctactgtaa gggaaagaat gaaacaagct    720
gagcctgagc cagcagcaga tggggtggga gcagcatctc gagacctgga aaaacatgga    780
gcaatcacaa gtagcaatac agcaactaat aacgctgctt gtgcctggct agaagcacaa    840
gaggaagagg aagtgggttt tccagtcaga cctcaggtac cttttaagacc aatgacttac    900 aagggagctt tagatcttag ccactttta aaagaaaagg ggggactgga agggttaatt    960
tactccccaa aaagacaaga gatccttgat ctgtgggtct accacacaca aggctacttc   1020
cctgattggc agaactacac accagggcca ggggtcagat atccactgac ctttggatgg   1080
tgcttcaagt tagtaccagt tgaaccagat gaagaagaga acagcagcct gttacaccct   1140
gcgagcctgc atgggacaga ggacacggag agagaagtgt taaagtggaa gtttgacagc   1200
catctagcat ttcatcacaa ggcccgagag ctgcatccgg agtactacaa agactgcgcg   1260
gccgtcatca ccctgtggca gcgcccctg gtggccctga tcgagatctg caccgagatg   1320
gagaaggagg gcaagatcag caagatcggc cccgccggcc tgaagaagaa gaagagcgtg   1380
accgtgctgg acgtgggcga cgcctacttc agcgtgcccc tggataagga cttccgcaag   1440
tacaccgcct tcaccatccc cagcatctgg aagggcagcc ccgccatctt ccagagcagc   1500
atgaccaaga agcagaaccc cgacatcgtg atctaccagt acatggacga cctgtacgtg   1560
cccatcgtgc tgcccgagaa ggacagctgg ctggtgggca agctgaactg gccagccag   1620 atctacgccg gcatcaaggt gaagcagctg atcctgaagg agcccgtgca cggcgtgtac   1680
gagcccatcg tgggcgccga gaccttctac gtggacggcg ccgccaaccg cgccggcaac   1740
ctgtgggtga ccgtgtacta cggcgtgccc gtgtggaagg aggccaccac caccctggtg   1800
gagcgctacc tgcgcgacca gcagctgctg ggcatctggg gctgcgcctg caccccctac   1860
gacatcaacc agatgctgcg cggccctggc cgcgccttcg tgaccatccg ccagggcagc   1920
ctggcggccg tgggcgcaag agcctccgtg ctgagcggcg agagctgga caagtgggag   1980 aagatccgcc tgcgccccgg cggcaagaag aagtaccagc tgaagcacat cgtgtgggcc   2040
agccgcgagc tggagcgctt cgccgtgaac cccggcctgc tcgagaccag cgaaggctgc   2100
cgccagatca tgggccagct ccagcccagc ctccagaccg gcagcgagga gctgcgcagc   2160
ctgtacaaca ccgtggccac cctgtactgc gtgcaccaga agatcgaggt gaaggacacc   2220
aaggaggccc tggacaaggt ggaggaggag cagaacaaca gcaagaagaa ggcccagcag   2280
gaggccgccg acgccggcaa ccgcaaccaa gtcagccaga actacccat cgtgcagaac   2340 ctgcagggcc agatggtgca ccaggccatc agccccgca ccctgaacgc ctgggtgaag   2400
gtggtggagg agaaggcctt cagccccgag gtgatcccca tgttcagcgc cctgagcgag   2460
ggcgctaccc ccaggacct gaacaccatg ctgaacaccg tgggcggcca ccaggccgcc   2520
atgcagatgc tgaaggagac catcaacgag gaggccgccg agtgggaccg cctgcacccc   2580
gtgcacgccg gcccatcgc ccccggccag atgcgcgagc ccgcggcag cgacatcgcc   2640 ggcaccacca gcaccctcca ggagcagatc ggctggatga ccaacaaccc ccccatcccc   2700
gtgggcgaga tctacaagcg ctggatcatc ctgggcctga caagatcgt ccgcatgtac   2760 agccccacca gcatcctgga catcaagcag ggccccaagg agcccttccg cgactacgtg   2820
gaccgcttct acaagaccct gcgcgccgag caggccaccc aggaggtgaa gaactggatg   2880
accgagaccc tgctggtgca gaacgccaac cccgactgca gaccatcct caaggccctg   2940
```

```
ggacccgccg ccaccctgga ggagatgatg accgcctgcc aaggcgtggg cggccccggc    3000
cacaaggccc gcgtgctgtg a                                              3021

<210> SEQ ID NO 23
<211> LENGTH: 3021
<212> TYPE: DNA
<213> ORGANISM: Artificial Sequence
<220> FEATURE:
<223> OTHER INFORMATION: Hybrid protein cds comprised of Rev-Nef-Tat,
      CTL and truncated Gag protein (RNT-CTL-optp17/24)

<400> SEQUENCE: 23
atggcaggaa gaagcggaga cagcgacgaa gagctcctca agacagtcag actcatcaag      60
tttctctacc aaagcaaccc tcctcccagc aacgagggga cccgacaggc ccgaagaaat     120
cgaagaagaa ggtggagaga gagacagagg cagatccgtt cgattagtga gcggattctt     180 agcactttc tgggacgacc tgcggagcct gtgcctcttc agctaccgcc gcttgagaga      240
cttactcttg attgtagcga agattgtgga aactctggga cgcaggggggt gggaagtcct    300 caagtattgg tggaatctcc tgcagtattg gagccaggaa ctaaagaaac tagtgtgggc    360
aagtggtcaa atgtagtgg atggcctact gtaaggaaa gaatgaaaca agctgagcct      420
gagccagcag cagatggggt gggagcagca tctcgagacc tggaaaaaca tggagcaatc    480
acaagtagca atacagcaac taataacgct gcttgtgcct ggctagaagc acaagaggaa    540
gaggaagtgg gttttccagt cagacctcag gtacctttaa gaccaatgac ttacaaggga    600
gctttagatc ttagccactt ttaaaaagaa aaggggggac tggaagggtt aatttactcc    660
ccaaaaagac aagagatcct tgatctgtgg gtctaccaca caaggcta cttccctgat     720 tggcagaact acacaccagg ccaggggtc agatatccac tgacctttgg atggtgcttc    780
aagttagtac cagttgaacc agatgaagaa gagaacagca gcctgttaca ccctgcgagc    840
ctgcatggga cagaggacac ggagagagaa gtgttaaagt ggaagtttga cagccatcta    900
gcatttcatc acaaggcccg agagctgcat ccggagtact acaaagactg caagcttgag    960
ccagtagatc ctagactaga gccctggaag catccaggaa gtcagcctag acccccttgt    1020
accaattgct attgtaaaaa gtgttgcctt cattgccaag tttgtttcac aagaaaaggc    1080
ttaggcatct cctatggcag gaagaagcgg agacagcgac gaagagctcc tcaagacagt    1140
cagactcatc aagtttctct accaaagcaa ccctcctccc agcaacgagg ggacccgaca    1200
ggcccgaaga atcgaagaa gaaggtggag agagagacag aggcagatcc gttcgatgcg    1260
gccgtcatca ccctgtggca gcgcccctg gtggccctga tcgagatctg caccgagatg    1320
gagaaggagg gcaagatcag caagatcggc ccgccggcc tgaagaagaa gaagagcgtg    1380
accgtgctgg acgtgggcga cgcctacttc agcgtgcccc tggataagga cttccgcaag    1440
tacaccgcct tcaccatccc cagcatctgg aagggcagcc ccgccatctt ccagagcagc    1500
atgaccaaga agcagaaccc cgacatcgtg atctaccagt acatggacga cctgtacgtg    1560
cccatcgtgc tgcccgagaa ggacagctgg ctggtgggca agctgaactg ggccagccag    1620
atctacgccg gcatcaaggt gaagcagctg atcctgaagg agcccgtgca ggcgtgtac    1680 gagcccatcg tgggcgccga gaccttctac gtggacggcg ccgccaaccg cgccggcaac    1740
ctgtgggtga ccgtgtacta cggcgtgccc gtgtggaagg aggccaccac caccctggtg    1800
gagcgctacc tgcgcgacca gcagctgctg gcatctggg gctgcgcctg caccccctac    1860
gacatcaacc agatgctgcg cggccctggc cgcgccttcg tgaccatccg ccagggcagc    1920
ctggcggccg tgggcgcaag agcctccgtg ctgagcggcg gagagctgga caagtgggag    1980
```

```
aagatccgcc tgcgcccgg cggcaagaag aagtaccagc tgaagcacat cgtgtgggcc    2040
agccgcgagc tggagcgctt cgccgtgaac cccggcctgc tcgagaccag cgaaggctgc    2100
cgccagatca tgggccagct ccagcccagc ctccagaccg gcagcgagga gctgcgcagc    2160
ctgtacaaca ccgtggccac cctgtactgc gtgcaccaga agatcgaggt gaaggacacc    2220
aaggaggccc tggacaaggt ggaggaggag cagaacaaca gcaagaagaa ggcccagcag    2280
gaggccgccg acgccggcaa ccgcaaccaa gtcagccaga actaccccat cgtgcagaac    2340
ctgcagggcc agatggtgca ccaggccatc agccccgca ccctgaacgc ctgggtgaag    2400
gtggtggagg agaaggcctt cagccccgag gtgatcccca tgttcagcgc cctgagcgag    2460
ggcgctaccc cccaggacct gaacaccatg ctgaacaccg tgggcggcca ccaggccgcc    2520
atgcagatgc tgaaggagac catcaacgag gaggccgccg agtgggaccg cctgcacccc    2580
gtgcacgccg gcccatcgc ccccggccag atgcgcgagc cccgcggcag cgacatcgcc    2640
ggcaccacca gcacctccca ggagcagatc ggctggatga ccaacaaccc ccccatcccc    2700
gtgggcgaga tctacaagcg ctggatcatc ctgggcctga caagatcgt ccgcatgtac    2760 agccccacca gcatcctgga catcaagcag ggccccaagg agcccttccg cgactacgtg    2820
gaccgcttct acaagaccct gcgcgccgag caggccaccc aggaggtgaa gaactggatg    2880
accgagaccc tgctggtgca gaacgccaac cccgactgca gaccatcct caaggccctg    2940 ggacccgccg ccaccctgga ggagatgatg accgcctgcc aaggcgtggg cggccccggc    3000
cacaaggccc gcgtgctgtg a                                              3021
```

<210> SEQ ID NO 24
<211> LENGTH: 3021
<212> TYPE: DNA
<213> ORGANISM: Artificial Sequence
<220> FEATURE:
<223> OTHER INFORMATION: Hybrid protein cds comprised of Rev-Nef-Tat,
      truncated Gag protein and CTL (RNT-optp17/24-CTL)

<400> SEQUENCE: 24

```
atggcaggaa gaagcggaga cagcgacgaa gagctcctca agacagtcag actcatcaag     60
tttctctacc aaagcaaccc tcctcccagc aacgagggga cccgacaggc ccgaagaaat    120
cgaagaagaa ggtggagaga gagacagagg cagatccgtt cgattagtga gcggattctt    180
agcacttttc tgggacgacc tgcggagcct gtgcctcttc agctaccgcc gcttgagaga    240
cttactcttg attgtagcga agattgtgga aactctggga gcaggggt gggaagtcct    300 caagtattgg tggaatctcc tgcagtattg gagccaggaa ctaaagaaac tagtgtgggc    360
aagtggtcaa aatgtagtgg atggcctact gtaaggaaa gaatgaaaca agctgagcct    420
gagccagcag cagatggggt gggagcagca tctcgagacc tggaaaaaca tggagcaatc    480
acaagtagca atacagcaac taataacgct gcttgtgcct ggctagaagc acaagaggaa    540
gaggaagtgg gttttccagt cagacctcag gtacctttaa gaccaatgac ttacaaggga    600
gctttagatc ttagccactt tttaaaagaa aaggggggac tggaagggtt aatttactcc    660
ccaaaaagac aagagatcct tgatctgtgg gtctaccaca cacaaggcta cttccctgat    720
tggcagaact acacaccagg gccagggtc agatatccac tgacctttgg atggtgcttc    780
aagttagtac cagttgaacc agatgaagaa gagaacagca gcctgttaca ccctgcgagc    840
ctgcatggga cagaggacac ggagagagaa gtgttaaagt ggaagtttga cagccatcta    900
gcatttcatc acaaggcccg agagctgcat ccggagtact acaaagactg caagcttgag    960
```

```
ccagtagatc ctagactaga gccctggaag catccaggaa gtcagcctag gacccttgt    1020
accaattgct attgtaaaaa gtgttgcctt cattgccaag tttgtttcac aagaaaaggc    1080
ttaggcatct cctatggcag gaagaagcgg agacagcgac gaagagctcc tcaagacagt    1140
cagactcatc aagtttctct accaaagcaa ccctcctccc agcaacgagg ggaccccgaca    1200
ggcccgaaga aatcgaagaa gaaggtggag agagagacag aggcagatcc gttcgatgcg    1260
gccgtgggcg caagagcctc cgtgctgagc ggcggagagc tggacaagtg ggagaagatc    1320
cgcctgcgcc ccggcggcaa gaagaagtac cagctgaagc acatcgtgtg ggccagccgc    1380
gagctggagc gcttcgccgt gaaccccggc ctgctcgaga ccagcgaagg ctgccgccag    1440
atcatgggcc agctccagcc cagcctccag accggcagcg aggagctgcg cagcctgtac    1500
aacaccgtgg ccaccctgta ctgcgtgcac cagaagatcg aggtgaagga caccaaggag    1560
gccctggaca aggtggagga ggagcagaac aacagcaaga gaaggcccca gcaggaggcc    1620
gccgacgccg gcaaccgcaa ccaagtcagc cagaactacc ccatcgtgca gaacctgcag    1680
ggccagatgg tgcaccaggc catcagcccc cgcaccctga cgcctgggt gaaggtggtg    1740
gaggagaagg ccttcagccc cgaggtgatc cccatgttca gcgccctaag cgagggcgct    1800
accccccagg acctgaacac catgctgaac accgtgggcg gccaccaggc cgccatgcag    1860
atgctgaagg agaccatcaa cgaggaggcc gccgagtggg accgcctgca ccccgtgcac    1920
gccgggccca tcgcccccgg ccagatgcgc gagccccgcg gcagcgacat cgccggcacc    1980
accagcaccc tccaggagca gatcggctgg atgaccaaca ccccccccat ccccgtgggc    2040
gagatctaca gcgctggat catcctgggc ctgaacaaga tcgtccgcat gtacagcccc    2100
accagcatcc tggacatcaa gcagggcccc aaggagccct tccgcgacta cgtggaccgc    2160
ttctacaaga ccctgcgcgc cgagcaggcc acccaggagg tgaagaactg gatgaccgag    2220
accctgctgg tgcagaacgc caaccccgac tgcaagacca tcctcaaggc cctgggaccc    2280
gccgccaccc tggaggagat gatgaccgcc tgccaaggcg tgggcggccc cggccacaag    2340
gcccgcgtgc tggcggccgt catcaccctg tggcagcgcc ccctggtggc cctgatcgag    2400
atctgcaccg agatggagaa ggagggcaag atcagcaaga tcggcccgc cggcctgaag    2460
aagaagaaga gcgtgaccgt gctggacgtg ggcgacgcct acttcagcgt gcccctggat    2520
aaggacttcc gcaagtacac cgccttcacc atccccagca tctggaaggg cagccccgcc    2580
atcttccaga gcagcatgac caagaagcag aaccccgaca tcgtgatcta ccagtacatg    2640
gacgacctgt acgtgcccat cgtgctgccc gagaaggaca gctggctggt gggcaagctg    2700
aactgggcca gccagatcta cgccggcatc aaggtgaagc agctgatcct gaaggagccc    2760
gtgcacggcg tgtacgagcc catcgtgggc gccgagacct ctacgtgga cggcgccgcc    2820
aaccgcgccg gcaacctgtg ggtgaccgtg tactacggcg tgcccgtgtg gaaggaggcc    2880
accaccaccc tggtggagcg ctacctgcgc gaccagcagc tgctgggcat ctggggctgc    2940
gcctgcaccc cctacgacat caaccagatg ctgcgcggcc ctggccgcgc cttcgtgacc    3000
atccgccagg gcagcctgta g                                              3021
```

<210> SEQ ID NO 25
<211> LENGTH: 419
<212> TYPE: PRT
<213> ORGANISM: Artificial Sequence
<220> FEATURE:
<223> OTHER INFORMATION: Hybrid protein comprised of Nef-Tat-Rev (NTR)

<400> SEQUENCE: 25

-continued

```
Met Val Gly Lys Trp Ser Lys Cys Ser Gly Trp Pro Thr Val Arg Glu
1               5                   10                  15
Arg Met Lys Gln Ala Glu Pro Glu Pro Ala Ala Asp Gly Val Gly Ala
            20                  25                  30
Ala Ser Arg Asp Leu Glu Lys His Gly Ala Ile Thr Ser Ser Asn Thr
        35                  40                  45
Ala Thr Asn Asn Ala Ala Cys Ala Trp Leu Glu Ala Gln Glu Glu Glu
    50                  55                  60
Glu Val Gly Phe Pro Val Arg Pro Gln Val Pro Leu Arg Pro Met Thr
65                  70                  75                  80
Tyr Lys Gly Ala Leu Asp Leu Ser His Phe Leu Lys Glu Lys Gly Gly
                85                  90                  95
Leu Glu Gly Leu Ile Tyr Ser Pro Lys Arg Gln Glu Ile Leu Asp Leu
            100                 105                 110
Trp Val Tyr His Thr Gln Gly Tyr Phe Pro Asp Trp Gln Asn Tyr Thr
        115                 120                 125
Pro Gly Pro Gly Val Arg Tyr Pro Leu Thr Phe Gly Trp Cys Phe Lys
    130                 135                 140
Leu Val Pro Val Glu Pro Asp Glu Glu Asn Ser Ser Leu Leu His
145                 150                 155                 160
Pro Ala Ser Leu His Gly Thr Glu Asp Thr Glu Arg Glu Val Leu Lys
                165                 170                 175
Trp Lys Phe Asp Ser His Leu Ala Phe His His Lys Ala Arg Glu Leu
            180                 185                 190
His Pro Glu Tyr Tyr Lys Asp Cys Thr Ser Ala Gly Arg Ser Gly Asp
        195                 200                 205
Ser Asp Glu Glu Leu Leu Lys Thr Val Arg Leu Ile Lys Phe Leu Tyr
210                 215                 220
Gln Ser Asn Pro Pro Ser Asn Glu Gly Thr Arg Gln Ala Arg Arg
225                 230                 235                 240
Asn Arg Arg Arg Arg Trp Arg Glu Arg Gln Arg Ile Arg Ser Ile
                245                 250                 255
Ser Glu Arg Ile Leu Ser Thr Phe Leu Gly Arg Pro Ala Glu Pro Val
            260                 265                 270
Pro Leu Gln Leu Pro Pro Leu Glu Arg Leu Thr Leu Asp Cys Ser Glu
        275                 280                 285
Asp Cys Gly Asn Ser Gly Thr Gln Gly Val Gly Ser Pro Gln Val Leu
    290                 295                 300
Val Glu Ser Pro Ala Val Leu Glu Pro Gly Thr Lys Glu Lys Leu Glu
305                 310                 315                 320
Pro Val Asp Pro Arg Leu Glu Pro Trp Lys His Pro Gly Ser Gln Pro
                325                 330                 335
Arg Thr Pro Cys Thr Asn Cys Tyr Cys Lys Lys Cys Cys Leu His Cys
            340                 345                 350
Gln Val Cys Phe Thr Arg Lys Gly Leu Gly Ile Ser Tyr Gly Arg Lys
        355                 360                 365
Lys Arg Arg Gln Arg Arg Ala Pro Gln Asp Ser Gln Thr His Gln
    370                 375                 380
Val Ser Leu Pro Lys Gln Pro Ser Ser Gln Arg Gly Asp Pro Thr
385                 390                 395                 400
Gly Pro Lys Lys Ser Lys Lys Lys Val Glu Arg Glu Thr Glu Ala Asp
                405                 410                 415
Pro Phe Asp
```

<210> SEQ ID NO 26
<211> LENGTH: 419
<212> TYPE: PRT
<213> ORGANISM: Artificial Sequence
<220> FEATURE:
<223> OTHER INFORMATION: Hybrid protein comprised of Tat-Rev-Nef (TRN)

<400> SEQUENCE: 26

```
Met Glu Pro Val Asp Pro Arg Leu Glu Pro Trp Lys His Pro Gly Ser
1               5                   10                  15

Gln Pro Arg Thr Pro Cys Thr Asn Cys Tyr Cys Lys Lys Cys Cys Leu
            20                  25                  30

His Cys Gln Val Cys Phe Thr Arg Lys Gly Leu Gly Ile Ser Tyr Gly
        35                  40                  45

Arg Lys Lys Arg Arg Gln Arg Arg Ala Pro Gln Asp Ser Gln Thr
 50                  55                  60

His Gln Val Ser Leu Pro Lys Gln Pro Ser Ser Gln Gln Arg Gly Asp
65                  70                  75                  80

Pro Thr Gly Pro Lys Lys Ser Lys Lys Val Glu Arg Glu Thr Glu
                85                  90                  95

Ala Asp Pro Phe Asp Thr Ser Ala Gly Arg Ser Gly Asp Ser Asp Glu
            100                 105                 110

Glu Leu Leu Lys Thr Val Arg Leu Ile Lys Phe Leu Tyr Gln Ser Asn
        115                 120                 125

Pro Pro Pro Ser Asn Glu Gly Thr Arg Gln Ala Arg Arg Asn Arg Arg
    130                 135                 140

Arg Arg Trp Arg Glu Arg Gln Arg Gln Ile Arg Ser Ile Ser Glu Arg
145                 150                 155                 160

Ile Leu Ser Thr Phe Leu Gly Arg Pro Ala Glu Pro Val Pro Leu Gln
                165                 170                 175

Leu Pro Pro Leu Glu Arg Leu Thr Leu Asp Cys Ser Glu Asp Cys Gly
            180                 185                 190

Asn Ser Gly Thr Gln Gly Val Gly Ser Pro Gln Val Leu Val Glu Ser
        195                 200                 205

Pro Ala Val Leu Glu Pro Gly Thr Lys Glu Lys Leu Val Gly Lys Trp
    210                 215                 220

Ser Lys Cys Ser Gly Trp Pro Thr Val Arg Glu Arg Met Lys Gln Ala
225                 230                 235                 240

Glu Pro Glu Pro Ala Ala Asp Gly Val Gly Ala Ala Ser Arg Asp Leu
                245                 250                 255

Glu Lys His Gly Ala Ile Thr Ser Ser Asn Thr Ala Thr Asn Asn Ala
            260                 265                 270

Ala Cys Ala Trp Leu Glu Ala Gln Glu Glu Glu Val Gly Phe Pro
        275                 280                 285

Val Arg Pro Gln Val Pro Leu Arg Pro Met Thr Tyr Lys Gly Ala Leu
    290                 295                 300

Asp Leu Ser His Phe Leu Lys Glu Lys Gly Gly Leu Glu Gly Leu Ile
305                 310                 315                 320

Tyr Ser Pro Lys Arg Gln Glu Ile Leu Asp Leu Trp Val Tyr His Thr
                325                 330                 335

Gln Gly Tyr Phe Pro Asp Trp Gln Asn Tyr Thr Pro Gly Pro Gly Val
            340                 345                 350

Arg Tyr Pro Leu Thr Phe Gly Trp Cys Phe Lys Leu Val Pro Val Glu
        355                 360                 365

Pro Asp Glu Glu Glu Asn Ser Ser Leu Leu His Pro Ala Ser Leu His
```

```
              370             375             380
Gly Thr Glu Asp Thr Glu Arg Glu Val Leu Lys Trp Lys Phe Asp Ser
385                 390                 395                 400

His Leu Ala Phe His His Lys Ala Arg Glu Leu His Pro Glu Tyr Tyr
                405                 410                 415

Lys Asp Cys

<210> SEQ ID NO 27
<211> LENGTH: 419
<212> TYPE: PRT
<213> ORGANISM: Artificial Sequence
<220> FEATURE:
<223> OTHER INFORMATION: Hybrid protein comprised of Rev-Tat-Nef (RTN)

<400> SEQUENCE: 27

Met Ala Gly Arg Ser Gly Asp Ser Asp Glu Glu Leu Leu Lys Thr Val
1               5                   10                  15

Arg Leu Ile Lys Phe Leu Tyr Gln Ser Asn Pro Pro Ser Asn Glu
            20                  25                  30

Gly Thr Arg Gln Ala Arg Arg Asn Arg Arg Arg Trp Arg Glu Arg
                35                  40                  45

Gln Arg Gln Ile Arg Ser Ile Ser Glu Arg Ile Leu Ser Thr Phe Leu
50                  55                  60

Gly Arg Pro Ala Glu Pro Val Pro Leu Gln Leu Pro Pro Leu Glu Arg
65                  70                  75                  80

Leu Thr Leu Asp Cys Ser Glu Asp Cys Gly Asn Ser Gly Thr Gln Gly
                85                  90                  95

Val Gly Ser Pro Gln Val Leu Val Glu Ser Pro Ala Val Leu Glu Pro
                100                 105                 110

Gly Thr Lys Glu Thr Ser Glu Pro Val Asp Pro Arg Leu Glu Pro Trp
            115                 120                 125

Lys His Pro Gly Ser Gln Pro Arg Thr Pro Cys Thr Asn Cys Tyr Cys
            130                 135                 140

Lys Lys Cys Cys Leu His Cys Gln Val Cys Phe Thr Arg Lys Gly Leu
145                 150                 155                 160

Gly Ile Ser Tyr Gly Arg Lys Lys Arg Arg Gln Arg Arg Ala Pro
                165                 170                 175

Gln Asp Ser Gln Thr His Gln Val Ser Leu Pro Lys Gln Pro Ser Ser
            180                 185                 190

Gln Gln Arg Gly Asp Pro Thr Gly Pro Lys Ser Lys Lys Lys Val
            195                 200                 205

Glu Arg Glu Thr Glu Ala Asp Pro Phe Asp Lys Leu Val Gly Lys Trp
210                 215                 220

Ser Lys Cys Ser Gly Trp Pro Thr Val Arg Glu Arg Met Lys Gln Ala
225                 230                 235                 240

Glu Pro Glu Pro Ala Ala Asp Gly Val Gly Ala Ala Ser Arg Asp Leu
                245                 250                 255

Glu Lys His Gly Ala Ile Thr Ser Ser Asn Thr Ala Thr Asn Asn Ala
            260                 265                 270

Ala Cys Ala Trp Leu Glu Ala Gln Glu Glu Glu Val Gly Phe Pro
            275                 280                 285

Val Arg Pro Gln Val Pro Leu Arg Pro Met Thr Tyr Lys Gly Ala Leu
        290                 295                 300

Asp Leu Ser His Phe Leu Lys Glu Lys Gly Gly Leu Glu Gly Leu Ile
305                 310                 315                 320
```

Tyr Ser Pro Lys Arg Gln Glu Ile Leu Asp Leu Trp Val Tyr His Thr
              325                 330                 335

Gln Gly Tyr Phe Pro Asp Trp Gln Asn Tyr Thr Pro Gly Pro Gly Val
              340                 345                 350

Arg Tyr Pro Leu Thr Phe Gly Trp Cys Phe Lys Leu Val Pro Val Glu
              355                 360                 365

Pro Asp Glu Glu Glu Asn Ser Ser Leu Leu His Pro Ala Ser Leu His
              370                 375                 380

Gly Thr Glu Asp Thr Glu Arg Glu Val Leu Lys Trp Lys Phe Asp Ser
385                 390                 395                 400

His Leu Ala Phe His His Lys Ala Arg Glu Leu His Pro Glu Tyr Tyr
              405                 410                 415

Lys Asp Cys

<210> SEQ ID NO 28
<211> LENGTH: 419
<212> TYPE: PRT
<213> ORGANISM: Artificial Sequence
<220> FEATURE:
<223> OTHER INFORMATION: Hybrid protein comprised of Tat-Nef-Rev (TNR)

<400> SEQUENCE: 28

Met Glu Pro Val Asp Pro Arg Leu Glu Pro Trp Lys His Pro Gly Ser
1               5                   10                  15

Gln Pro Arg Thr Pro Cys Thr Asn Cys Tyr Cys Lys Lys Cys Cys Leu
              20                  25                  30

His Cys Gln Val Cys Phe Thr Arg Lys Gly Leu Gly Ile Ser Tyr Gly
              35                  40                  45

Arg Lys Lys Arg Arg Gln Arg Arg Ala Pro Gln Asp Ser Gln Thr
50                  55                  60

His Gln Val Ser Leu Pro Lys Gln Pro Ser Ser Gln Arg Gly Asp
65                  70                  75                  80

Pro Thr Gly Pro Lys Lys Ser Lys Lys Lys Val Glu Arg Glu Thr Glu
              85                  90                  95

Ala Asp Pro Phe Asp Thr Ser Val Gly Lys Trp Ser Lys Cys Ser Gly
              100                 105                 110

Trp Pro Thr Val Arg Glu Arg Met Lys Gln Ala Glu Pro Glu Pro Ala
              115                 120                 125

Ala Asp Gly Val Gly Ala Ala Ser Arg Asp Leu Glu Lys His Gly Ala
              130                 135                 140

Ile Thr Ser Ser Asn Thr Ala Thr Asn Asn Ala Ala Cys Ala Trp Leu
145                 150                 155                 160

Glu Ala Gln Glu Glu Glu Val Gly Phe Pro Val Arg Pro Gln Val
              165                 170                 175

Pro Leu Arg Pro Met Thr Tyr Lys Gly Ala Leu Asp Leu Ser His Phe
              180                 185                 190

Leu Lys Glu Lys Gly Gly Leu Glu Gly Leu Ile Tyr Ser Pro Lys Arg
              195                 200                 205

Gln Glu Ile Leu Asp Leu Trp Val Tyr His Thr Gln Gly Tyr Phe Pro
              210                 215                 220

Asp Trp Gln Asn Tyr Thr Pro Gly Pro Gly Val Arg Tyr Pro Leu Thr
225                 230                 235                 240

Phe Gly Trp Cys Phe Lys Leu Val Pro Val Glu Pro Asp Glu Glu Glu
              245                 250                 255

Asn Ser Ser Leu Leu His Pro Ala Ser Leu His Gly Thr Glu Asp Thr
              260                 265                 270

```
Glu Arg Glu Val Leu Lys Trp Lys Phe Asp Ser His Leu Ala Phe His
                275                 280                 285

His Lys Ala Arg Glu Leu His Pro Glu Tyr Tyr Lys Asp Cys Lys Leu
        290                 295                 300

Ala Gly Arg Ser Gly Asp Ser Asp Glu Glu Leu Leu Lys Thr Val Arg
305                 310                 315                 320

Leu Ile Lys Phe Leu Tyr Gln Ser Asn Pro Pro Ser Asn Glu Gly
                325                 330                 335

Thr Arg Gln Ala Arg Arg Asn Arg Arg Arg Trp Arg Glu Arg Gln
                340                 345                 350

Arg Gln Ile Arg Ser Ile Ser Glu Arg Ile Leu Ser Thr Phe Leu Gly
                355                 360                 365

Arg Pro Ala Glu Pro Val Pro Leu Gln Leu Pro Pro Leu Glu Arg Leu
        370                 375                 380

Thr Leu Asp Cys Ser Glu Asp Cys Gly Asn Ser Gly Thr Gln Gly Val
385                 390                 395                 400

Gly Ser Pro Gln Val Leu Val Glu Ser Pro Ala Val Leu Glu Pro Gly
                405                 410                 415

Thr Lys Glu

<210> SEQ ID NO 29
<211> LENGTH: 419
<212> TYPE: PRT
<213> ORGANISM: Artificial Sequence
<220> FEATURE:
<223> OTHER INFORMATION: Hybrid protein comprised of Rev-Nef-Tat (RNT)

<400> SEQUENCE: 29

Met Ala Gly Arg Ser Gly Asp Ser Asp Glu Glu Leu Leu Lys Thr Val
1               5                   10                  15

Arg Leu Ile Lys Phe Leu Tyr Gln Ser Asn Pro Pro Ser Asn Glu
                20                  25                  30

Gly Thr Arg Gln Ala Arg Arg Asn Arg Arg Arg Trp Arg Glu Arg
            35                  40                  45

Gln Arg Gln Ile Arg Ser Ile Ser Glu Arg Ile Leu Ser Thr Phe Leu
50                  55                  60

Gly Arg Pro Ala Glu Pro Val Pro Leu Gln Leu Pro Pro Leu Glu Arg
65                  70                  75                  80

Leu Thr Leu Asp Cys Ser Glu Asp Cys Gly Asn Ser Gly Thr Gln Gly
                85                  90                  95

Val Gly Ser Pro Gln Val Leu Val Glu Ser Pro Ala Val Leu Glu Pro
                100                 105                 110

Gly Thr Lys Glu Thr Ser Val Gly Lys Trp Ser Lys Cys Ser Gly Trp
            115                 120                 125

Pro Thr Val Arg Glu Arg Met Lys Gln Ala Glu Pro Glu Pro Ala Ala
        130                 135                 140

Asp Gly Val Gly Ala Ala Ser Arg Asp Leu Glu Lys His Gly Ala Ile
145                 150                 155                 160

Thr Ser Ser Asn Thr Ala Thr Asn Asn Ala Ala Cys Ala Trp Leu Glu
                165                 170                 175

Ala Gln Glu Glu Glu Val Gly Phe Pro Val Arg Pro Gln Val Pro
                180                 185                 190

Leu Arg Pro Met Thr Tyr Lys Gly Ala Leu Asp Leu Ser His Phe Leu
            195                 200                 205

Lys Glu Lys Gly Gly Leu Glu Gly Leu Ile Tyr Ser Pro Lys Arg Gln
```

```
                  210                 215                 220
Glu Ile Leu Asp Leu Trp Val Tyr His Thr Gln Gly Tyr Phe Pro Asp
225                 230                 235                 240

Trp Gln Asn Tyr Thr Pro Gly Pro Gly Val Arg Tyr Pro Leu Thr Phe
                245                 250                 255

Gly Trp Cys Phe Lys Leu Val Pro Val Glu Pro Asp Glu Glu Glu Asn
            260                 265                 270

Ser Ser Leu Leu His Pro Ala Ser Leu His Gly Thr Glu Asp Thr Glu
        275                 280                 285

Arg Glu Val Leu Lys Trp Lys Phe Asp Ser His Leu Ala Phe His His
    290                 295                 300

Lys Ala Arg Glu Leu His Pro Glu Tyr Tyr Lys Asp Cys Lys Leu Glu
305                 310                 315                 320

Pro Val Asp Pro Arg Leu Glu Pro Trp Lys His Pro Gly Ser Gln Pro
                325                 330                 335

Arg Thr Pro Cys Thr Asn Cys Tyr Cys Lys Lys Cys Cys Leu His Cys
            340                 345                 350

Gln Val Cys Phe Thr Arg Lys Gly Leu Gly Ile Ser Tyr Gly Arg Lys
        355                 360                 365

Lys Arg Arg Gln Arg Arg Ala Pro Gln Asp Ser Gln Thr His Gln
    370                 375                 380

Val Ser Leu Pro Lys Gln Pro Ser Ser Gln Arg Gly Asp Pro Thr
385                 390                 395                 400

Gly Pro Lys Lys Ser Lys Lys Lys Val Glu Arg Glu Thr Glu Ala Asp
                405                 410                 415

Pro Phe Asp

<210> SEQ ID NO 30
<211> LENGTH: 387
<212> TYPE: PRT
<213> ORGANISM: Artificial Sequence
<220> FEATURE:
<223> OTHER INFORMATION: Protein comprised of Immunodominant parts of
      the Nef-Tat-Rev(NTR)

<400> SEQUENCE: 30

Met Gly Trp Pro Thr Val Arg Glu Arg Met Lys Gln Ala Pro Glu
1               5                   10                  15

Pro Ala Ala Asp Gly Val Gly Ala Ala Ser Arg Asp Leu Glu Lys His
                20                  25                  30

Gly Ala Ile Thr Ser Ser Asn Thr Ala Thr Asn Ala Ala Cys Ala
            35                  40                  45

Trp Leu Glu Ala Gln Glu Glu Glu Val Gly Phe Pro Val Arg Pro
    50                  55                  60

Gln Val Pro Leu Arg Pro Met Thr Tyr Lys Gly Ala Leu Asp Leu Ser
65                  70                  75                  80

His Phe Leu Lys Glu Lys Gly Gly Leu Glu Gly Leu Ile Tyr Ser Pro
                85                  90                  95

Lys Arg Gln Glu Ile Leu Asp Leu Trp Val Tyr His Thr Gln Gly Tyr
            100                 105                 110

Phe Pro Asp Trp Gln Asn Tyr Thr Pro Gly Pro Gly Val Arg Tyr Pro
        115                 120                 125

Leu Thr Phe Gly Trp Cys Phe Lys Leu Val Pro Val Glu Pro Asp Glu
    130                 135                 140

Glu Glu Asn Ser Ser Leu Leu His Pro Ala Ser Leu His Gly Thr Glu
145                 150                 155                 160
```

Asp Thr Glu Arg Glu Val Leu Lys Trp Lys Phe Asp Ser His Leu Ala
            165                 170                 175

Phe His His Lys Ala Arg Glu Leu His Pro Glu Tyr Tyr Lys Asp Cys
            180                 185                 190

Ala Leu Ala Ala Val Glu Pro Val Asp Pro Arg Leu Glu Pro Trp Lys
            195                 200                 205

His Pro Gly Ser Gln Pro Arg Thr Pro Cys Thr Asn Cys Tyr Cys Lys
    210                 215                 220

Lys Cys Cys Leu His Cys Gln Val Cys Phe Thr Arg Lys Gly Leu Gly
225                 230                 235                 240

Ile Ser Tyr Gly Arg Lys Lys Arg Arg Gln Arg Arg Ala Pro Gln
                245                 250                 255

Asp Ser Gln Thr His Gln Val Ser Leu Pro Lys Gln Pro Ser Ser Gln
            260                 265                 270

Gln Arg Gly Asp Pro Thr Gly Pro Lys Lys Ser Gly Leu Ala Ile Leu
        275                 280                 285

Leu Ser Asp Glu Glu Leu Leu Lys Thr Val Arg Leu Ile Lys Phe Leu
    290                 295                 300

Tyr Gln Ser Asn Pro Pro Ser Asn Glu Gly Thr Arg Gln Ala Arg
305                 310                 315                 320

Arg Asn Arg Arg Arg Trp Arg Glu Arg Gln Arg Gln Ile Arg Ser
                325                 330                 335

Ile Ser Glu Arg Ile Leu Ser Thr Phe Leu Gly Arg Pro Ala Glu Pro
            340                 345                 350

Val Pro Leu Gln Leu Pro Pro Leu Glu Arg Leu Thr Leu Asp Cys Ser
            355                 360                 365

Glu Asp Cys Gly Asn Ser Gly Thr Gln Gly Val Gly Ser Pro Gln Val
    370                 375                 380

Leu Val Glu
385

<210> SEQ ID NO 31
<211> LENGTH: 390
<212> TYPE: PRT
<213> ORGANISM: Artificial Sequence
<220> FEATURE:
<223> OTHER INFORMATION: Protein comprised of Immunodominant parts of
      the Nef-Tat-Rev separated by protease sites(NTR)

<400> SEQUENCE: 31

Met Gly Trp Pro Thr Val Arg Glu Arg Met Lys Gln Ala Glu Pro Glu
1               5                   10                  15

Pro Ala Ala Asp Gly Val Gly Ala Ala Ser Arg Asp Leu Glu Lys His
            20                  25                  30

Gly Ala Ile Thr Ser Ser Asn Thr Ala Thr Asn Asn Ala Ala Cys Ala
        35                  40                  45

Trp Leu Glu Ala Gln Glu Glu Glu Val Gly Phe Pro Val Arg Pro
    50                  55                  60

Gln Val Pro Leu Arg Pro Met Thr Tyr Lys Gly Ala Leu Asp Leu Ser
65                  70                  75                  80

His Phe Leu Lys Glu Lys Gly Gly Leu Glu Gly Leu Ile Tyr Ser Pro
                85                  90                  95

Lys Arg Gln Glu Ile Leu Asp Leu Trp Val Tyr His Thr Gln Gly Tyr
            100                 105                 110

Phe Pro Asp Trp Gln Asn Tyr Thr Pro Gly Pro Gly Val Arg Tyr Pro
        115                 120                 125

Leu Thr Phe Gly Trp Cys Phe Lys Leu Val Pro Val Glu Pro Asp Glu
         130                 135                 140

Glu Glu Asn Ser Ser Leu Leu His Pro Ala Ser Leu His Gly Thr Glu
145                 150                 155                 160

Asp Thr Glu Arg Glu Val Leu Lys Trp Lys Phe Asp Ser His Leu Ala
                165                 170                 175

Phe His His Lys Ala Arg Glu Leu His Pro Glu Tyr Tyr Lys Asp Cys
            180                 185                 190

Ala Leu Ala Phe Lys Arg Val Glu Pro Val Asp Pro Arg Leu Glu Pro
        195                 200                 205

Trp Lys His Pro Gly Ser Gln Pro Arg Thr Pro Cys Thr Asn Cys Tyr
    210                 215                 220

Cys Lys Lys Cys Cys Leu His Cys Gln Val Cys Phe Thr Arg Lys Gly
225                 230                 235                 240

Leu Gly Ile Ser Tyr Gly Arg Lys Lys Arg Gln Arg Arg Arg Ala
                245                 250                 255

Pro Gln Asp Ser Gln Thr His Gln Val Ser Leu Pro Lys Gln Pro Ser
            260                 265                 270

Ser Gln Gln Arg Gly Asp Pro Thr Gly Pro Lys Lys Ser Val Arg Glu
                275                 280                 285

Lys Arg Leu Leu Ser Asp Glu Glu Leu Leu Lys Thr Val Arg Leu Ile
290                 295                 300

Lys Phe Leu Tyr Gln Ser Asn Pro Pro Ser Asn Glu Gly Thr Arg
305                 310                 315                 320

Gln Ala Arg Arg Asn Arg Arg Arg Trp Arg Glu Arg Gln Arg Gln
            325                 330                 335

Ile Arg Ser Ile Ser Glu Arg Ile Leu Ser Thr Phe Leu Gly Arg Pro
        340                 345                 350

Ala Glu Pro Val Pro Leu Gln Leu Pro Pro Leu Glu Arg Leu Thr Leu
    355                 360                 365

Asp Cys Ser Glu Asp Cys Gly Asn Ser Gly Thr Gln Gly Val Gly Ser
370                 375                 380

Pro Gln Val Leu Val Glu
385                 390

<210> SEQ ID NO 32
<211> LENGTH: 386
<212> TYPE: PRT
<213> ORGANISM: Artificial Sequence
<220> FEATURE:
<223> OTHER INFORMATION: Protein comprised of Immunodominant parts of
      the regulatory proteins Nef-Tat-Rev started from aa1 of Nef(N11TR)

<400> SEQUENCE: 32

Met Trp Pro Thr Val Arg Glu Arg Met Lys Gln Ala Glu Pro Glu Pro
1               5                   10                  15

Ala Ala Asp Gly Val Gly Ala Ala Ser Arg Asp Leu Glu Lys His Gly
            20                  25                  30

Ala Ile Thr Ser Ser Asn Thr Ala Thr Asn Ala Ala Cys Ala Trp
        35                  40                  45

Leu Glu Ala Gln Glu Glu Glu Val Gly Phe Pro Val Arg Pro Gln
50                  55                  60

Val Pro Leu Arg Pro Met Thr Tyr Lys Gly Ala Leu Asp Leu Ser His
65                  70                  75                  80

Phe Leu Lys Glu Lys Gly Gly Leu Glu Gly Leu Ile Tyr Ser Pro Lys
                85                  90                  95

```
Arg Gln Glu Ile Leu Asp Leu Trp Val Tyr His Thr Gln Gly Tyr Phe
                100                 105                 110

Pro Asp Trp Gln Asn Tyr Thr Pro Gly Pro Gly Val Arg Tyr Pro Leu
            115                 120                 125

Thr Phe Gly Trp Cys Phe Lys Leu Val Pro Val Pro Asp Glu Glu
    130                 135                 140

Glu Asn Ser Ser Leu Leu His Pro Ala Ser Leu His Gly Thr Glu Asp
145                 150                 155                 160

Thr Glu Arg Glu Val Leu Lys Trp Lys Phe Asp Ser His Leu Ala Phe
                165                 170                 175

His His Lys Ala Arg Glu Leu His Pro Glu Tyr Tyr Lys Asp Cys Ala
            180                 185                 190

Leu Ala Ala Val Glu Pro Val Asp Pro Arg Leu Glu Pro Trp Lys His
        195                 200                 205

Pro Gly Ser Gln Pro Arg Thr Pro Cys Thr Asn Cys Tyr Cys Lys Lys
    210                 215                 220

Cys Cys Leu His Cys Gln Val Cys Phe Thr Arg Lys Gly Leu Gly Ile
225                 230                 235                 240

Ser Tyr Gly Arg Lys Lys Arg Arg Gln Arg Arg Ala Pro Gln Asp
                245                 250                 255

Ser Gln Thr His Gln Val Ser Leu Pro Lys Gln Pro Ser Ser Gln Gln
            260                 265                 270

Arg Gly Asp Pro Thr Gly Pro Lys Lys Ser Gly Leu Ala Ile Leu Leu
        275                 280                 285

Ser Asp Glu Glu Leu Leu Lys Thr Val Arg Leu Ile Lys Phe Leu Tyr
    290                 295                 300

Gln Ser Asn Pro Pro Ser Asn Glu Gly Thr Arg Gln Ala Arg Arg
305                 310                 315                 320

Asn Arg Arg Arg Arg Trp Arg Glu Arg Gln Arg Gln Ile Arg Ser Ile
                325                 330                 335

Ser Glu Arg Ile Leu Ser Thr Phe Leu Gly Arg Pro Ala Glu Pro Val
            340                 345                 350

Pro Leu Gln Leu Pro Pro Leu Glu Arg Leu Thr Leu Asp Cys Ser Glu
        355                 360                 365

Asp Cys Gly Asn Ser Gly Thr Gln Gly Val Gly Ser Pro Gln Val Leu
    370                 375                 380

Val Glu
385

<210> SEQ ID NO 33
<211> LENGTH: 389
<212> TYPE: PRT
<213> ORGANISM: Artificial Sequence
<220> FEATURE:
<223> OTHER INFORMATION: Protein comprised of Immunodominant parts of
      the regulatory proteins Nef-Tat-Rev started from aa1 of Nef
      separated by protease sites(N11TR)

<400> SEQUENCE: 33

Met Trp Pro Thr Val Arg Glu Arg Met Lys Gln Ala Glu Pro Glu Pro
1               5                   10                  15

Ala Ala Asp Gly Val Gly Ala Ala Ser Arg Asp Leu Glu Lys His Gly
            20                  25                  30

Ala Ile Thr Ser Ser Asn Thr Ala Thr Asn Ala Ala Cys Ala Trp
        35                  40                  45

Leu Glu Ala Gln Glu Glu Glu Glu Val Gly Phe Pro Val Arg Pro Gln
```

```
    50                  55                  60

Val Pro Leu Arg Pro Met Thr Tyr Lys Gly Ala Leu Asp Leu Ser His
65                  70                  75                  80

Phe Leu Lys Glu Lys Gly Gly Leu Glu Gly Leu Ile Tyr Ser Pro Lys
                85                  90                  95

Arg Gln Glu Ile Leu Asp Leu Trp Val Tyr His Thr Gln Gly Tyr Phe
            100                 105                 110

Pro Asp Trp Gln Asn Tyr Thr Pro Gly Pro Gly Val Arg Tyr Pro Leu
        115                 120                 125

Thr Phe Gly Trp Cys Phe Lys Leu Val Pro Val Glu Pro Asp Glu Glu
    130                 135                 140

Glu Asn Ser Ser Leu Leu His Pro Ala Ser Leu His Gly Thr Glu Asp
145                 150                 155                 160

Thr Glu Arg Glu Val Leu Lys Trp Lys Phe Asp Ser His Leu Ala Phe
                165                 170                 175

His His Lys Ala Arg Glu Leu His Pro Glu Tyr Tyr Lys Asp Cys Ala
            180                 185                 190

Leu Ala Phe Lys Arg Val Glu Pro Val Asp Pro Arg Leu Glu Pro Trp
        195                 200                 205

Lys His Pro Gly Ser Gln Pro Arg Thr Pro Cys Thr Asn Cys Tyr Cys
    210                 215                 220

Lys Lys Cys Cys Leu His Cys Gln Val Cys Phe Thr Arg Lys Gly Leu
225                 230                 235                 240

Gly Ile Ser Tyr Gly Arg Lys Lys Arg Arg Gln Arg Arg Arg Ala Pro
                245                 250                 255

Gln Asp Ser Gln Thr His Gln Val Ser Leu Pro Lys Gln Pro Ser Ser
            260                 265                 270

Gln Gln Arg Gly Asp Pro Thr Gly Pro Lys Lys Ser Val Arg Glu Lys
        275                 280                 285

Arg Leu Leu Ser Asp Glu Glu Leu Leu Lys Thr Val Arg Leu Ile Lys
    290                 295                 300

Phe Leu Tyr Gln Ser Asn Pro Pro Pro Ser Asn Glu Gly Thr Arg Gln
305                 310                 315                 320

Ala Arg Arg Asn Arg Arg Arg Arg Trp Arg Glu Arg Gln Arg Gln Ile
                325                 330                 335

Arg Ser Ile Ser Glu Arg Ile Leu Ser Thr Phe Leu Gly Arg Pro Ala
            340                 345                 350

Glu Pro Val Pro Leu Gln Leu Pro Pro Leu Glu Arg Leu Thr Leu Asp
        355                 360                 365

Cys Ser Glu Asp Cys Gly Asn Ser Gly Thr Gln Gly Val Gly Ser Pro
    370                 375                 380

Gln Val Leu Val Glu
385

<210> SEQ ID NO 34
<211> LENGTH: 220
<212> TYPE: PRT
<213> ORGANISM: Artificial Sequence
<220> FEATURE:
<223> OTHER INFORMATION: Protein comprised of Cytotoxic T-cell epitopes
      of Pol and Env genes(CTL)

<400> SEQUENCE: 34

Met Ile Thr Leu Trp Gln Arg Pro Leu Val Ala Leu Ile Glu Ile Cys
1               5                   10                  15

Thr Glu Met Glu Lys Glu Gly Lys Ile Ser Lys Ile Gly Pro Ala Gly
```

```
                    20                  25                  30
Leu Lys Lys Lys Lys Ser Val Thr Val Leu Asp Val Gly Asp Ala Tyr
             35                  40                  45

Phe Ser Val Pro Leu Asp Lys Asp Phe Arg Lys Tyr Thr Ala Phe Thr
         50                  55                  60

Ile Pro Ser Ile Trp Lys Gly Ser Pro Ala Ile Phe Gln Ser Ser Met
 65                  70                  75                  80

Thr Lys Lys Gln Asn Pro Asp Ile Val Ile Tyr Gln Tyr Met Asp Asp
                 85                  90                  95

Leu Tyr Val Pro Ile Val Leu Pro Glu Lys Asp Ser Trp Leu Val Gly
             100                 105                 110

Lys Leu Asn Trp Ala Ser Gln Ile Tyr Ala Gly Ile Lys Val Lys Gln
         115                 120                 125

Leu Ile Leu Lys Glu Pro Val His Gly Val Tyr Glu Pro Ile Val Gly
     130                 135                 140

Ala Glu Thr Phe Tyr Val Asp Gly Ala Ala Asn Arg Ala Gly Asn Leu
145                 150                 155                 160

Trp Val Thr Val Tyr Tyr Gly Val Pro Val Trp Lys Glu Ala Thr Thr
                 165                 170                 175

Thr Leu Val Glu Arg Tyr Leu Arg Asp Gln Gln Leu Leu Gly Ile Trp
             180                 185                 190

Gly Cys Ala Cys Thr Pro Tyr Asp Ile Asn Gln Met Leu Arg Gly Pro
         195                 200                 205

Gly Arg Ala Phe Val Thr Ile Arg Gln Gly Ser Leu
     210                 215                 220

<210> SEQ ID NO 35
<211> LENGTH: 421
<212> TYPE: PRT
<213> ORGANISM: Artificial Sequence
<220> FEATURE:
<223> OTHER INFORMATION: Truncated Gag protein sequence(dgag)

<400> SEQUENCE: 35

Met Leu Asp Lys Trp Glu Lys Ile Arg Leu Arg Pro Gly Gly Lys Lys
 1               5                  10                  15

Lys Tyr Gln Leu Lys His Ile Val Trp Ala Ser Arg Glu Leu Glu Arg
                 20                  25                  30

Phe Ala Val Asn Pro Gly Leu Leu Glu Thr Ser Glu Gly Cys Arg Gln
             35                  40                  45

Ile Met Gly Gln Leu Gln Pro Ser Leu Gln Thr Gly Ser Glu Glu Leu
         50                  55                  60

Arg Ser Leu Tyr Asn Thr Val Ala Thr Leu Tyr Cys Val His Gln Lys
 65                  70                  75                  80

Ile Glu Val Lys Asp Thr Lys Glu Ala Leu Asp Lys Val Glu Glu Glu
                 85                  90                  95

Gln Asn Asn Ser Lys Lys Lys Ala Gln Gln Glu Ala Ala Asp Ala Gly
             100                 105                 110

Asn Arg Asn Gln Val Ser Gln Asn Tyr Pro Ile Val Gln Asn Leu Gln
         115                 120                 125

Gly Gln Met Val His Gln Ala Ile Ser Pro Arg Thr Leu Asn Ala Trp
     130                 135                 140

Val Lys Val Val Glu Glu Lys Ala Phe Ser Pro Glu Val Ile Pro Met
145                 150                 155                 160

Phe Ser Ala Leu Ser Glu Gly Ala Thr Pro Gln Asp Leu Asn Thr Met
                 165                 170                 175
```

Leu Asn Thr Val Gly Gly His Gln Ala Ala Met Gln Met Leu Lys Glu
            180                 185                 190

Thr Ile Asn Glu Glu Ala Ala Glu Trp Asp Arg Leu His Pro Val His
        195                 200                 205

Ala Gly Pro Ile Ala Pro Gly Gln Met Arg Glu Pro Arg Gly Ser Asp
    210                 215                 220

Ile Ala Gly Thr Thr Ser Thr Leu Gln Glu Gln Ile Gly Trp Met Thr
225                 230                 235                 240

Asn Asn Pro Pro Ile Pro Val Gly Glu Ile Tyr Lys Arg Trp Ile Ile
                245                 250                 255

Leu Gly Leu Asn Lys Ile Val Arg Met Tyr Ser Pro Thr Ser Ile Leu
            260                 265                 270

Asp Ile Lys Gln Gly Pro Lys Glu Pro Phe Arg Asp Tyr Val Asp Arg
        275                 280                 285

Phe Tyr Lys Thr Leu Arg Ala Glu Gln Ala Thr Gln Glu Val Lys Asn
    290                 295                 300

Trp Met Thr Glu Thr Leu Leu Val Gln Asn Ala Asn Pro Asp Cys Lys
305                 310                 315                 320

Thr Ile Leu Lys Ala Leu Gly Pro Ala Ala Thr Leu Glu Glu Met Met
                325                 330                 335

Thr Ala Cys Gln Gly Val Gly Gly Pro Gly His Lys Ala Arg Val Leu
            340                 345                 350

Ala Glu Ala Met Ser Gln Val Thr Gly Ser Ala Ala Ile Met Met Gln
        355                 360                 365

Arg Gly Asn Phe Arg Asn Gln Arg Lys Thr Val Lys Cys Phe Asn Cys
    370                 375                 380

Gly Lys Glu Gly His Ile Ala Arg Asn Cys Arg Ala Pro Arg Lys Lys
385                 390                 395                 400

Gly Cys Trp Lys Cys Gly Lys Glu Gly His Gln Met Lys Asp Cys Thr
                405                 410                 415

Glu Arg Gln Ala Asn
            420

<210> SEQ ID NO 36
<211> LENGTH: 363
<212> TYPE: PRT
<213> ORGANISM: Artificial Sequence
<220> FEATURE:
<223> OTHER INFORMATION: Synthetic p17/24 protein of Gag gene(Syn 17/24)

<400> SEQUENCE: 36

Met Gly Ala Arg Ala Ser Val Leu Ser Gly Gly Glu Leu Asp Lys Trp
1               5                   10                  15

Glu Lys Ile Arg Leu Arg Pro Gly Gly Lys Lys Tyr Gln Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Met Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Lys Ile Glu Val Lys Asp
                85                  90                  95

Thr Lys Glu Ala Leu Asp Lys Val Glu Glu Glu Gln Asn Asn Ser Lys
            100                 105                 110

```
Lys Lys Ala Gln Gln Glu Ala Ala Asp Ala Gly Asn Arg Asn Gln Val
        115                 120                 125

Ser Gln Asn Tyr Pro Ile Val Gln Asn Leu Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Leu His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Lys Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Thr Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu
        355                 360

<210> SEQ ID NO 37
<211> LENGTH: 363
<212> TYPE: PRT
<213> ORGANISM: Artificial Sequence
<220> FEATURE:
<223> OTHER INFORMATION: Synthetic p17/24 protein of Gag gene optimized
      for expression in eukaryotic cells(optp 17/24)

<400> SEQUENCE: 37

Met Gly Ala Arg Ala Ser Val Leu Ser Gly Gly Glu Leu Asp Lys Trp
1               5                   10                  15

Glu Lys Ile Arg Leu Arg Pro Gly Gly Lys Lys Tyr Gln Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Met Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Lys Ile Glu Val Lys Asp
                85                  90                  95

Thr Lys Glu Ala Leu Asp Lys Val Glu Glu Glu Gln Asn Asn Ser Lys
            100                 105                 110
```

```
Lys Lys Ala Gln Gln Glu Ala Ala Asp Ala Gly Asn Arg Asn Gln Val
        115                 120                 125

Ser Gln Asn Tyr Pro Ile Val Gln Asn Leu Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
                180                 185                 190

Gly His Gln Ala Ala Met Gln Met Leu Lys Glu Thr Ile Asn Glu Glu
            195                 200                 205

Ala Ala Glu Trp Asp Arg Leu His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
                260                 265                 270

Ile Val Arg Met Tyr Ser Pro Thr Ser Ile Leu Asp Ile Lys Gln Gly
            275                 280                 285

Pro Lys Glu Pro Phe Arg Asp Tyr Val Asp Arg Phe Tyr Lys Thr Leu
        290                 295                 300

Arg Ala Glu Gln Ala Thr Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
                340                 345                 350

Val Gly Gly Pro Gly His Lys Ala Arg Val Leu
            355                 360

<210> SEQ ID NO 38
<211> LENGTH: 641
<212> TYPE: PRT
<213> ORGANISM: Artificial Sequence
<220> FEATURE:
<223> OTHER INFORMATION: Hybrid protein comprised of Tat-Rev-Nef
      and CTL(TRN-CTL)

<400> SEQUENCE: 38

Met Glu Pro Val Asp Pro Arg Leu Glu Pro Trp Lys His Pro Gly Ser
1               5                   10                  15

Gln Pro Arg Thr Pro Cys Thr Asn Cys Tyr Cys Lys Lys Cys Cys Leu
            20                  25                  30

His Cys Gln Val Cys Phe Thr Arg Lys Gly Leu Gly Ile Ser Tyr Gly
        35                  40                  45

Arg Lys Lys Arg Arg Gln Arg Arg Ala Pro Gln Asp Ser Gln Thr
    50                  55                  60

His Gln Val Ser Leu Pro Lys Gln Pro Ser Ser Gln Arg Gly Asp
65                  70                  75                  80

Pro Thr Gly Pro Lys Lys Ser Lys Lys Lys Val Glu Arg Glu Thr Glu
                85                  90                  95

Ala Asp Pro Phe Asp Thr Ser Ala Gly Arg Ser Gly Asp Ser Asp Glu
                100                 105                 110
```

-continued

```
Glu Leu Leu Lys Thr Val Arg Leu Ile Lys Phe Leu Tyr Gln Ser Asn
            115                 120                 125

Pro Pro Pro Ser Asn Glu Gly Thr Arg Gln Ala Arg Arg Asn Arg Arg
        130                 135                 140

Arg Arg Trp Arg Glu Arg Gln Arg Gln Ile Arg Ser Ile Ser Glu Arg
145                 150                 155                 160

Ile Leu Ser Thr Phe Leu Gly Arg Pro Ala Glu Pro Val Pro Leu Gln
                165                 170                 175

Leu Pro Pro Leu Glu Arg Leu Thr Leu Asp Cys Ser Glu Asp Cys Gly
            180                 185                 190

Asn Ser Gly Thr Gln Gly Val Gly Ser Pro Gln Val Leu Val Glu Ser
        195                 200                 205

Pro Ala Val Leu Glu Pro Gly Thr Lys Glu Lys Leu Val Gly Lys Trp
210                 215                 220

Ser Lys Cys Ser Gly Trp Pro Thr Val Arg Glu Arg Met Lys Gln Ala
225                 230                 235                 240

Glu Pro Glu Pro Ala Ala Asp Gly Val Gly Ala Ala Ser Arg Asp Leu
                245                 250                 255

Glu Lys His Gly Ala Ile Thr Ser Ser Asn Thr Ala Thr Asn Asn Ala
            260                 265                 270

Ala Cys Ala Trp Leu Glu Ala Gln Glu Glu Glu Val Gly Phe Pro
        275                 280                 285

Val Arg Pro Gln Val Pro Leu Arg Pro Met Thr Tyr Lys Gly Ala Leu
290                 295                 300

Asp Leu Ser His Phe Leu Lys Glu Lys Gly Gly Leu Glu Gly Leu Ile
305                 310                 315                 320

Tyr Ser Pro Lys Arg Gln Glu Ile Leu Asp Leu Trp Val Tyr His Thr
                325                 330                 335

Gln Gly Tyr Phe Pro Asp Trp Gln Asn Tyr Thr Pro Gly Pro Gly Val
            340                 345                 350

Arg Tyr Pro Leu Thr Phe Gly Trp Cys Phe Lys Leu Val Pro Val Glu
        355                 360                 365

Pro Asp Glu Glu Glu Asn Ser Ser Leu Leu His Pro Ala Ser Leu His
370                 375                 380

Gly Thr Glu Asp Thr Glu Arg Glu Val Leu Lys Trp Lys Phe Asp Ser
385                 390                 395                 400

His Leu Ala Phe His His Lys Ala Arg Glu Leu His Pro Glu Tyr Tyr
                405                 410                 415

Lys Asp Cys Ala Ala Val Ile Thr Leu Trp Gln Arg Pro Leu Val Ala
            420                 425                 430

Leu Ile Glu Ile Cys Thr Glu Met Glu Lys Glu Gly Lys Ile Ser Lys
        435                 440                 445

Ile Gly Pro Ala Gly Leu Lys Lys Lys Ser Val Thr Val Leu Asp
450                 455                 460

Val Gly Asp Ala Tyr Phe Ser Val Pro Leu Asp Lys Asp Phe Arg Lys
465                 470                 475                 480

Tyr Thr Ala Phe Thr Ile Pro Ser Ile Trp Lys Gly Ser Pro Ala Ile
                485                 490                 495

Phe Gln Ser Ser Met Thr Lys Lys Gln Asn Pro Asp Ile Val Ile Tyr
            500                 505                 510

Gln Tyr Met Asp Asp Leu Tyr Val Pro Ile Val Leu Pro Glu Lys Asp
        515                 520                 525

Ser Trp Leu Val Gly Lys Leu Asn Trp Ala Ser Gln Ile Tyr Ala Gly
530                 535                 540
```

```
Ile Lys Val Lys Gln Leu Ile Leu Lys Glu Pro Val His Gly Val Tyr
545                 550                 555                 560

Glu Pro Ile Val Gly Ala Glu Thr Phe Tyr Val Asp Gly Ala Ala Asn
            565                 570                 575

Arg Ala Gly Asn Leu Trp Val Thr Val Tyr Tyr Gly Val Pro Val Trp
            580                 585                 590

Lys Glu Ala Thr Thr Thr Leu Val Glu Arg Tyr Leu Arg Asp Gln Gln
        595                 600                 605

Leu Leu Gly Ile Trp Gly Cys Ala Cys Thr Pro Tyr Asp Ile Asn Gln
    610                 615                 620

Met Leu Arg Gly Pro Gly Arg Ala Phe Val Thr Ile Arg Gln Gly Ser
625                 630                 635                 640

Leu
```

<210> SEQ ID NO 39
<211> LENGTH: 641
<212> TYPE: PRT
<213> ORGANISM: Artificial Sequence
<220> FEATURE:
<223> OTHER INFORMATION: Hybrid protein comprised of Rev-Nef-Tat
      and CTL(RNT-CTL)

<400> SEQUENCE: 39

```
Met Ala Gly Arg Ser Gly Asp Ser Asp Glu Glu Leu Leu Lys Thr Val
1               5                   10                  15

Arg Leu Ile Lys Phe Leu Tyr Gln Ser Asn Pro Pro Ser Asn Glu
            20                  25                  30

Gly Thr Arg Gln Ala Arg Arg Asn Arg Arg Arg Trp Arg Glu Arg
            35                  40                  45

Gln Arg Gln Ile Arg Ser Ile Ser Glu Arg Ile Leu Ser Thr Phe Leu
    50                  55                  60

Gly Arg Pro Ala Glu Pro Val Pro Leu Gln Leu Pro Pro Leu Glu Arg
65                  70                  75                  80

Leu Thr Leu Asp Cys Ser Glu Asp Cys Gly Asn Ser Gly Thr Gln Gly
                85                  90                  95

Val Gly Ser Pro Gln Val Leu Val Glu Ser Pro Ala Val Leu Glu Pro
            100                 105                 110

Gly Thr Lys Glu Thr Ser Val Gly Lys Trp Ser Lys Cys Ser Gly Trp
            115                 120                 125

Pro Thr Val Arg Glu Arg Met Lys Gln Ala Glu Pro Glu Pro Ala Ala
    130                 135                 140

Asp Gly Val Gly Ala Ala Ser Arg Asp Leu Glu Lys His Gly Ala Ile
145                 150                 155                 160

Thr Ser Ser Asn Thr Ala Thr Asn Asn Ala Ala Cys Ala Trp Leu Glu
                165                 170                 175

Ala Gln Glu Glu Glu Val Gly Phe Pro Val Arg Pro Gln Val Pro
            180                 185                 190

Leu Arg Pro Met Thr Tyr Lys Gly Ala Leu Asp Leu Ser His Phe Leu
    195                 200                 205

Lys Glu Lys Gly Gly Leu Glu Gly Leu Ile Tyr Ser Pro Lys Arg Gln
210                 215                 220

Glu Ile Leu Asp Leu Trp Val Tyr His Thr Gln Gly Tyr Phe Pro Asp
225                 230                 235                 240

Trp Gln Asn Tyr Thr Pro Gly Pro Gly Val Arg Tyr Pro Leu Thr Phe
                245                 250                 255
```

```
Gly Trp Cys Phe Lys Leu Val Pro Val Glu Pro Asp Glu Glu Asn
            260                 265                 270
Ser Ser Leu Leu His Pro Ala Ser Leu His Gly Thr Glu Asp Thr Glu
275                 280                 285
Arg Glu Val Leu Lys Trp Lys Phe Asp Ser His Leu Ala Phe His His
            290                 295                 300
Lys Ala Arg Glu Leu His Pro Glu Tyr Tyr Lys Asp Cys Lys Leu Glu
305                 310                 315                 320
Pro Val Asp Pro Arg Leu Glu Pro Trp Lys His Pro Gly Ser Gln Pro
                325                 330                 335
Arg Thr Pro Cys Thr Asn Cys Tyr Cys Lys Lys Cys Cys Leu His Cys
            340                 345                 350
Gln Val Cys Phe Thr Arg Lys Gly Leu Gly Ile Ser Tyr Gly Arg Lys
            355                 360                 365
Lys Arg Arg Gln Arg Arg Ala Pro Gln Asp Ser Gln Thr His Gln
370                 375                 380
Val Ser Leu Pro Lys Gln Pro Ser Ser Gln Arg Gly Asp Pro Thr
385                 390                 395                 400
Gly Pro Lys Lys Ser Lys Lys Lys Val Glu Arg Glu Thr Glu Ala Asp
                405                 410                 415
Pro Phe Asp Ala Ala Val Ile Thr Leu Trp Gln Arg Pro Leu Val Ala
                420                 425                 430
Leu Ile Glu Ile Cys Thr Glu Met Glu Lys Glu Gly Lys Ile Ser Lys
            435                 440                 445
Ile Gly Pro Ala Gly Leu Lys Lys Lys Ser Val Thr Val Leu Asp
450                 455                 460
Val Gly Asp Ala Tyr Phe Ser Val Pro Leu Asp Lys Asp Phe Arg Lys
465                 470                 475                 480
Tyr Thr Ala Phe Thr Ile Pro Ser Ile Trp Lys Gly Ser Pro Ala Ile
                485                 490                 495
Phe Gln Ser Ser Met Thr Lys Lys Gln Asn Pro Asp Ile Val Ile Tyr
                500                 505                 510
Gln Tyr Met Asp Asp Leu Tyr Val Pro Ile Val Leu Pro Glu Lys Asp
            515                 520                 525
Ser Trp Leu Val Gly Lys Leu Asn Trp Ala Ser Gln Ile Tyr Ala Gly
530                 535                 540
Ile Lys Val Lys Gln Leu Ile Leu Lys Glu Pro Val His Gly Val Tyr
545                 550                 555                 560
Glu Pro Ile Val Gly Ala Glu Thr Phe Tyr Val Asp Gly Ala Ala Asn
                565                 570                 575
Arg Ala Gly Asn Leu Trp Val Thr Val Tyr Tyr Gly Val Pro Val Trp
            580                 585                 590
Lys Glu Ala Thr Thr Thr Leu Val Glu Arg Tyr Leu Arg Asp Gln Gln
            595                 600                 605
Leu Leu Gly Ile Trp Gly Cys Ala Cys Thr Pro Tyr Asp Ile Asn Gln
            610                 615                 620
Met Leu Arg Gly Pro Gly Arg Ala Phe Val Thr Ile Arg Gln Gly Ser
625                 630                 635                 640
Leu

<210> SEQ ID NO 40
<211> LENGTH: 842
<212> TYPE: PRT
<213> ORGANISM: Artificial Sequence
<220> FEATURE:
```

```
<223> OTHER INFORMATION: Hybrid protein cds comprised of Tat-Rev-Nef
      and truncated Gag protein(TRN-dgag)

<400> SEQUENCE: 40

Met Glu Pro Val Asp Pro Arg Leu Glu Pro Trp Lys His Pro Gly Ser
1               5                   10                  15

Gln Pro Arg Thr Pro Cys Thr Asn Cys Tyr Cys Lys Lys Cys Cys Leu
                20                  25                  30

His Cys Gln Val Cys Phe Thr Arg Lys Gly Leu Gly Ile Ser Tyr Gly
            35                  40                  45

Arg Lys Lys Arg Arg Gln Arg Arg Ala Pro Gln Asp Ser Gln Thr
50                  55                  60

His Gln Val Ser Leu Pro Lys Gln Pro Ser Ser Gln Gln Arg Gly Asp
65                  70                  75                  80

Pro Thr Gly Pro Lys Lys Ser Lys Lys Lys Val Glu Arg Glu Thr Glu
                85                  90                  95

Ala Asp Pro Phe Asp Thr Ser Ala Gly Arg Ser Gly Asp Ser Asp Glu
                100                 105                 110

Glu Leu Leu Lys Thr Val Arg Leu Ile Lys Phe Leu Tyr Gln Ser Asn
            115                 120                 125

Pro Pro Pro Ser Asn Glu Gly Thr Arg Gln Ala Arg Arg Asn Arg Arg
130                 135                 140

Arg Arg Trp Arg Glu Arg Gln Arg Gln Ile Arg Ser Ile Ser Glu Arg
145                 150                 155                 160

Ile Leu Ser Thr Phe Leu Gly Arg Pro Ala Glu Pro Val Pro Leu Gln
                165                 170                 175

Leu Pro Pro Leu Glu Arg Leu Thr Leu Asp Cys Ser Glu Asp Cys Gly
                180                 185                 190

Asn Ser Gly Thr Gln Gly Val Gly Ser Pro Gln Val Leu Val Glu Ser
            195                 200                 205

Pro Ala Val Leu Glu Pro Gly Thr Lys Glu Lys Leu Val Gly Lys Trp
210                 215                 220

Ser Lys Cys Ser Gly Trp Pro Thr Val Arg Glu Arg Met Lys Gln Ala
225                 230                 235                 240

Glu Pro Glu Pro Ala Ala Asp Gly Val Gly Ala Ala Ser Arg Asp Leu
                245                 250                 255

Glu Lys His Gly Ala Ile Thr Ser Ser Asn Thr Ala Thr Asn Asn Ala
            260                 265                 270

Ala Cys Ala Trp Leu Glu Ala Gln Glu Glu Glu Val Gly Phe Pro
275                 280                 285

Val Arg Pro Gln Val Pro Leu Arg Pro Met Thr Tyr Lys Gly Ala Leu
290                 295                 300

Asp Leu Ser His Phe Leu Lys Glu Lys Gly Gly Leu Glu Gly Leu Ile
305                 310                 315                 320

Tyr Ser Pro Lys Arg Gln Glu Ile Leu Asp Leu Trp Val Tyr His Thr
                325                 330                 335

Gln Gly Tyr Phe Pro Asp Trp Gln Asn Tyr Thr Pro Gly Pro Gly Val
            340                 345                 350

Arg Tyr Pro Leu Thr Phe Gly Trp Cys Phe Lys Leu Val Pro Val Glu
            355                 360                 365

Pro Asp Glu Glu Glu Asn Ser Ser Leu Leu His Pro Ala Ser Leu His
370                 375                 380

Gly Thr Glu Asp Thr Glu Arg Glu Val Leu Lys Trp Lys Phe Asp Ser
385                 390                 395                 400
```

-continued

```
His Leu Ala Phe His His Lys Ala Arg Glu Leu His Pro Glu Tyr Tyr
                405                 410                 415
Lys Asp Cys Ala Ala Val Leu Asp Lys Trp Glu Lys Ile Arg Leu Arg
            420                 425                 430
Pro Gly Gly Lys Lys Lys Tyr Gln Leu Lys His Ile Val Trp Ala Ser
        435                 440                 445
Arg Glu Leu Glu Arg Phe Ala Val Asn Pro Gly Leu Leu Glu Thr Ser
    450                 455                 460
Glu Gly Cys Arg Gln Ile Met Gly Gln Leu Gln Pro Ser Leu Gln Thr
465                 470                 475                 480
Gly Ser Glu Glu Leu Arg Ser Leu Tyr Asn Thr Val Ala Thr Leu Tyr
                485                 490                 495
Cys Val His Gln Lys Ile Glu Val Lys Asp Thr Lys Glu Ala Leu Asp
            500                 505                 510
Lys Val Glu Glu Glu Gln Asn Asn Ser Lys Lys Ala Gln Gln Glu
        515                 520                 525
Ala Ala Asp Ala Gly Asn Arg Asn Gln Val Ser Gln Asn Tyr Pro Ile
    530                 535                 540
Val Gln Asn Leu Gln Gly Gln Met Val His Gln Ala Ile Ser Pro Arg
545                 550                 555                 560
Thr Leu Asn Ala Trp Val Lys Val Val Glu Glu Lys Ala Phe Ser Pro
                565                 570                 575
Glu Val Ile Pro Met Phe Ser Ala Leu Ser Glu Gly Ala Thr Pro Gln
            580                 585                 590
Asp Leu Asn Thr Met Leu Asn Thr Val Gly Gly His Gln Ala Ala Met
        595                 600                 605
Gln Met Leu Lys Glu Thr Ile Asn Glu Glu Ala Ala Glu Trp Asp Arg
    610                 615                 620
Leu His Pro Val His Ala Gly Pro Ile Ala Pro Gly Gln Met Arg Glu
625                 630                 635                 640
Pro Arg Gly Ser Asp Ile Ala Gly Thr Thr Ser Thr Leu Gln Glu Gln
                645                 650                 655
Ile Gly Trp Met Thr Asn Asn Pro Pro Ile Pro Val Gly Glu Ile Tyr
            660                 665                 670
Lys Arg Trp Ile Ile Leu Gly Leu Asn Lys Ile Val Arg Met Tyr Ser
        675                 680                 685
Pro Thr Ser Ile Leu Asp Ile Lys Gln Gly Pro Lys Glu Pro Phe Arg
    690                 695                 700
Asp Tyr Val Asp Arg Phe Tyr Lys Thr Leu Arg Ala Glu Gln Ala Thr
705                 710                 715                 720
Gln Glu Val Lys Asn Trp Met Thr Glu Thr Leu Leu Val Gln Asn Ala
                725                 730                 735
Asn Pro Asp Cys Lys Thr Ile Leu Lys Ala Leu Gly Pro Ala Ala Thr
            740                 745                 750
Leu Glu Glu Met Met Thr Ala Cys Gln Gly Val Gly Gly Pro Gly His
        755                 760                 765
Lys Ala Arg Val Leu Ala Glu Ala Met Ser Gln Val Thr Gly Ser Ala
    770                 775                 780
Ala Ile Met Met Gln Arg Gly Asn Phe Arg Asn Gln Arg Lys Thr Val
785                 790                 795                 800
Lys Cys Phe Asn Cys Gly Lys Glu Gly His Ile Ala Arg Asn Cys Arg
                805                 810                 815
Ala Pro Arg Lys Lys Gly Cys Trp Lys Cys Gly Lys Glu Gly His Gln
            820                 825                 830
```

Met Lys Asp Cys Thr Glu Arg Gln Ala Asn
        835                 840

<210> SEQ ID NO 41
<211> LENGTH: 1064
<212> TYPE: PRT
<213> ORGANISM: Artificial Sequence
<220> FEATURE:
<223> OTHER INFORMATION: Hybrid protein cds comprised of Tat-Rev-Nef,
      CTL and truncated Gag protein(TRN-TCL-dgag)

<400> SEQUENCE: 41

Met Glu Pro Val Asp Pro Arg Leu Glu Pro Trp Lys His Pro Gly Ser
1               5                   10                  15

Gln Pro Arg Thr Pro Cys Thr Asn Cys Tyr Cys Lys Lys Cys Cys Leu
            20                  25                  30

His Cys Gln Val Cys Phe Thr Arg Lys Gly Leu Gly Ile Ser Tyr Gly
        35                  40                  45

Arg Lys Lys Arg Arg Gln Arg Arg Ala Pro Gln Asp Ser Gln Thr
    50                  55                  60

His Gln Val Ser Leu Pro Lys Gln Pro Ser Ser Gln Gln Arg Gly Asp
65              70                  75                  80

Pro Thr Gly Pro Lys Lys Ser Lys Lys Lys Val Glu Arg Glu Thr Glu
                85                  90                  95

Ala Asp Pro Phe Asp Thr Ser Ala Gly Arg Ser Gly Asp Ser Asp Glu
            100                 105                 110

Glu Leu Leu Lys Thr Val Arg Leu Ile Lys Phe Leu Tyr Gln Ser Asn
        115                 120                 125

Pro Pro Pro Ser Asn Glu Gly Thr Arg Gln Ala Arg Arg Asn Arg Arg
    130                 135                 140

Arg Arg Trp Arg Glu Arg Gln Arg Gln Ile Arg Ser Ile Ser Glu Arg
145                 150                 155                 160

Ile Leu Ser Thr Phe Leu Gly Arg Pro Ala Glu Pro Val Pro Leu Gln
                165                 170                 175

Leu Pro Pro Leu Glu Arg Leu Thr Leu Asp Cys Ser Glu Asp Cys Gly
            180                 185                 190

Asn Ser Gly Thr Gln Gly Val Gly Ser Pro Gln Val Leu Val Glu Ser
        195                 200                 205

Pro Ala Val Leu Glu Pro Gly Thr Lys Glu Lys Leu Val Gly Lys Trp
    210                 215                 220

Ser Lys Cys Ser Gly Trp Pro Thr Val Arg Glu Arg Met Lys Gln Ala
225                 230                 235                 240

Glu Pro Glu Pro Ala Ala Asp Gly Val Gly Ala Ala Ser Arg Asp Leu
                245                 250                 255

Glu Lys His Gly Ala Ile Thr Ser Ser Asn Thr Ala Thr Asn Asn Ala
            260                 265                 270

Ala Cys Ala Trp Leu Glu Ala Gln Glu Glu Glu Glu Val Gly Phe Pro
        275                 280                 285

Val Arg Pro Gln Val Pro Leu Arg Pro Met Thr Tyr Lys Gly Ala Leu
    290                 295                 300

Asp Leu Ser His Phe Leu Lys Glu Lys Gly Gly Leu Glu Gly Leu Ile
305                 310                 315                 320

Tyr Ser Pro Lys Arg Gln Glu Ile Leu Asp Leu Trp Val Tyr His Thr
                325                 330                 335

Gln Gly Tyr Phe Pro Asp Trp Gln Asn Tyr Thr Pro Gly Pro Gly Val
            340                 345                 350

```
Arg Tyr Pro Leu Thr Phe Gly Trp Cys Phe Lys Leu Val Pro Val Glu
        355                 360                 365

Pro Asp Glu Glu Glu Asn Ser Ser Leu Leu His Pro Ala Ser Leu His
        370                 375                 380

Gly Thr Glu Asp Thr Glu Arg Glu Val Leu Lys Trp Lys Phe Asp Ser
385                 390                 395                 400

His Leu Ala Phe His His Lys Ala Arg Glu Leu His Pro Glu Tyr Tyr
                405                 410                 415

Lys Asp Cys Ala Ala Val Ile Thr Leu Trp Gln Arg Pro Leu Val Ala
                420                 425                 430

Leu Ile Glu Ile Cys Thr Glu Met Glu Lys Glu Gly Lys Ile Ser Lys
        435                 440                 445

Ile Gly Pro Ala Gly Leu Lys Lys Lys Ser Val Thr Val Leu Asp
        450                 455                 460

Val Gly Asp Ala Tyr Phe Ser Val Pro Leu Asp Lys Asp Phe Arg Lys
465                 470                 475                 480

Tyr Thr Ala Phe Thr Ile Pro Ser Ile Trp Lys Gly Ser Pro Ala Ile
                485                 490                 495

Phe Gln Ser Ser Met Thr Lys Lys Gln Asn Pro Asp Ile Val Ile Tyr
                500                 505                 510

Gln Tyr Met Asp Asp Leu Tyr Val Pro Ile Val Leu Pro Glu Lys Asp
        515                 520                 525

Ser Trp Leu Val Gly Lys Leu Asn Trp Ala Ser Gln Ile Tyr Ala Gly
        530                 535                 540

Ile Lys Val Lys Gln Leu Ile Leu Lys Glu Pro Val His Gly Val Tyr
545                 550                 555                 560

Glu Pro Ile Val Gly Ala Glu Thr Phe Tyr Val Asp Gly Ala Ala Asn
                565                 570                 575

Arg Ala Gly Asn Leu Trp Val Thr Val Tyr Tyr Gly Val Pro Val Trp
                580                 585                 590

Lys Glu Ala Thr Thr Thr Leu Val Glu Arg Tyr Leu Arg Asp Gln Gln
        595                 600                 605

Leu Leu Gly Ile Trp Gly Cys Ala Cys Thr Pro Tyr Asp Ile Asn Gln
        610                 615                 620

Met Leu Arg Gly Pro Gly Arg Ala Phe Val Thr Ile Arg Gln Gly Ser
625                 630                 635                 640

Leu Ala Ala Val Leu Asp Lys Trp Glu Lys Ile Arg Leu Arg Pro Gly
                645                 650                 655

Gly Lys Lys Lys Tyr Gln Leu Lys His Ile Val Trp Ala Ser Arg Glu
                660                 665                 670

Leu Glu Arg Phe Ala Val Asn Pro Gly Leu Leu Glu Thr Ser Glu Gly
        675                 680                 685

Cys Arg Gln Ile Met Gly Gln Leu Gln Pro Ser Leu Gln Thr Gly Ser
        690                 695                 700

Glu Glu Leu Arg Ser Leu Tyr Asn Thr Val Ala Thr Leu Tyr Cys Val
705                 710                 715                 720

His Gln Lys Ile Glu Val Lys Asp Thr Lys Glu Ala Leu Asp Lys Val
                725                 730                 735

Glu Glu Glu Gln Asn Asn Ser Lys Lys Lys Ala Gln Gln Glu Ala Ala
        740                 745                 750

Asp Ala Gly Asn Arg Asn Gln Val Ser Gln Asn Tyr Pro Ile Val Gln
        755                 760                 765

Asn Leu Gln Gly Gln Met Val His Gln Ala Ile Ser Pro Arg Thr Leu
```

```
                        770                 775                 780
Asn Ala Trp Val Lys Val Val Glu Glu Lys Ala Phe Ser Pro Glu Val
785                 790                 795                 800

Ile Pro Met Phe Ser Ala Leu Ser Glu Gly Ala Thr Pro Gln Asp Leu
                805                 810                 815

Asn Thr Met Leu Asn Thr Val Gly Gly His Gln Ala Ala Met Gln Met
                820                 825                 830

Leu Lys Glu Thr Ile Asn Glu Glu Ala Ala Glu Trp Asp Arg Leu His
                835                 840                 845

Pro Val His Ala Gly Pro Ile Ala Pro Gly Gln Met Arg Glu Pro Arg
850                 855                 860

Gly Ser Asp Ile Ala Gly Thr Thr Ser Thr Leu Gln Glu Gln Ile Gly
865                 870                 875                 880

Trp Met Thr Asn Asn Pro Pro Ile Pro Val Gly Glu Ile Tyr Lys Arg
                885                 890                 895

Trp Ile Ile Leu Gly Leu Asn Lys Ile Val Arg Met Tyr Ser Pro Thr
                900                 905                 910

Ser Ile Leu Asp Ile Lys Gln Gly Pro Lys Glu Pro Phe Arg Asp Tyr
                915                 920                 925

Val Asp Arg Phe Tyr Lys Thr Leu Arg Ala Glu Gln Ala Thr Gln Glu
                930                 935                 940

Val Lys Asn Trp Met Thr Glu Thr Leu Leu Val Gln Asn Ala Asn Pro
945                 950                 955                 960

Asp Cys Lys Thr Ile Leu Lys Ala Leu Gly Pro Ala Ala Thr Leu Glu
                965                 970                 975

Glu Met Met Thr Ala Cys Gln Gly Val Gly Gly Pro Gly His Lys Ala
                980                 985                 990

Arg Val Leu Ala Glu Ala Met Ser Gln Val Thr Gly Ser Ala Ala Ile
                995                 1000                1005

Met Met Gln Arg Gly Asn Phe Arg Asn Gln Arg Lys Thr Val Lys
        1010                1015                1020

Cys Phe Asn Cys Gly Lys Glu Gly His Ile Ala Arg Asn Cys Arg
        1025                1030                1035

Ala Pro Arg Lys Lys Gly Cys Trp Lys Cys Gly Lys Glu Gly His
        1040                1045                1050

Gln Met Lys Asp Cys Thr Glu Arg Gln Ala Asn
        1055                1060

<210> SEQ ID NO 42
<211> LENGTH: 1064
<212> TYPE: PRT
<213> ORGANISM: Artificial Sequence
<220> FEATURE:
<223> OTHER INFORMATION: Hybrid protein comprised of Tat-Rev-Nef,
      CTL and truncated Gag protein(TRN-CTL-dgag)

<400> SEQUENCE: 42

Met Ala Gly Arg Ser Gly Asp Ser Asp Glu Glu Leu Leu Lys Thr Val
1               5                   10                  15

Arg Leu Ile Lys Phe Leu Tyr Gln Ser Asn Pro Pro Ser Asn Glu
                20                  25                  30

Gly Thr Arg Gln Ala Arg Arg Asn Arg Arg Arg Trp Arg Glu Arg
                35                  40                  45

Gln Arg Gln Ile Arg Ser Ile Ser Glu Arg Ile Leu Ser Thr Phe Leu
50                  55                  60

Gly Arg Pro Ala Glu Pro Val Pro Leu Gln Leu Pro Pro Leu Glu Arg
```

```
            65                  70                  75                  80
Leu Thr Leu Asp Cys Ser Glu Asp Cys Gly Asn Ser Gly Thr Gln Gly
                85                  90                  95

Val Gly Ser Pro Gln Val Leu Val Glu Ser Pro Ala Val Leu Glu Pro
            100                 105                 110

Gly Thr Lys Glu Thr Ser Val Gly Lys Trp Ser Lys Cys Ser Gly Trp
            115                 120                 125

Pro Thr Val Arg Glu Arg Met Lys Gln Ala Glu Pro Glu Pro Ala Ala
            130                 135                 140

Asp Gly Val Gly Ala Ala Ser Arg Asp Leu Glu Lys His Gly Ala Ile
145                 150                 155                 160

Thr Ser Ser Asn Thr Ala Thr Asn Asn Ala Ala Cys Ala Trp Leu Glu
                165                 170                 175

Ala Gln Glu Glu Glu Val Gly Phe Pro Val Arg Pro Gln Val Pro
            180                 185                 190

Leu Arg Pro Met Thr Tyr Lys Gly Ala Leu Asp Leu Ser His Phe Leu
            195                 200                 205

Lys Glu Lys Gly Gly Leu Glu Gly Leu Ile Tyr Ser Pro Lys Arg Gln
            210                 215                 220

Glu Ile Leu Asp Leu Trp Val Tyr His Thr Gln Gly Tyr Phe Pro Asp
225                 230                 235                 240

Trp Gln Asn Tyr Thr Pro Gly Pro Gly Val Arg Tyr Pro Leu Thr Phe
                245                 250                 255

Gly Trp Cys Phe Lys Leu Val Pro Val Glu Pro Asp Glu Glu Glu Asn
            260                 265                 270

Ser Ser Leu Leu His Pro Ala Ser Leu His Gly Thr Glu Asp Thr Glu
            275                 280                 285

Arg Glu Val Leu Lys Trp Lys Phe Asp Ser His Leu Ala Phe His His
            290                 295                 300

Lys Ala Arg Glu Leu His Pro Glu Tyr Tyr Lys Asp Cys Lys Leu Glu
305                 310                 315                 320

Pro Val Asp Pro Arg Leu Glu Pro Trp Lys His Pro Gly Ser Gln Pro
            325                 330                 335

Arg Thr Pro Cys Thr Asn Cys Tyr Cys Lys Lys Cys Cys Leu His Cys
            340                 345                 350

Gln Val Cys Phe Thr Arg Lys Gly Leu Gly Ile Ser Tyr Gly Arg Lys
            355                 360                 365

Lys Arg Arg Gln Arg Arg Arg Ala Pro Gln Asp Ser Gln Thr His Gln
            370                 375                 380

Val Ser Leu Pro Lys Gln Pro Ser Ser Gln Arg Gly Asp Pro Thr
385                 390                 395                 400

Gly Pro Lys Lys Ser Lys Lys Lys Val Glu Arg Glu Thr Glu Ala Asp
                405                 410                 415

Pro Phe Asp Ala Ala Val Ile Thr Leu Trp Gln Arg Pro Leu Val Ala
            420                 425                 430

Leu Ile Glu Ile Cys Thr Glu Met Glu Lys Glu Gly Lys Ile Ser Lys
            435                 440                 445

Ile Gly Pro Ala Gly Leu Lys Lys Lys Ser Val Thr Val Leu Asp
            450                 455                 460

Val Gly Asp Ala Tyr Phe Ser Val Pro Leu Asp Lys Asp Phe Arg Lys
465                 470                 475                 480

Tyr Thr Ala Phe Thr Ile Pro Ser Ile Trp Lys Gly Ser Pro Ala Ile
                485                 490                 495
```

-continued

```
Phe Gln Ser Ser Met Thr Lys Lys Gln Asn Pro Asp Ile Val Ile Tyr
                500                 505                 510
Gln Tyr Met Asp Asp Leu Tyr Val Pro Ile Val Leu Pro Glu Lys Asp
            515                 520                 525
Ser Trp Leu Val Gly Lys Leu Asn Trp Ala Ser Gln Ile Tyr Ala Gly
        530                 535                 540
Ile Lys Val Lys Gln Leu Ile Leu Lys Glu Pro Val His Gly Val Tyr
545                 550                 555                 560
Glu Pro Ile Val Gly Ala Glu Thr Phe Tyr Val Asp Gly Ala Ala Asn
                565                 570                 575
Arg Ala Gly Asn Leu Trp Val Thr Val Tyr Tyr Gly Val Pro Val Trp
            580                 585                 590
Lys Glu Ala Thr Thr Thr Leu Val Glu Arg Tyr Leu Arg Asp Gln Gln
        595                 600                 605
Leu Leu Gly Ile Trp Gly Cys Ala Cys Thr Pro Tyr Asp Ile Asn Gln
    610                 615                 620
Met Leu Arg Gly Pro Gly Arg Ala Phe Val Thr Ile Arg Gln Gly Ser
625                 630                 635                 640
Leu Ala Ala Val Leu Asp Lys Trp Glu Lys Ile Arg Leu Arg Pro Gly
                645                 650                 655
Gly Lys Lys Lys Tyr Gln Leu Lys His Ile Val Trp Ala Ser Arg Glu
            660                 665                 670
Leu Glu Arg Phe Ala Val Asn Pro Gly Leu Leu Glu Thr Ser Glu Gly
        675                 680                 685
Cys Arg Gln Ile Met Gly Gln Leu Gln Pro Ser Leu Gln Thr Gly Ser
    690                 695                 700
Glu Glu Leu Arg Ser Leu Tyr Asn Thr Val Ala Thr Leu Tyr Cys Val
705                 710                 715                 720
His Gln Lys Ile Glu Val Lys Asp Thr Lys Glu Ala Leu Asp Lys Val
                725                 730                 735
Glu Glu Glu Gln Asn Asn Ser Lys Lys Lys Ala Gln Gln Glu Ala Ala
            740                 745                 750
Asp Ala Gly Asn Arg Asn Gln Val Ser Gln Asn Tyr Pro Ile Val Gln
        755                 760                 765
Asn Leu Gln Gly Gln Met Val His Gln Ala Ile Ser Pro Arg Thr Leu
    770                 775                 780
Asn Ala Trp Val Lys Val Val Glu Glu Lys Ala Phe Ser Pro Glu Val
785                 790                 795                 800
Ile Pro Met Phe Ser Ala Leu Ser Glu Gly Ala Thr Pro Gln Asp Leu
                805                 810                 815
Asn Thr Met Leu Asn Thr Val Gly Gly His Gln Ala Ala Met Gln Met
            820                 825                 830
Leu Lys Glu Thr Ile Asn Glu Glu Ala Ala Glu Trp Asp Arg Leu His
        835                 840                 845
Pro Val His Ala Gly Pro Ile Ala Pro Gly Gln Met Arg Glu Pro Arg
    850                 855                 860
Gly Ser Asp Ile Ala Gly Thr Thr Ser Thr Leu Gln Glu Gln Ile Gly
865                 870                 875                 880
Trp Met Thr Asn Asn Pro Pro Ile Pro Val Gly Glu Ile Tyr Lys Arg
                885                 890                 895
Trp Ile Ile Leu Gly Leu Asn Lys Ile Val Arg Met Tyr Ser Pro Thr
            900                 905                 910
Ser Ile Leu Asp Ile Lys Gln Gly Pro Lys Glu Pro Phe Arg Asp Tyr
        915                 920                 925
```

```
Val Asp Arg Phe Tyr Lys Thr Leu Arg Ala Glu Gln Ala Thr Gln Glu
        930                 935                 940

Val Lys Asn Trp Met Thr Glu Thr Leu Leu Val Gln Asn Ala Asn Pro
945                 950                 955                 960

Asp Cys Lys Thr Ile Leu Lys Ala Leu Gly Pro Ala Ala Thr Leu Glu
                965                 970                 975

Glu Met Met Thr Ala Cys Gln Gly Val Gly Gly Pro Gly His Lys Ala
                980                 985                 990

Arg Val Leu Ala Glu Ala Met Ser  Gln Val Thr Gly Ser  Ala Ala Ile
        995                 1000                1005

Met Met  Gln Arg Gly Asn Phe  Arg Asn Gln Arg Lys  Thr Val Lys
    1010                1015                1020

Cys Phe  Asn Cys Gly Lys Glu  Gly His Ile Ala Arg  Asn Cys Arg
    1025                1030                1035

Ala Pro  Arg Lys Lys Gly Cys  Trp Lys Cys Gly Lys  Glu Gly His
    1040                1045                1050

Gln Met  Lys Asp Cys Thr Glu  Arg Gln Ala Asn
    1055                1060

<210> SEQ ID NO 43
<211> LENGTH: 1064
<212> TYPE: PRT
<213> ORGANISM: Artificial Sequence
<220> FEATURE:
<223> OTHER INFORMATION: Hybrid protein comprised of Tat-Rev-Nef,
      truncated Gag protein and CTL (TRN-dgag-CTL)

<400> SEQUENCE: 43

Met Glu Pro Val Asp Pro Arg Leu Glu Pro Trp Lys His Pro Gly Ser
1               5                   10                  15

Gln Pro Arg Thr Pro Cys Thr Asn Cys Tyr Cys Lys Lys Cys Cys Leu
            20                  25                  30

His Cys Gln Val Cys Phe Thr Arg Lys Gly Leu Gly Ile Ser Tyr Gly
        35                  40                  45

Arg Lys Lys Arg Arg Gln Arg Arg Ala Pro Gln Asp Ser Gln Thr
    50                  55                  60

His Gln Val Ser Leu Pro Lys Gln Pro Ser Ser Gln Arg Gly Asp
65                  70                  75                  80

Pro Thr Gly Pro Lys Lys Ser Lys Lys Val Glu Arg Glu Thr Glu
                85                  90                  95

Ala Asp Pro Phe Asp Thr Ser Ala Gly Arg Ser Gly Asp Ser Asp Glu
                100                 105                 110

Glu Leu Leu Lys Thr Val Arg Leu Ile Lys Phe Leu Tyr Gln Ser Asn
            115                 120                 125

Pro Pro Pro Ser Asn Glu Gly Thr Arg Gln Ala Arg Arg Asn Arg Arg
        130                 135                 140

Arg Arg Trp Arg Glu Arg Gln Arg Gln Ile Arg Ser Ile Ser Glu Arg
145                 150                 155                 160

Ile Leu Ser Thr Phe Leu Gly Arg Pro Ala Glu Pro Val Pro Leu Gln
                165                 170                 175

Leu Pro Pro Leu Glu Arg Leu Thr Leu Asp Cys Ser Glu Asp Cys Gly
            180                 185                 190

Asn Ser Gly Thr Gln Gly Val Gly Ser Pro Gln Val Leu Val Glu Ser
        195                 200                 205

Pro Ala Val Leu Glu Pro Gly Thr Lys Glu Lys Leu Val Gly Lys Trp
    210                 215                 220
```

```
Ser Lys Cys Ser Gly Trp Pro Thr Val Arg Glu Arg Met Lys Gln Ala
225                 230                 235                 240

Glu Pro Glu Pro Ala Ala Asp Gly Val Gly Ala Ala Ser Arg Asp Leu
            245                 250                 255

Glu Lys His Gly Ala Ile Thr Ser Ser Asn Thr Ala Thr Asn Asn Ala
        260                 265                 270

Ala Cys Ala Trp Leu Glu Ala Gln Glu Glu Glu Val Gly Phe Pro
    275                 280                 285

Val Arg Pro Gln Val Pro Leu Arg Pro Met Thr Tyr Lys Gly Ala Leu
290                 295                 300

Asp Leu Ser His Phe Leu Lys Glu Lys Gly Gly Leu Glu Gly Leu Ile
305                 310                 315                 320

Tyr Ser Pro Lys Arg Gln Glu Ile Leu Asp Leu Trp Val Tyr His Thr
                325                 330                 335

Gln Gly Tyr Phe Pro Asp Trp Gln Asn Tyr Thr Pro Gly Pro Gly Val
            340                 345                 350

Arg Tyr Pro Leu Thr Phe Gly Trp Cys Phe Lys Leu Val Pro Val Glu
        355                 360                 365

Pro Asp Glu Glu Glu Asn Ser Ser Leu Leu His Pro Ala Ser Leu His
    370                 375                 380

Gly Thr Glu Asp Thr Glu Arg Glu Val Leu Lys Trp Lys Phe Asp Ser
385                 390                 395                 400

His Leu Ala Phe His His Lys Ala Arg Glu Leu His Pro Glu Tyr Tyr
                405                 410                 415

Lys Asp Cys Ala Ala Val Leu Asp Lys Trp Glu Lys Ile Arg Leu Arg
            420                 425                 430

Pro Gly Gly Lys Lys Tyr Gln Leu Lys His Ile Val Trp Ala Ser
        435                 440                 445

Arg Glu Leu Glu Arg Phe Ala Val Asn Pro Gly Leu Leu Glu Thr Ser
    450                 455                 460

Glu Gly Cys Arg Gln Ile Met Gly Gln Leu Gln Pro Ser Leu Gln Thr
465                 470                 475                 480

Gly Ser Glu Glu Leu Arg Ser Leu Tyr Asn Thr Val Ala Thr Leu Tyr
                485                 490                 495

Cys Val His Gln Lys Ile Glu Val Lys Asp Thr Lys Glu Ala Leu Asp
            500                 505                 510

Lys Val Glu Glu Glu Gln Asn Asn Ser Lys Lys Ala Gln Gln Glu
        515                 520                 525

Ala Ala Asp Ala Gly Asn Arg Asn Gln Val Ser Gln Asn Tyr Pro Ile
    530                 535                 540

Val Gln Asn Leu Gln Gly Gln Met Val His Gln Ala Ile Ser Pro Arg
545                 550                 555                 560

Thr Leu Asn Ala Trp Val Lys Val Val Glu Glu Lys Ala Phe Ser Pro
                565                 570                 575

Glu Val Ile Pro Met Phe Ser Ala Leu Ser Glu Gly Ala Thr Pro Gln
            580                 585                 590

Asp Leu Asn Thr Met Leu Asn Thr Val Gly Gly His Gln Ala Ala Met
        595                 600                 605

Gln Met Leu Lys Glu Thr Ile Asn Glu Glu Ala Ala Glu Trp Asp Arg
    610                 615                 620

Leu His Pro Val His Ala Gly Pro Ile Ala Pro Gly Gln Met Arg Glu
625                 630                 635                 640

Pro Arg Gly Ser Asp Ile Ala Gly Thr Thr Ser Thr Leu Gln Glu Gln
```

645                 650                 655
Ile Gly Trp Met Thr Asn Asn Pro Pro Ile Pro Val Gly Glu Ile Tyr
                660                 665                 670

Lys Arg Trp Ile Ile Leu Gly Leu Asn Lys Ile Val Arg Met Tyr Ser
                675                 680                 685

Pro Thr Ser Ile Leu Asp Ile Lys Gln Gly Pro Lys Glu Pro Phe Arg
                690                 695                 700

Asp Tyr Val Asp Arg Phe Tyr Lys Thr Leu Arg Ala Glu Gln Ala Thr
705                 710                 715                 720

Gln Glu Val Lys Asn Trp Met Thr Glu Thr Leu Leu Val Gln Asn Ala
                725                 730                 735

Asn Pro Asp Cys Lys Thr Ile Leu Lys Ala Leu Gly Pro Ala Ala Thr
                740                 745                 750

Leu Glu Glu Met Met Thr Ala Cys Gln Gly Val Gly Gly Pro Gly His
                755                 760                 765

Lys Ala Arg Val Leu Ala Glu Ala Met Ser Gln Val Thr Gly Ser Ala
                770                 775                 780

Ala Ile Met Met Gln Arg Gly Asn Phe Arg Asn Gln Arg Lys Thr Val
785                 790                 795                 800

Lys Cys Phe Asn Cys Gly Lys Glu Gly His Ile Ala Arg Asn Cys Arg
                805                 810                 815

Ala Pro Arg Lys Lys Gly Cys Trp Lys Cys Gly Lys Glu Gly His Gln
                820                 825                 830

Met Lys Asp Cys Thr Glu Arg Gln Ala Asn Ala Ala Val Ile Thr Leu
                835                 840                 845

Trp Gln Arg Pro Leu Val Ala Leu Ile Glu Ile Cys Thr Glu Met Glu
                850                 855                 860

Lys Glu Gly Lys Ile Ser Lys Ile Gly Pro Ala Gly Leu Lys Lys Lys
865                 870                 875                 880

Lys Ser Val Thr Val Leu Asp Val Gly Asp Ala Tyr Phe Ser Val Pro
                885                 890                 895

Leu Asp Lys Asp Phe Arg Lys Tyr Thr Ala Phe Thr Ile Pro Ser Ile
                900                 905                 910

Trp Lys Gly Ser Pro Ala Ile Phe Gln Ser Ser Met Thr Lys Lys Gln
                915                 920                 925

Asn Pro Asp Ile Val Ile Tyr Gln Tyr Met Asp Asp Leu Tyr Val Pro
                930                 935                 940

Ile Val Leu Pro Glu Lys Asp Ser Trp Leu Val Gly Lys Leu Asn Trp
945                 950                 955                 960

Ala Ser Gln Ile Tyr Ala Gly Ile Lys Val Lys Gln Leu Ile Leu Lys
                965                 970                 975

Glu Pro Val His Gly Val Tyr Glu Pro Ile Val Gly Ala Glu Thr Phe
                980                 985                 990

Tyr Val Asp Gly Ala Ala Asn Arg Ala Gly Asn Leu Trp Val Thr Val
                995                 1000                1005

Tyr Tyr Gly Val Pro Val Trp Lys Glu Ala Thr Thr Thr Leu Val
                1010                1015                1020

Glu Arg Tyr Leu Arg Asp Gln Gln Leu Leu Gly Ile Trp Gly Cys
                1025                1030                1035

Ala Cys Thr Pro Tyr Asp Ile Asn Gln Met Leu Arg Gly Pro Gly
                1040                1045                1050

Arg Ala Phe Val Thr Ile Arg Gln Gly Ser Leu
                1055                1060

-continued

```
<210> SEQ ID NO 44
<211> LENGTH: 1064
<212> TYPE: PRT
<213> ORGANISM: Artificial Sequence
<220> FEATURE:
<223> OTHER INFORMATION: Hybrid protein comprised of Rev-Nef-Tat,
      truncated Gag protein and CTL(RNT-dgag-CTL)

<400> SEQUENCE: 44

Met Ala Gly Arg Ser Gly Asp Ser Asp Glu Glu Leu Leu Lys Thr Val
1               5                   10                  15

Arg Leu Ile Lys Phe Leu Tyr Gln Ser Asn Pro Pro Ser Asn Glu
            20                  25                  30

Gly Thr Arg Gln Ala Arg Arg Asn Arg Arg Arg Trp Arg Glu Arg
                35                  40                  45

Gln Arg Gln Ile Arg Ser Ile Ser Glu Arg Ile Leu Ser Thr Phe Leu
    50                  55                  60

Gly Arg Pro Ala Glu Pro Val Pro Leu Gln Leu Pro Pro Leu Glu Arg
65                  70                  75                  80

Leu Thr Leu Asp Cys Ser Glu Asp Cys Gly Asn Ser Gly Thr Gln Gly
                85                  90                  95

Val Gly Ser Pro Gln Val Leu Val Glu Ser Pro Ala Val Leu Glu Pro
                100                 105                 110

Gly Thr Lys Glu Thr Ser Val Gly Lys Trp Ser Lys Cys Ser Gly Trp
                115                 120                 125

Pro Thr Val Arg Glu Arg Met Lys Gln Ala Glu Pro Glu Pro Ala Ala
                130                 135                 140

Asp Gly Val Gly Ala Ala Ser Arg Asp Leu Glu Lys His Gly Ala Ile
145                 150                 155                 160

Thr Ser Ser Asn Thr Ala Thr Asn Asn Ala Ala Cys Ala Trp Leu Glu
                165                 170                 175

Ala Gln Glu Glu Glu Val Gly Phe Pro Val Arg Pro Gln Val Pro
                180                 185                 190

Leu Arg Pro Met Thr Tyr Lys Gly Ala Leu Asp Leu Ser His Phe Leu
                195                 200                 205

Lys Glu Lys Gly Gly Leu Glu Gly Leu Ile Tyr Ser Pro Lys Arg Gln
                210                 215                 220

Glu Ile Leu Asp Leu Trp Val Tyr His Thr Gln Gly Tyr Phe Pro Asp
225                 230                 235                 240

Trp Gln Asn Tyr Thr Pro Gly Pro Gly Val Arg Tyr Pro Leu Thr Phe
                245                 250                 255

Gly Trp Cys Phe Lys Leu Val Pro Val Glu Pro Asp Glu Glu Glu Asn
                260                 265                 270

Ser Ser Leu Leu His Pro Ala Ser Leu His Gly Thr Glu Asp Thr Glu
                275                 280                 285

Arg Glu Val Leu Lys Trp Lys Phe Asp Ser His Leu Ala Phe His His
                290                 295                 300

Lys Ala Arg Glu Leu His Pro Glu Tyr Tyr Lys Asp Cys Lys Leu Glu
305                 310                 315                 320

Pro Val Asp Pro Arg Leu Glu Pro Trp Lys His Pro Gly Ser Gln Pro
                325                 330                 335

Arg Thr Pro Cys Thr Asn Cys Tyr Cys Lys Lys Cys Cys Leu His Cys
                340                 345                 350

Gln Val Cys Phe Thr Arg Lys Gly Leu Gly Ile Ser Tyr Gly Arg Lys
                355                 360                 365
```

-continued

```
Lys Arg Arg Gln Arg Arg Ala Pro Gln Asp Ser Gln Thr His Gln
370                 375                 380
Val Ser Leu Pro Lys Gln Pro Ser Ser Gln Gln Arg Gly Asp Pro Thr
385                 390                 395                 400
Gly Pro Lys Lys Ser Lys Lys Val Glu Arg Glu Thr Glu Ala Asp
                405                 410                 415
Pro Phe Asp Ala Ala Val Leu Asp Lys Trp Glu Lys Ile Arg Leu Arg
            420                 425                 430
Pro Gly Gly Lys Lys Tyr Gln Leu Lys His Ile Val Trp Ala Ser
            435                 440                 445
Arg Glu Leu Glu Arg Phe Ala Val Asn Pro Gly Leu Leu Glu Thr Ser
450                 455                 460
Glu Gly Cys Arg Gln Ile Met Gly Gln Leu Gln Pro Ser Leu Gln Thr
465                 470                 475                 480
Gly Ser Glu Glu Leu Arg Ser Leu Tyr Asn Thr Val Ala Thr Leu Tyr
                485                 490                 495
Cys Val His Gln Lys Ile Glu Val Lys Asp Thr Lys Glu Ala Leu Asp
            500                 505                 510
Lys Val Glu Glu Glu Gln Asn Asn Ser Lys Lys Ala Gln Gln Glu
            515                 520                 525
Ala Ala Asp Ala Gly Asn Arg Asn Gln Val Ser Gln Asn Tyr Pro Ile
530                 535                 540
Val Gln Asn Leu Gln Gly Gln Met Val His Gln Ala Ile Ser Pro Arg
545                 550                 555                 560
Thr Leu Asn Ala Trp Val Lys Val Val Glu Glu Lys Ala Phe Ser Pro
                565                 570                 575
Glu Val Ile Pro Met Phe Ser Ala Leu Ser Glu Gly Ala Thr Pro Gln
            580                 585                 590
Asp Leu Asn Thr Met Leu Asn Thr Val Gly Gly His Gln Ala Ala Met
            595                 600                 605
Gln Met Leu Lys Glu Thr Ile Asn Glu Glu Ala Ala Glu Trp Asp Arg
610                 615                 620
Leu His Pro Val His Ala Gly Pro Ile Ala Pro Gly Gln Met Arg Glu
625                 630                 635                 640
Pro Arg Gly Ser Asp Ile Ala Gly Thr Thr Ser Thr Leu Gln Glu Gln
                645                 650                 655
Ile Gly Trp Met Thr Asn Asn Pro Pro Ile Pro Val Gly Glu Ile Tyr
            660                 665                 670
Lys Arg Trp Ile Ile Leu Gly Leu Asn Lys Ile Val Arg Met Tyr Ser
            675                 680                 685
Pro Thr Ser Ile Leu Asp Ile Lys Gln Gly Pro Lys Glu Pro Phe Arg
690                 695                 700
Asp Tyr Val Asp Arg Phe Tyr Lys Thr Leu Arg Ala Glu Gln Ala Thr
705                 710                 715                 720
Gln Glu Val Lys Asn Trp Met Thr Glu Thr Leu Leu Val Gln Asn Ala
                725                 730                 735
Asn Pro Asp Cys Lys Thr Ile Leu Lys Ala Leu Gly Pro Ala Ala Thr
            740                 745                 750
Leu Glu Glu Met Met Thr Ala Cys Gln Gly Val Gly Gly Pro Gly His
            755                 760                 765
Lys Ala Arg Val Leu Ala Glu Ala Met Ser Gln Val Thr Gly Ser Ala
770                 775                 780
Ala Ile Met Met Gln Arg Gly Asn Phe Arg Asn Gln Arg Lys Thr Val
785                 790                 795                 800
```

Lys Cys Phe Asn Cys Gly Lys Glu Gly His Ile Ala Arg Asn Cys Arg
                805                 810                 815

Ala Pro Arg Lys Gly Cys Trp Lys Cys Gly Lys Glu Gly His Gln
            820                 825                 830

Met Lys Asp Cys Thr Glu Arg Gln Ala Asn Ala Ala Val Ile Thr Leu
                835                 840                 845

Trp Gln Arg Pro Leu Val Ala Leu Ile Glu Ile Cys Thr Glu Met Glu
            850                 855                 860

Lys Glu Gly Lys Ile Ser Lys Ile Gly Pro Ala Gly Leu Lys Lys Lys
865                 870                 875                 880

Lys Ser Val Thr Val Leu Asp Val Gly Asp Ala Tyr Phe Ser Val Pro
                885                 890                 895

Leu Asp Lys Asp Phe Arg Lys Tyr Thr Ala Phe Thr Ile Pro Ser Ile
            900                 905                 910

Trp Lys Gly Ser Pro Ala Ile Phe Gln Ser Ser Met Thr Lys Lys Gln
            915                 920                 925

Asn Pro Asp Ile Val Ile Tyr Gln Tyr Met Asp Asp Leu Tyr Val Pro
930                 935                 940

Ile Val Leu Pro Glu Lys Asp Ser Trp Leu Val Gly Lys Leu Asn Trp
945                 950                 955                 960

Ala Ser Gln Ile Tyr Ala Gly Ile Lys Val Lys Gln Leu Ile Leu Lys
                965                 970                 975

Glu Pro Val His Gly Val Tyr Glu Pro Ile Val Gly Ala Glu Thr Phe
            980                 985                 990

Tyr Val Asp Gly Ala Ala Asn Arg Ala Gly Asn Leu Trp Val Thr Val
            995                 1000                1005

Tyr Tyr Gly Val Pro Val Trp Lys Glu Ala Thr Thr Thr Leu Val
    1010                1015                1020

Glu Arg Tyr Leu Arg Asp Gln Gln Leu Leu Gly Ile Trp Gly Cys
    1025                1030                1035

Ala Cys Thr Pro Tyr Asp Ile Asn Gln Met Leu Arg Gly Pro Gly
    1040                1045                1050

Arg Ala Phe Val Thr Ile Arg Gln Gly Ser Leu
    1055                1060

<210> SEQ ID NO 45
<211> LENGTH: 1006
<212> TYPE: PRT
<213> ORGANISM: Artificial Sequence
<220> FEATURE:
<223> OTHER INFORMATION: Hybrid protein cds comprised of Tat-Rev-Nef,
      truncated Gag protein and CTL(TRN-optp17/24-CTL )

<400> SEQUENCE: 45

Met Glu Pro Val Asp Pro Arg Leu Glu Pro Trp Lys His Pro Gly Ser
1               5                   10                  15

Gln Pro Arg Thr Pro Cys Thr Asn Cys Tyr Cys Lys Lys Cys Cys Leu
                20                  25                  30

His Cys Gln Val Cys Phe Thr Arg Lys Gly Leu Gly Ile Ser Tyr Gly
            35                  40                  45

Arg Lys Lys Arg Arg Gln Arg Arg Ala Pro Gln Asp Ser Gln Thr
50                  55                  60

His Gln Val Ser Leu Pro Lys Gln Pro Ser Ser Gln Arg Gly Asp
65                  70                  75                  80

Pro Thr Gly Pro Lys Lys Ser Lys Lys Val Glu Arg Glu Thr Glu
                85                  90                  95

```
Ala Asp Pro Phe Asp Thr Ser Ala Gly Arg Ser Gly Asp Ser Asp Glu
            100                 105                 110
Glu Leu Leu Lys Thr Val Arg Leu Ile Lys Phe Leu Tyr Gln Ser Asn
            115                 120                 125
Pro Pro Pro Ser Asn Glu Gly Thr Arg Gln Ala Arg Arg Asn Arg Arg
            130                 135                 140
Arg Arg Trp Arg Glu Arg Gln Arg Gln Ile Arg Ser Ile Ser Glu Arg
145                 150                 155                 160
Ile Leu Ser Thr Phe Leu Gly Arg Pro Ala Glu Pro Val Pro Leu Gln
                165                 170                 175
Leu Pro Pro Leu Glu Arg Leu Thr Leu Asp Cys Ser Glu Asp Cys Gly
            180                 185                 190
Asn Ser Gly Thr Gln Gly Val Gly Ser Pro Gln Val Leu Val Glu Ser
            195                 200                 205
Pro Ala Val Leu Glu Pro Gly Thr Lys Glu Lys Leu Val Gly Lys Trp
            210                 215                 220
Ser Lys Cys Ser Gly Trp Pro Thr Val Arg Glu Arg Met Lys Gln Ala
225                 230                 235                 240
Glu Pro Glu Pro Ala Ala Asp Gly Val Gly Ala Ala Ser Arg Asp Leu
                245                 250                 255
Glu Lys His Gly Ala Ile Thr Ser Ser Asn Thr Ala Thr Asn Asn Ala
            260                 265                 270
Ala Cys Ala Trp Leu Glu Ala Gln Glu Glu Glu Val Gly Phe Pro
            275                 280                 285
Val Arg Pro Gln Val Pro Leu Arg Pro Met Thr Tyr Lys Gly Ala Leu
            290                 295                 300
Asp Leu Ser His Phe Leu Lys Glu Lys Gly Gly Leu Glu Gly Leu Ile
305                 310                 315                 320
Tyr Ser Pro Lys Arg Gln Glu Ile Leu Asp Leu Trp Val Tyr His Thr
                325                 330                 335
Gln Gly Tyr Phe Pro Asp Trp Gln Asn Tyr Thr Pro Gly Pro Gly Val
            340                 345                 350
Arg Tyr Pro Leu Thr Phe Gly Trp Cys Phe Lys Leu Val Pro Val Glu
            355                 360                 365
Pro Asp Glu Glu Glu Asn Ser Ser Leu Leu His Pro Ala Ser Leu His
            370                 375                 380
Gly Thr Glu Asp Thr Glu Arg Glu Val Leu Lys Trp Lys Phe Asp Ser
385                 390                 395                 400
His Leu Ala Phe His His Lys Ala Arg Glu Leu His Pro Glu Tyr Tyr
                405                 410                 415
Lys Asp Cys Ala Ala Val Gly Ala Arg Ala Ser Val Leu Ser Gly Gly
            420                 425                 430
Glu Leu Asp Lys Trp Glu Lys Ile Arg Leu Arg Pro Gly Gly Lys Lys
            435                 440                 445
Lys Tyr Gln Leu Lys His Ile Val Trp Ala Ser Arg Glu Leu Glu Arg
            450                 455                 460
Phe Ala Val Asn Pro Gly Leu Leu Glu Thr Ser Glu Gly Cys Arg Gln
465                 470                 475                 480
Ile Met Gly Gln Leu Gln Pro Ser Leu Gln Thr Gly Ser Glu Glu Leu
                485                 490                 495
Arg Ser Leu Tyr Asn Thr Val Ala Thr Leu Tyr Cys Val His Gln Lys
            500                 505                 510
Ile Glu Val Lys Asp Thr Lys Glu Ala Leu Asp Lys Val Glu Glu Glu
```

```
                515                 520                 525
Gln Asn Asn Ser Lys Lys Ala Gln Gln Glu Ala Ala Asp Ala Gly
        530                 535                 540
Asn Arg Asn Gln Val Ser Gln Asn Tyr Pro Ile Val Gln Asn Leu Gln
545                 550                 555                 560
Gly Gln Met Val His Gln Ala Ile Ser Pro Arg Thr Leu Asn Ala Trp
                565                 570                 575
Val Lys Val Val Glu Glu Lys Ala Phe Ser Pro Glu Val Ile Pro Met
        580                 585                 590
Phe Ser Ala Leu Ser Glu Gly Ala Thr Pro Gln Asp Leu Asn Thr Met
        595                 600                 605
Leu Asn Thr Val Gly Gly His Gln Ala Ala Met Gln Met Leu Lys Glu
    610                 615                 620
Thr Ile Asn Glu Glu Ala Ala Glu Trp Asp Arg Leu His Pro Val His
625                 630                 635                 640
Ala Gly Pro Ile Ala Pro Gly Gln Met Arg Glu Pro Arg Gly Ser Asp
                645                 650                 655
Ile Ala Gly Thr Thr Ser Thr Leu Gln Glu Gln Ile Gly Trp Met Thr
            660                 665                 670
Asn Asn Pro Pro Ile Pro Val Gly Glu Ile Tyr Lys Arg Trp Ile Ile
        675                 680                 685
Leu Gly Leu Asn Lys Ile Val Arg Met Tyr Ser Pro Thr Ser Ile Leu
    690                 695                 700
Asp Ile Lys Gln Gly Pro Lys Glu Pro Phe Arg Asp Tyr Val Asp Arg
705                 710                 715                 720
Phe Tyr Lys Thr Leu Arg Ala Glu Gln Ala Thr Gln Glu Val Lys Asn
                725                 730                 735
Trp Met Thr Glu Thr Leu Leu Val Gln Asn Ala Asn Pro Asp Cys Lys
            740                 745                 750
Thr Ile Leu Lys Ala Leu Gly Pro Ala Ala Thr Leu Glu Glu Met Met
        755                 760                 765
Thr Ala Cys Gln Gly Val Gly Gly Pro Gly His Lys Ala Arg Val Leu
770                 775                 780
Ala Ala Val Ile Thr Leu Trp Gln Arg Pro Leu Val Ala Leu Ile Glu
785                 790                 795                 800
Ile Cys Thr Glu Met Glu Lys Glu Gly Lys Ile Ser Lys Ile Gly Pro
                805                 810                 815
Ala Gly Leu Lys Lys Lys Lys Ser Val Thr Val Leu Asp Val Gly Asp
            820                 825                 830
Ala Tyr Phe Ser Val Pro Leu Asp Lys Asp Phe Arg Lys Tyr Thr Ala
        835                 840                 845
Phe Thr Ile Pro Ser Ile Trp Lys Gly Ser Pro Ala Ile Phe Gln Ser
    850                 855                 860
Ser Met Thr Lys Lys Gln Asn Pro Asp Ile Val Ile Tyr Gln Tyr Met
865                 870                 875                 880
Asp Asp Leu Tyr Val Pro Ile Val Leu Pro Glu Lys Asp Ser Trp Leu
                885                 890                 895
Val Gly Lys Leu Asn Trp Ala Ser Gln Ile Tyr Ala Gly Ile Lys Val
            900                 905                 910
Lys Gln Leu Ile Leu Lys Glu Pro Val His Gly Val Tyr Glu Pro Ile
        915                 920                 925
Val Gly Ala Glu Thr Phe Tyr Val Asp Gly Ala Ala Asn Arg Ala Gly
    930                 935                 940
```

```
Asn Leu Trp Val Thr Val Tyr Tyr Gly Val Pro Val Trp Lys Glu Ala
945                 950                 955                 960

Thr Thr Thr Leu Val Glu Arg Tyr Leu Arg Asp Gln Gln Leu Leu Gly
                965                 970                 975

Ile Trp Gly Cys Ala Cys Thr Pro Tyr Asp Ile Asn Gln Met Leu Arg
            980                 985                 990

Gly Pro Gly Arg Ala Phe Val Thr Ile Arg Gln Gly Ser Leu
        995                 1000                1005

<210> SEQ ID NO 46
<211> LENGTH: 1006
<212> TYPE: PRT
<213> ORGANISM: Artificial Sequence
<220> FEATURE:
<223> OTHER INFORMATION: Hybrid protein cdscomprised of Tat-Rev-Nef,
      CTL and truncated Gag protein (TRN-CTL-optp17/24)

<400> SEQUENCE: 46

Met Glu Pro Val Asp Pro Arg Leu Glu Pro Trp Lys His Pro Gly Ser
1               5                   10                  15

Gln Pro Arg Thr Pro Cys Thr Asn Cys Tyr Cys Lys Lys Cys Cys Leu
            20                  25                  30

His Cys Gln Val Cys Phe Thr Arg Lys Gly Leu Gly Ile Ser Tyr Gly
        35                  40                  45

Arg Lys Lys Arg Arg Gln Arg Arg Ala Pro Gln Asp Ser Gln Thr
50                  55                  60

His Gln Val Ser Leu Pro Lys Gln Pro Ser Ser Gln Gln Arg Gly Asp
65                  70                  75                  80

Pro Thr Gly Pro Lys Lys Ser Lys Lys Val Glu Arg Glu Thr Glu
                85                  90                  95

Ala Asp Pro Phe Asp Thr Ser Ala Gly Arg Ser Gly Asp Ser Asp Glu
            100                 105                 110

Glu Leu Leu Lys Thr Val Arg Leu Ile Lys Phe Leu Tyr Gln Ser Asn
        115                 120                 125

Pro Pro Pro Ser Asn Glu Gly Thr Arg Gln Ala Arg Arg Asn Arg Arg
    130                 135                 140

Arg Arg Trp Arg Glu Arg Gln Arg Gln Ile Arg Ser Ile Ser Glu Arg
145                 150                 155                 160

Ile Leu Ser Thr Phe Leu Gly Arg Pro Ala Glu Pro Val Pro Leu Gln
                165                 170                 175

Leu Pro Pro Leu Glu Arg Leu Thr Leu Asp Cys Ser Glu Asp Cys Gly
            180                 185                 190

Asn Ser Gly Thr Gln Gly Val Gly Ser Pro Gln Val Leu Val Glu Ser
        195                 200                 205

Pro Ala Val Leu Glu Pro Gly Thr Lys Glu Lys Leu Val Gly Lys Trp
    210                 215                 220

Ser Lys Cys Ser Gly Trp Pro Thr Val Arg Glu Arg Met Lys Gln Ala
225                 230                 235                 240

Glu Pro Glu Pro Ala Ala Asp Gly Val Gly Ala Ala Ser Arg Asp Leu
                245                 250                 255

Glu Lys His Gly Ala Ile Thr Ser Ser Asn Thr Ala Thr Asn Asn Ala
            260                 265                 270

Ala Cys Ala Trp Leu Glu Ala Gln Glu Glu Glu Val Gly Phe Pro
        275                 280                 285

Val Arg Pro Gln Val Pro Leu Arg Pro Met Thr Tyr Lys Gly Ala Leu
    290                 295                 300
```

```
Asp Leu Ser His Phe Leu Lys Glu Lys Gly Gly Leu Glu Gly Leu Ile
305                 310                 315                 320

Tyr Ser Pro Lys Arg Gln Glu Ile Leu Asp Leu Trp Val Tyr His Thr
            325                 330                 335

Gln Gly Tyr Phe Pro Asp Trp Gln Asn Tyr Thr Pro Gly Pro Gly Val
            340                 345                 350

Arg Tyr Pro Leu Thr Phe Gly Trp Cys Phe Lys Leu Val Pro Val Glu
            355                 360                 365

Pro Asp Glu Glu Asn Ser Ser Leu Leu His Pro Ala Ser Leu His
370                 375                 380

Gly Thr Glu Asp Thr Glu Arg Glu Val Leu Lys Trp Lys Phe Asp Ser
385                 390                 395                 400

His Leu Ala Phe His His Lys Ala Arg Glu Leu His Pro Glu Tyr Tyr
                405                 410                 415

Lys Asp Cys Ala Ala Val Ile Thr Leu Trp Gln Arg Pro Leu Val Ala
                420                 425                 430

Leu Ile Glu Ile Cys Thr Glu Met Glu Lys Glu Gly Lys Ile Ser Lys
            435                 440                 445

Ile Gly Pro Ala Gly Leu Lys Lys Lys Ser Val Thr Val Leu Asp
450                 455                 460

Val Gly Asp Ala Tyr Phe Ser Val Pro Leu Asp Lys Asp Phe Arg Lys
465                 470                 475                 480

Tyr Thr Ala Phe Thr Ile Pro Ser Ile Trp Lys Gly Ser Pro Ala Ile
                485                 490                 495

Phe Gln Ser Ser Met Thr Lys Lys Gln Asn Pro Asp Ile Val Ile Tyr
                500                 505                 510

Gln Tyr Met Asp Asp Leu Tyr Val Pro Ile Val Leu Pro Glu Lys Asp
            515                 520                 525

Ser Trp Leu Val Gly Lys Leu Asn Trp Ala Ser Gln Ile Tyr Ala Gly
530                 535                 540

Ile Lys Val Lys Gln Leu Ile Leu Lys Glu Pro Val His Gly Val Tyr
545                 550                 555                 560

Glu Pro Ile Val Gly Ala Glu Thr Phe Tyr Val Asp Gly Ala Ala Asn
                565                 570                 575

Arg Ala Gly Asn Leu Trp Val Thr Val Tyr Tyr Gly Val Pro Val Trp
                580                 585                 590

Lys Glu Ala Thr Thr Thr Leu Val Glu Arg Tyr Leu Arg Asp Gln Gln
                595                 600                 605

Leu Leu Gly Ile Trp Gly Cys Ala Cys Thr Pro Tyr Asp Ile Asn Gln
            610                 615                 620

Met Leu Arg Gly Pro Gly Arg Ala Phe Val Thr Ile Arg Gln Gly Ser
625                 630                 635                 640

Leu Ala Ala Val Gly Ala Arg Ala Ser Val Leu Ser Gly Gly Glu Leu
                645                 650                 655

Asp Lys Trp Glu Lys Ile Arg Leu Arg Pro Gly Gly Lys Lys Lys Tyr
            660                 665                 670

Gln Leu Lys His Ile Val Trp Ala Ser Arg Glu Leu Glu Arg Phe Ala
            675                 680                 685

Val Asn Pro Gly Leu Leu Glu Thr Ser Glu Gly Cys Arg Gln Ile Met
            690                 695                 700

Gly Gln Leu Gln Pro Ser Leu Gln Thr Gly Ser Glu Glu Leu Arg Ser
705                 710                 715                 720

Leu Tyr Asn Thr Val Ala Thr Leu Tyr Cys Val His Gln Lys Ile Glu
                725                 730                 735
```

```
Val Lys Asp Thr Lys Glu Ala Leu Asp Lys Val Glu Glu Gln Asn
            740                 745                 750

Asn Ser Lys Lys Ala Gln Gln Glu Ala Ala Asp Ala Gly Asn Arg
            755                 760                 765

Asn Gln Val Ser Gln Asn Tyr Pro Ile Val Gln Asn Leu Gln Gly Gln
            770                 775                 780

Met Val His Gln Ala Ile Ser Pro Arg Thr Leu Asn Ala Trp Val Lys
785                 790                 795                 800

Val Val Glu Glu Lys Ala Phe Ser Pro Glu Val Ile Pro Met Phe Ser
            805                 810                 815

Ala Leu Ser Glu Gly Ala Thr Pro Gln Asp Leu Asn Thr Met Leu Asn
            820                 825                 830

Thr Val Gly Gly His Gln Ala Ala Met Gln Met Leu Lys Glu Thr Ile
            835                 840                 845

Asn Glu Glu Ala Ala Glu Trp Asp Arg Leu His Pro Val His Ala Gly
850                 855                 860

Pro Ile Ala Pro Gly Gln Met Arg Glu Pro Arg Gly Ser Asp Ile Ala
865                 870                 875                 880

Gly Thr Thr Ser Thr Leu Gln Glu Gln Ile Gly Trp Met Thr Asn Asn
                885                 890                 895

Pro Pro Ile Pro Val Gly Glu Ile Tyr Lys Arg Trp Ile Ile Leu Gly
            900                 905                 910

Leu Asn Lys Ile Val Arg Met Tyr Ser Pro Thr Ser Ile Leu Asp Ile
            915                 920                 925

Lys Gln Gly Pro Lys Glu Pro Phe Arg Asp Tyr Val Asp Arg Phe Tyr
930                 935                 940

Lys Thr Leu Arg Ala Glu Gln Ala Thr Gln Glu Val Lys Asn Trp Met
945                 950                 955                 960

Thr Glu Thr Leu Leu Val Gln Asn Ala Asn Pro Asp Cys Lys Thr Ile
                965                 970                 975

Leu Lys Ala Leu Gly Pro Ala Ala Thr Leu Glu Glu Met Met Thr Ala
            980                 985                 990

Cys Gln Gly Val Gly Gly Pro Gly  His Lys Ala Arg Val  Leu
            995                 1000                1005

<210> SEQ ID NO 47
<211> LENGTH: 1006
<212> TYPE: PRT
<213> ORGANISM: Artificial Sequence
<220> FEATURE:
<223> OTHER INFORMATION: Hybrid protein comprised of Rev-Nef-Tat,
      CTL and truncated Gag protein (RNT-CTL-optp17/24)

<400> SEQUENCE: 47

Met Ala Gly Arg Ser Gly Asp Ser Asp Glu Glu Leu Leu Lys Thr Val
1               5                   10                  15

Arg Leu Ile Lys Phe Leu Tyr Gln Ser Asn Pro Pro Ser Asn Glu
            20                  25                  30

Gly Thr Arg Gln Ala Arg Arg Asn Arg Arg Arg Trp Arg Glu Arg
            35                  40                  45

Gln Arg Gln Ile Arg Ser Ile Ser Glu Arg Ile Leu Ser Thr Phe Leu
    50                  55                  60

Gly Arg Pro Ala Glu Pro Val Pro Leu Gln Leu Pro Pro Leu Glu Arg
65              70                  75                  80

Leu Thr Leu Asp Cys Ser Glu Asp Cys Gly Asn Ser Gly Thr Gln Gly
                85                  90                  95
```

-continued

```
Val Gly Ser Pro Gln Val Leu Val Glu Ser Pro Ala Val Leu Glu Pro
            100                 105                 110
Gly Thr Lys Glu Thr Ser Val Gly Lys Trp Ser Lys Cys Ser Gly Trp
        115                 120                 125
Pro Thr Val Arg Glu Arg Met Lys Gln Ala Glu Pro Glu Pro Ala Ala
    130                 135                 140
Asp Gly Val Gly Ala Ala Ser Arg Asp Leu Glu Lys His Gly Ala Ile
145                 150                 155                 160
Thr Ser Ser Asn Thr Ala Thr Asn Asn Ala Ala Cys Ala Trp Leu Glu
                165                 170                 175
Ala Gln Glu Glu Glu Glu Val Gly Phe Pro Val Arg Pro Gln Val Pro
            180                 185                 190
Leu Arg Pro Met Thr Tyr Lys Gly Ala Leu Asp Leu Ser His Phe Leu
        195                 200                 205
Lys Glu Lys Gly Gly Leu Glu Gly Leu Ile Tyr Ser Pro Lys Arg Gln
    210                 215                 220
Glu Ile Leu Asp Leu Trp Val Tyr His Thr Gln Gly Tyr Phe Pro Asp
225                 230                 235                 240
Trp Gln Asn Tyr Thr Pro Gly Pro Gly Val Arg Tyr Pro Leu Thr Phe
                245                 250                 255
Gly Trp Cys Phe Lys Leu Val Pro Val Glu Pro Asp Glu Glu Glu Asn
            260                 265                 270
Ser Ser Leu Leu His Pro Ala Ser Leu His Gly Thr Glu Asp Thr Glu
        275                 280                 285
Arg Glu Val Leu Lys Trp Lys Phe Asp Ser His Leu Ala Phe His His
    290                 295                 300
Lys Ala Arg Glu Leu His Pro Glu Tyr Tyr Lys Asp Cys Lys Leu Glu
305                 310                 315                 320
Pro Val Asp Pro Arg Leu Glu Pro Trp Lys His Pro Gly Ser Gln Pro
                325                 330                 335
Arg Thr Pro Cys Thr Asn Cys Tyr Cys Lys Lys Cys Leu His Cys
        340                 345                 350
Gln Val Cys Phe Thr Arg Lys Gly Leu Gly Ile Ser Tyr Gly Arg Lys
        355                 360                 365
Lys Arg Arg Gln Arg Arg Ala Pro Gln Asp Ser Gln Thr His Gln
    370                 375                 380
Val Ser Leu Pro Lys Gln Pro Ser Ser Gln Arg Gly Asp Pro Thr
385                 390                 395                 400
Gly Pro Lys Lys Ser Lys Lys Val Glu Arg Glu Thr Glu Ala Asp
                405                 410                 415
Pro Phe Asp Ala Ala Val Ile Thr Leu Trp Gln Arg Pro Leu Val Ala
            420                 425                 430
Leu Ile Glu Ile Cys Thr Glu Met Glu Lys Glu Gly Lys Ile Ser Lys
        435                 440                 445
Ile Gly Pro Ala Gly Leu Lys Lys Lys Ser Val Thr Val Leu Asp
    450                 455                 460
Val Gly Asp Ala Tyr Phe Ser Val Pro Leu Asp Lys Asp Phe Arg Lys
465                 470                 475                 480
Tyr Thr Ala Phe Thr Ile Pro Ser Ile Trp Lys Gly Ser Pro Ala Ile
                485                 490                 495
Phe Gln Ser Ser Met Thr Lys Lys Gln Asn Pro Asp Ile Val Ile Tyr
            500                 505                 510
Gln Tyr Met Asp Asp Leu Tyr Val Pro Ile Val Leu Pro Glu Lys Asp
```

```
            515                 520                 525
Ser Trp Leu Val Gly Lys Leu Asn Trp Ala Ser Gln Ile Tyr Ala Gly
530                 535                 540

Ile Lys Val Lys Gln Leu Ile Leu Lys Glu Pro Val His Gly Val Tyr
545                 550                 555                 560

Glu Pro Ile Val Gly Ala Glu Thr Phe Tyr Val Asp Gly Ala Ala Asn
                    565                 570                 575

Arg Ala Gly Asn Leu Trp Val Thr Val Tyr Tyr Gly Val Pro Val Trp
                580                 585                 590

Lys Glu Ala Thr Thr Thr Leu Val Glu Arg Tyr Leu Arg Asp Gln Gln
                595                 600                 605

Leu Leu Gly Ile Trp Gly Cys Ala Cys Thr Pro Tyr Asp Ile Asn Gln
610                 615                 620

Met Leu Arg Gly Pro Gly Arg Ala Phe Val Thr Ile Arg Gln Gly Ser
625                 630                 635                 640

Leu Ala Ala Val Gly Ala Arg Ala Ser Val Leu Ser Gly Gly Glu Leu
                645                 650                 655

Asp Lys Trp Glu Lys Ile Arg Leu Arg Pro Gly Gly Lys Lys Lys Tyr
                660                 665                 670

Gln Leu Lys His Ile Val Trp Ala Ser Arg Glu Leu Glu Arg Phe Ala
                675                 680                 685

Val Asn Pro Gly Leu Leu Glu Thr Ser Glu Gly Cys Arg Gln Ile Met
690                 695                 700

Gly Gln Leu Gln Pro Ser Leu Gln Thr Gly Ser Glu Glu Leu Arg Ser
705                 710                 715                 720

Leu Tyr Asn Thr Val Ala Thr Leu Tyr Cys Val His Gln Lys Ile Glu
                725                 730                 735

Val Lys Asp Thr Lys Glu Ala Leu Asp Lys Val Glu Glu Glu Gln Asn
                740                 745                 750

Asn Ser Lys Lys Lys Ala Gln Gln Glu Ala Ala Asp Ala Gly Asn Arg
                755                 760                 765

Asn Gln Val Ser Gln Asn Tyr Pro Ile Val Gln Asn Leu Gln Gly Gln
                770                 775                 780

Met Val His Gln Ala Ile Ser Pro Arg Thr Leu Asn Ala Trp Val Lys
785                 790                 795                 800

Val Val Glu Glu Lys Ala Phe Ser Pro Glu Val Ile Pro Met Phe Ser
                805                 810                 815

Ala Leu Ser Glu Gly Ala Thr Pro Gln Asp Leu Asn Thr Met Leu Asn
                820                 825                 830

Thr Val Gly Gly His Gln Ala Ala Met Gln Met Leu Lys Glu Thr Ile
                835                 840                 845

Asn Glu Glu Ala Ala Glu Trp Asp Arg Leu His Pro Val His Ala Gly
                850                 855                 860

Pro Ile Ala Pro Gly Gln Met Arg Glu Pro Arg Gly Ser Asp Ile Ala
865                 870                 875                 880

Gly Thr Thr Ser Thr Leu Gln Glu Gln Ile Gly Trp Met Thr Asn Asn
                    885                 890                 895

Pro Pro Ile Pro Val Gly Glu Ile Tyr Lys Arg Trp Ile Ile Leu Gly
                900                 905                 910

Leu Asn Lys Ile Val Arg Met Tyr Ser Pro Thr Ser Ile Leu Asp Ile
                915                 920                 925

Lys Gln Gly Pro Lys Glu Pro Phe Arg Asp Tyr Val Asp Arg Phe Tyr
                930                 935                 940
```

```
Lys Thr Leu Arg Ala Glu Gln Ala Thr Gln Glu Val Lys Asn Trp Met
945                 950                 955                 960

Thr Glu Thr Leu Leu Val Gln Asn Ala Asn Pro Asp Cys Lys Thr Ile
            965                 970                 975

Leu Lys Ala Leu Gly Pro Ala Ala Thr Leu Glu Glu Met Met Thr Ala
        980                 985                 990

Cys Gln Gly Val Gly Gly Pro Gly  His Lys Ala Arg Val  Leu
        995              1000                 1005

<210> SEQ ID NO 48
<211> LENGTH: 1006
<212> TYPE: PRT
<213> ORGANISM: Artificial Sequence
<220> FEATURE:
<223> OTHER INFORMATION: Hybrid protein comprised of Rev-Nef-Tat,
      truncated Gag protein and CTL (RNT-optp17/24-CTL)

<400> SEQUENCE: 48

Met Ala Gly Arg Ser Gly Asp Ser Asp Glu Glu Leu Leu Lys Thr Val
1               5                   10                  15

Arg Leu Ile Lys Phe Leu Tyr Gln Ser Asn Pro Pro Ser Asn Glu
            20                  25                  30

Gly Thr Arg Gln Ala Arg Arg Asn Arg Arg Arg Arg Trp Arg Glu Arg
            35                  40                  45

Gln Arg Gln Ile Arg Ser Ile Ser Glu Arg Ile Leu Ser Thr Phe Leu
50                  55                  60

Gly Arg Pro Ala Glu Pro Val Pro Leu Gln Leu Pro Pro Leu Glu Arg
65                  70                  75                  80

Leu Thr Leu Asp Cys Ser Glu Asp Cys Gly Asn Ser Gly Thr Gln Gly
                85                  90                  95

Val Gly Ser Pro Gln Val Leu Val Glu Ser Pro Ala Val Leu Glu Pro
            100                 105                 110

Gly Thr Lys Glu Thr Ser Val Gly Lys Trp Ser Lys Cys Ser Gly Trp
            115                 120                 125

Pro Thr Val Arg Glu Arg Met Lys Gln Ala Glu Pro Glu Pro Ala Ala
        130                 135                 140

Asp Gly Val Gly Ala Ala Ser Arg Asp Leu Glu Lys His Gly Ala Ile
145                 150                 155                 160

Thr Ser Ser Asn Thr Ala Thr Asn Asn Ala Ala Cys Ala Trp Leu Glu
                165                 170                 175

Ala Gln Glu Glu Glu Glu Val Gly Phe Pro Val Arg Pro Gln Val Pro
            180                 185                 190

Leu Arg Pro Met Thr Tyr Lys Gly Ala Leu Asp Leu Ser His Phe Leu
        195                 200                 205

Lys Glu Lys Gly Gly Leu Glu Gly Leu Ile Tyr Ser Pro Lys Arg Gln
    210                 215                 220

Glu Ile Leu Asp Leu Trp Val Tyr His Thr Gln Gly Tyr Phe Pro Asp
225                 230                 235                 240

Trp Gln Asn Tyr Thr Pro Gly Pro Gly Val Arg Tyr Pro Leu Thr Phe
                245                 250                 255

Gly Trp Cys Phe Lys Leu Val Pro Val Glu Pro Asp Glu Glu Glu Asn
            260                 265                 270

Ser Ser Leu Leu His Pro Ala Ser Leu His Gly Thr Glu Asp Thr Glu
        275                 280                 285

Arg Glu Val Leu Lys Trp Lys Phe Asp Ser His Leu Ala Phe His His
    290                 295                 300
```

```
        -continued

Lys Ala Arg Glu Leu His Pro Glu Tyr Tyr Lys Asp Cys Lys Leu Glu
305                 310                 315                 320

Pro Val Asp Pro Arg Leu Glu Pro Trp Lys His Pro Gly Ser Gln Pro
            325                 330                 335

Arg Thr Pro Cys Thr Asn Cys Tyr Cys Lys Lys Cys Cys Leu His Cys
                340                 345                 350

Gln Val Cys Phe Thr Arg Lys Gly Leu Gly Ile Ser Tyr Gly Arg Lys
            355                 360                 365

Lys Arg Arg Gln Arg Arg Ala Pro Gln Asp Ser Gln Thr His Gln
370                 375                 380

Val Ser Leu Pro Lys Gln Pro Ser Ser Gln Gln Arg Gly Asp Pro Thr
385                 390                 395                 400

Gly Pro Lys Lys Ser Lys Lys Lys Val Glu Arg Glu Thr Glu Ala Asp
            405                 410                 415

Pro Phe Asp Ala Ala Val Gly Ala Arg Ala Ser Val Leu Ser Gly Gly
            420                 425                 430

Glu Leu Asp Lys Trp Glu Lys Ile Arg Leu Arg Pro Gly Gly Lys Lys
            435                 440                 445

Lys Tyr Gln Leu Lys His Ile Val Trp Ala Ser Arg Glu Leu Glu Arg
450                 455                 460

Phe Ala Val Asn Pro Gly Leu Leu Glu Thr Ser Glu Gly Cys Arg Gln
465                 470                 475                 480

Ile Met Gly Gln Leu Gln Pro Ser Leu Gln Thr Gly Ser Glu Glu Leu
            485                 490                 495

Arg Ser Leu Tyr Asn Thr Val Ala Thr Leu Tyr Cys Val His Gln Lys
            500                 505                 510

Ile Glu Val Lys Asp Thr Lys Glu Ala Leu Asp Lys Val Glu Glu Glu
            515                 520                 525

Gln Asn Asn Ser Lys Lys Lys Ala Gln Glu Ala Ala Asp Ala Gly
            530                 535                 540

Asn Arg Asn Gln Val Ser Gln Asn Tyr Pro Ile Val Gln Asn Leu Gln
545                 550                 555                 560

Gly Gln Met Val His Gln Ala Ile Ser Pro Arg Thr Leu Asn Ala Trp
                565                 570                 575

Val Lys Val Val Glu Glu Lys Ala Phe Ser Pro Glu Val Ile Pro Met
            580                 585                 590

Phe Ser Ala Leu Ser Glu Gly Ala Thr Pro Gln Asp Leu Asn Thr Met
            595                 600                 605

Leu Asn Thr Val Gly Gly His Gln Ala Ala Met Gln Met Leu Lys Glu
            610                 615                 620

Thr Ile Asn Glu Glu Ala Ala Glu Trp Asp Arg Leu His Pro Val His
625                 630                 635                 640

Ala Gly Pro Ile Ala Pro Gly Gln Met Arg Glu Pro Arg Gly Ser Asp
                645                 650                 655

Ile Ala Gly Thr Thr Ser Thr Leu Gln Glu Gln Ile Gly Trp Met Thr
                660                 665                 670

Asn Asn Pro Pro Ile Pro Val Gly Glu Ile Tyr Lys Arg Trp Ile Ile
            675                 680                 685

Leu Gly Leu Asn Lys Ile Val Arg Met Tyr Ser Pro Thr Ser Ile Leu
            690                 695                 700

Asp Ile Lys Gln Gly Pro Lys Glu Pro Phe Arg Asp Tyr Val Asp Arg
705                 710                 715                 720

Phe Tyr Lys Thr Leu Arg Ala Glu Gln Ala Thr Gln Glu Val Lys Asn
                725                 730                 735
```

```
Trp Met Thr Glu Thr Leu Leu Val Gln Asn Ala Asn Pro Asp Cys Lys
            740                 745                 750
Thr Ile Leu Lys Ala Leu Gly Pro Ala Ala Thr Leu Glu Glu Met Met
            755                 760                 765
Thr Ala Cys Gln Gly Val Gly Pro Gly His Lys Ala Arg Val Leu
770                 775                 780
Ala Ala Val Ile Thr Leu Trp Gln Arg Pro Leu Val Ala Leu Ile Glu
785                 790                 795                 800
Ile Cys Thr Glu Met Glu Lys Glu Gly Lys Ile Ser Lys Ile Gly Pro
                    805                 810                 815
Ala Gly Leu Lys Lys Lys Ser Val Thr Val Leu Asp Val Gly Asp
                820                 825                 830
Ala Tyr Phe Ser Val Pro Leu Asp Lys Asp Phe Arg Lys Tyr Thr Ala
            835                 840                 845
Phe Thr Ile Pro Ser Ile Trp Lys Gly Ser Pro Ala Ile Phe Gln Ser
850                 855                 860
Ser Met Thr Lys Lys Gln Asn Pro Asp Ile Val Ile Tyr Gln Tyr Met
865                 870                 875                 880
Asp Asp Leu Tyr Val Pro Ile Val Leu Pro Glu Lys Asp Ser Trp Leu
                    885                 890                 895
Val Gly Lys Leu Asn Trp Ala Ser Gln Ile Tyr Ala Gly Ile Lys Val
                900                 905                 910
Lys Gln Leu Ile Leu Lys Glu Pro Val His Gly Val Tyr Glu Pro Ile
            915                 920                 925
Val Gly Ala Glu Thr Phe Tyr Val Asp Gly Ala Ala Asn Arg Ala Gly
930                 935                 940
Asn Leu Trp Val Thr Val Tyr Tyr Gly Val Pro Val Trp Lys Glu Ala
945                 950                 955                 960
Thr Thr Thr Leu Val Glu Arg Tyr Leu Arg Asp Gln Gln Leu Leu Gly
                    965                 970                 975
Ile Trp Gly Cys Ala Cys Thr Pro Tyr Asp Ile Asn Gln Met Leu Arg
                980                 985                 990
Gly Pro Gly Arg Ala Phe Val Thr  Ile Arg Gln Gly Ser  Leu
            995                 1000                1005
```

<210> SEQ ID NO 49
<211> LENGTH: 7945
<212> TYPE: DNA
<213> ORGANISM: Bovine papillomavirus
<220> FEATURE:
<221> NAME/KEY: misc_feature
<222> LOCATION: 1205
<223> OTHER INFORMATION: n = A,T,C or G

<400> SEQUENCE: 49

| | | | | |
|---|---|---|---|---|
| gttaacaata atcacaccat caccgttttt tcaagcggga aaaatagcc agctaactat | 60 |
| aaaaagctgc tgacagaccc cggttttcac atggacctga aaccttttgc aagaaccaat | 120 |
| ccattctcag ggttggattg tctgtggtgc agagagcctc ttacagaagt tgatgctttt | 180 |
| aggtgcatgg tcaaagactt tcatgttgta attcgggaag gctgtagata tggtgcatgt | 240 |
| accatttgtc ttgaaaactg tttagctact gaaagaagac tttggcaagg tgttccagta | 300 |
| acaggtgagg aagctgaatt attgcatggc aaaacacttg ataggctttg cataagatgc | 360 |
| tgctactgtg ggggcaaact aacaaaaaat gaaaaacatc ggcatgtgct ttttaatgag | 420 |
| cctttctgca aaaccagagc taacataatt agaggacgct gctacgactg ctgcagacat | 480 |

-continued

```
ggttcaaggt ccaaatac cc atagaaactt ggatgattca cctgcaggac cgttgctgat      540
tttaagtcca tgtgcaggca cacctaccag gtctcctgca gcacctgatg cacctgattt      600
cagacttccg tgccatttcg gccgtcctac taggaagcga ggtcccacta cccctccgct      660
ttcctctccc ggaaaactgt gtgcaacagg gccacgtcga gtgtattctg tgactgtctg      720
ctgtggaaac tgcggaaaag agctgacttt tgctgtgaag accagctcga cgtccctgct      780
tggatttgaa caccttttaa actcagattt agacctcttg tgtccacgtt gtgaatctcg      840
cgagcgtcat ggcaaacgat aaaggtagca attgggattc gggcttggga tgctcatatc      900
tgctgactga ggcagaatgt gaaagtgaca aagagaatga ggaacccggg gcaggtgtag      960
aactgtctgt ggaatctgat cggtatgata gccaggatga ggattttgtt gacaatgcat     1020
cagtctttca gggaaatcac ctggaggtct tccaggcatt agagaaaaag gcgggtgagg     1080
agcagatttt aaatttgaaa agaaaagtat tggggagttc gcaaacagc agcggttccg      1140 aagcatctga aactccagtt aaaagacgga aatcaggagc aaagcgaaga ttatttgctg     1200
aaaangaagc taaccgtgtt cttacgcccc tccaggtaca gggggagggg gaggggaggc     1260
aagaacttaa tgaggagcag gcaattagtc atctacatct gcagcttgtt aaatctaaaa     1320
atgctacagt ttttaagctg gggctcttta aatctttgtt cctttgtagc ttccatgata     1380
ttacgaggtt gtttaagaat gataagacca ctaatcagca atgggtgctg gctgtgtttg     1440
gccttgcaga ggtgtttttt gaggcgagtt tcgaactcct aaagaagcag tgtagttttc     1500
tgcagatgca aaaagatct catgaaggag gaacttgtgc agtttactta atctgcttta      1560
acacagctaa aagcagagaa acagtccgga atctgatggc aaacacgcta aatgtaagag     1620
aagagtgttt gatgctgcag ccagctaaaa ttcgaggact cagcgcagct ctattctggt     1680
ttaaaagtag tttgtcaccc gctacactta aacatggtgc tttacctgag tggatacggg     1740
cgcaaactac tctgaacgag agcttgcaga ccgagaaatt cgacttcgga actatggtgc     1800
aatgggccta tgatcacaaa tatgctgagg agtctaaaat agcctatgaa tatgctttgg     1860
ctgcaggatc tgatagcaat gcacgggctt ttttagcaac taacagccaa gctaagcatg     1920
tgaaggactg tgcaactatg gtaagacact atctaagagc tgaaacacaa gcattaagca     1980
tgcctgcata tattaaagct aggtgcaagc tggcaactgg ggaaggaagc tggaagtcta     2040
tcctaacttt ttttaactat cagaatattg aattaattac ctttattaat gctttaaagc     2100
tctggctaaa aggaattcca aaaaaaact gtttagcatt tattggccct ccaaacacag      2160
gcaagtctat gctctgcaac tcattaattc attttttggg tggtagtgtt ttatcttttg     2220
ccaaccataa aagtcacttt tggcttgctt ccctagcaga tactagagct gctttagtag     2280
atgatgctac tcatgcttgc tggaggtact ttgacacata cctcagaaat gcattggatg     2340
gctaccctgt cagtattgat agaaaacaca aagcagcggt tcaaattaaa gctccacccc     2400
tcctggtaac cagtaatatt gatgtgcagg cagaggacag atatttgtac ttgcatagtc     2460
gggtgcaaac ctttcgcttt gagcagccat gcacagatga atcgggtgag caacctttta     2520
atattactga tgcagattgg aaatcttttt ttgtaaggtt atgggggcgt ttagacctga     2580
ttgacgagga ggaggatagt gaagaggatg agacagcat gcgaacgttt acatgtagcg      2640
caagaaacac aaatgcagtt gattgagaaa agtagtgata agttgcaaga tcatatactg     2700
tactggactg ctgttagaac tgagaacaca ctgctttatg ctgcaaggaa aaagggggtg     2760
actgtcctag gacactgcag agtaccacac tctgtagttt gtcaagagag agccaagcag     2820
gccattgaaa tgcagttgtc tttgcaggag ttaagcaaaa ctgagtttgg ggatgaacca     2880
```

```
tggtctttgc ttgacacaag ctgggaccga tatatgtcag aacctaaacg gtgctttaag    2940
aaaggcgcca gggtggtaga ggtggagttt gatggaaatg caagcaatac aaactggtac    3000
actgtctaca gcaatttgta catgcgcaca gaggacggct ggcagcttgc gaaggctggg    3060
gctgacggaa ctgggctcta ctactgcacc atggccggtg ctggacgcat ttactattct    3120
cgctttggtg acgaggcagc cagatttagt acaacagggc attactctgt aagagatcag    3180
gacagagtgt atgctggtgt ctcatccacc tcttctgatt ttagagatcg cccagacgga    3240
gtctgggtcg catccgaagg acctgaagga gaccctgcag gaaagaagc cgagccagcc     3300 cagcctgtct cttctttgct cggctccccc gcctgcggtc ccatcagagc aggcctcggt    3360
tgggtacggg acggtcctcg ctcgcacccc tacaattttc ctgcaggctc gggggctct    3420 attctccgct cttcctccac cccgtgcagg gcacggtacc ggtggacttg gcatcaaggc    3480
aggaagaaga ggagcagtcg cccgactcca cagaggaaga accagtgact ctcccaaggc    3540
gcaccaccaa tgatggattc cacctgttaa aggcaggagg gtcatgcttt gctctaattt    3600
caggaactgc taaccaggta aagtgctatc gctttcgggt gaaaagaac catagacatc    3660 gctacgagaa ctgcaccacc acctggttca cagttgctga caacggtgct gaaagacaag    3720
gacaagcaca aatactgatc acctttggat cgccaagtca aaggcaagac tttctgaaac    3780
atgtaccact acctcctgga atgaacattt ccggctttac agccagcttg gacttctgat    3840
cactgccatt gccttttctt catctgactg gtgtactatg ccaaatctat ggtttctatt    3900
gttcttggga ctagttgctg caatgcaact gctgctatta ctgttcttac tcttgttttt    3960
tcttgtatac tgggatcatt ttgagtgctc ctgtacaggt ctgccctttt aatgccttta    4020
catcactggc tattggctgt gttttttactg ttgtgtggat ttgatttgtt ttatatactg    4080
tatgaagttt tttcatttgt gcttgtattg ctgtttgtaa gttttttact agagtttgta    4140
ttccccctgc tcagatttta tatggtttaa gctgcagcaa taaaaatgag tgcacgaaaa    4200
agagtaaaac gtgccagtgc ctatgacctg tacaggacat gcaagcaagc gggcacatgt    4260
ccaccagatg tgataccaaa ggtagaagga gatactatag cagataaaat tttgaaattt    4320
gggggtcttg caatctactt aggagggcta ggaataggaa catggtctac tggaaggggtt   4380 gctgcaggtg gatcaccaag gtacacacca ctccgaacag cagggtccac atcatcgctt    4440
gcatcaatag gatccagagc tgtaacagca gggacccgcc ccagtatagg tgcgggcatt    4500
cctttagaca ccccttgaaac tcttgggcc ttgcgtccag gggtgtatga ggacactgtg    4560
ctaccagagg ccctgcaat agtcactcct gatgctgttc ctgcagattc agggcttgat    4620
gccctgtcca taggtacaga ctcgtccacg gagaccctca ttactctgct agagcctgag    4680
ggtcccgagg acatagcggt tcttgagctg caacccctgg accgtccaac ttggcaagta    4740
agcaatgctg ttcatcagtc ctctgcatac cacgcccctc tgcagctgca atcgtccatt    4800
gcagaaacat ctggtttaga aaatattttt gtaggaggct cgggtttagg ggatacagga    4860
ggagaaaaca ttgaactgac atacttcggg tccccacgaa caagcacgcc ccgcagtatt    4920
gcctctaaat cacgtggcat tttaaactgg ttcagtaaac ggtactacac acaggtgccc    4980
acggaagatc ctgaagtgtt ttcatcccaa acatttgcaa acccactgta tgaagcagaa    5040
ccagctgtgc ttaagggacc tagtggacgt gttggactca gtcaggttta taaacctgat    5100
acacttacaa cacgtagcgg gacagaggtg ggaccacagc tacatgtcag gtactcattg    5160
agtactatac atgaagatgt agaagcaatc cctacacag ttgatgaaaa tacacaggga    5220
cttgcattcg taccttgca tgaagagcaa gcaggttttg aggagataga attagatgat    5280
```

```
tttagtgaga cacatagact gctacctcag aacacctctt ctacacctgt tggtagtggt   5340
gtacgaagaa gcctcattcc aactcaggaa tttagtgcaa cacggcctac aggtgttgta   5400
acctatggct cacctgacac ttactctgct agcccagtta ctgaccctga ttctacctct   5460
cctagtctag ttatcgatga cactactact acaccaatca ttataattga tgggcacaca   5520
gttgatttgt acagcagtaa ctacaccttg catccctcct tgttgaggaa acgaaaaaaa   5580
cggaaacatg cctaattttt tttgcagatg gcgttgtggc aacaaggcca gaagctgtat   5640
ctccctccaa cccctgtaag caaggtgctt tgcagtgaaa cctatgtgca agaaaaagc    5700
attttttatc atgcagaaac ggagcgcctg ctaactatag gacatccata ttacccagtg   5760
tctatcgggg ccaaaactgt tcctaaggtc tctgcaaatc agtatagggt atttaaaata   5820
caactacctg atcccaatca atttgcacta cctgacagga ctgttcacaa cccaagtaaa   5880
gagcggctgg tgtgggcagt cataggtgtg caggtgtcca gagggcagcc tcttggaggt   5940
actgtaactg ggcaccccac ttttaatgct ttgcttgatg cagaaaatgt gaatagaaaa   6000
gtcaccaccc aaacaacaga tgacaggaaa caaacaggcc tagatgctaa gcaacaacag   6060
attctgttgc taggctgtac ccctgctgaa ggggaatatt ggacaacagc ccgtccatgt   6120
gttactgatc gtctagaaaa tggcgcctgc cctcctcttg aattaaaaaa caagcacata   6180
gaagatgggg atatgatgga aatttgggttt ggtgcagcca acttcaaaga aattaatgca   6240
agtaaatcag atctacctct tgacattcaa aatgagatct gcttgtaccc agactacctc   6300
aaaatggctg aggacgctgc tggtaatagc atgttctttt ttgcaaggaa agaacaggtg   6360
tatgttagac acatctggac cagagggggc tcggagaaag aagcccctac cacagatttt   6420
tatttaaaga ataataaagg ggatgccacc cttaaaatac ccagtgtgca ttttggtagt   6480
cccagtggct cactagtctc aactgataat caaattttta atcggcccta ctggctattc   6540
cgtgcccagg gcatgaacaa tggaattgca tggaataatt tattgttttt aacagtgggg   6600
gacaatacac gtggtactaa tcttaccata agtgtagcct cagatggaac cccactaaca   6660
gagtatgata gctcaaaatt caatgtatac catagacata tggaagaata taagctagcc   6720
tttatattag agctatgctc tgtggaaatc acagctcaaa ctgtgtcaca tctgcaagga   6780
cttatgccct ctgtgcttga aaattgggaa ataggtgtgc agcctcctac ctcatcgata   6840
ttagaggaca cctatcgcta tatagagtct cctgcaacta aatgtgcaag caatgtaatt   6900
cctgcaaaag aagacccta tgcagggttt aagttttgga acatagatct aaagaaaag    6960
ctttctttgg acttagatca atttcccttg ggaagaagat ttttagcaca gcaagggca    7020
ggatgttcaa ctgtgagaaa acgaagaatt agccaaaaaa cttccagtaa gcctgcaaaa   7080
aaaaaaaaaa aataaaagct aagtttctat aaatgttctg taaatgtaaa acagaaggta   7140
agtcaactgc acctaataaa aatcacttaa tagcaatgtg ctgtgtcagt tgtttattgg   7200
aaccacaccc ggtacacatc ctgtccagca tttgcagtgc gtgcattgaa ttattgtgct   7260
ggctagactt catggcgcct ggcaccgaat cctgccttct cagcgaaaat gaataattgc   7320
tttgttggca agaaactaag catcaatggg acgcgtgcaa agcaccggcg gcggtagatg   7380
cggggtaagt actgaatttt aattcgacct atcccggtaa agcgaaagcg acacgctttt   7440
ttttcacaca tagcgggacc gaacacgtta taagtatcga ttaggtctat ttttgtctct   7500
ctgtcggaac cagaactggt aaaagtttcc attgcgtctg ggcttgtcta tcattgcgtc   7560
tctatggttt ttggaggatt agacggggcc accagtaatg gtgcatagcg gatgtctgta   7620
ccgccatcgg tgcaccgata taggtttggg gctccccaag ggactgctgg gatgacagct   7680
```

```
tcatattata ttgaatgggc gcataatcag cttaattggt gaggacaagc tacaagttgt    7740
aacctgatct ccacaaagta cgttgccggt cggggtcaaa ccgtcttcgg tgctcgaaac    7800
cgccttaaac tacagacagg tcccagccaa gtaggcggat caaaacctca aaaaggcggg    7860
agccaatcaa aatgcagcat tatattttaa gctcaccgaa accggtaagt aaagactatg    7920
tattttttcc cagtgaataa ttgtt                                          7945
```

<210> SEQ ID NO 50
<211> LENGTH: 306
<212> TYPE: PRT
<213> ORGANISM: bovine papillomavirus type 1

<400> SEQUENCE: 50

```
Met Glu Thr Ala Cys Glu Arg Leu His Val Ala Gln Glu Thr Gln Met
 1               5                  10                  15

Gln Leu Ile Glu Lys Ser Ser Asp Lys Leu Gln Asp His Ile Leu Tyr
            20                  25                  30

Trp Thr Ala Val Arg Thr Glu Asn Thr Leu Leu Tyr Ala Ala Arg Lys
        35                  40                  45

Lys Gly Val Thr Val Leu Gly His Cys Arg Val Pro His Ser Val Val
    50                  55                  60

Cys Gln Glu Arg Ala Lys Gln Ala Ile Glu Met Gln Leu Ser Leu Gln
65                  70                  75                  80

Glu Leu Ser Lys Thr Glu Phe Gly Asp Glu Pro Trp Ser Leu Leu Asp
                85                  90                  95

Thr Ser Trp Asp Arg Tyr Met Ser Glu Pro Lys Arg Cys Phe Lys Lys
            100                 105                 110

Gly Ala Arg Val Val Glu Val Glu Phe Asp Gly Asn Ala Ser Asn Thr
        115                 120                 125

Asn Trp Tyr Thr Val Tyr Ser Asn Leu Tyr Met Arg Thr Glu Asp Gly
    130                 135                 140

Trp Gln Leu Ala Lys Ala Gly Ala Asp Gly Thr Gly Leu Tyr Tyr Cys
145                 150                 155                 160

Thr Met Ala Gly Ala Gly Arg Ile Tyr Tyr Ser Arg Phe Gly Asp Glu
                165                 170                 175

Ala Ala Arg Phe Ser Thr Thr Gly His Tyr Ser Val Arg Asp Gln Asp
            180                 185                 190

Arg Val Tyr Ala Gly Val Ser Ser Thr Ser Ser Asp Phe Arg Asp Arg
        195                 200                 205

Pro Asp Gly Val Trp Val Ala Ser Glu Gly Pro Glu Gly Asp Pro Ala
    210                 215                 220

Gly Lys Glu Ala Glu Pro Ala Gln Pro Val Ser Ser Leu Leu Gly Ser
225                 230                 235                 240

Pro Ala Cys Gly Pro Ile Arg Ala Gly Leu Gly Trp Val Arg Asp Gly
                245                 250                 255

Pro Arg Ser His Pro Tyr Asn Phe Pro Ala Gly Ser Gly Gly Ser Ile
            260                 265                 270

Leu Arg Ser Ser Thr Pro Cys Arg Ala Arg Tyr Arg Trp Thr Trp
        275                 280                 285

His Gln Gly Arg Lys Lys Arg Ser Ser Arg Pro Thr Pro Gln Arg Lys
    290                 295                 300

Asn Gln
305
```

<210> SEQ ID NO 51

-continued

```
<211> LENGTH: 622
<212> TYPE: DNA
<213> ORGANISM: Human herpesvirus 4

<400> SEQUENCE: 51
gggtatcata tgctgactgt atatgcatga ggatagcata tgctacccgg atacagatta        60
ggatagcata tactacccag atatagatta ggatagcata tgctacccag atatagatta       120
ggatagccta tgctacccag atataaatta ggatagcata tactacccag atatagatta       180
ggatagcata tgctacccag atatagatta ggatagccta tgctacccag atatagatta       240
ggatagcata tgctacccag atatagatta ggatagcata tgctatccag atatttgggt       300
agtatatgct acccagatat aaattaggat agcatatact accctaatct ctattaggat       360
agcatatgct acccggatac agattaggat agcatatact acccagatat agattaggat       420
agcatatgct acccagatat agattaggat agcctatgct acccagatat aaattaggat       480
agcatatact acccagatat agattaggat agcatatgct acccagatat agattaggat       540
agcctatgct acccagatat agattaggat agcatatgct atccagatat ttgggtagta       600
tatgctaccc atggcaacat ta                                                622

<210> SEQ ID NO 52
<211> LENGTH: 641
<212> TYPE: PRT
<213> ORGANISM: Human herpesvirus 4

<400> SEQUENCE: 52

Met Ser Asp Glu Gly Pro Gly Thr Gly Pro Gly Asn Gly Leu Gly Glu
  1               5                  10                  15

Lys Gly Asp Thr Ser Gly Pro Glu Gly Ser Gly Gly Ser Gly Pro Gln
             20                  25                  30

Arg Arg Gly Gly Asp Asn His Gly Arg Gly Arg Gly Arg Gly Arg Gly
         35                  40                  45

Arg Gly Gly Gly Arg Pro Gly Ala Pro Gly Gly Ser Gly Ser Gly Pro
     50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                 85                  90                  95

Gly Ala Gly Ala Gly Gly Ala Gly Ala Gly Gly Ala Gly Ala Gly Gly
            100                 105                 110

Gly Gly Ala Gly Gly Ala Gly Gly Ala Gly Ala Gly Gly Ala Gly Gly
        115                 120                 125

Gly Ala Gly Ala Gly Gly Ala Gly Gly Ala Gly Gly Ala Gly Gly Ala
    130                 135                 140

Gly Gly Gly Ala Gly Ala Gly Gly Ala Gly Gly Ala Gly Ala Gly Gly
145                 150                 155                 160

Gly Gly Ala Gly Gly Ala Gly Gly Ala Gly Gly Ala Gly Gly Ala Gly
                165                 170                 175

Ala Gly Gly Gly Ala Gly Gly Ala Gly Ala Gly Gly Gly Ala Gly Gly
            180                 185                 190

Ala Gly Gly Ala Gly Ala Gly Gly Ala Gly Ala Gly Gly Gly Ala Gly
        195                 200                 205

Gly Ala Gly Gly Ala Gly Ala Gly Ala Gly Ala Gly Gly Gly Gly Ala
    210                 215                 220

Gly Gly Ala Gly Gly Ala Gly Ala Gly Gly Ala Gly Ala Gly Gly Ala
225                 230                 235                 240
```

```
Gly Ala Gly Gly Ala Gly Ala Gly Gly Ala Gly Ala Gly
            245                 250                 255
Gly Ala Gly Gly Ala Gly Ala Gly Gly Ala Gly Ala Gly
            260                 265                 270
Gly Gly Ala Gly Gly Ala Gly Ala Gly Gly Ala Gly Ala Gly
                275                 280                 285
Ala Gly Gly Ala Gly Gly Ala Gly Ala Gly Gly Ala Gly
        290                 295                 300
Ala Gly Gly Ala Gly Gly Ala Gly Ala Gly Gly Ala Gly
305                 310                 315                 320
Gly Ala Gly Ala Gly Gly Gly Arg Gly Arg Gly Ser Gly Gly
                325                 330                 335
Arg Gly Arg Gly Gly Ser Gly Gly Arg Gly Arg Gly Ser Gly Gly
            340                 345                 350
Arg Arg Gly Arg Gly Arg Glu Arg Ala Arg Gly Gly Ser Arg Glu Arg
            355                 360                 365
Ala Arg Gly Arg Gly Arg Gly Arg Gly Glu Lys Arg Pro Arg Ser Pro
    370                 375                 380
Ser Ser Gln Ser Ser Ser Ser Gly Ser Pro Pro Arg Arg Pro Pro Pro
385                 390                 395                 400
Gly Arg Arg Pro Phe Phe His Pro Val Gly Glu Ala Asp Tyr Phe Glu
                405                 410                 415
Tyr His Gln Glu Gly Gly Pro Asp Gly Glu Pro Asp Val Pro Pro Gly
                420                 425                 430
Ala Ile Glu Gln Gly Pro Ala Asp Asp Pro Gly Glu Gly Pro Ser Thr
            435                 440                 445
Gly Pro Arg Gly Gln Gly Asp Gly Gly Arg Arg Lys Lys Gly Gly Trp
        450                 455                 460
Phe Gly Lys His Arg Gly Gln Gly Gly Ser Asn Pro Lys Phe Glu Asn
465                 470                 475                 480
Ile Ala Glu Gly Leu Arg Ala Leu Leu Ala Arg Ser His Val Glu Arg
                485                 490                 495
Thr Thr Asp Glu Gly Thr Trp Val Ala Gly Val Phe Val Tyr Gly Gly
                500                 505                 510
Ser Lys Thr Ser Leu Tyr Asn Leu Arg Arg Gly Thr Ala Leu Ala Ile
            515                 520                 525
Pro Gln Cys Arg Leu Thr Pro Leu Ser Arg Leu Pro Phe Gly Met Ala
        530                 535                 540
Pro Gly Pro Gly Pro Gln Pro Gly Pro Leu Arg Glu Ser Ile Val Cys
545                 550                 555                 560
Tyr Phe Met Val Phe Leu Gln Thr His Ile Phe Ala Glu Val Leu Lys
                565                 570                 575
Asp Ala Ile Lys Asp Leu Val Met Thr Lys Pro Ala Pro Thr Cys Asn
                580                 585                 590
Ile Arg Val Thr Val Cys Ser Phe Asp Asp Gly Val Asp Leu Pro Pro
            595                 600                 605
Trp Phe Pro Pro Met Val Glu Gly Ala Ala Glu Gly Asp Asp Gly
        610                 615                 620
Asp Asp Gly Asp Glu Gly Gly Asp Gly Asp Glu Gly Glu Glu Gly Gln
625                 630                 635                 640
Glu
```

EXPRESSION VECTORS AND USES THEREOF

This application claims the benefit of priority under 35 U.S.C. §119(a) to Finnish patent application 20010922 filed on May 3, 2001 in the Finnish Patent Office, which is incorporated by reference herein in its entirety.

1. FIELD OF THE INVENTION

The present invention relates to novel vectors, to DNA vaccines and gene therapeutics containing said vectors, to methods for the preparation of the vectors and DNA vaccines and gene therapeutics containing the vectors, and to therapeutic uses of said vectors. More specifically, the present invention relates to novel vectors comprising (a) an expression cassette of a gene of a nuclear-anchoring protein, which contains (i) a DNA binding domain capable of binding to a specific DNA sequence and (ii) a functional domain capable of binding to a nuclear component and (b) a multimerized DNA forming a binding site for the anchoring protein of a nuclear-anchoring protein, and optionally (c) one or more expression cassettes of a DNA sequence of interest. In particular the invention relates to vectors that lack a papilloma virus origin of replication. The invention also relates to vectors that lack an origin of replication functional in a mammalian cell. The invention further relates to methods for expressing a DNA sequence of interest in a subject.

2. BACKGROUND OF THE INVENTION

Transfer of autologous or heterologous genes into animal or human organisms with suitable vectors is emerging as a technique with immense potential to cure diseases with a genetic background or to prevent or cure infectious diseases. Several types of viral and non-viral vectors have been developed and tested in animals and in human subjects to deliver a gene/genes that are defective by mutations and therefore non-functional. Examples of such vectors include Adenovirus vectors, Herpes virus vectors, Retrovirus vectors, Lentivirus vectors and Adeno-associated vectors.

Vaccination has proven to be a highly effective and economical method to prevent a disease caused by infectious agents. Since the introduction of the Vaccinia virus as an attenuated vaccine against the smallpox virus (Variola), vaccines against a multitude of human pathogens have been developed and taken into routine use. Today small pox has been eradicated by vaccinations and the same is to be expected shortly for the poliovirus. Several childhood diseases, such as pertussis, diphtheria and tetanus, can be effectively prevented by vaccinations.

In general, the most successful viral vaccines are live avirulent mutants of the disease-causing viruses. The key to the success of this approach is the fact that a living virus targets the same organs, the same type and similar number of cells, and therefore, by multiplying in the recipient, elicits a long-lasting immune response without causing the disease or causing only a mild disease. In effect, a live attenuated vaccine produces a subclinical infection, the nature's own way of immunizing. As a result, a full immune response will be induced, including humoral, cellular and innate responses, providing a long lasting and sometimes a life-long immune protection against the pathogen.

Although live attenuated vaccines are most potent, they can cause harmful side effects. Thus, an attenuated viral vaccine can revert to a virulent strain or in cases where the attenuated virus is apathogenic in adults it can still cause a disease in infants or in disabled persons. This is true in the case of viruses causing chronic infections, such as Human Immunodeficiency Virus type 1 and 2. Vaccines composed of viral and bacterial proteins or immunogenic peptides are less likely to cause unwanted side effects but may not be as potent as the live vaccines. This is especially the case with vaccines against microbes causing chronic infections, such as certain viruses and intracellular bacteria.

The strength and type of immune response is, however, also dependent on how the viral proteins are processed and how they are presented to the immune system by antigen presenting cells (APCs), such as macrophages and dendritic cells. Protein and peptide antigens are taken up by APCs via endocytosis, processed to small immunogenic peptides through an endosomal pathway and presented to T-lymphocytes (T-cells) by MHC (major histocompatibility complex) class II antigens [in man HLAs (human leukocyte antigens) class II]. In contrast, proteins synthesized de novo in APCs or in possible target cells for an immune response, will be processed through a cytoplasmic pathway and presented to T-cells by MHC class I antigens (in man HLAs class I). In general, the presentation of immunogenic peptides through the class II pathway will lead to the activation of the helper/inducer T-cells, which in turn will lead to the activation of B-cells and to antibody response. In contrast, presentation through class I MHC favors the induction of cytotoxic T-lymphocytes (CTLs), which are capable of recognition and destruction of virally infected cells.

In early 1990's, a method to mimic the antigen processing and presentation that was normally achieved by live attenuated vaccines was introduced [Ulmer, J. B. et al Science 259 (1993) 1745-1749]. It was shown that an injection of eukaryotic expression vectors in the form of circular DNA into the muscle induced take-up of this DNA by the muscle cells (and probably others) and was able to induce the expression of the gene of interest, and to raise an immune response, especially a cellular immune response in the form of CTLs, to the protein encoded by the inserted gene. Since that observation, DNA immunization has become a standard method to induce immune responses to foreign proteins in experimental animals and human studies with several DNA vaccines are underway.

Generally, the DNA vectors used in these vaccine studies contain a cloning site for the gene of interest, a strong viral promoter, such as the immediate early promoter of the CMV virus, in order to drive the expression of the gene of interest, a polyadenylation region, and an antibiotic resistance gene and a bacterial replication origin for the propagation of the DNA vector (plasmid) in bacterial cells.

With the vectors described above it is possible to obtain a detectable level of expression of the gene of interest after administering the vector to experimental animals or to humans, either by a direct injection to muscle or to skin with a particle bombardment technique or by applying the vector in a solution directly to mucous membranes. However, the expression obtained by these vectors is short lived: the vectors tend to disappear from the transfected cells little by little and are not transferred to daughter cells in a dividing cell population. The short-term expression of the gene of interest and limited number of cells targeted are probably the major reasons, why only temporary immune responses are observed in subjects immunized with DNA vectors described above. Thus, for example, Boyer et al. observed only temporary immune responses to HIV-1 Env and Rev proteins in human subjects, who were immunized several times with a vector similar to the those described above [Boyer, J. D., J Infect Dis 181 (2000) 476-483].

There is a growing interest in developing novel products useful in gene therapy and DNA vaccination. For instance papilloma virus vectors carrying the expression cassette for the gene of interest have been suggested to be useful candidates.

To date more than 70 subtypes of human papilloma viruses (HPVS) and many different animal papilloma viruses have been identified [zur Hausen, H. and de Villiers E., Annu Rev Microbiol 48 (1994) 427-447; Bernard, H., et al., Curr Top Microbiol Immunol 186 (1994) 33-54]. All papilloma viruses share a similar genome organization and the positioning of all of the translational open reading frames (ORFs) is highly conserved.

Papilloma viruses infect squamous epithelial cells of skin or mucosa at different body sites and induce the formation of benign tumors, which in some cases can progress to malignancy. The papilloma virus genomes are replicated and maintained in the infected cells as multicopy nuclear plasmids. The replication, episomal maintenance, expression of the late genes and virus assembly are tightly coupled to the differentiation of the epithelial tissue: the papilloma virus DNA episomal replication takes place during the initial amplificational replication and the second, i.e. latent, and the third, i.e. vegetative, replications in the differentiating epithelium [Howley, P. M.; Papillomavirinae: the viruses and their replication. In Virology, Fields, B. C., Knipe, D. M., Howley, P. M., Eds., Lippincott-Raven Publishers, Philadelphia, USA, 1996, 2. Edition, p. 2045-2076].

Two viral factors encoded by the E1 and E2 open reading frames have been shown to be necessary and sufficient for the initiation of the DNA replication from the papilloma virus origin in the cells [Ustav, M. and Stenlund, A., EMBO J 10 (1991) 449-57; Ustav, M., et al., EMBO J 10 (1991) 4321-4329; Ustav, E., et al., Proc Natl Acad Sci USA 90 (1993) 898-902].

Functional origins for the initiation of the DNA replication have been defined for BPV1 [Ustav, M., et al., EMBO J 10 (1991) 4321-4329], HPV1a [Gopalakrishnan, V. and Khan, S., supra], HPV11 [Russell, J., Botchan, M., J Virol 69 (1995) 651-660], HPV18 [Sverdrup, F. and Khan, S., J Virol 68 (1995) 1319-1323:Sverdrup, F. and Khan, S., J Virol 68 (1994) 505-509] and many others. Characteristically, all these origin fragments have a high A/T content, and they contain several overlapping individual E1 protein recognition sequences, which together constitute the E1 binding site [Ustav, M., et al., EMBO J 10 (1991) 4321-4329; Holt, S., et al., J Virol 68 (1994) 1094-1102; Holt, S. and Wilson, V., J Virol 69 (1995) 6525-3652; Sedman, T., et al. J Virol 71 (1997) 2887-2996]. In addition, these functional origin fragments contain an E2 binding site, which is essential for the initiation of DNA replication in vivo in most cases (Ustav, E., et al., supra). The E2 protein facilitates the first step of the origin recognition by E1. After the initial binding of monomeric E1 to the origin the multimerization of E1 is initiated. This leads to the formation of the complex with the ori melting activity. It has been suggested that E2 has no influence on the following stages of the initiation of the DNA replication [Lusky, M., et al., Proc Natl Acad Sci USA 91 (1994) 8895-8899].

The BPV 1 E2 ORF encodes three proteins that originate from selective promoter usage and alternative mRNA splicing [Lambert, P., et al., Annu Rev Genet 22 (1988) 235-258]. All these proteins can form homo- and heterodimers with each other and bind specifically to a 12 bp interrupted palindromic sequence 5'-ACC followed by NNNNNN followed by GGT-3 [Androphy, E., et al., Nature 325 (1987) 70-739].

There are 17 E2 binding sites in the BPV1 genome and up to four sites in the HPV genomes, which play a crucial role in the initiation of viral DNA replication (Ustav, E., et al., supra) and in the regulation of viral gene expression (Howley, P. M., Papillomavirinae: the viruses and their replication, in Virology, Fields, B. C., Knipe, D. M., Howley, P. M., Eds., Philadelphia: Lippincott-Raven Publishers, 1996. 2. edition, p. 2045-2076). Structural and mutational analyses have revealed three distinct functional domains in the full size E2 protein. The N-terminal part (residues 1 to 210) is an activation domain for transcription and replication. It is followed by the unstructured hinge region (residues 211 to 324) and the carboxy-terminal DNA binding-dimerization domain (residues 325 to 410) [Dostatni, N., et al., EMBO J 7 (1988) 3807-3816; Haugen, T., et al. EMBO J 7 (1988) 4245-4253; McBride, A., et al., EMBO J 7 (1988) 533-539; McBride, A., et al., Proc Natl Acad Sci USA 86 (1989) 510-514]. On the basis of X-ray crystallographical data, the DNA binding-dimerization domain of E2 has a structure of a dyad-symmetric eight-stranded antiparallel beta barrel, made up of two identical "half-barrel" subunits [Hegde, R., et al., Nature 359 (1992) 505-512; Hegde, R., J Nucl Med 36(6 Suppl) (1995) 25S -27S]. The functional elements of the transactivation domain of E2 have a very high structural integrity as confirmed by mutational analysis [Abroi, A., et al., J Virol 70 (1996) 6169-6179; Brokaw, J., et al., J Virol 71 (1996) 23-29; Grossel, M., et al., J Virol 70 (1996) 7264-7269; Ferguson, M. and Botchan, M., J Virol 70 (1996) 4193-4199] and by X-ray crystallography [Harris, S., and Botchan, M. R., Science 284 (1999) 1673-1677 and Antson, A. et al., Nature 403 (2000) 805-809]. In addition, X-ray crystallography shows that the N-terminal domain of the E2 protein forms a dimeric structure, where Arg 37 has an important function in dimer formation (Antson, A., et al., supra).

As has been described previously, bovine papillomavirus type 1 E2 protein in trans and its multiple binding sites in cis are both necessary and sufficient for the chromatin attachment of the episomal genetic elements. The phenomenon is suggested to provide a mechanism for partitioning viral genome during viral infection in the dividing cells [Ilves, I., et al., J Virol. 73 (1999) 4404-4412].

None of the papilloma vectors or other vectors disclosed so far fulfills the criteria and requirements set forth for an optimal vaccine, which are the same for DNA vaccines and for conventional vaccines. (It should be noted that these requirements are preferred but not necessary for use as a vaccine.) First, an optimal vaccine must produce protective immunity with minimal adverse effects. Thus the vaccine should be devoid of components, which are toxic and/or cause symptoms of the disease to the recipient. Second, an optimal vaccine must induce a pathogen-specific immune response, i.e. it must elicit a strong and measurable immune response to the desired pathogen without causing an immune response to other components of the vaccine. These two requirements imply that a vector to be used as a DNA vaccine should optimally only express the desired gene(s) and optimally should not replicate in the host or contain any sequences homologous with those of the recipient, since nucleotide sequences that are homologous between the vector and the host's genome may effect the integration of the vector into the host's genome. Third, an optimal vaccine must induce a right type of immune response; i.e. it must raise both humoral and cellular immune responses in order to act on the intracellular and extracellular pathogen. Finally, an optimal vaccine must be stable, i.e. it must retain its potency for a sufficiently long time in the body to raise the immune response in a vaccine formulation for use in various demanding circumstances duraing storage and preparation. Additionally, vaccines should be of reasonable price. Further, the route and the method of inoculation are important considerations for optimizing a DNA immunization.

When developing a DNA vaccine the stability of the expression of the desired gene is sometimes a major problem. Thus, the maintenance function or the persistance of the vector in the recipient cell has been focused on in the prior art, however, often at the cost of the safety. For example, Ohe, Y., et al.] [Hum Gene Ther 6(3) (1995) 325-333] disclose a papilloma virus vector capable of stable, high-level gene expression, which is suggested for use in gene therapy. Transforming early genes E5, E6, and E7 have been deleted from said vector, but it still contains nucleotide sequences encoding other papilloma viral genes, such as the E1 and E2 genes, which are involved in the replication of the virus. Thus, the vector produces several other papilloma proteins, which may elicit undesired immune responses and which induce a risk of the vector's integration in the recipient. Also, the vector is replicable, since it contains the E1 gene. Additionally, it is large in size and therefore subject to bacterial modification during preparation.

International Patent Application PCT/EE96/00004 (WO 97/24451) discloses vectors capable of a long-term maintenance in a host cell and methods using such vectors for obtaining long-term production of a gene product of interest in a mammalian host cell, which expresses E1 and E2. These vectors contain a minimal origin of replication of a papilloma virus (MO), a Minichromosome Maintenance Element (MME) of a papilloma virus and a gene encoding said gene product, the MO and MME consisting of a DNA sequence different from the natural papilloma virus sequence, and in some embodiments the E1 gene. Additionally, vectors containing an MME consisting essentially of ten E2 binding sites are disclosed in some examples. These vectors require the presence of the E1 protein either in the host or in the vector for the expression. This imparts the replication function to the vectors. These vectors also express the E1 protein in addition to the gene of interest and the E2 protein and contain sequences, such as rabbit β-globin sequences, which are partially homologous to human sequences causing a serious risk of integration to human genome, which reduces the potential of these vectors as DNA vaccines. Additionally, the vectors are unstable due to their size (ca 15 kb): at the preparation stage in a bacterial cell, the bacterial replication machinery tends to modify the vector by random slicing of the vector, which leads to unsatisfactory expression products including products totally lacking the gene of interest.

International Patent Application PCT/EE96/00004 (WO 97/24451) further discloses that E1 and E2 are the only viral proteins necessary for the episomal long-term replication of the vectors. Additionally, the maintenance function of the BPV1 genome is associated with the presence of minimal ori (MO), which is stated to be necessary, although not sufficient, for the long-term persistence or the stable maintenance of the vectors the cells. In addition, the cis-elements, i.e. the Minichromosome Maintenance Elements of the BPV1, are stated to be required for the stable replication of BPV1. In particular, multimeric E2 binding sites (E2BS) are stated to be necessary for the stable maintenance of the vectors.

There is a clear need for improved novel vectors, which would be useful as DNA vaccines.

An object of the invention is therefore to provide novel vectors, which are capable of a long-term maintenance in a large and increasing number of different cells of the host's body and thereby capable of providing a stable expression of the desired antigen(s).

Another object of the invention is to provide novel vectors, which are maintained for a long period of time in the cells that originally received the vector and transferred it to the daughter cells after mitotic cell division.

Yet another object of the invention is to provide novel vectors, which express in addition to the gene or genes of interest preferably only a gene necessary for a long-term maintenance in the recipient cells and thus are devoid of components that are toxic or cause symptoms of the disease to the recipient.

A further object of the invention is to provide novel vectors, which mimic attenuated live viral vaccines, especially in their function of multiplying in the body, without inducing any considerable signs of disease and without expressing undesired proteins, which may induce adverse reactions in a host injected with the DNA vaccine.

Still a further object of the invention is to provide novel vectors, which do not replicate in the recipient.

Still another object of the invention is to provide novel vectors, which induce both humoral and cellular immune responses when used as DNA vaccines.

Yet another object of the invention is to provide novel vectors, which are suitable for a large-scale production in bacterial cell.

Yet another object of the invention is to provide novel vectors, which are not host specific and thus enable the production in various bacterial cells.

An additional object of the invention is to provide novel vectors, which are useful as carrier vectors for a gene or genes of interest, A further object of the invention is to provide novel vectors, which are useful in gene therapy and as gene therapeutic agents and for the production of macromolecular drugs in vivo.

3. SUMMARY OF THE INVENTION

The present invention discloses novel vectors, which meet the requirements of a carrier vector of a gene or genes of interest or of an optimal DNA vaccination vector and which are preferably devoid of drawbacks and side effects of prior art vectors.

The present invention is based on the surprising finding that a vector (plasmid) carrying (i) an expression cassette of a DNA sequence encoding a nuclear-anchoring protein, and (ii) multiple copies of high affinity binding sites for said nuclear-anchoring protein spreads in proliferating cells. As a result, the number of vector-carrying cells increases even without the replication of the vector. When the vector additionally carries a gene or genes of interest, the number of such cells that express a gene or genes of interest similarly increases without the replication of the vector. Thus, the vector of the invention lacks a papilloma virus origin of replication. In a preferred embodiment, the vector of the invention lacks an origin of replication that functions in a mammalian cell.

Accordingly, the present invention discloses novel vectors useful as carrier vectors of a gene or genes of interest, in DNA vaccination and gene therapy and as gene therapeutic agents. In a specific embodiment, said vectors are capable of spreading and, if desired, of expressing a gene or genes of interest in an increasing number of cells for an extended time. The vectors of the present invention preferably express only a nuclear-anchoring protein, and, if desired, the gene or genes of interest, and optionally a selectable marker. However, they preferably lack any redundant, oncogenically transforming or potentially toxic sequences, thereby avoiding a severe drawback of the vectors previously disclosed or suggested for use as DNA vaccines, i.e. hypersensitivity reactions against other viral components. In certain embodiments of the invention, this is achieved by low level of the expressed nuclear-anchoring protein in the cells. At the same time, the vectors of the present invention induce both humoral and cellular immune responses, where the gene or genes of interest is included in the vector.

The vectors of the present invention are advantageous for use both in vitro (e.g., in the production level) and in vivo (e.g., vaccination).

The present invention relates to the subject matter of the invention as set forth in the attached claims.

The present invention relates to expression vectors comprising: (a) a DNA sequence encoding a nuclear-anchoring protein operatively linked to a heterologous promoter, said nuclear-anchoring protein comprising (i) a DNA binding domain which binds to a specific DNA sequence, and (ii) a functional domain that binds to a nuclear component, or a functional equivalent thereof; and (b) a multimerized DNA sequence forming a binding site for the nuclear anchoring protein, wherein said vector lacks a papilloma virus origin of replication. In a preferred embodiment a vector of the invention lacks an origin of replication functional in a mammalian cell.

In certain embodiments, the nuclear component is mitotic chromatin, the nuclear matrix, nuclear domain 10 (ND10), or nuclear domain POD.

In certain specific embodiments, the nuclear anchoring-protein is a chromatin-anchoring protein, and said functional domain binds mitotic chromatin.

In certain embodiments, the nuclear-anchoring protein contains a hinge or linker region.

In certain embodiments, the nuclear-anchoring protein is a natural protein of eukaryotic, prokaryotic, or viral origin. In certain specific embodiments, the natural protein is of viral origin.

In certain embodiments, the nuclear-anchoring protein is a natural protein of eukaryotic origin.

In certain embodiments, the nuclear-anchoring protein is that of a papilloma virus or an Epstein-Barr virus.

In specific embodiments, the nuclear-anchoring protein is the E2 protein of Bovine Papilloma Virus type 1 or Epstein-Barr Virus Nuclear Antigen 1.

In a specific embodiment, the nuclear-anchoring protein is the E2 protein of Bovine Papilloma Virus type 1.

In specific embodiments, the nuclear-anchoring protein is a High Mobility Group protein.

In certain embodiments, the nuclear-anchoring protein is a non-natural protein.

In certain embodiments, the nuclear-anchoring protein is a recombinant protein, a fusion protein, or a protein obtained by molecular modeling techniques.

In specific embodiments, the recombinant protein, fusion protein, or protein obtained by molecular modeling techniques contains any combination of a DNA binding domain which binds to said specific DNA sequence and a functional domain which binds to a nuclear component, wherein said functional domain which binds to a nuclear component is that of a papilloma virus, an Epstein-Barr-Virus, or a High Mobility Group protein.

In certain specific embodiments, the recombinant protein, fusion protein, or protein obtained by molecular modeling techniques contains any combination of a DNA binding domain which binds to said specific DNA sequence and a functional domain which binds to a nuclear component, wherein said functional domain which binds to a nuclear component is that of E2 protein of Bovine Papilloma Virus type 1, Epstein-Barr Virus Nuclear Antigen 1, or a High Mobility Group protein.

In certain embodiments, the vector further comprises one or more expression cassettes of a DNA sequence of interest.

In certain embodiments, the DNA sequence of interest is that of an infectious pathogen. In certain embodiments, the infectious pathogen is a virus. In certain specific embodiments, the virus is selected from the group consisting of Human Immunodeficiency Virus (HIV), Herpex Simplex Virus (HSV), Hepatitis C Virus, Influenzae Virus, and Enterovirus.

In certain embodiments, the DNA sequence of interest is that of a bacterium. In certain embodiments, the bacterium is selected from the group consisting of *Chlamydia trachomatis*, *Mycobacterium tuberculosis*, and *Mycoplasma pneumonia*. In a specific embodiment, the bacterium is Salmonella.

In certain embodiments, the DNA sequence of interest is that of a fungal pathogen. In certain embodiments, the fungal pathogen is *Candida albigans*.

In certain embodiments, the DNA sequence of interest is of HIV origin.

In specific embodiments, the DNA sequence of interest encodes a non-structural regulatory protein of HIV. In more specific embodiments, the non-structural regulatory protein of HIV is Nef, Tat or Rev. In a specific embodiment, the non-structural regulatory protein of HIV is Nef.

In certain embodiments, the DNA sequence of interest encodes a structural protein of HIV. In a specific embodiment, the DNA sequence of interest is the gene encoding HIV gp120/gp160.

In certain embodiments, the vector of the invention comprises a first expression cassette comprising a DNA sequence of interest which encodes Nef, Tat or Rev, and a second expression cassette comprising a DNA sequence of interest which encodes Nef, Tat or Rev.

In certain embodiments, the vector of the invention comprises a first expression cassette comprising a DNA sequence of interest which encodes Nef, Tat or Rev, and a second expression cassette comprising a DNA sequence of interest which encodes a structural protein of HIV.

In certain embodiments, the DNA sequence of interest encodes a protein associated with cancer.

In certain embodiments, the DNA sequence of interest encodes a protein associated with immune maturation, regulation of immune responses, or regulation of autoimmune responses. In a specific embodiment, the protein is APECED.

In a specific embodiment, the DNA sequence of interest is the Aire gene.

In certain embodiments, the DNA sequence of interest encodes a protein that is defective in any hereditary single gene disease.

In certain embodiments, the DNA sequence of interest encodes a macromolecular drug.

In certain embodiments, the DNA sequence of interest encodes a cytokine. In certain specific embodiments, the cytokine is an interleukin selected from the group consisting of IL1, IL2, IL4, IL6 and IL12. In certain other specific embodiments, the DNA sequence of interest encodes an interferon.

In certain embodiments, the DNA sequence of interest encodes a biologically active RNA molecule. In certain specific embodiments, the biologically active RNA molecule is selected from the group consisting of inhibitory antisense and ribozyme molecules. In certain specific embodiments, the inhibitory antisense or ribozyme molecules antagonize the function of an oncogene.

A vector of the invention for the use for production of a therapeutic macromolecular agent in vivo.

In certain embodiments, the invention provides a vector for use as a medicament.

In certain embodiments, the invention provides a vector for use as a carrier vector for a gene, genes, or a DNA sequence or DNA sequences of interest, such as a gene, genes, or a DNA sequence or DNA sequences encoding a protein or peptide of an infectious agent, a therapeutic agent, a macromolecular drug, or any combination thereof.

In certain specific embodiments, the invention provides a vector for use as a medicament for treating inherited or acquired genetic defects.

In certain embodiments, the invention provides a vector for use as a therapeutic DNA vaccine against an infectious agent.

In certain embodiments, the invention provides a vector for use as a therapeutic agent.

The invention further relates to methods for providing a protein to a subject, said method comprising administering to the subject a vector of the invention, wherein said vector (i) further comprises a second DNA sequence encoding the protein to be provided to the subject, which second DNA sequence is operably linked to a second promoter, and (ii) does not encode Bovine Papilloma Virus protein E1, and wherein said subject does not express Bovine Papilloma Virus protein E1.

The invention further relates to methods for inducing an immune response to a protein in a subject, said method comprising administering to the subject a vector of the invention wherein said vector (i) further comprises a second DNA sequence encoding said protein, which second DNA sequence is operably linked to a second promoter, and (ii) does not encode Bovine Papilloma Virus protein E1, and wherein said subject does not express Bovine Papilloma Virus protein E1.

The invention further relates to methods for treating an infectious disease in a subject in need of said treatment, said method comprising administering to said subject a therapeutically effective amount of a vector of the invention, wherein the DNA sequence of interest encodes a protein comprising an immunogenic epitope of an infectious agent.

The invention further relates to methods for treating an inherited or acquired genetic defect in a subject in need of said treatment, said method comprising: administering to said subject a therapeutically effective amount of a vector of the invention, wherein said DNA sequence of interest encodes a protein which is affected by said inherited or acquired genetic defect.

The invention further relates to methods for expressing a DNA sequence in a subject, said method comprising administering a vector of the invention to said subject.

The invention further relates to methods for expressing a DNA sequence in a subject, treating an inherited or acquired genetic defect, treating an infectious disease, inducing an immune-response to a protein, and providing a protein to a subject, wherein the vector of the invention does not encode Bovine Papilloma Virus protein E1, and wherein said subject does not express Bovine Papilloma Virus protein E1.

In certain embodiments, a vector of the invention is used for production of a protein encoded by said DNA sequence of interest in a cell or an organism.

The invention further provides a method for the preparation of a vector of claim 1, 2, or 17 comprising: (a) cultivating a host cell containing said vector and (b) recovering the vector. In a specific embodiment, the method for preparing a vector of the invention further comprises before step (a) a step of transforming said host cell with said vector. In certain specific embodiments, the host cell is a prokaryotic cell. In a specific embodiment, the host cell is an *Escherichia coli*.

The invention further relates to a host cell that is characterized by containing a vector of the invention. In certain embodiments, the host cell is a bacterial cell. In a certain other embodiments, the host cell is a mammalian cell.

The invention further relates to carrier vectors containing a vector of the invention.

The invention further relates to a pharmaceutical composition comprising a vector of the invention and a suitable pharmaceutical vehicle.

The invention further relates to a DNA vaccine containing a vector of the invention.

The invention further relates to a gene therapeutic agent containig a vector of the invention.

The invention further relates to a method for the preparation of a DNA vaccine, said method comprising combining a vector of the invention with a suitable pharmaceutical vehicle.

The invention further relates to a method for the preparation of an agent for use in gene therapy, said method comprising combining a vector of the invention with a suitable pharmaceutical vehicle.

4. DESCRIPTION OF THE FIGURES

Figure 26:
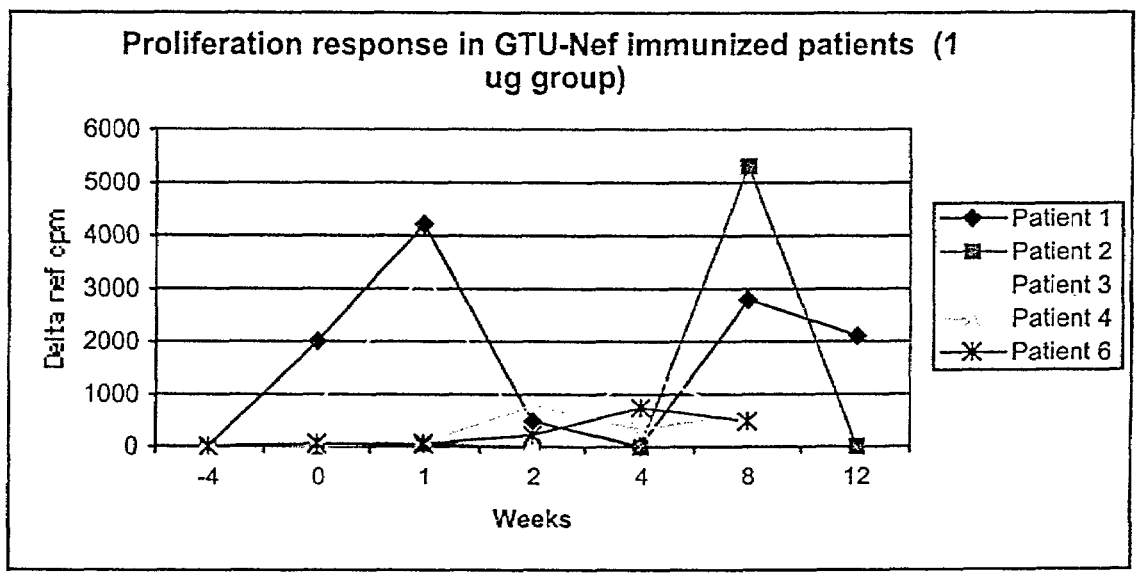

FIG. 26. T-cell responses towards recombinant Nef proteins (5 micrograms/well), measured by T-cell proliferation in five patients immunized with 1 microgram of GTU-Nef.

Figure 27:
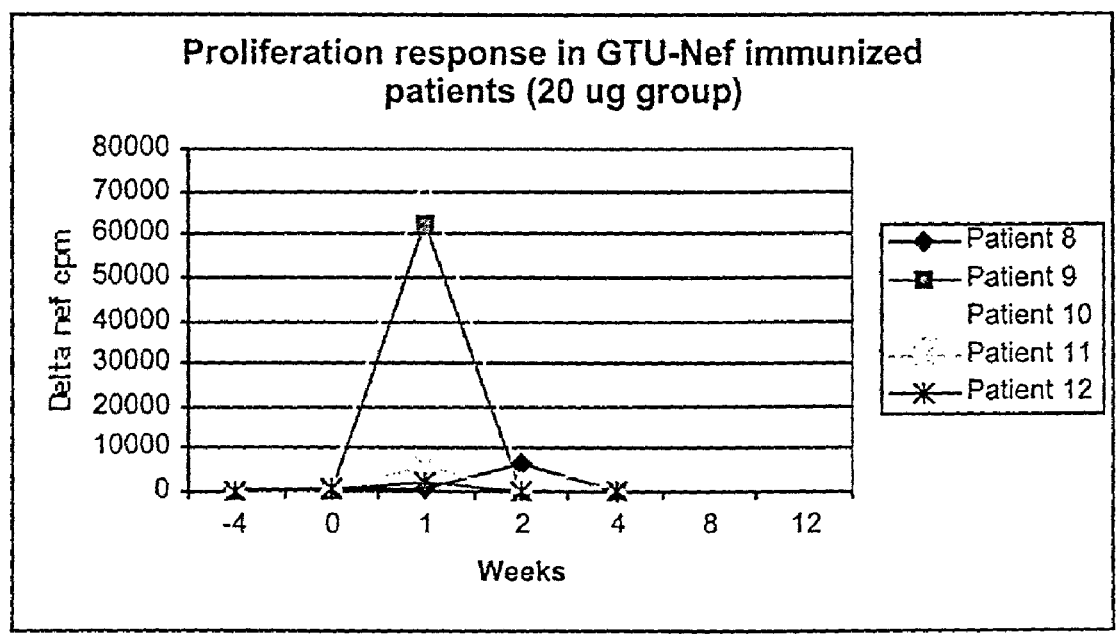

FIG. 27. T-cell responses towards recombinant Nef proteins (5 micrograms/well), measured by T-cell proliferation in five patients immunized with 20 micrograms of GTU-Nef.

Figure 28:
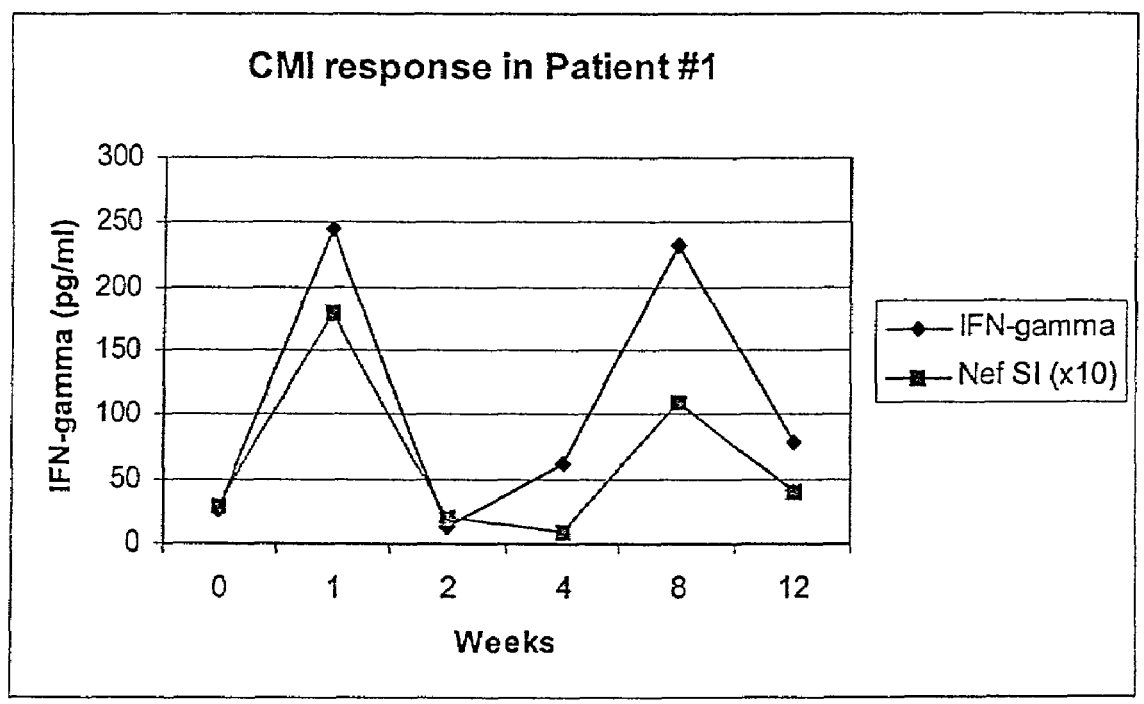

FIG. 28. T-cell responses towards recombinant Nef proteins (5 micrograms/well), measured by T-cell proliferation in patient #1 immunized with 1 microgram of GTU-Nef. The results are given as stimulation index of the T-cell proliferation assay (Nef SI) and as IFN-Gamma secretion to the supernatant.

Figure 29A:
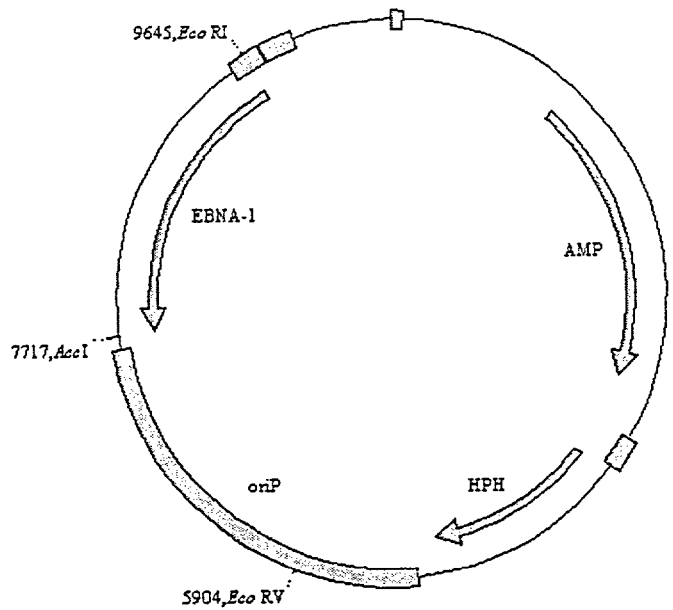
Figure 29B:
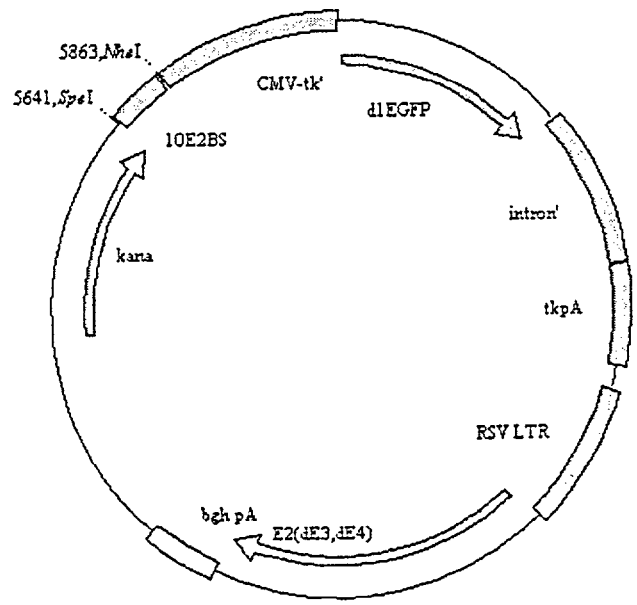
Figure 29C:
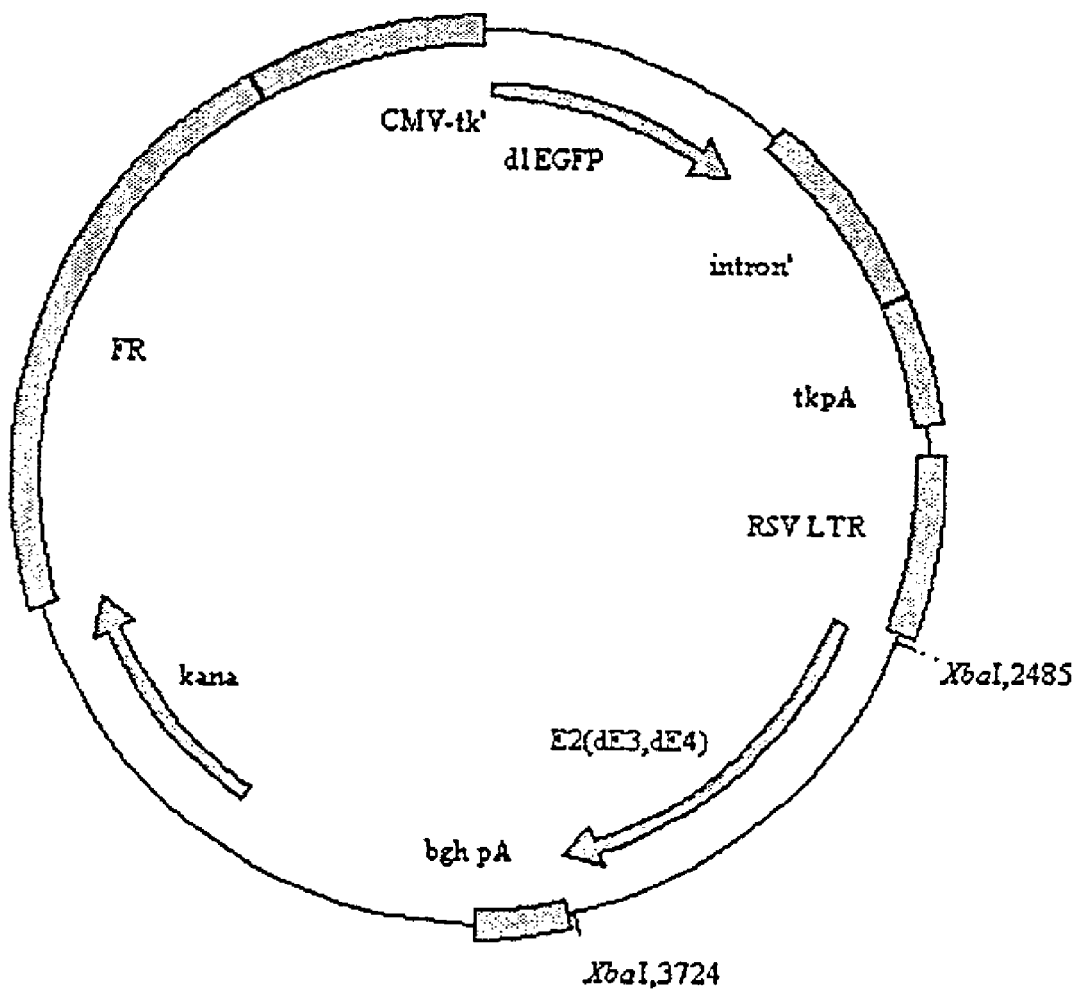

FIG. 29. (A) plasmid pEBO LPP; (B) plasmid s6E2d1EGFP; (C) plasmid FRE2d1EGFP

Figure 30:
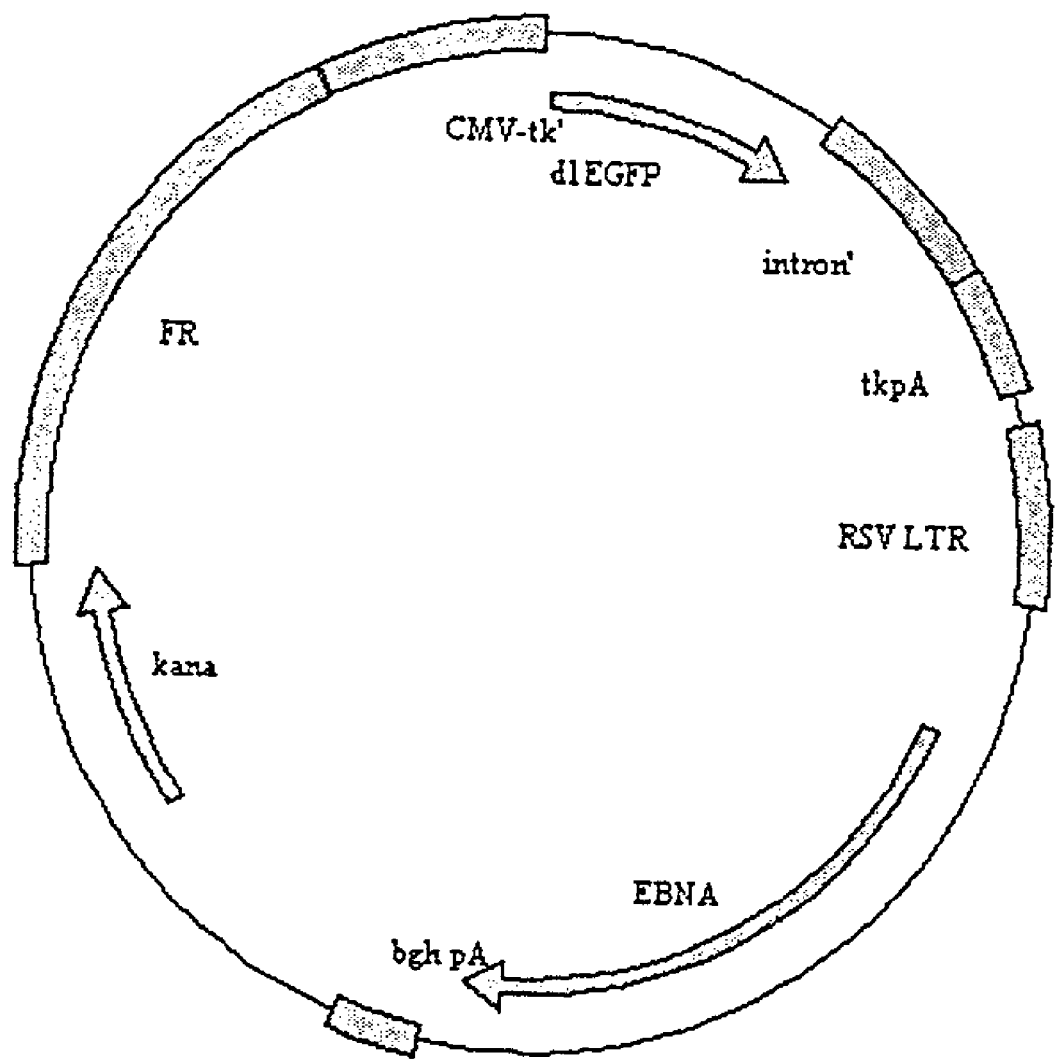

FIG. 30. Plasmid FREBNAd1EGFP

Figure 31:
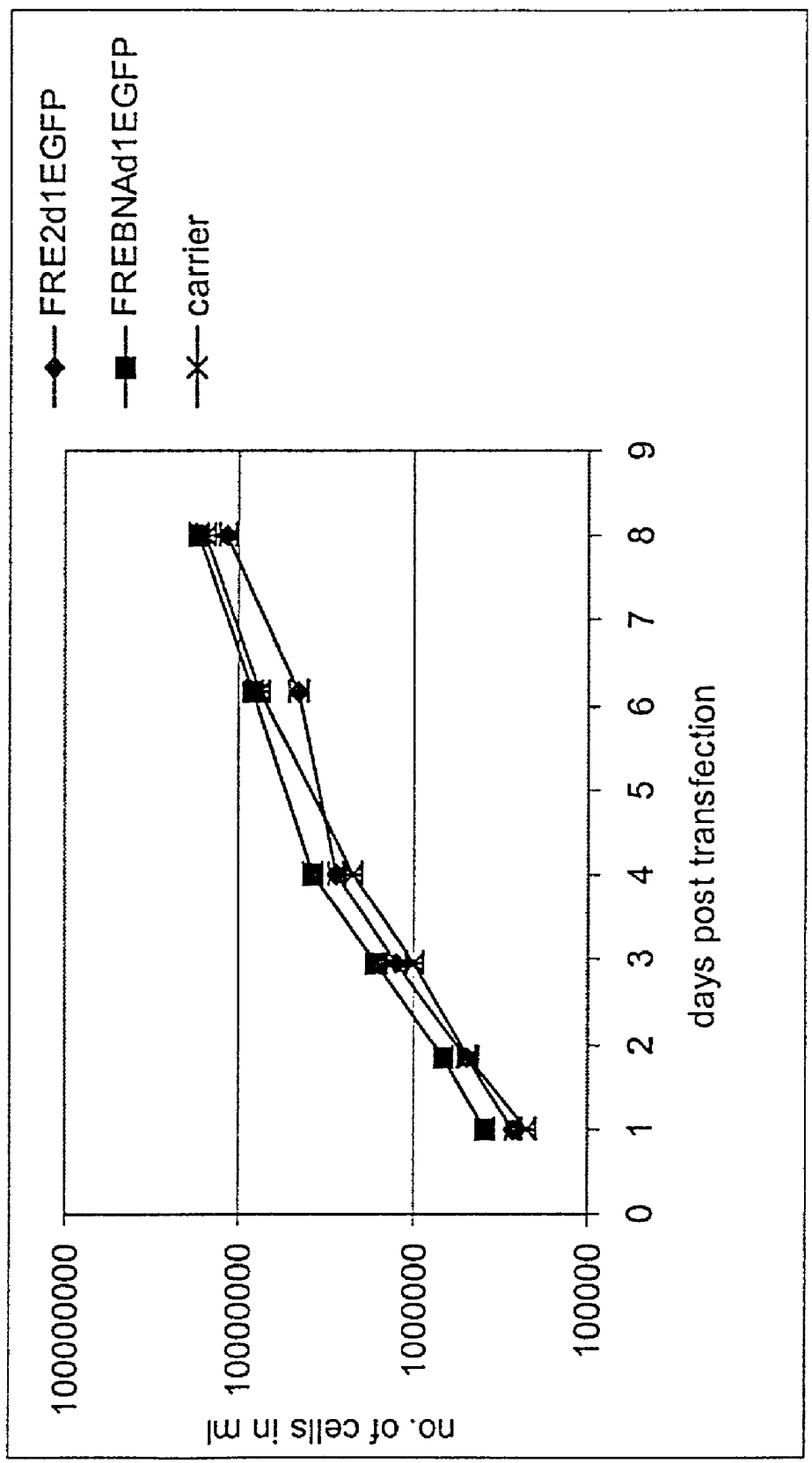

FIG. 31. Vectors did not interfere with cell proliferation

Figure 32:
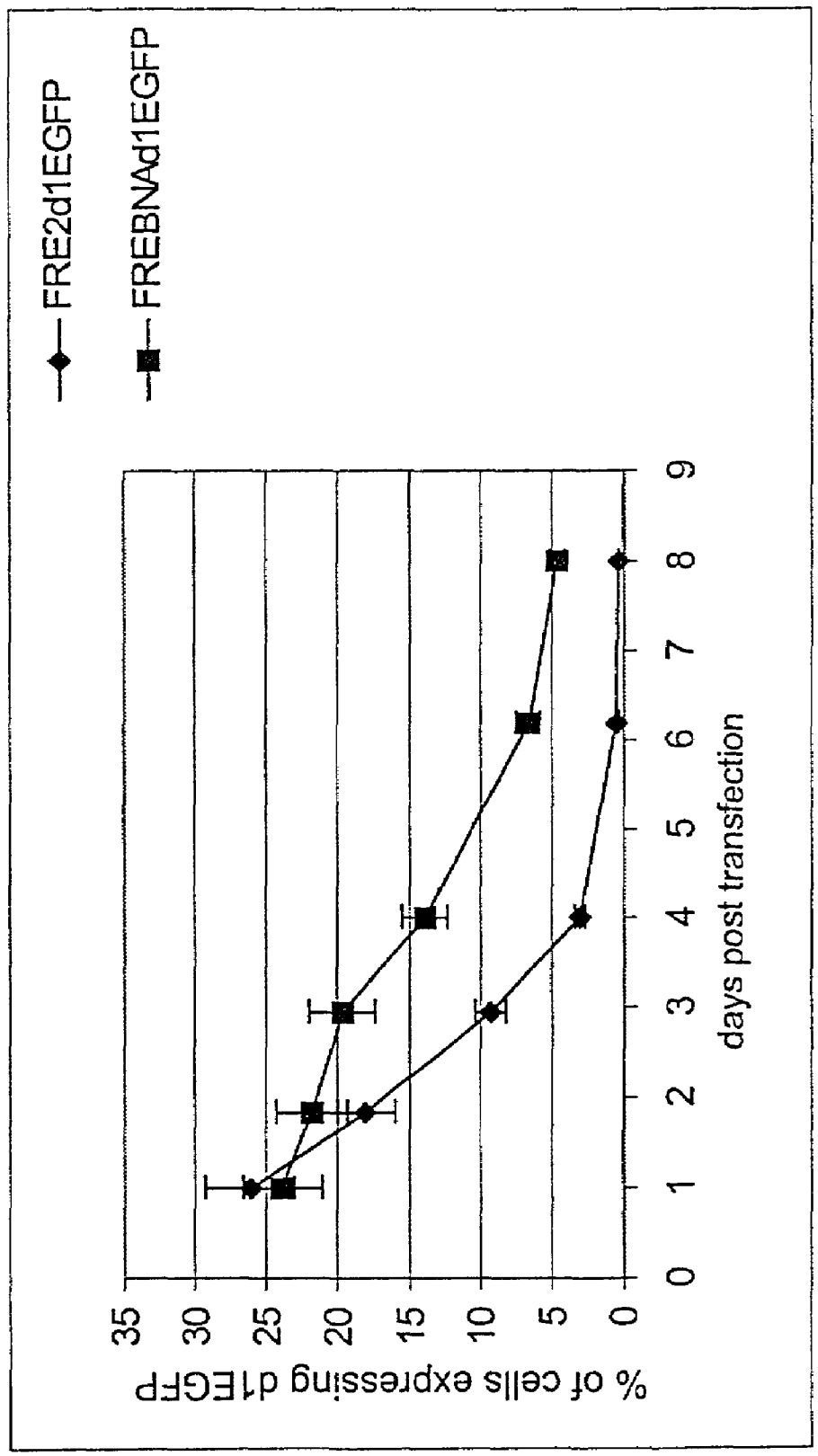

FIG. 32. Vectors were maintained in the cells with different kinetics

Figure 33:
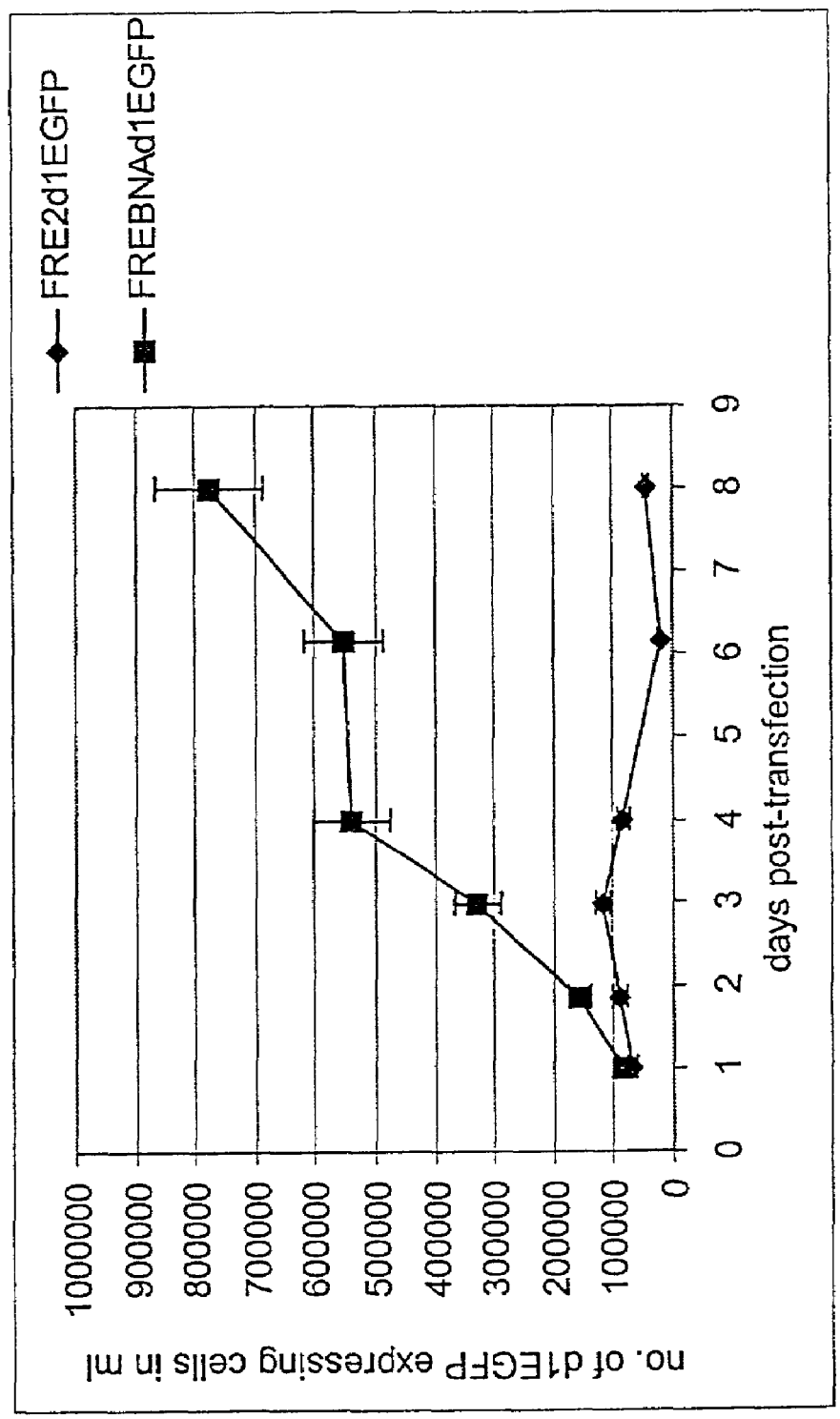

FIG. 33. Change of the number of d1EGFP expressing cells in time in transfected total population of cells FIG. 34. The identical results were obtained also in (A) human embryonic cell line 293; and (B) mouse cell line 3T6

Figure 35:
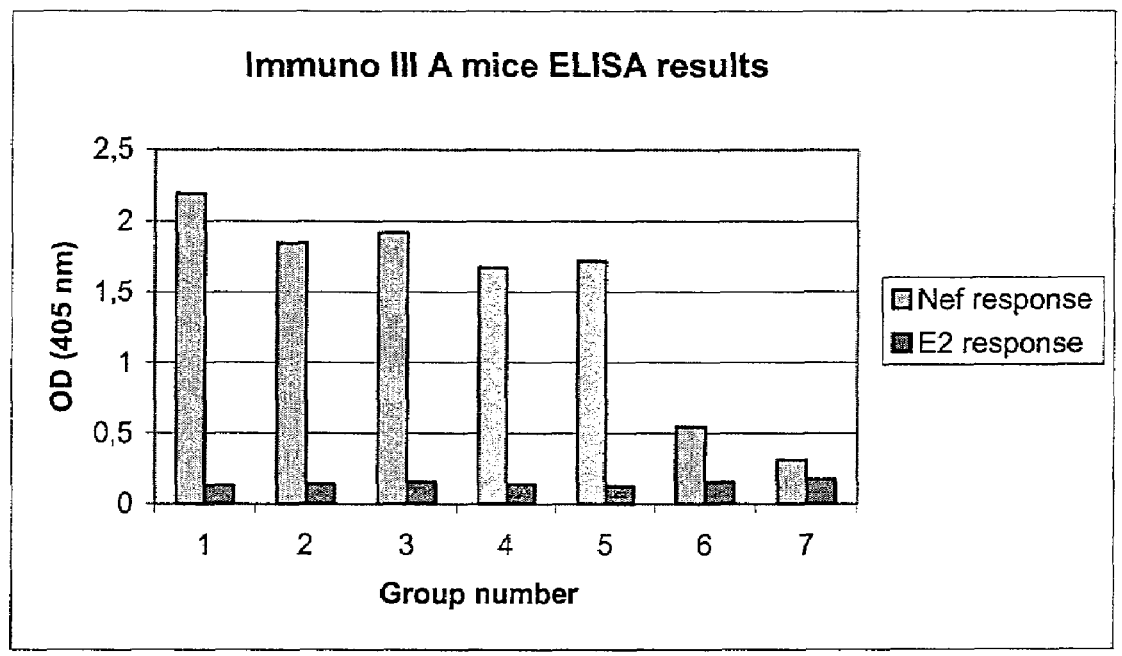

FIG. 35. Nef and E2 antibody response

Figure 36:
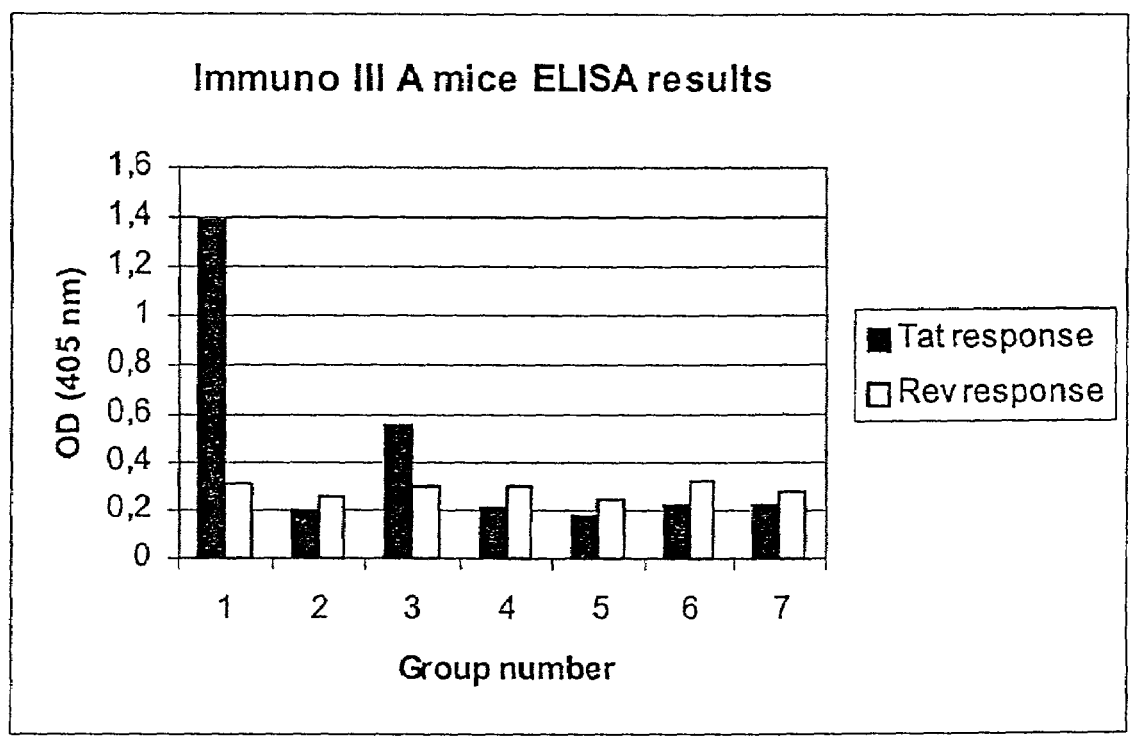

FIG. 36. Rev and Tat antibody response

Figure 37:
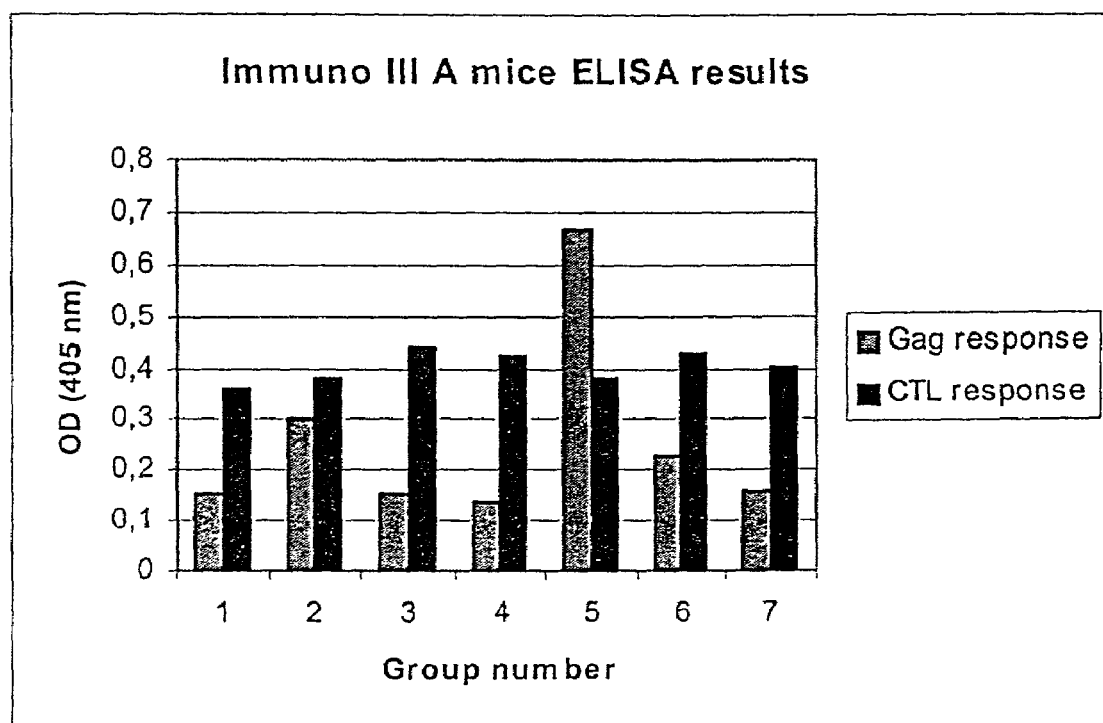
Figure 38A:
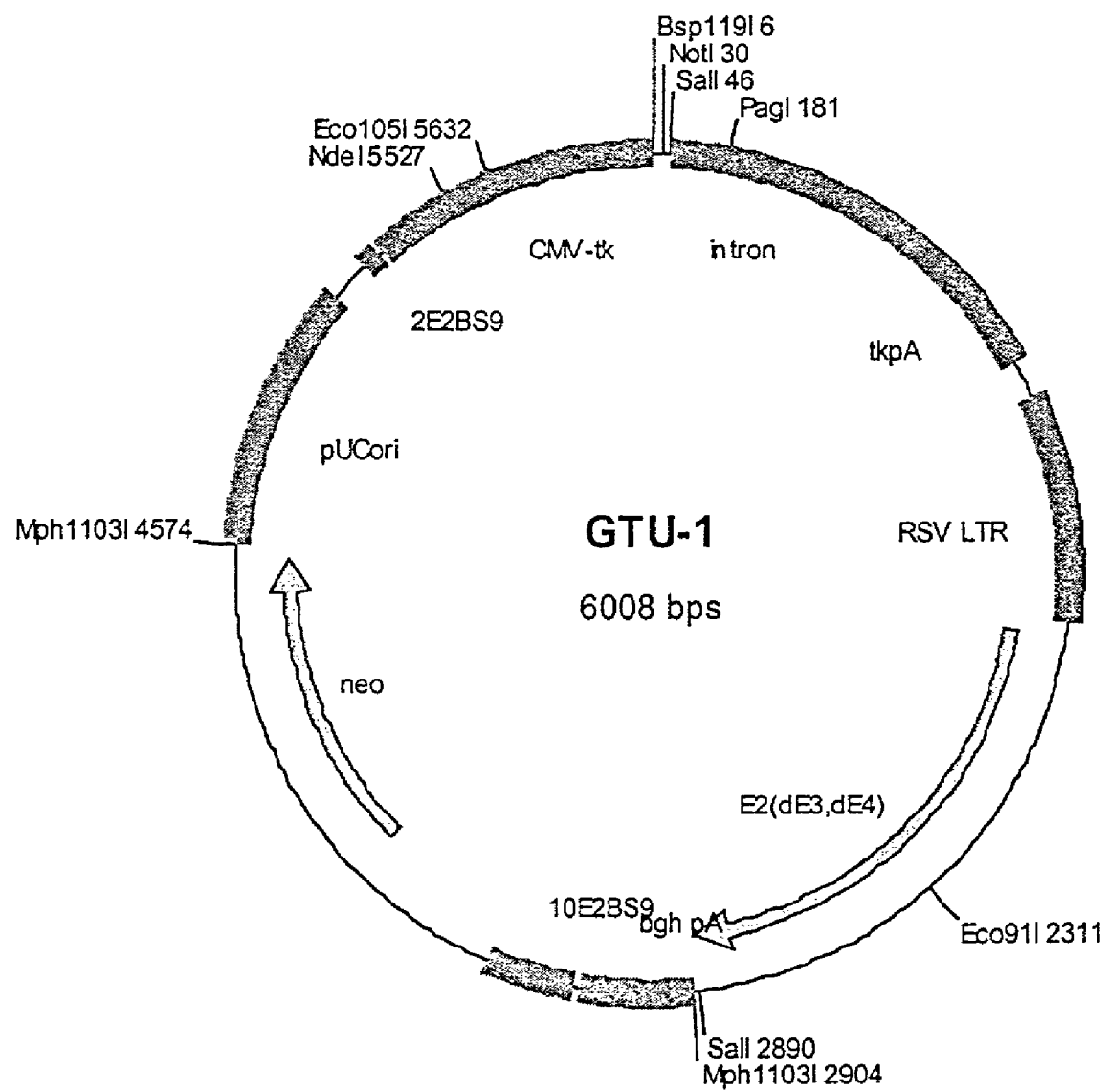
Figure 38B:
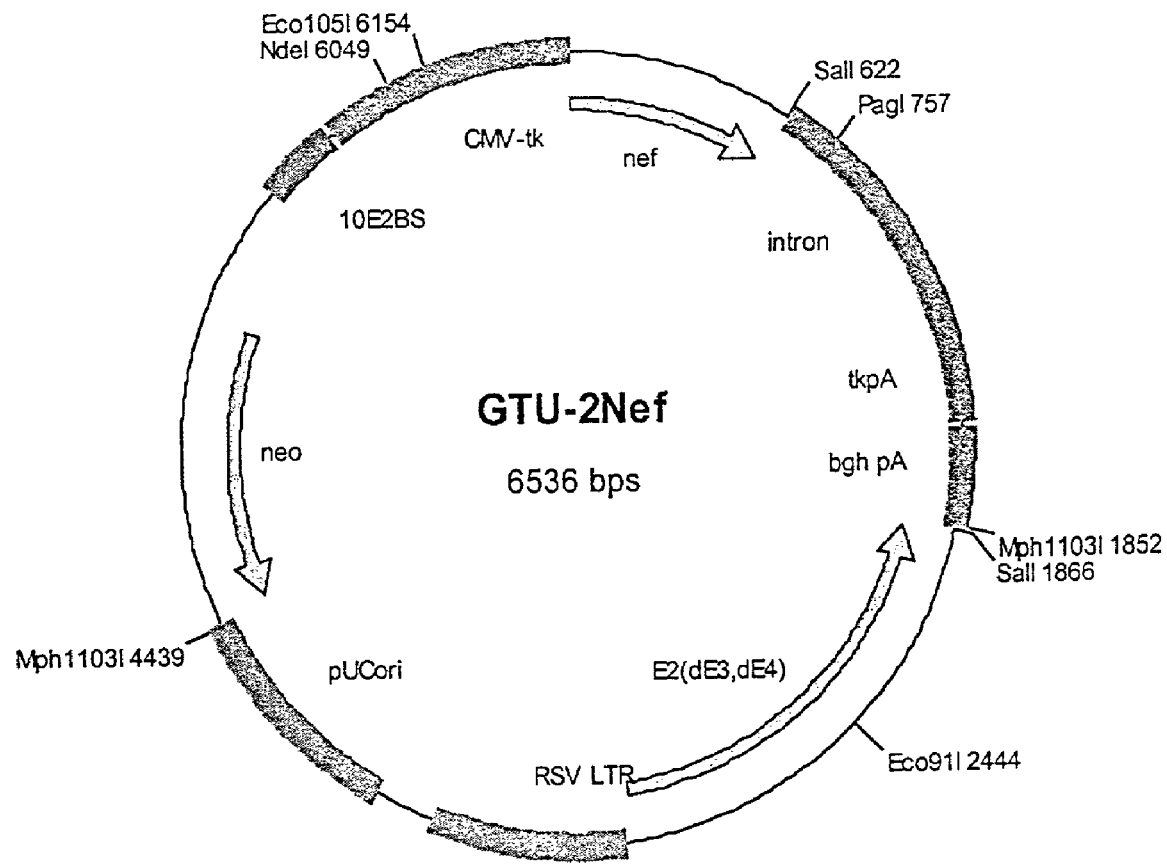
Figure 38C:
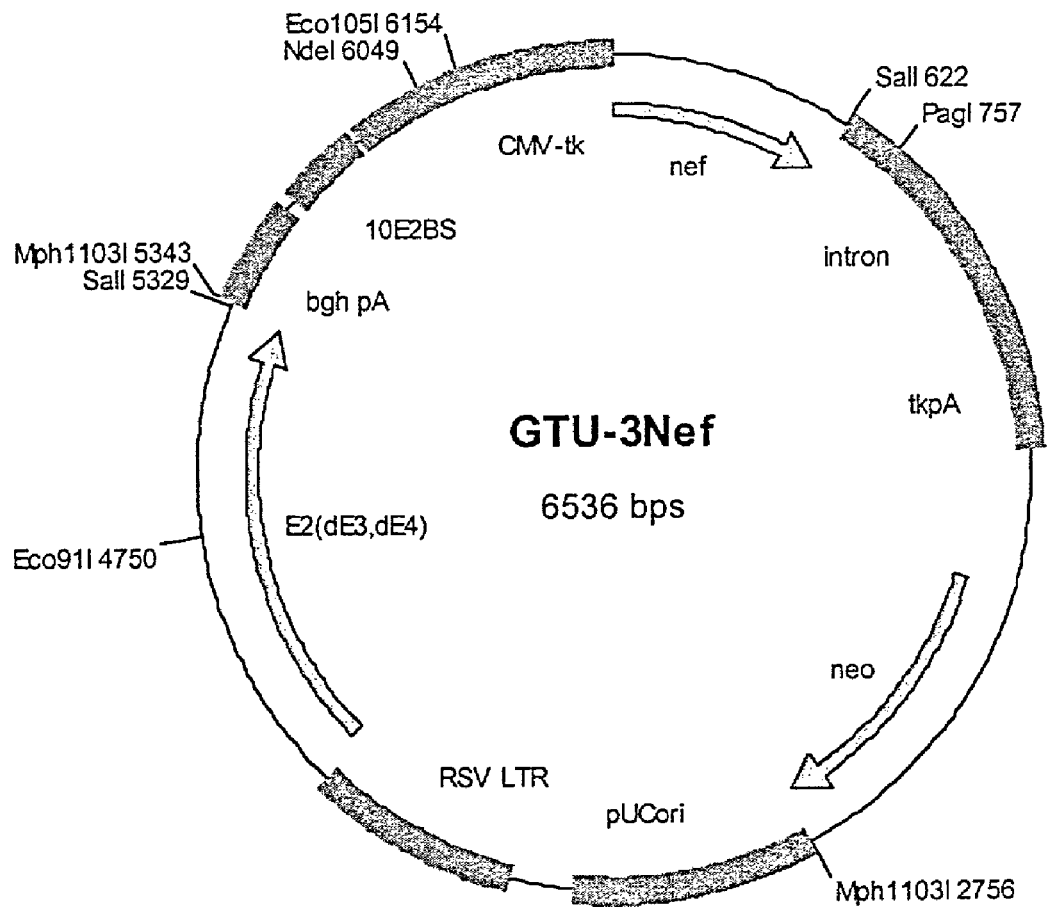
Figure 38D:
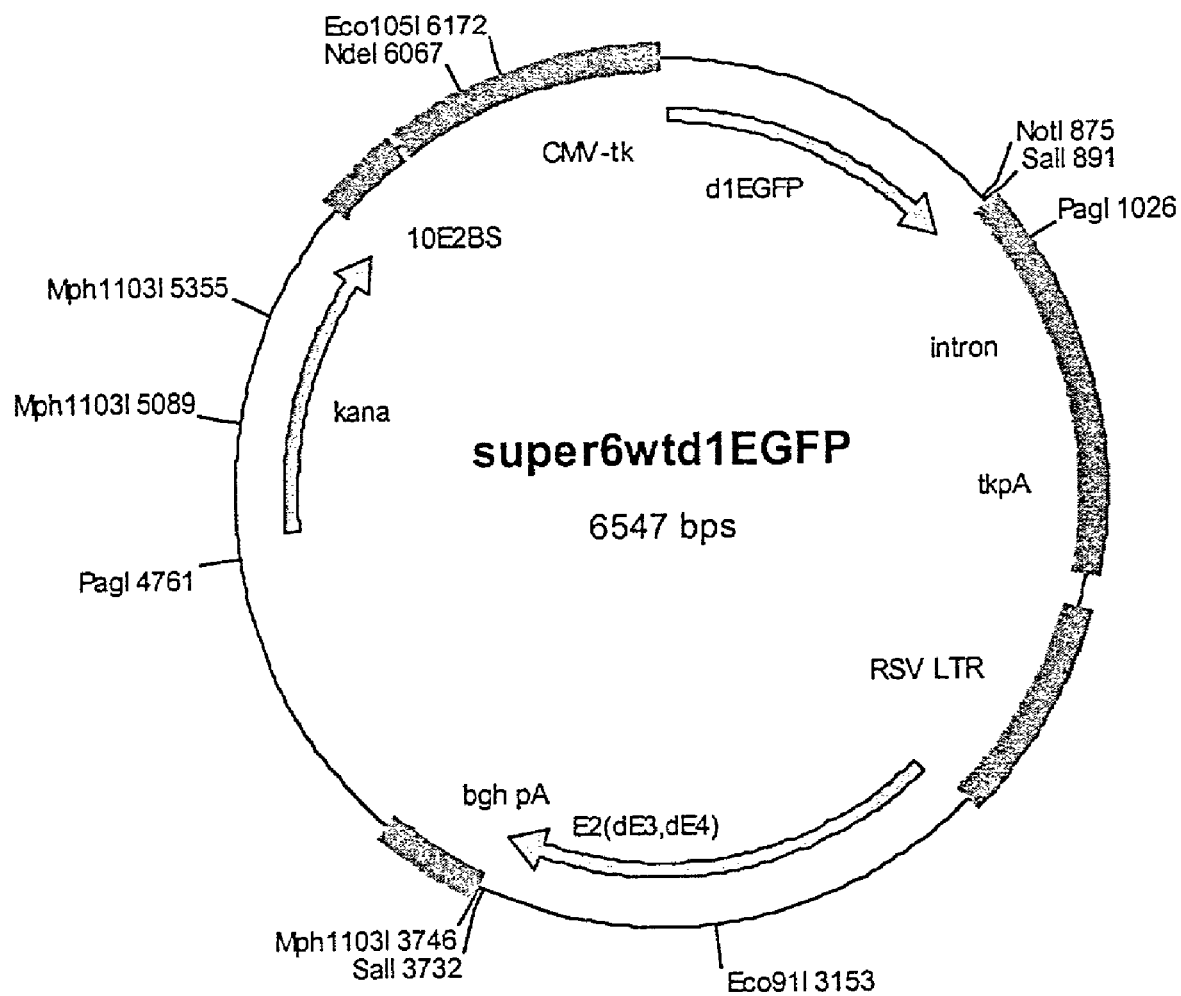
Figure 38E:
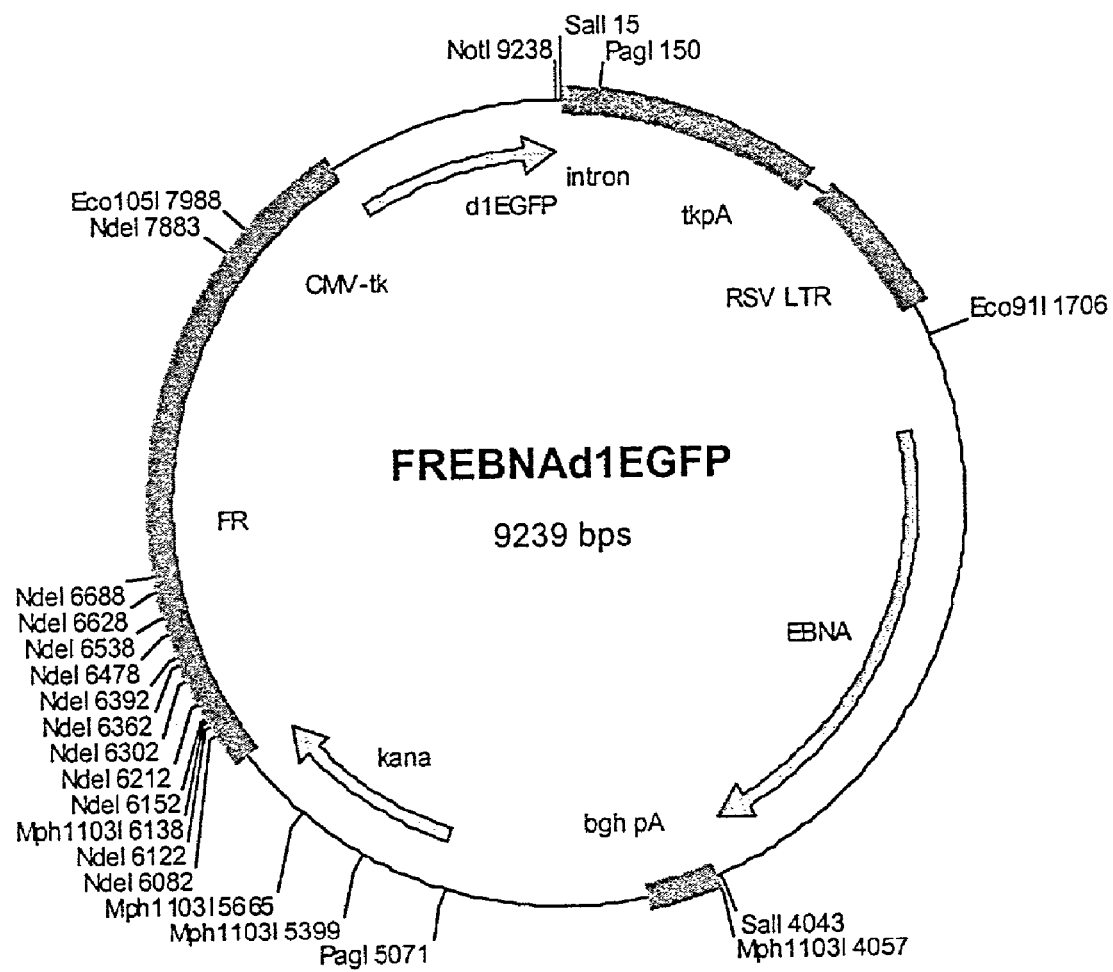
Figure 38F:
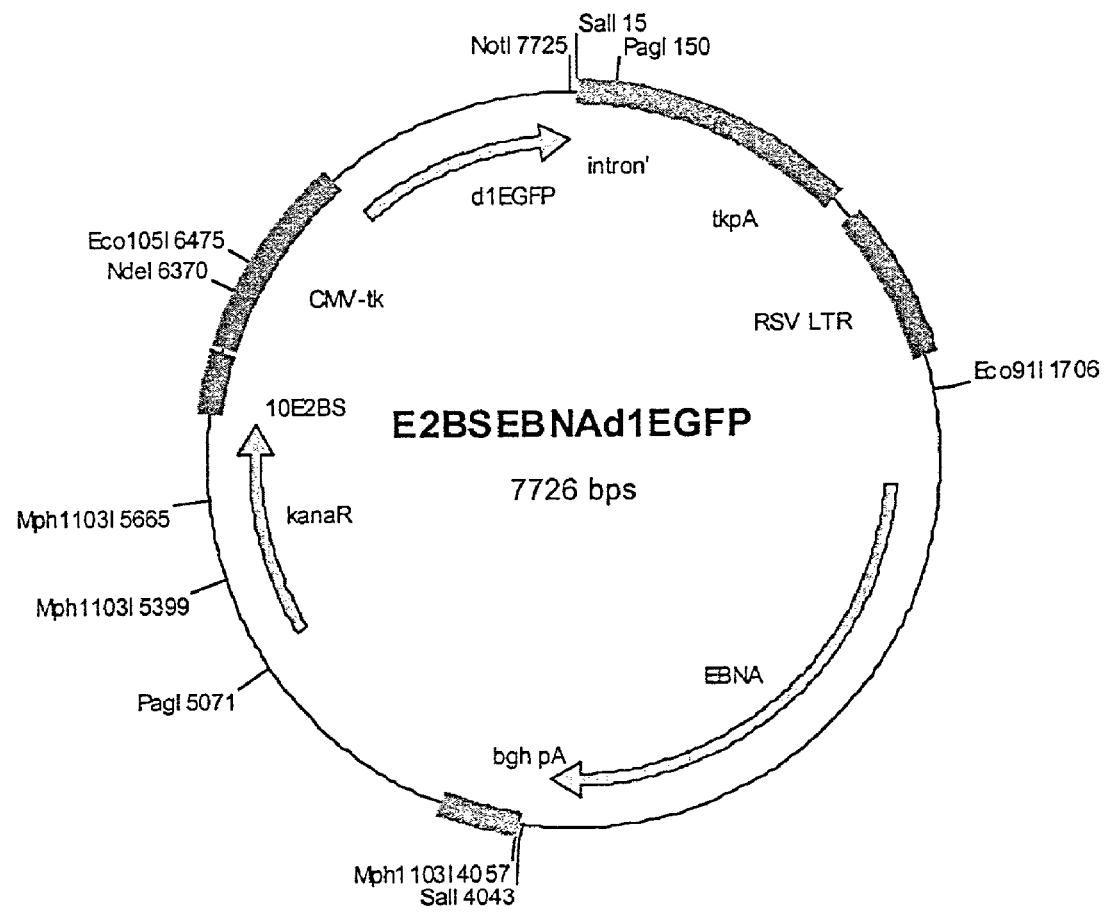
Figure 38G:
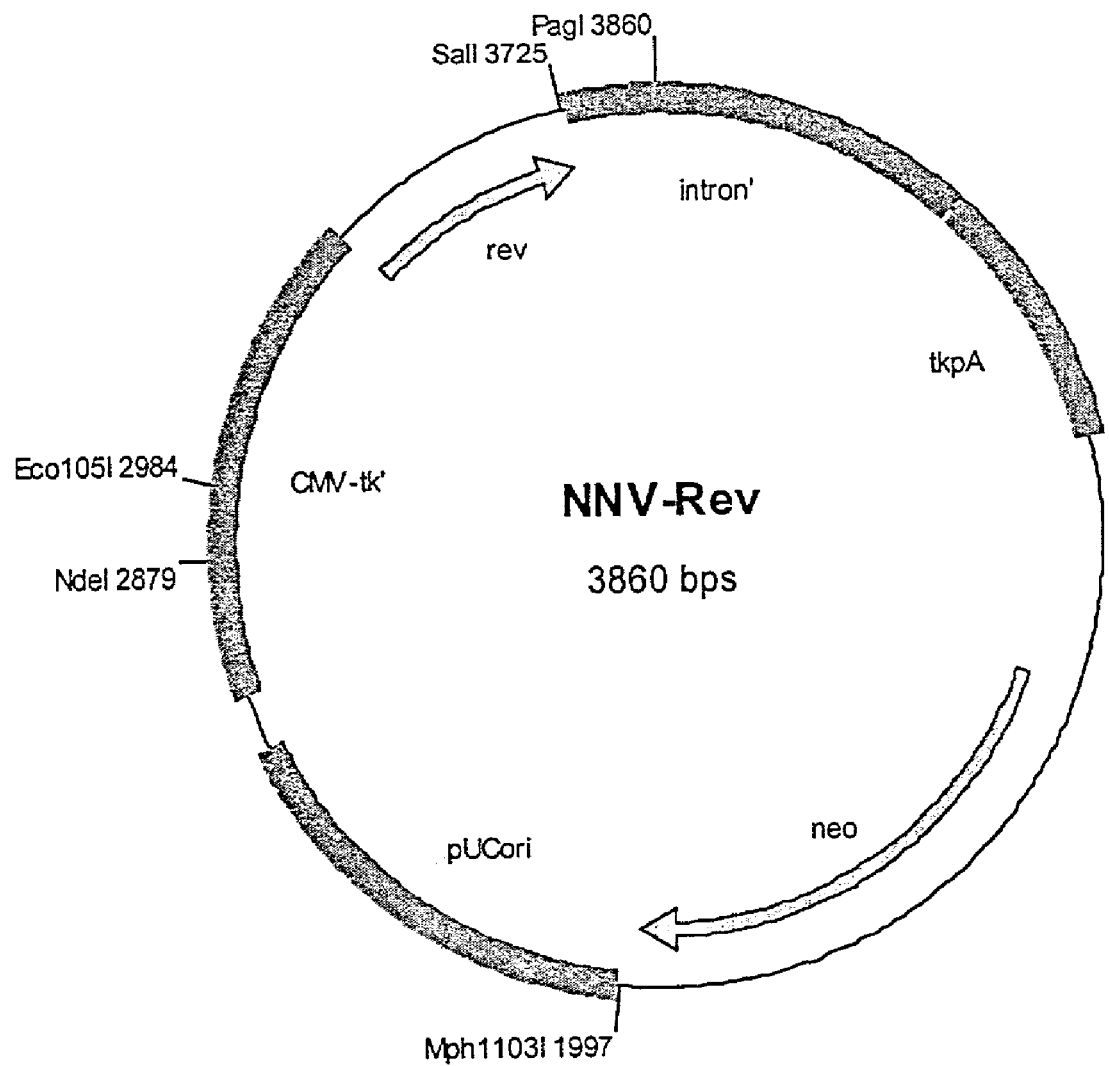

FIG. 37. Gag and CTL response

Figure 39A:
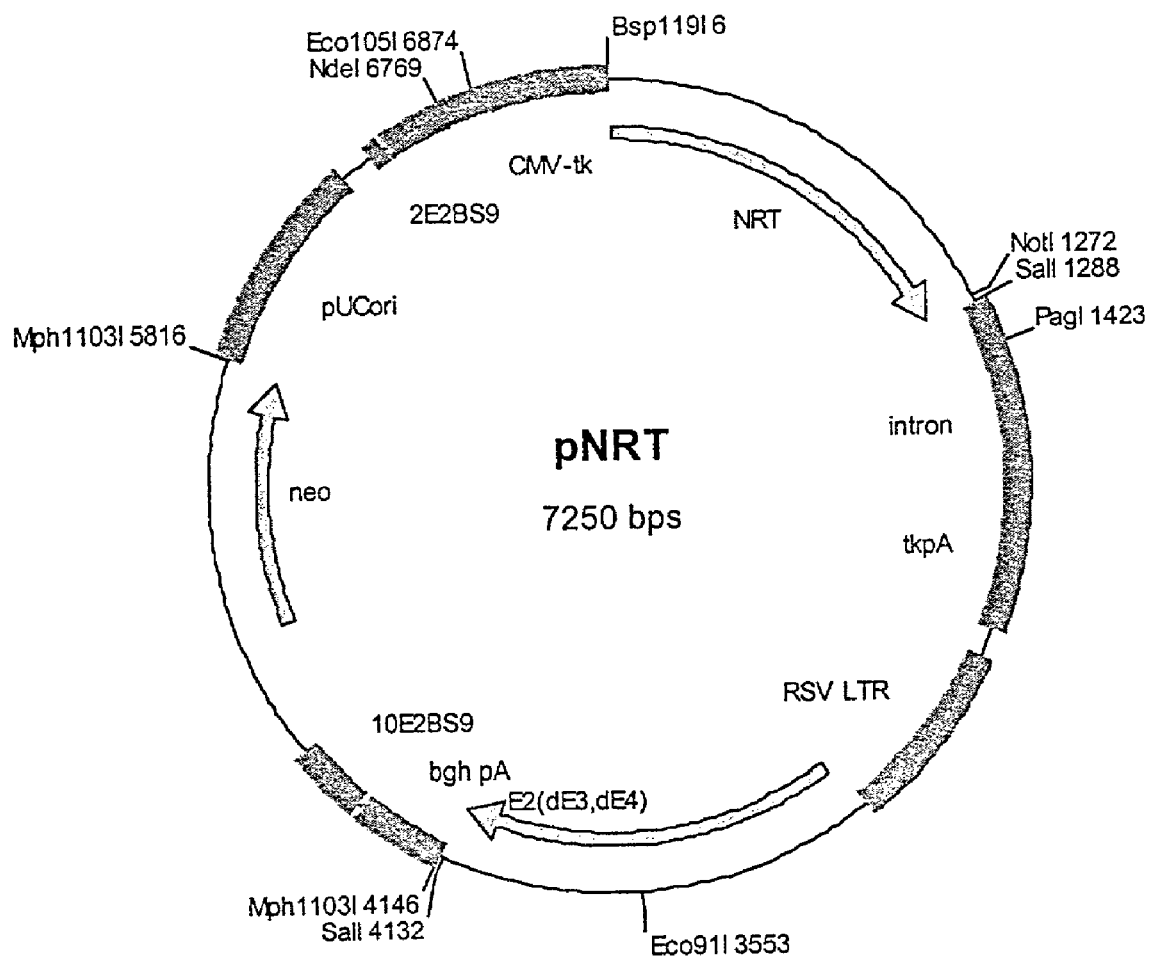
Figure 39B:
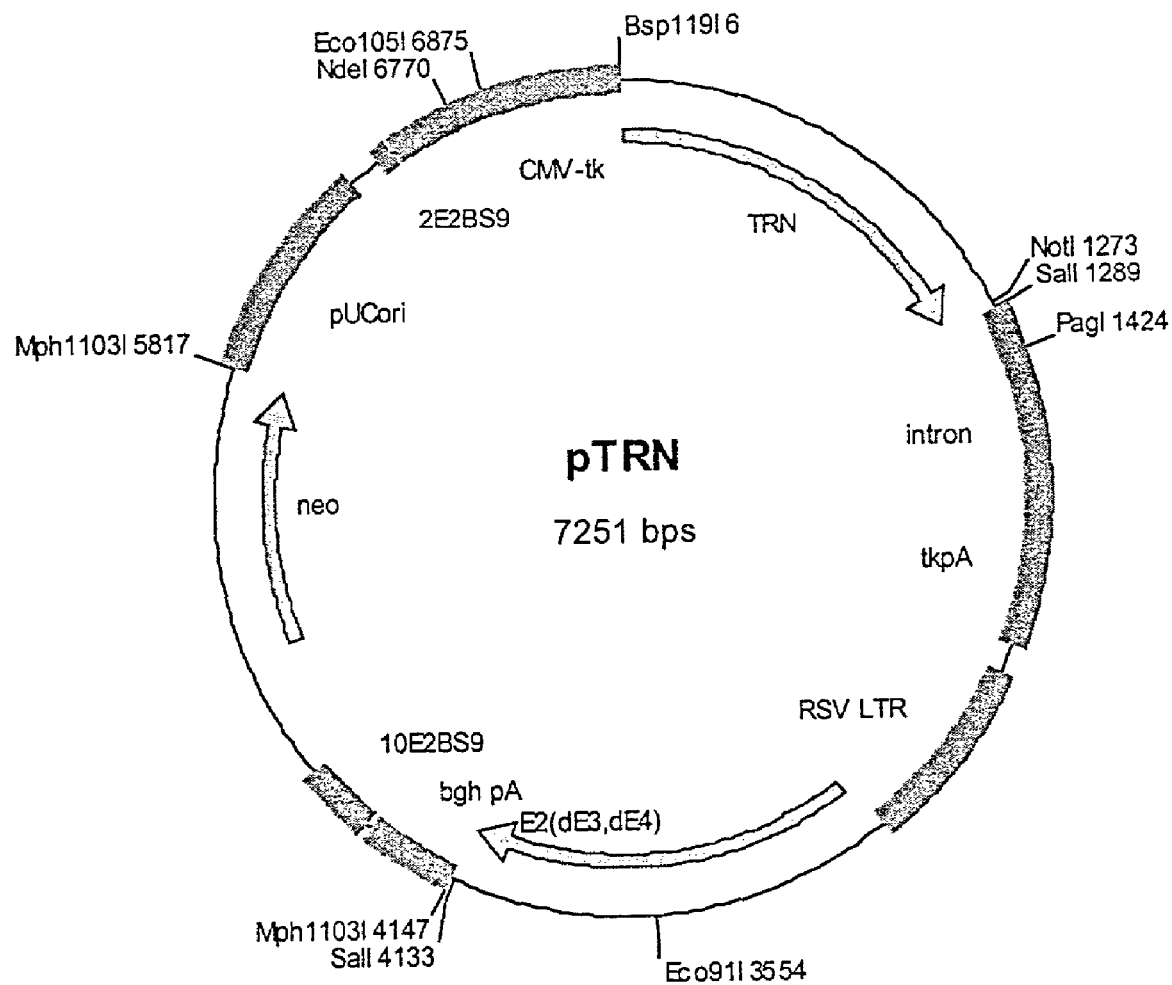
Figure 39C:
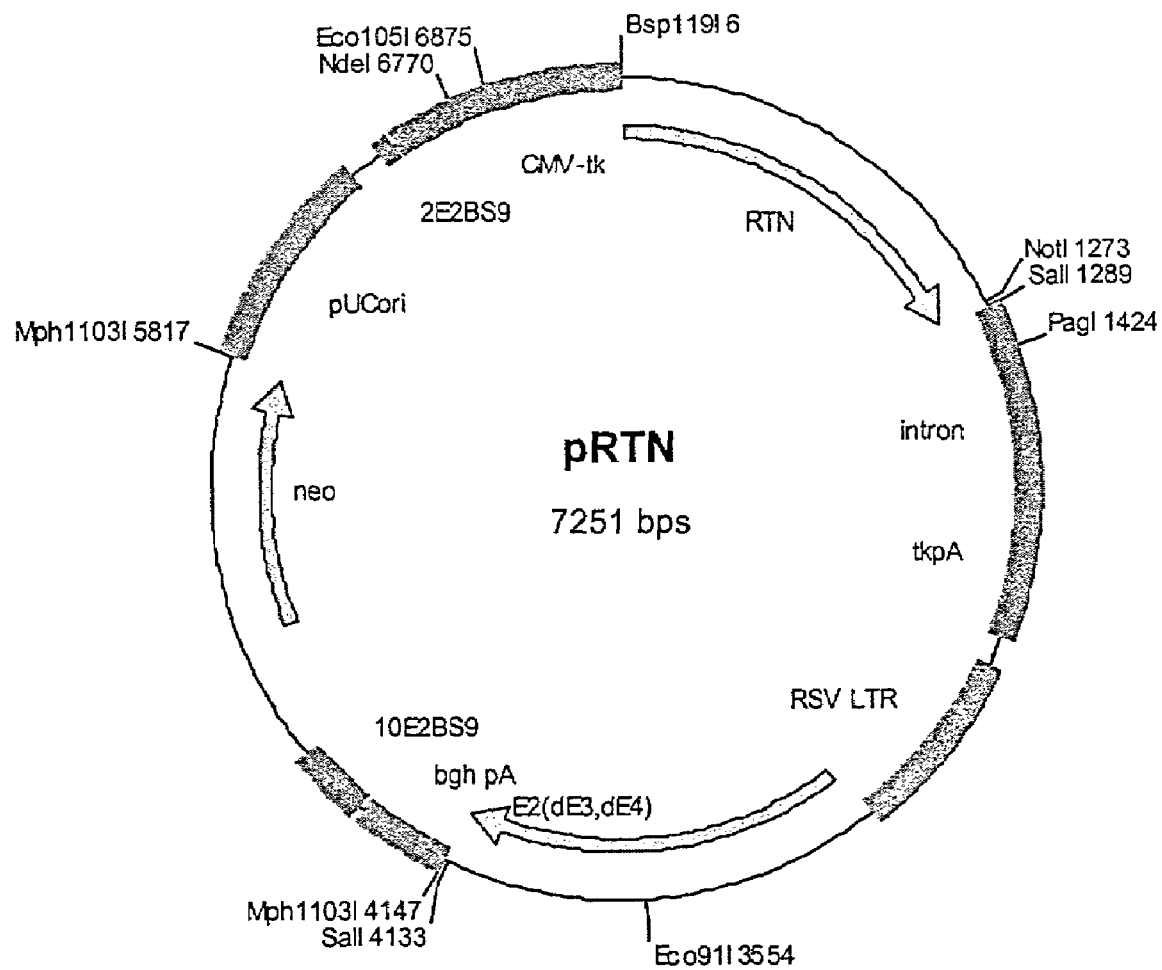
Figure 39D:
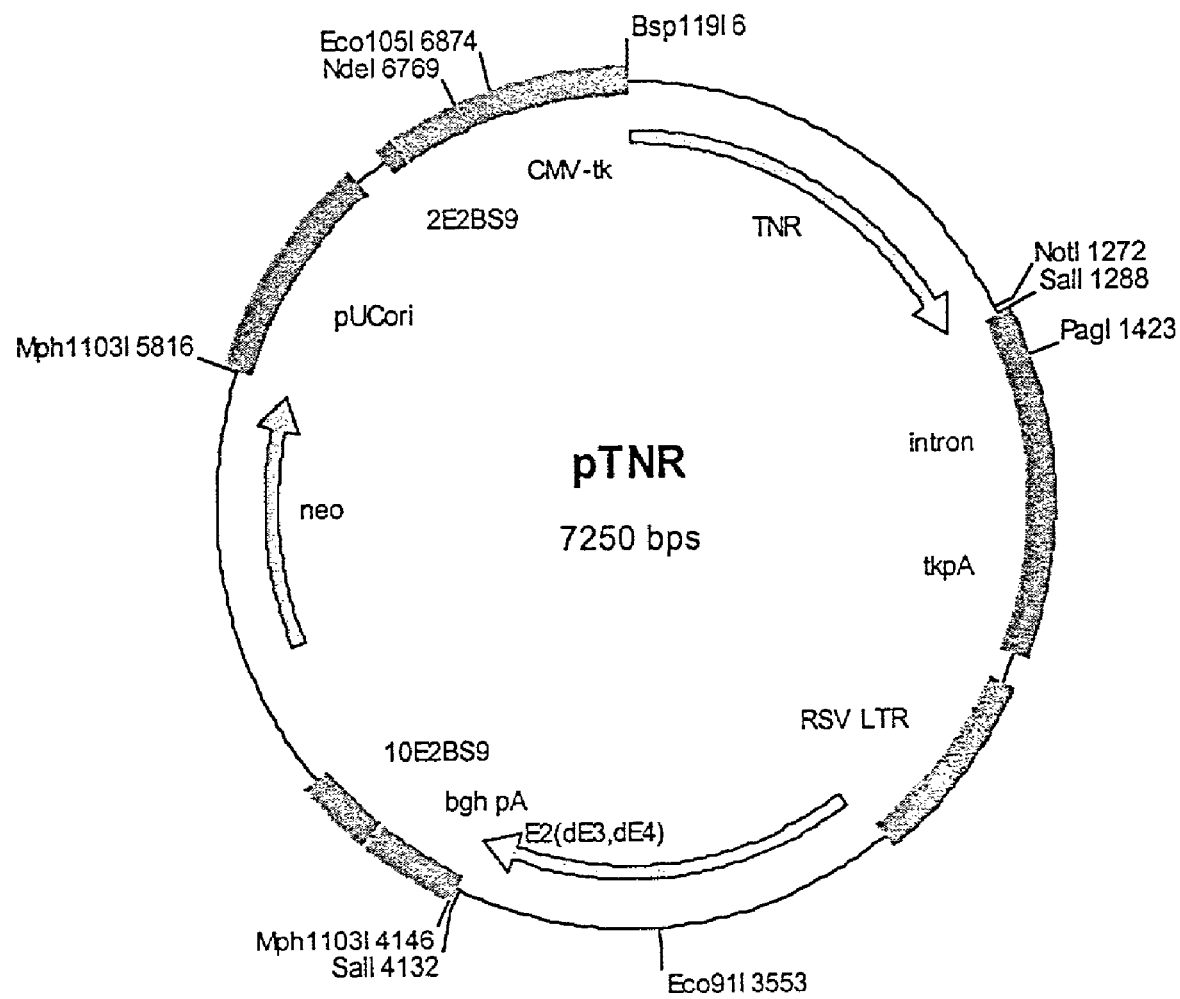
Figure 39E:
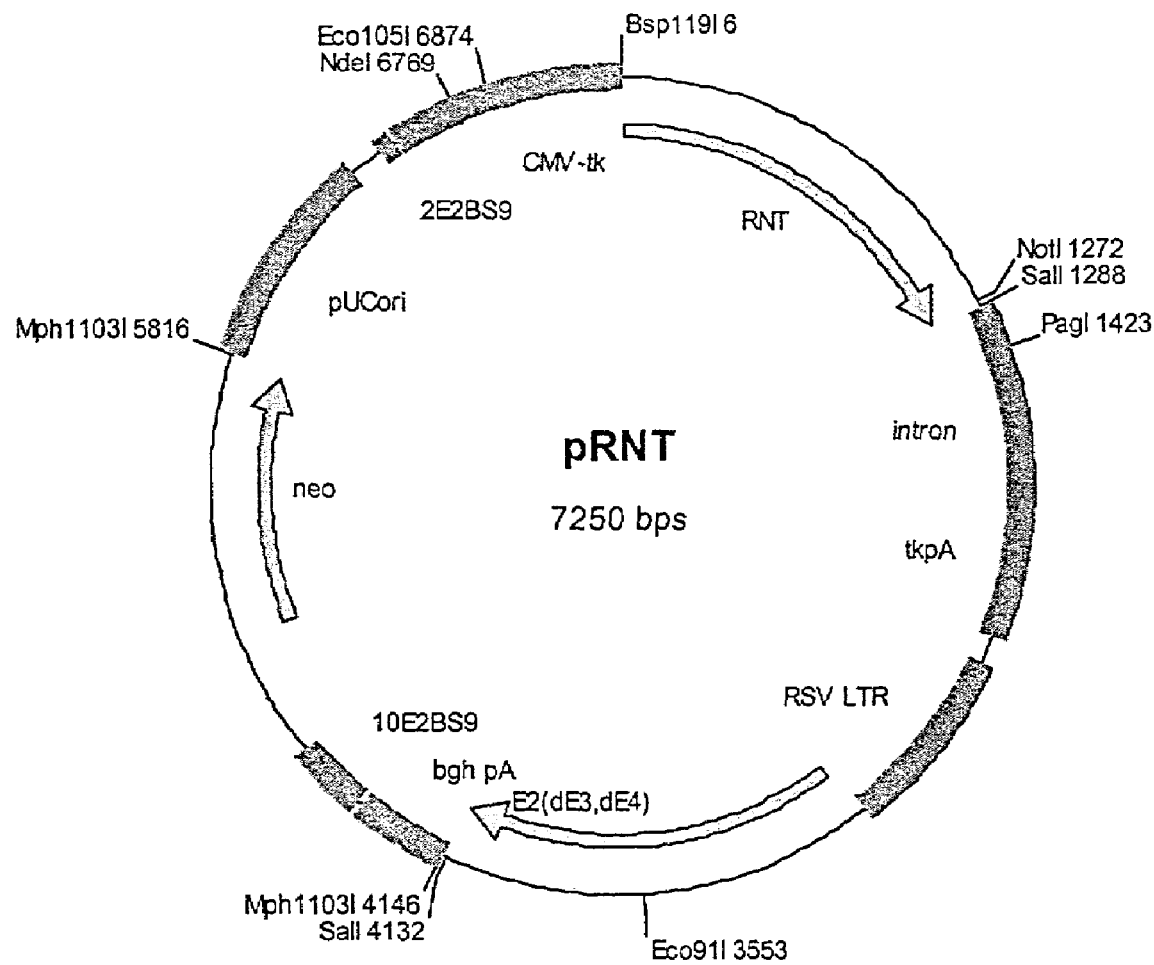
Figure 39F:
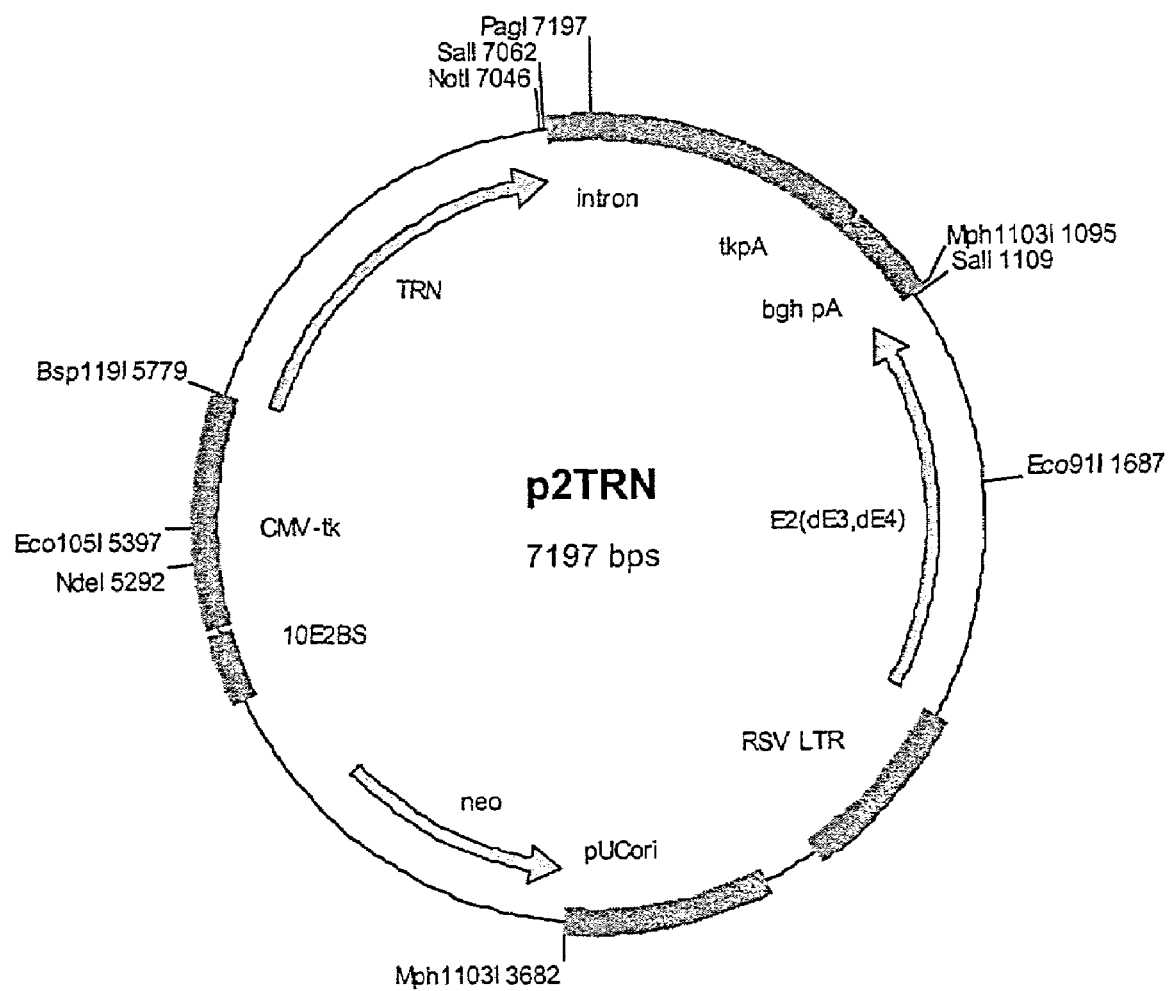
Figure 39G:
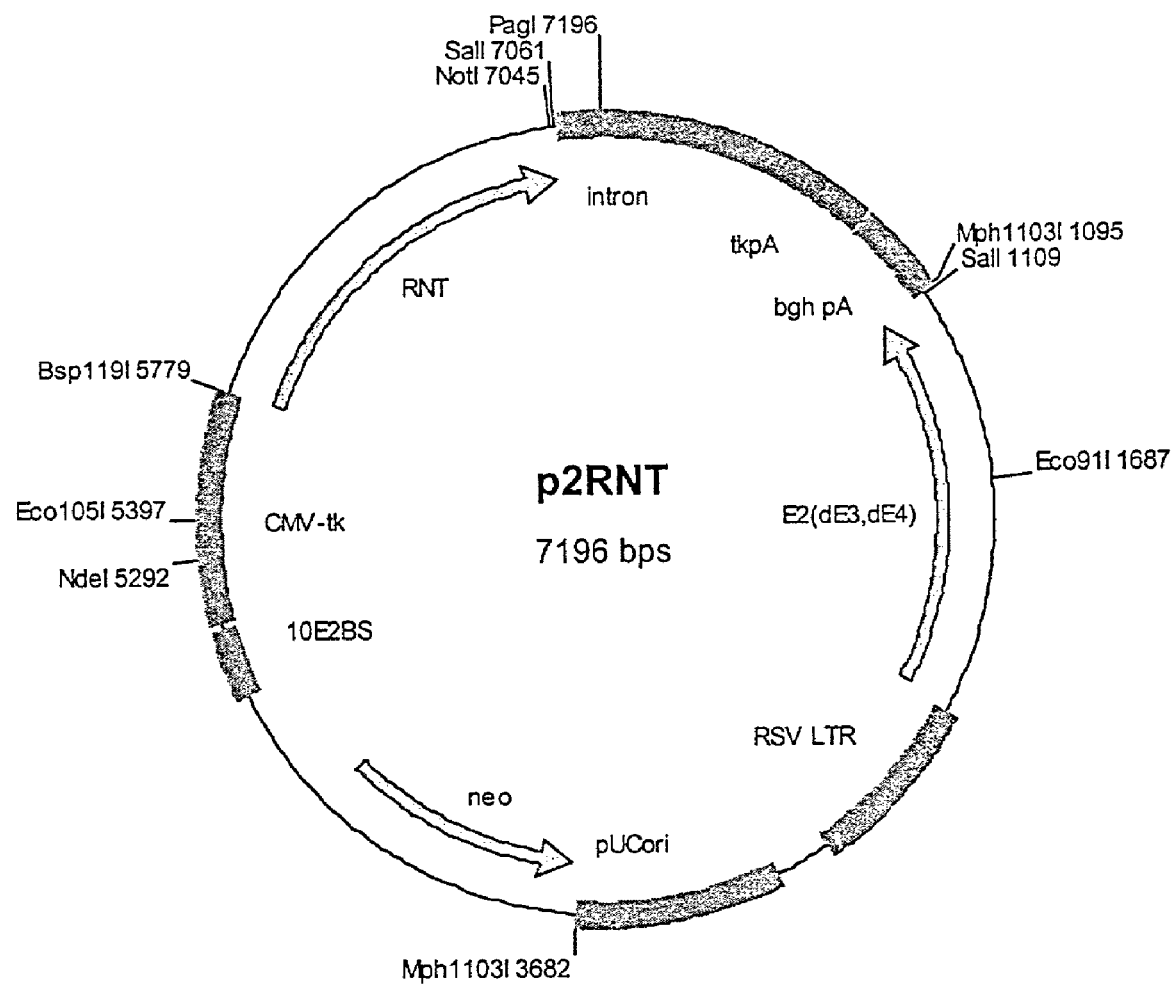
Figure 39H:
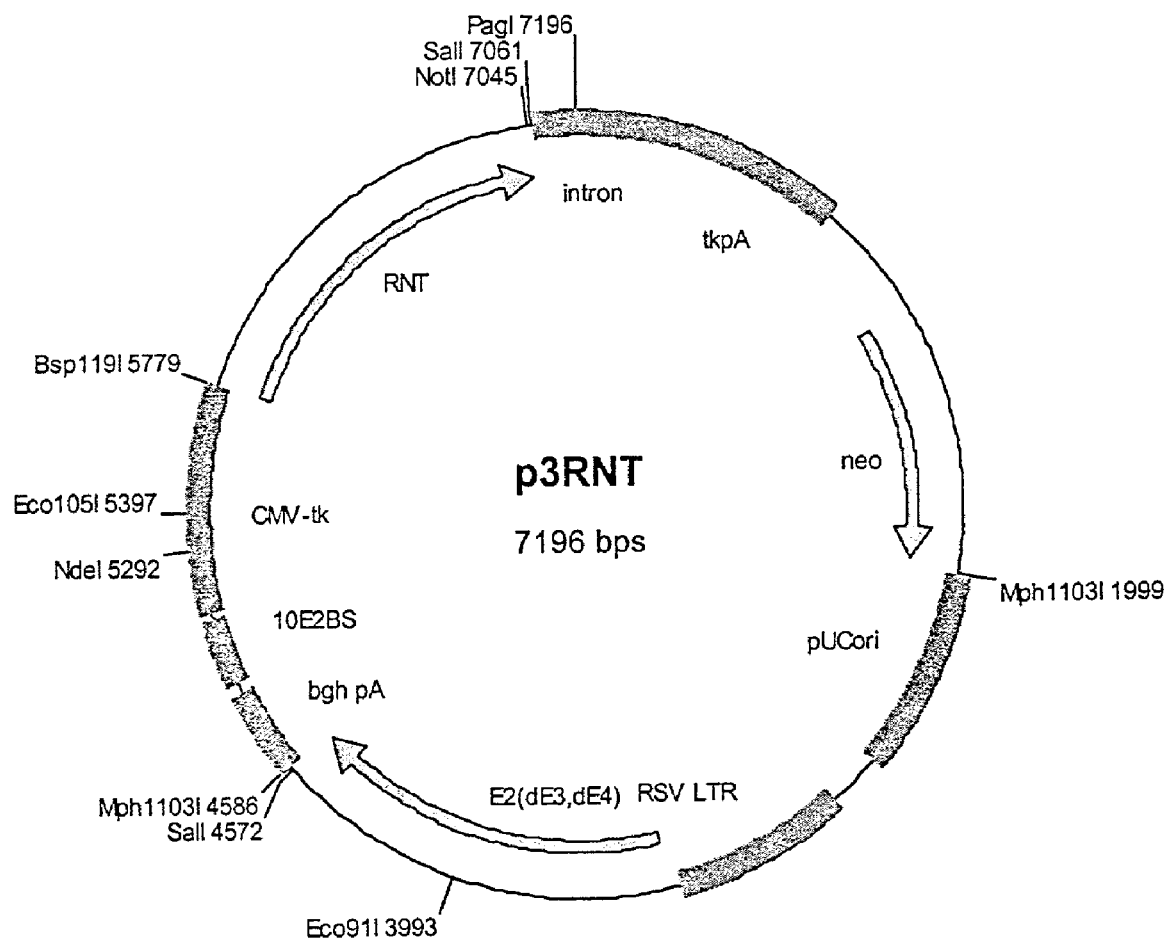
Figure 39:
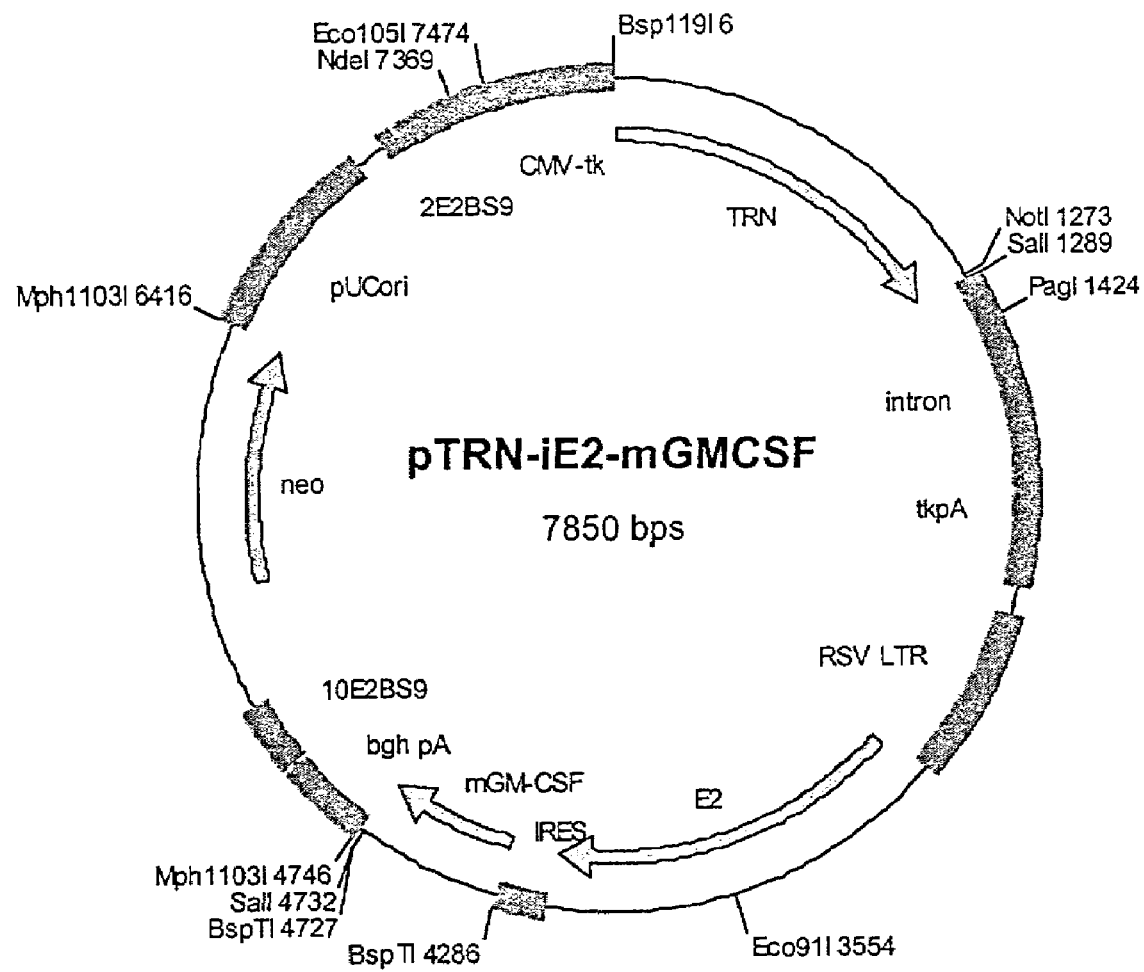
Figure 39J:
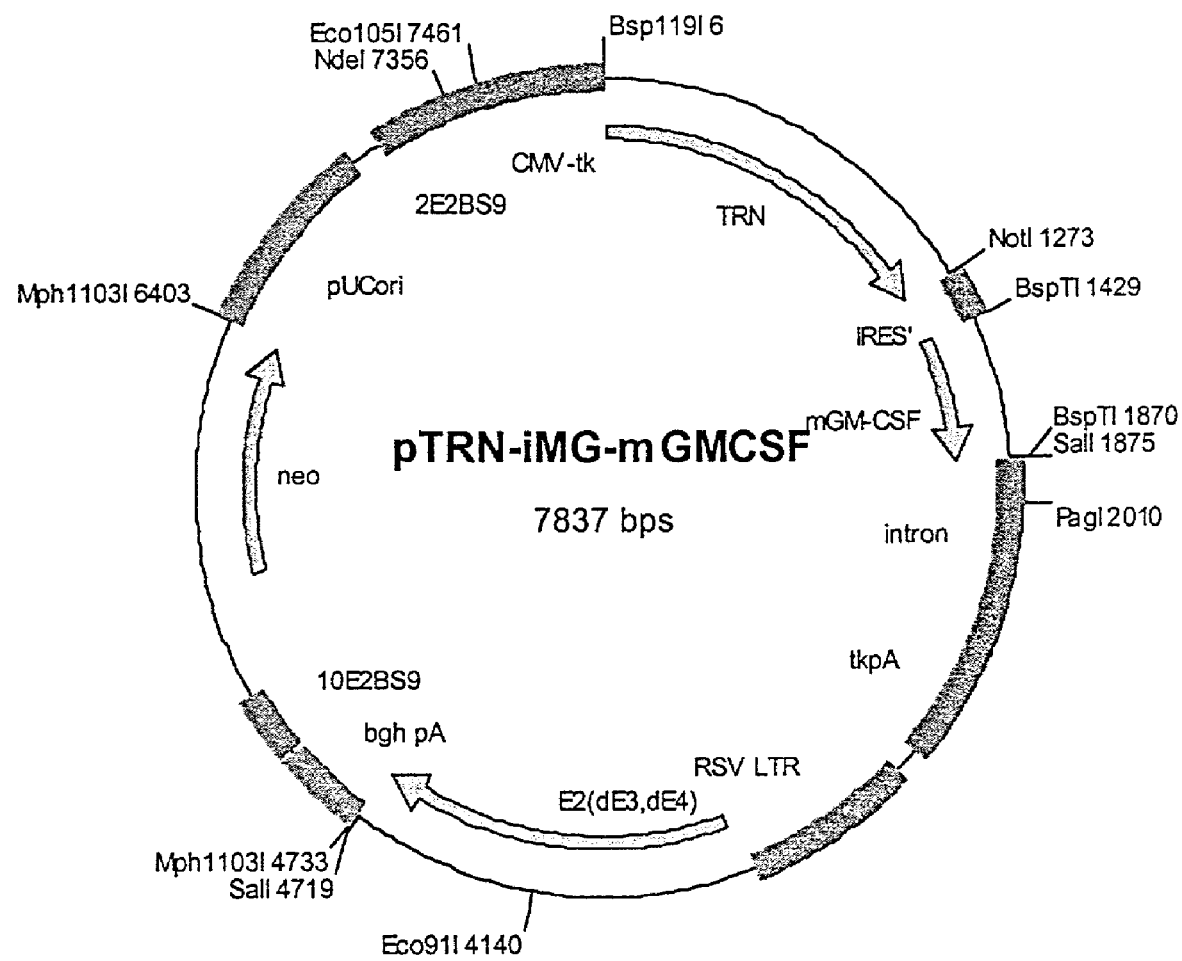
Figure 40A:
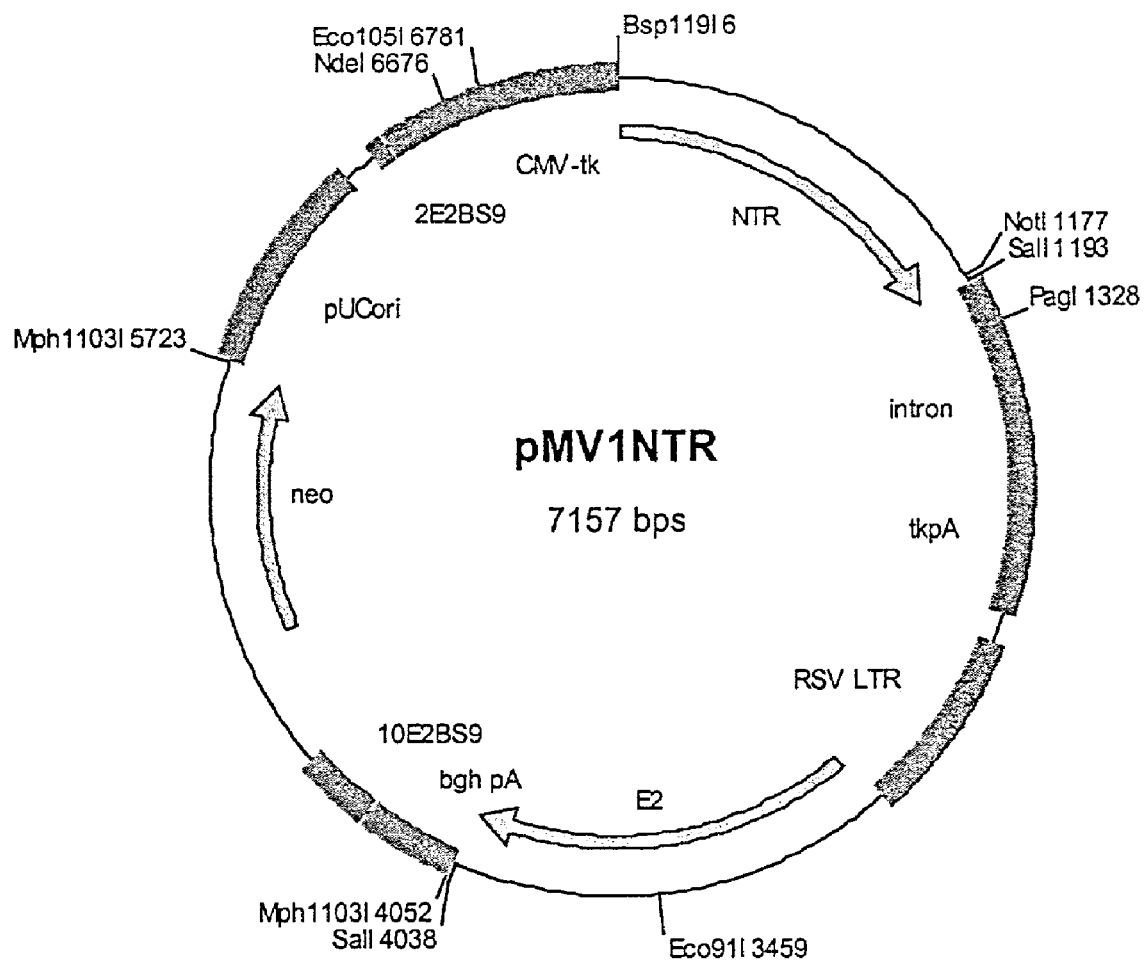
Figure 40B:
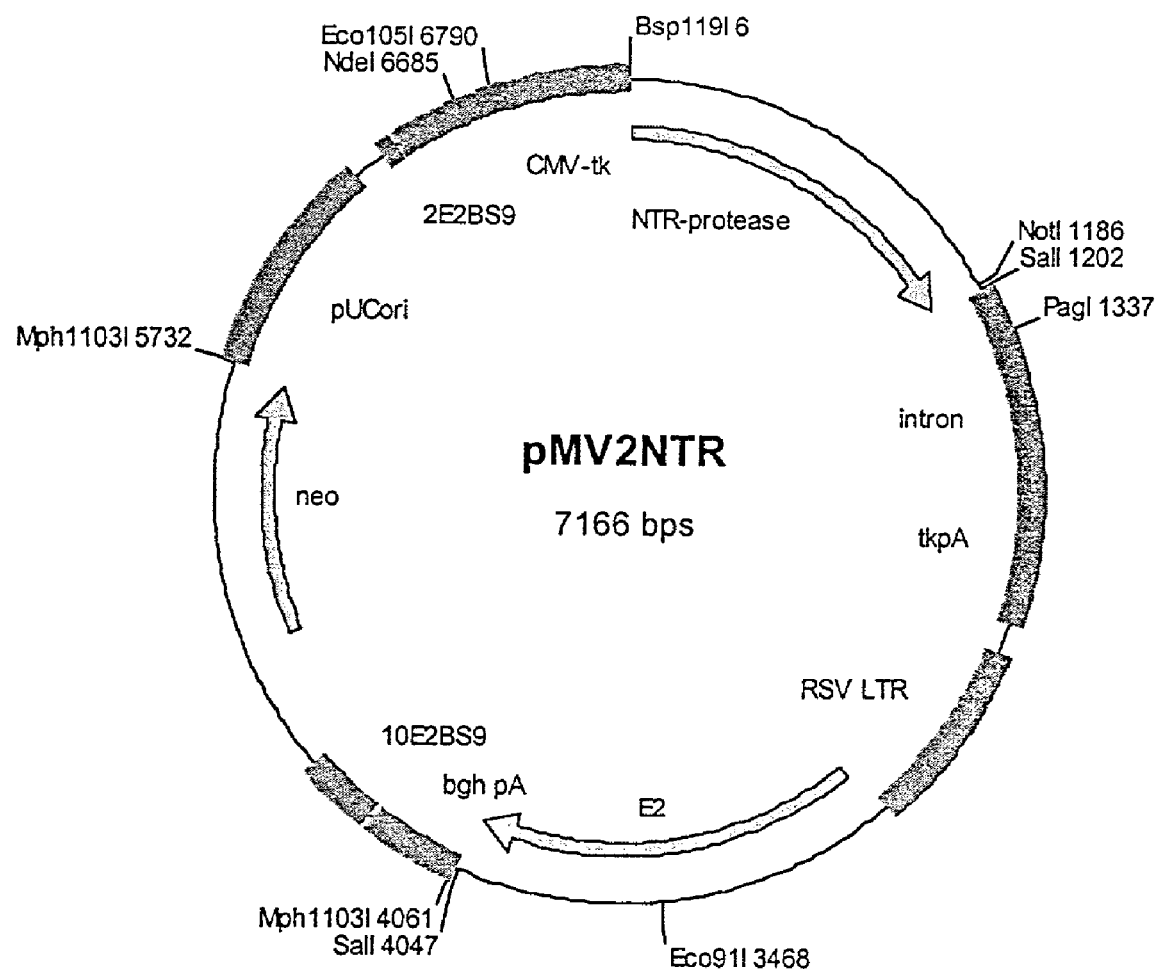
Figure 40C:
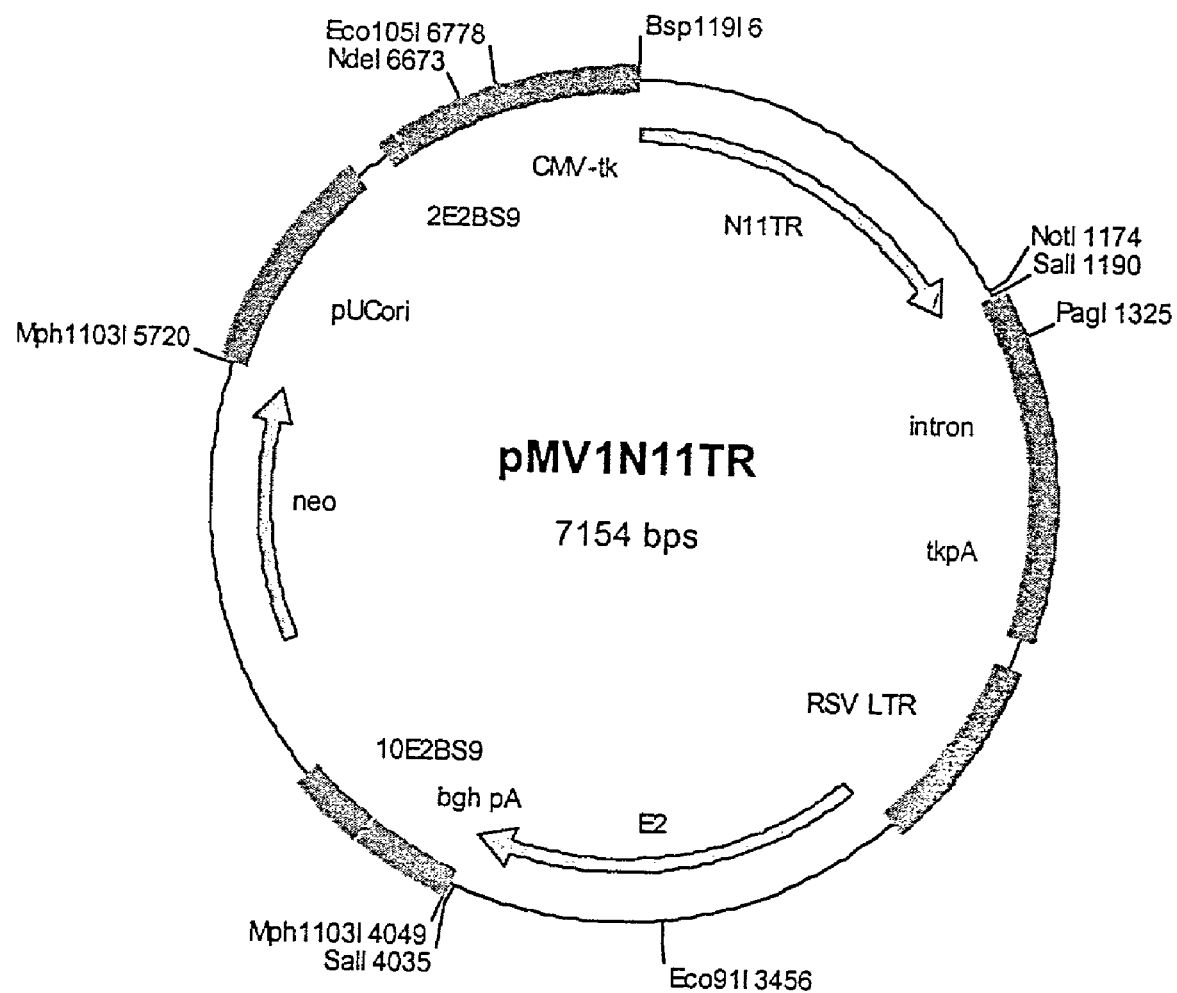
Figure 40D:
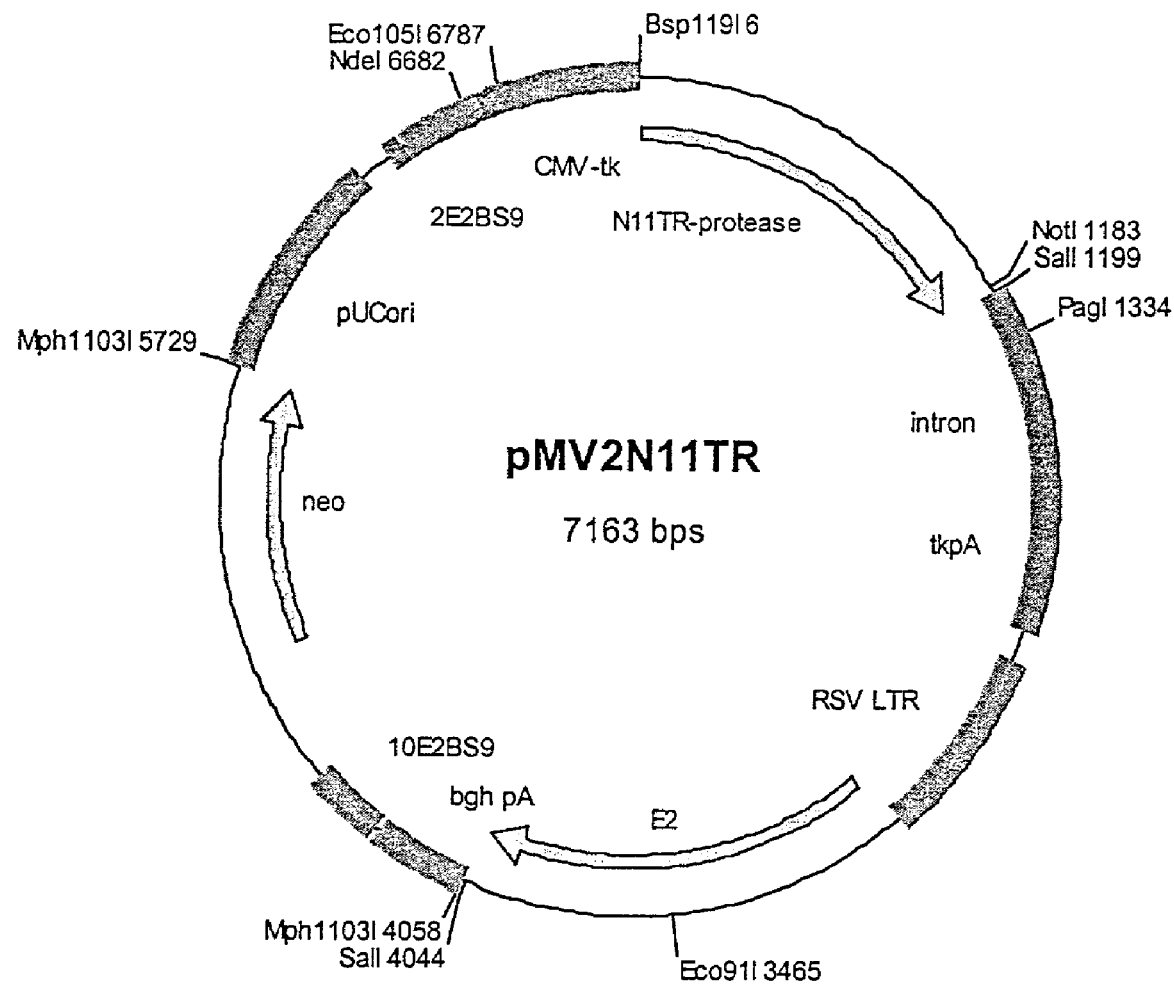
Figure 41A:
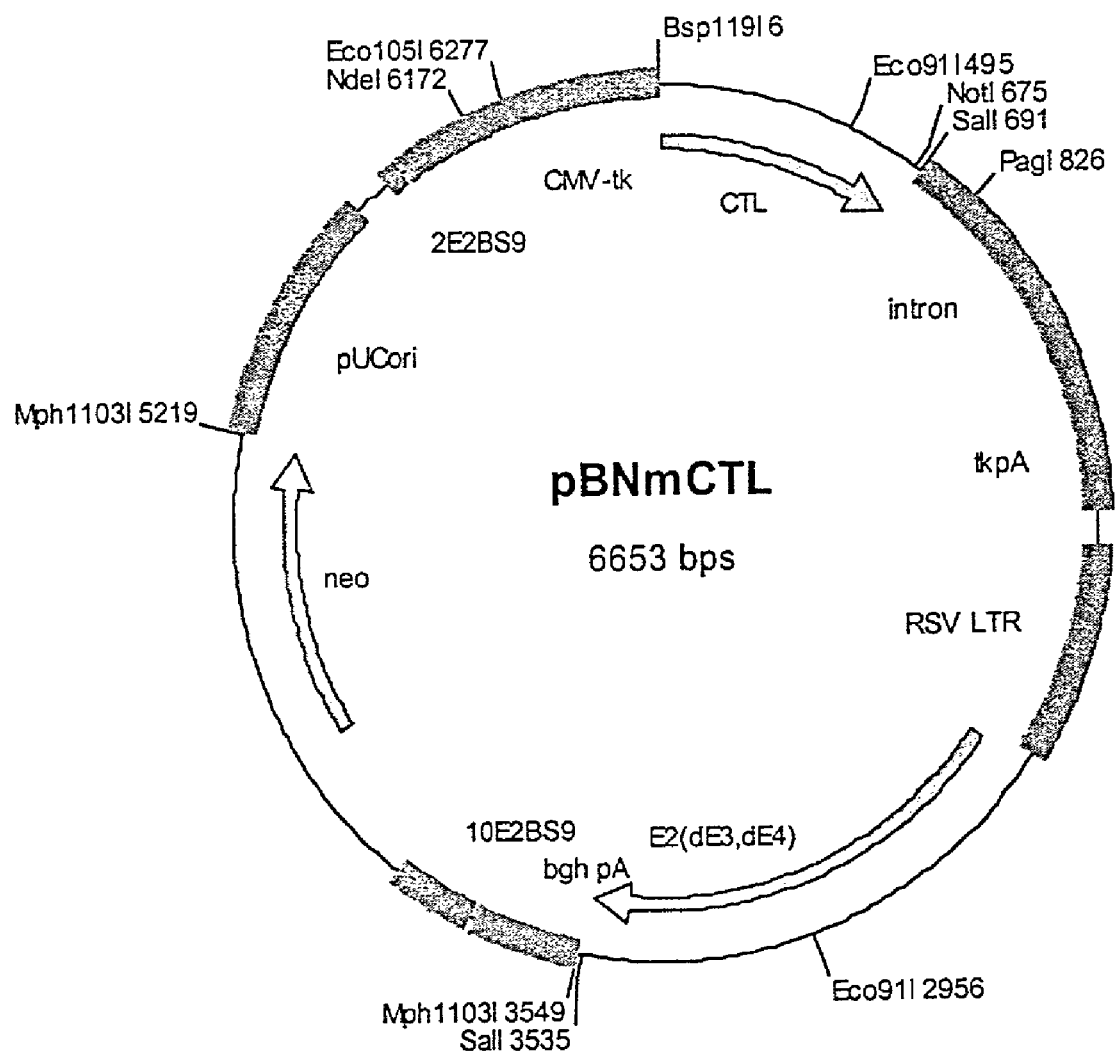
Figure 41B:
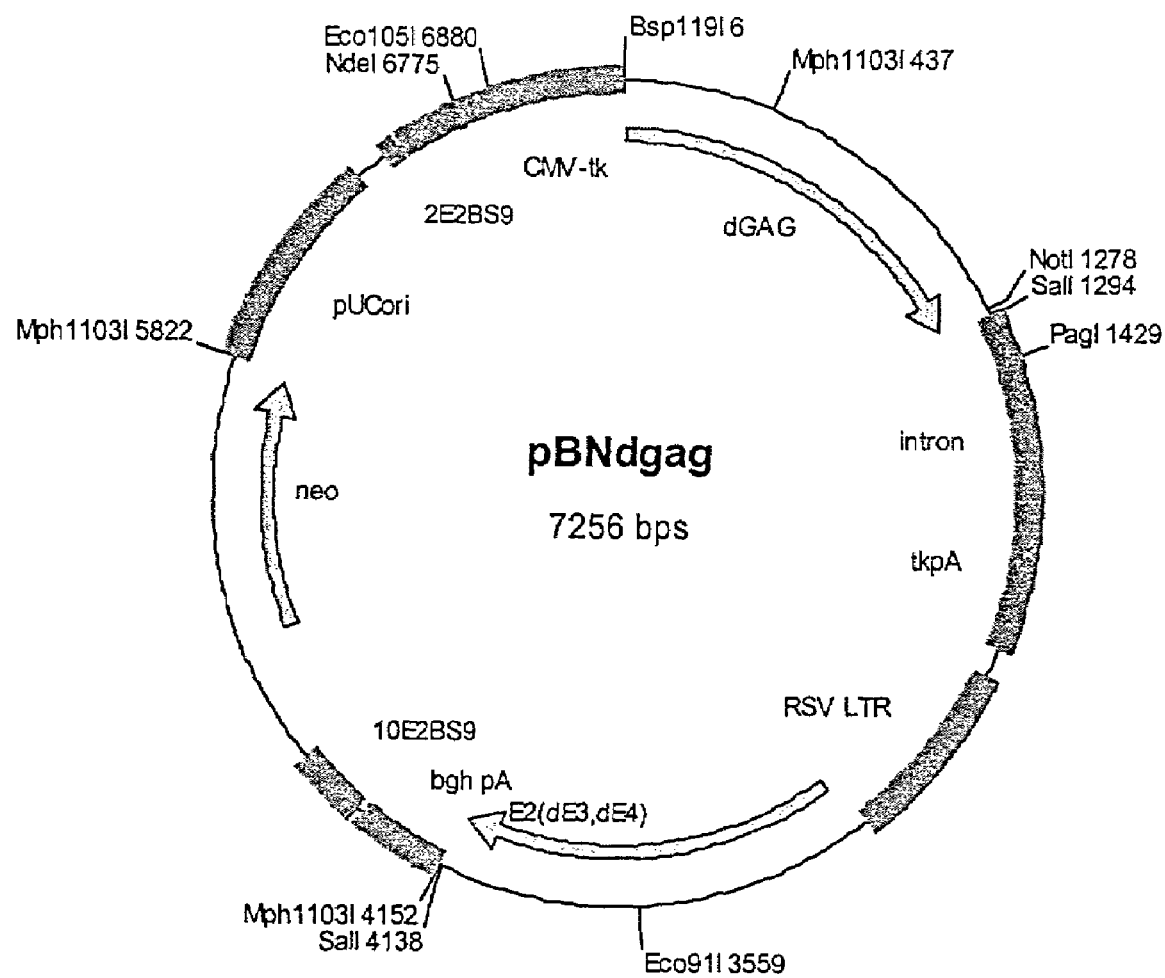
Figure 41C:
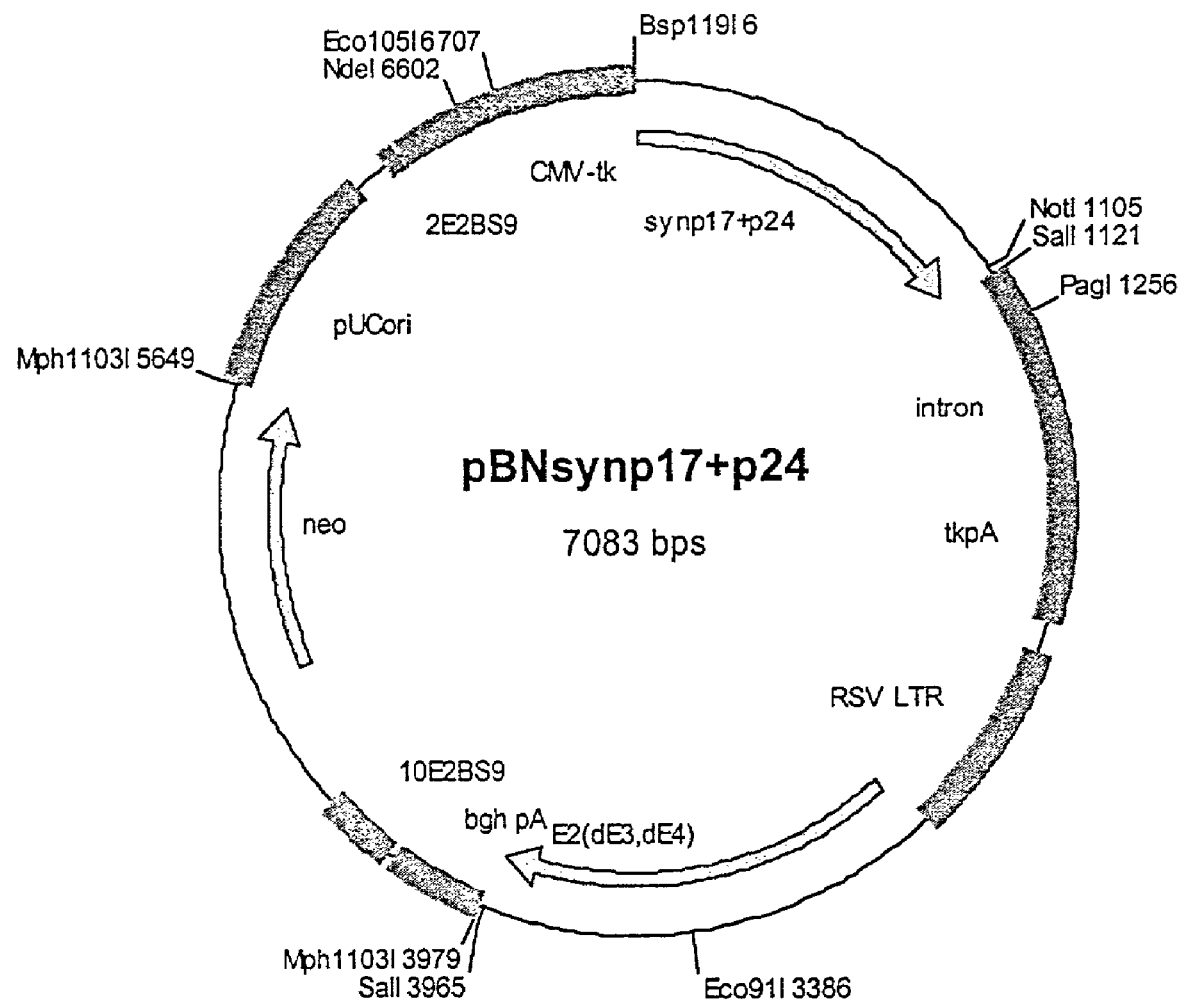
Figure 41D:
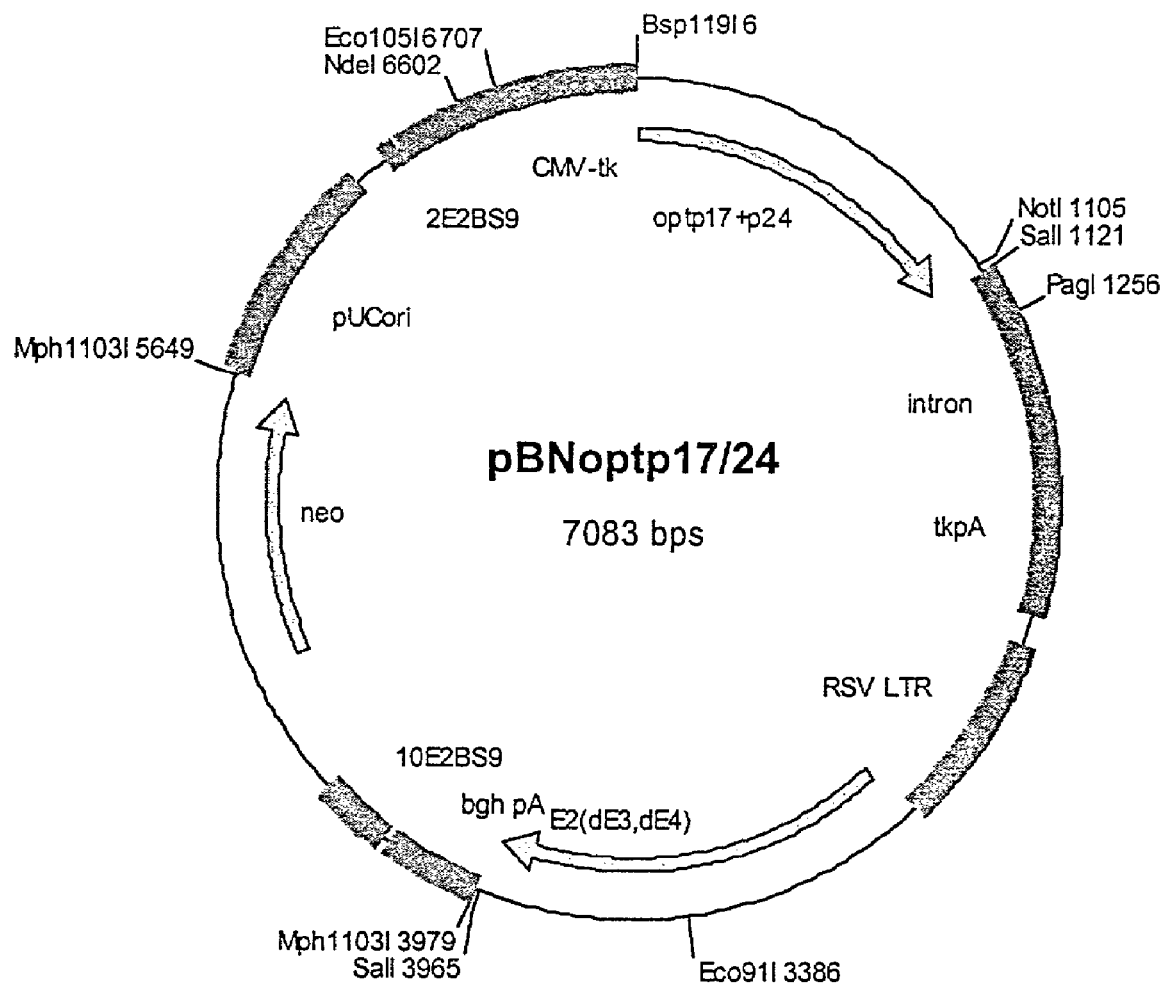
Figure 41E:
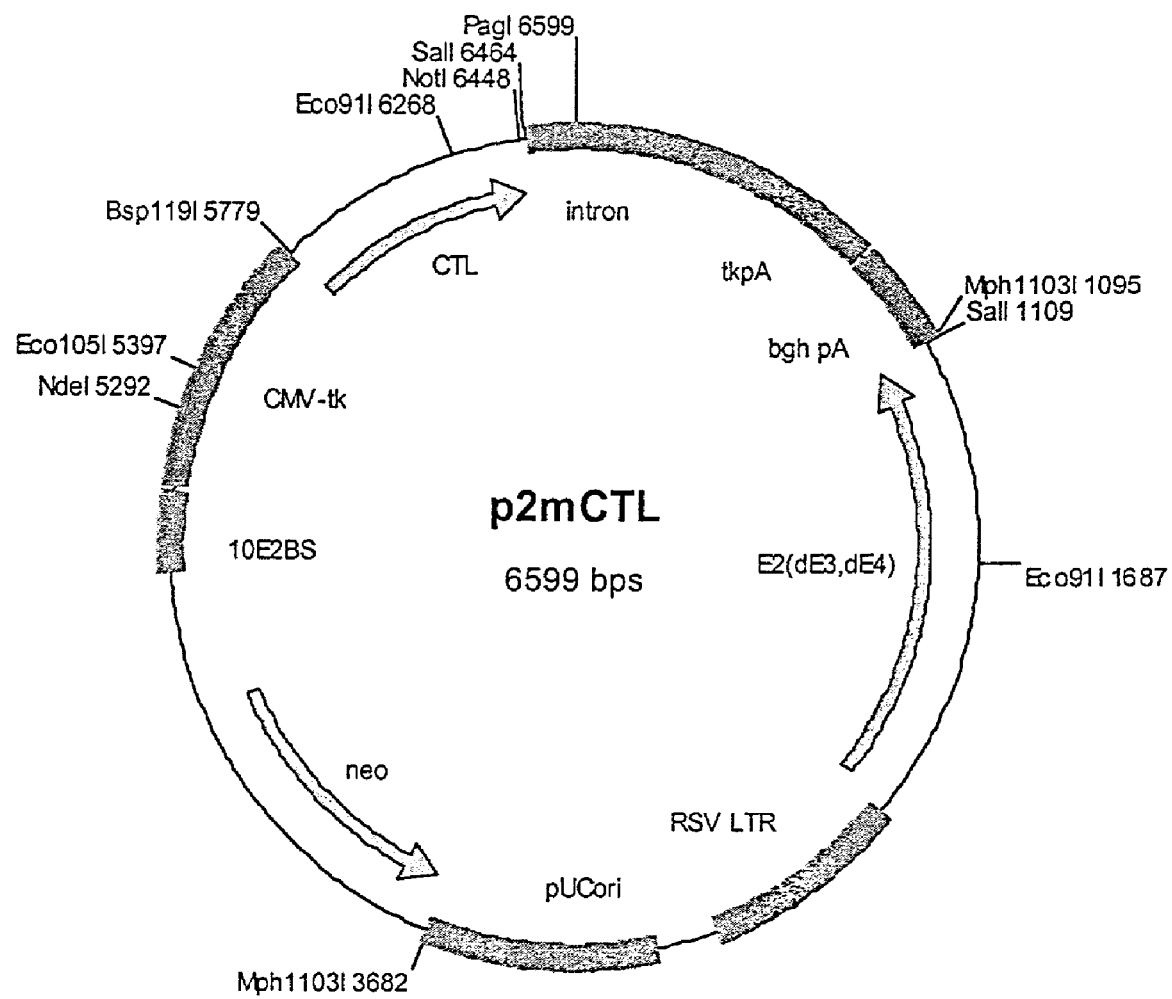
Figure 41F:
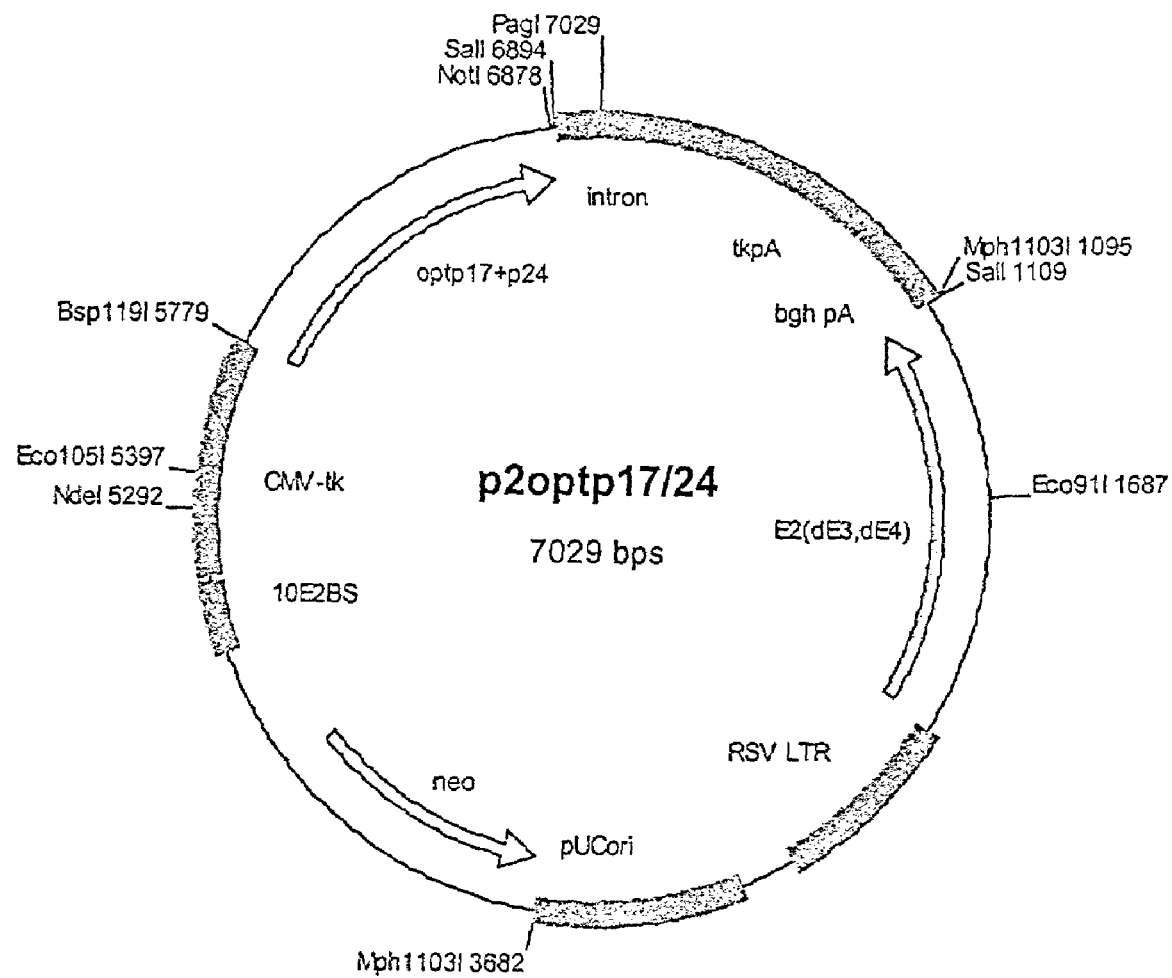
Figure 41G:
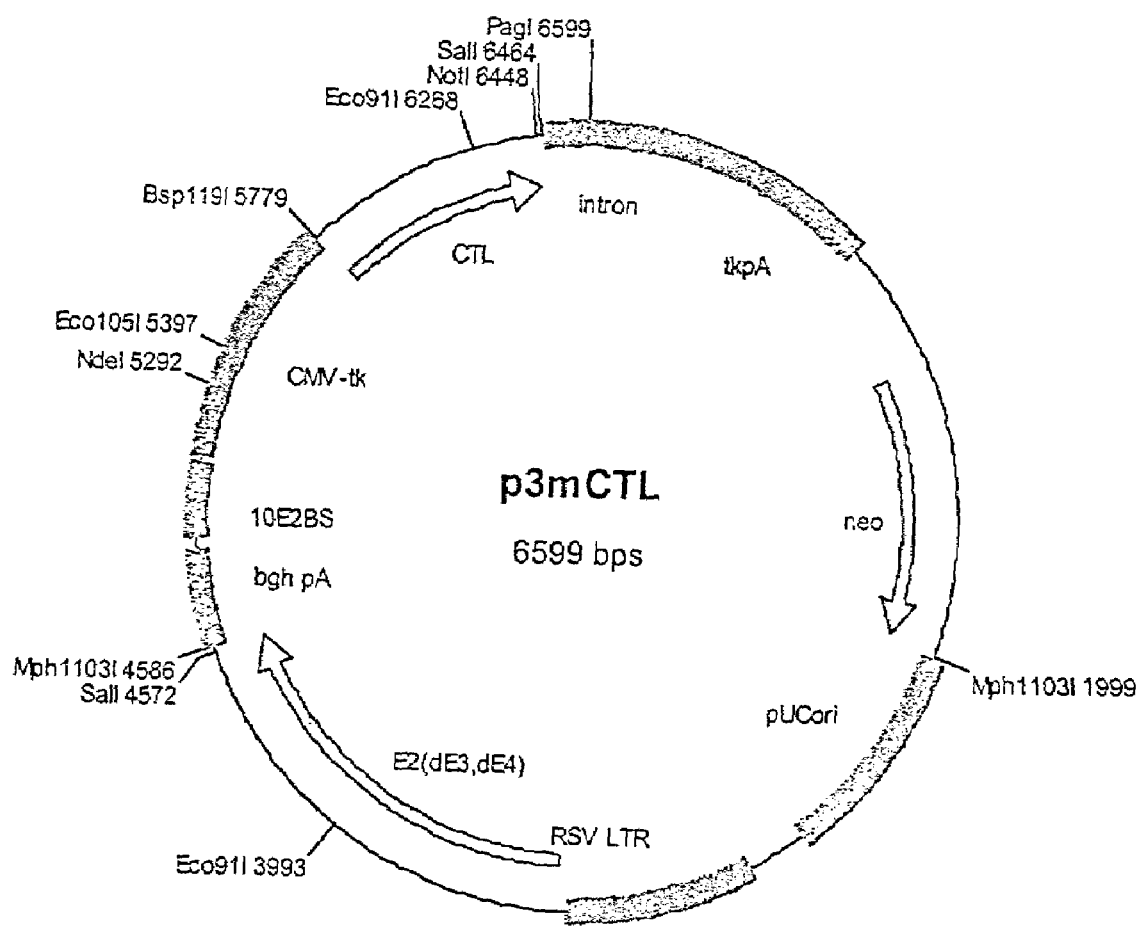
Figure 41H:
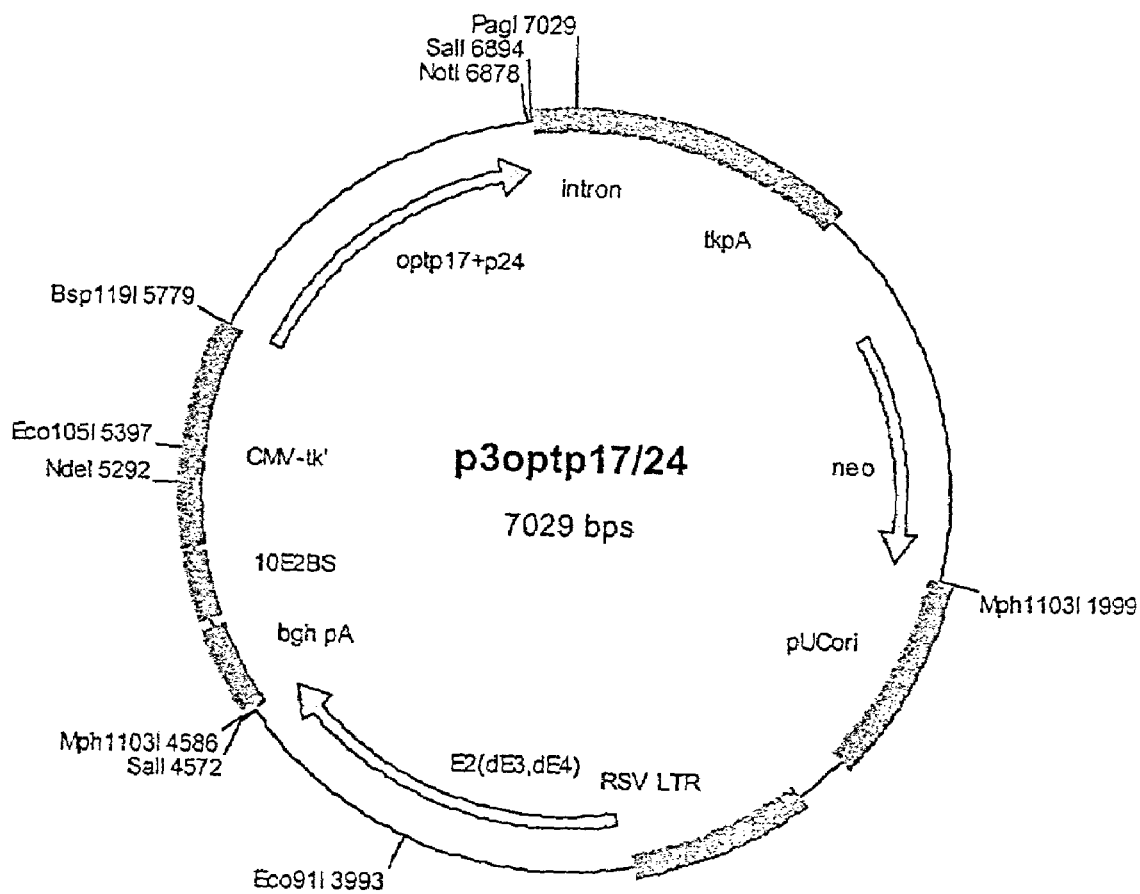

FIG. 38. (A) GTU-1; (B) GTU-2Nef; (C) GTU-3Nef; (D) super6 wtd1EGFP; (E) FREBNAd1EGFP; (F) E2BSEBNAd1EGFP; (G) NNV-Rev FIG. 39. (A) pNRT; (B) PTRN; (C) pRTN; (D) pTNR; (E) pRNT; (F) p2TRN; (G) p2RNT; (H) p3RNT; (I) pTRN-iE2-GMCSF; (J) pTRN-iMG-GMCSF FIG. 40. (A) pMV1NTR; (B) pMV2NTR; (C) pMV1N11TR; (D) pMV2N11TR FIG. 41. (A) pCTL; (B) pdgag; (C) psynp17/24; (D) poptp17/24; (E) p2mCTL; (F) p2optp17/24; (G) p3mCTL; (H) p3optp17/24

Figure 42A:
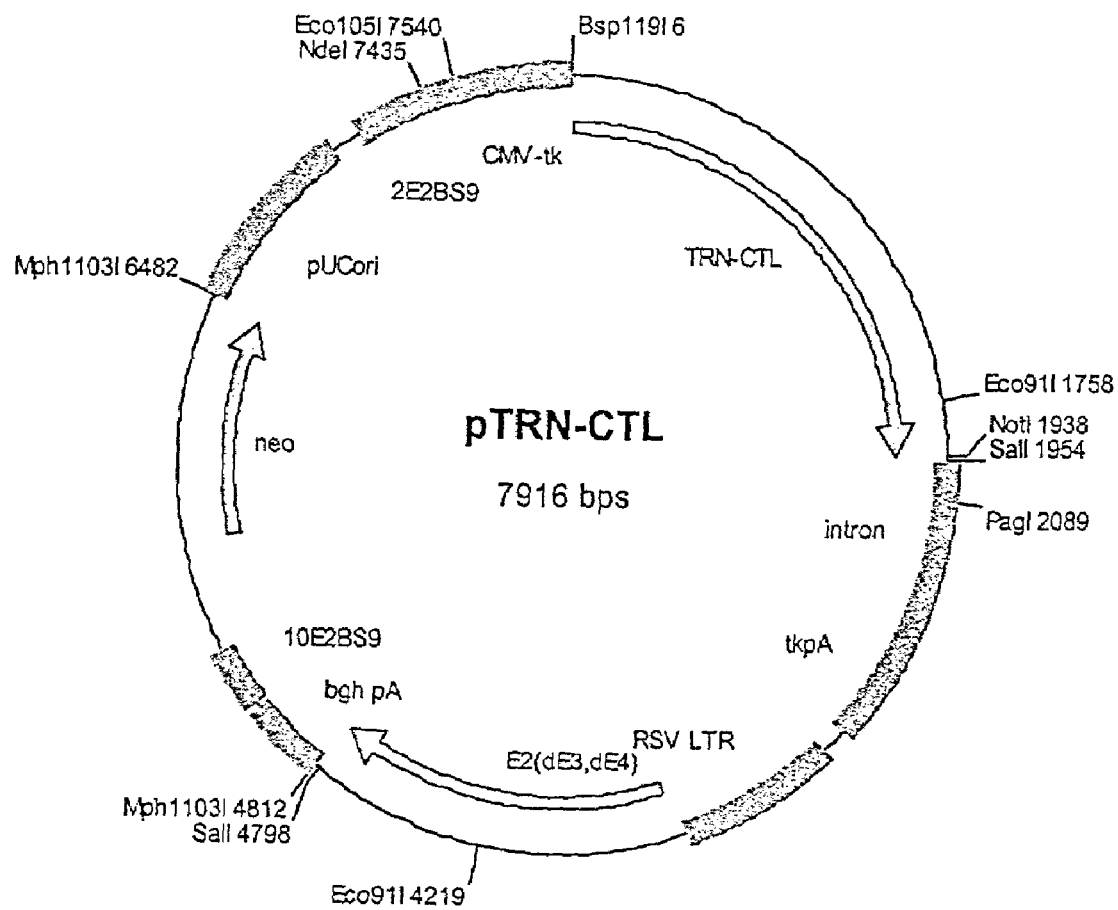
Figure 42B:
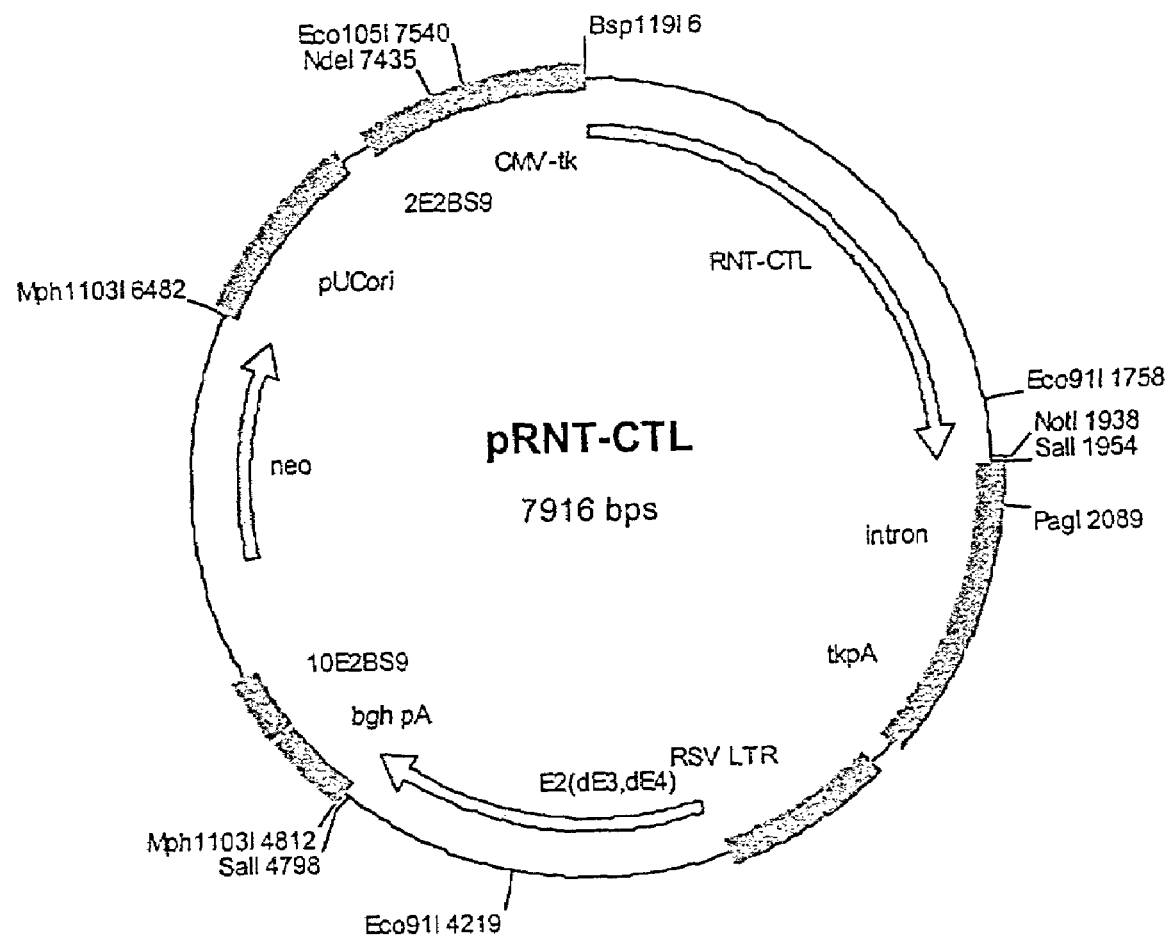
Figure 42C:
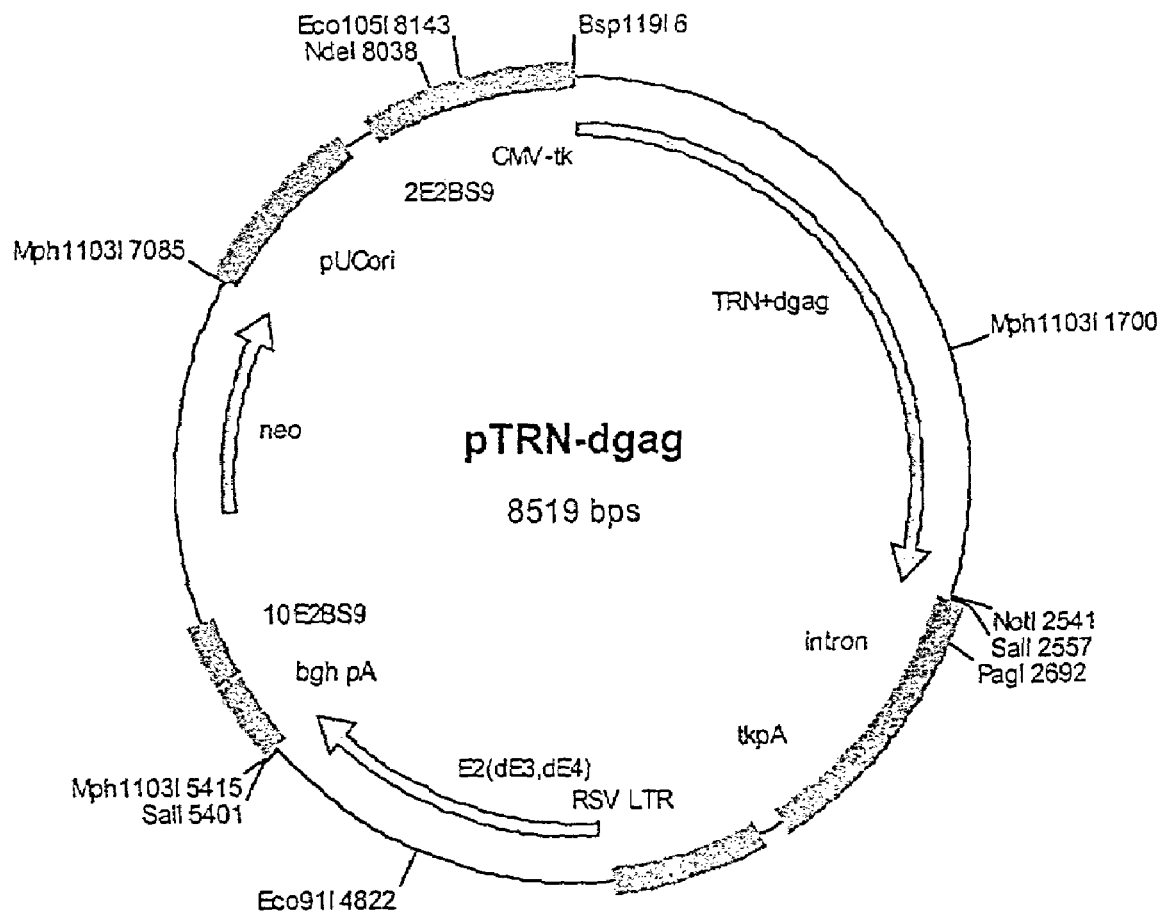
Figure 42D:
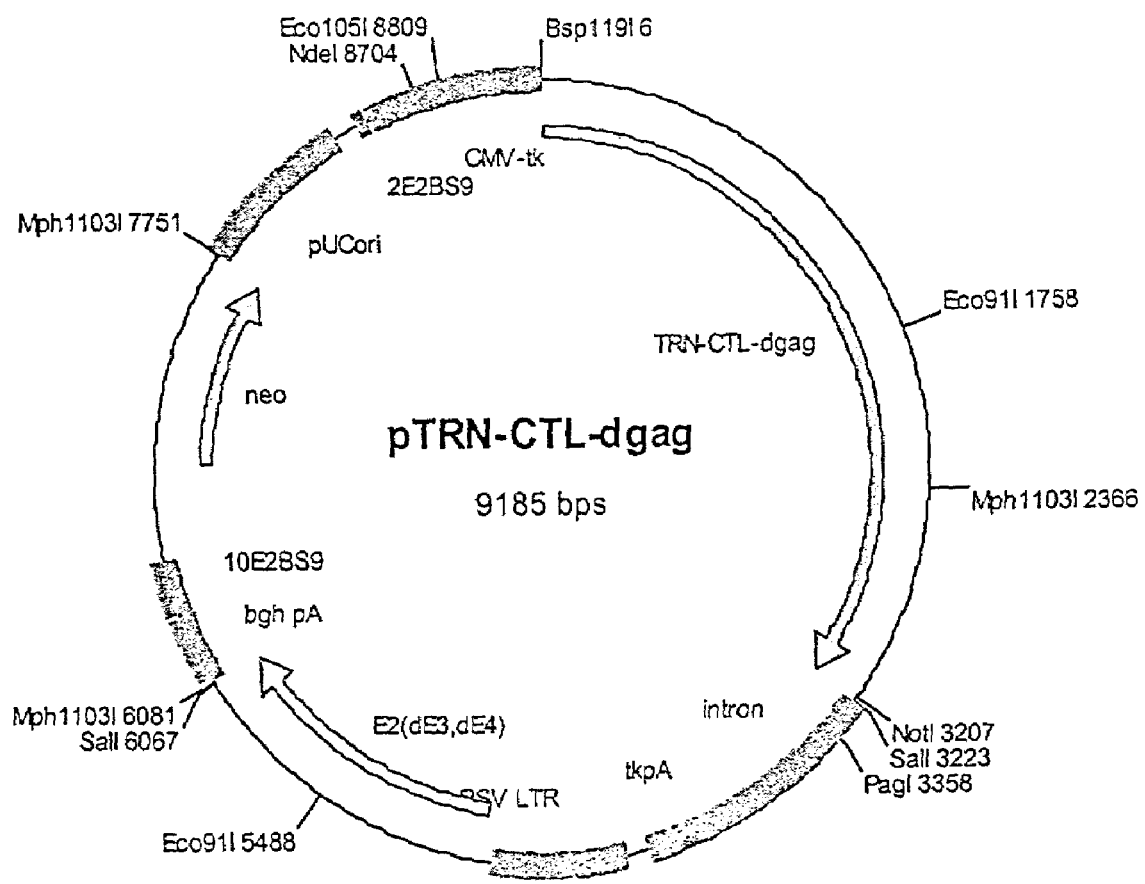
Figure 42E:
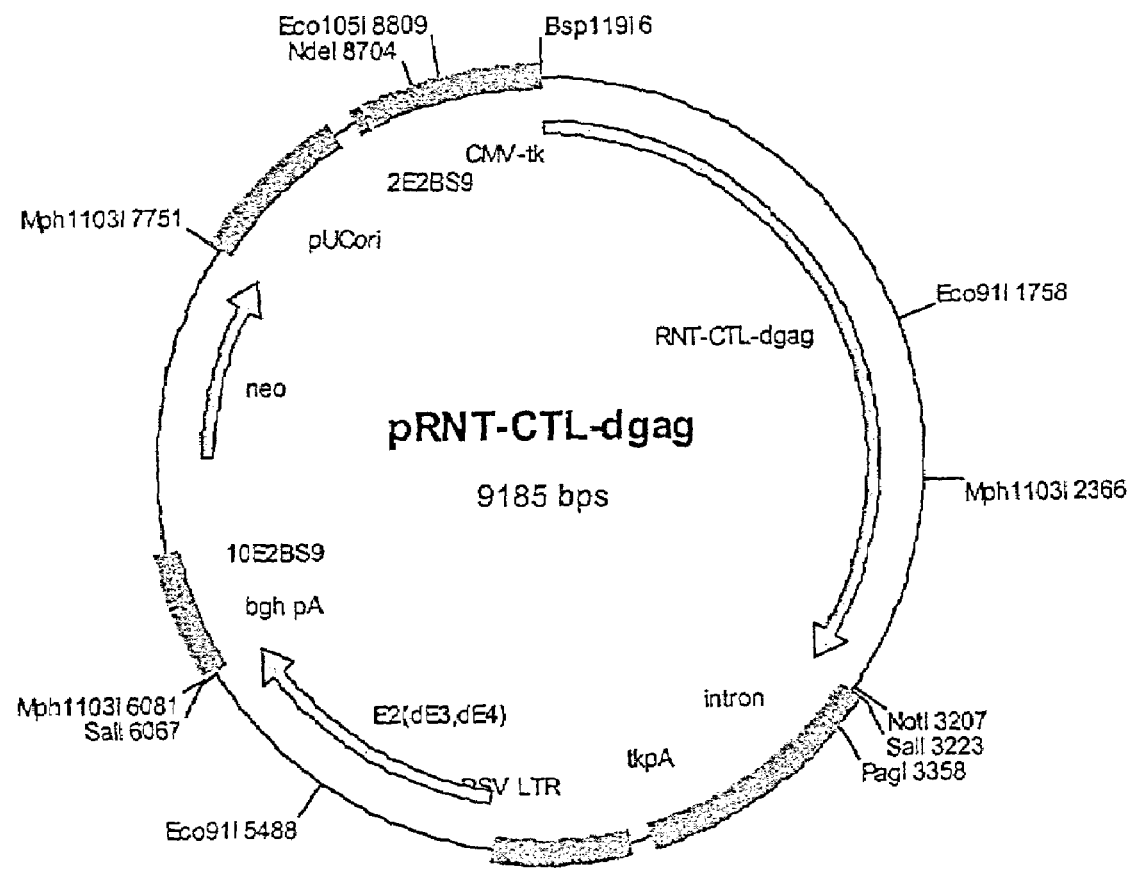
Figure 42F:
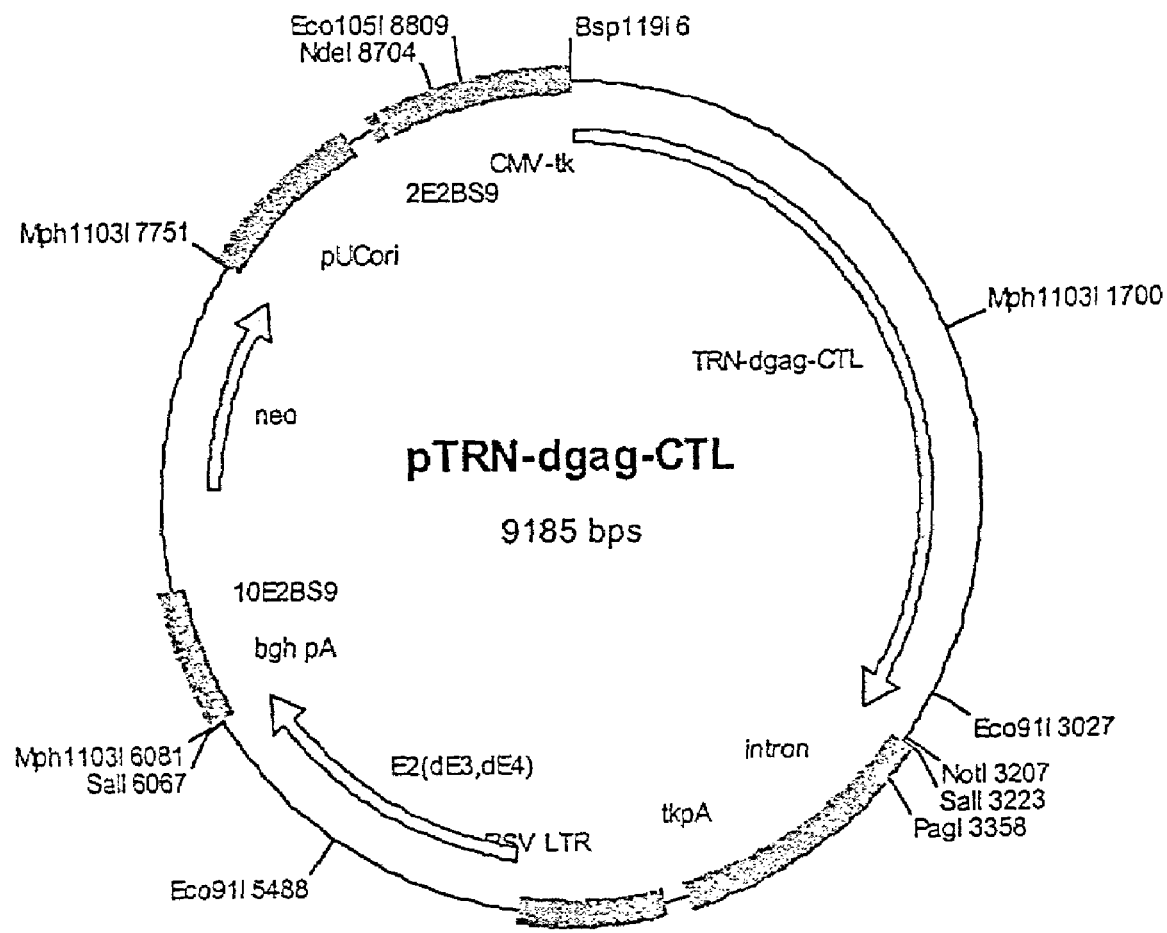
Figure 42G:
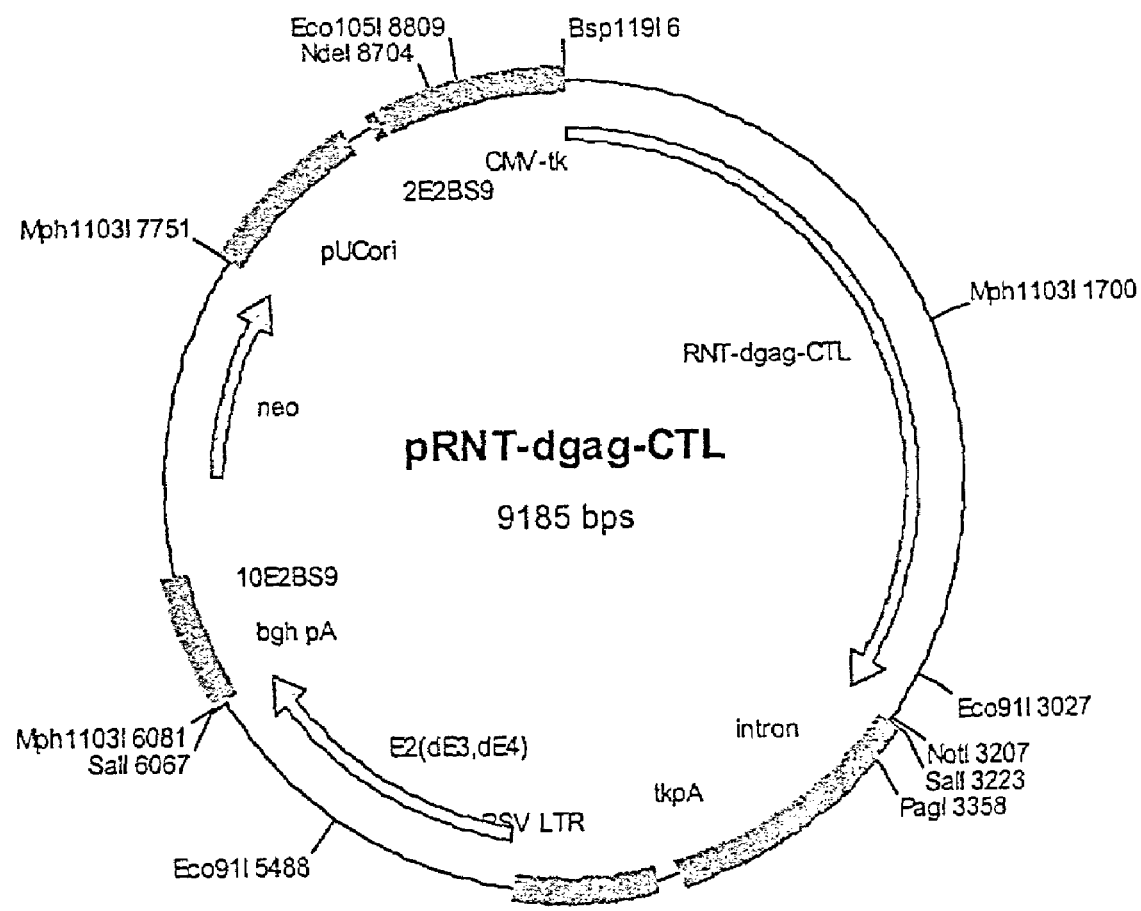
Figure 42H:
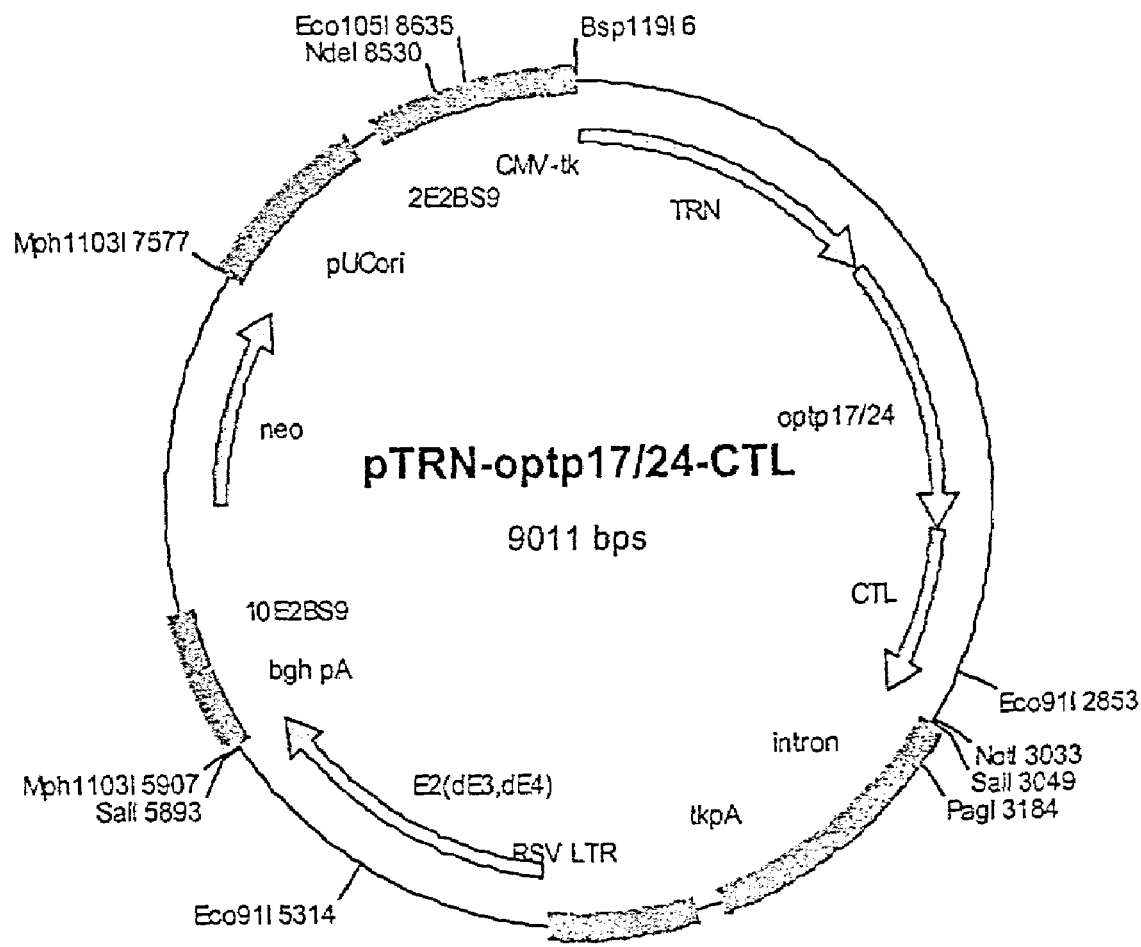
Figure 42:
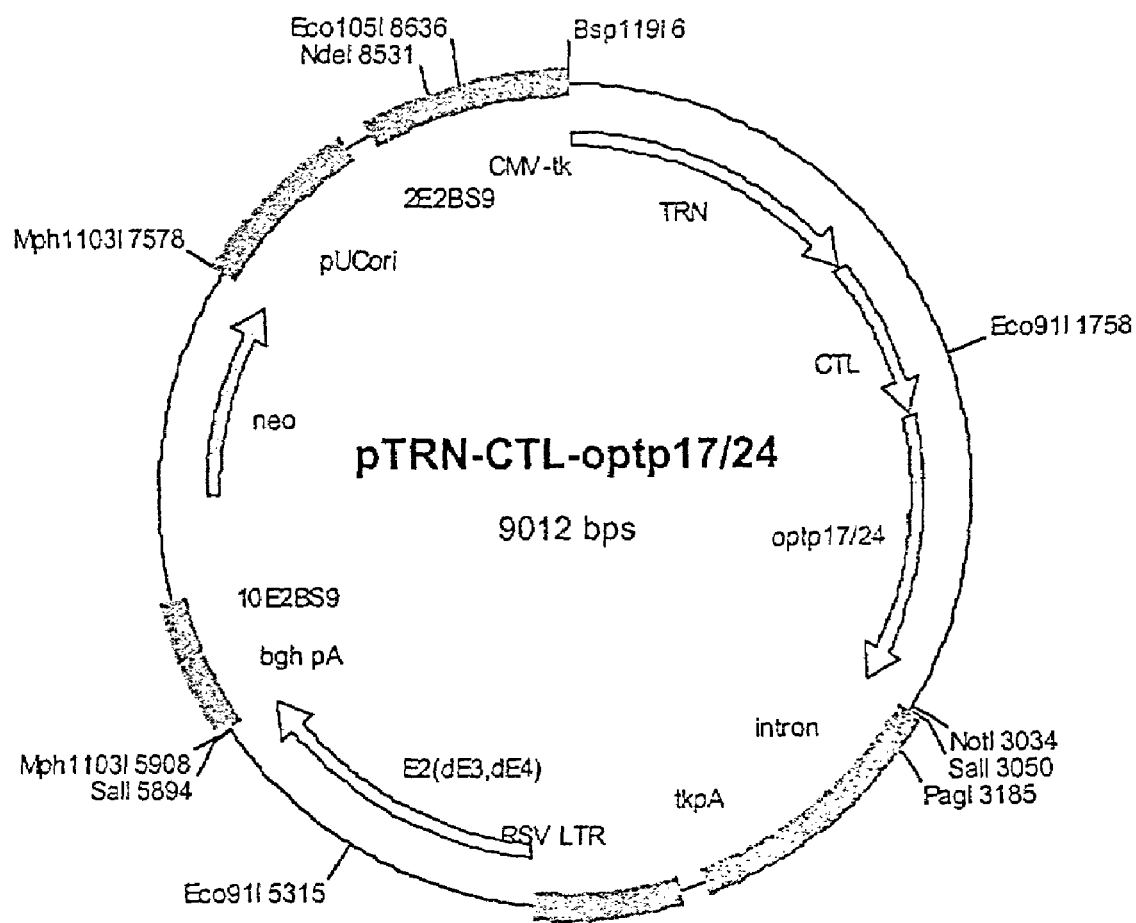
Figure 42J:
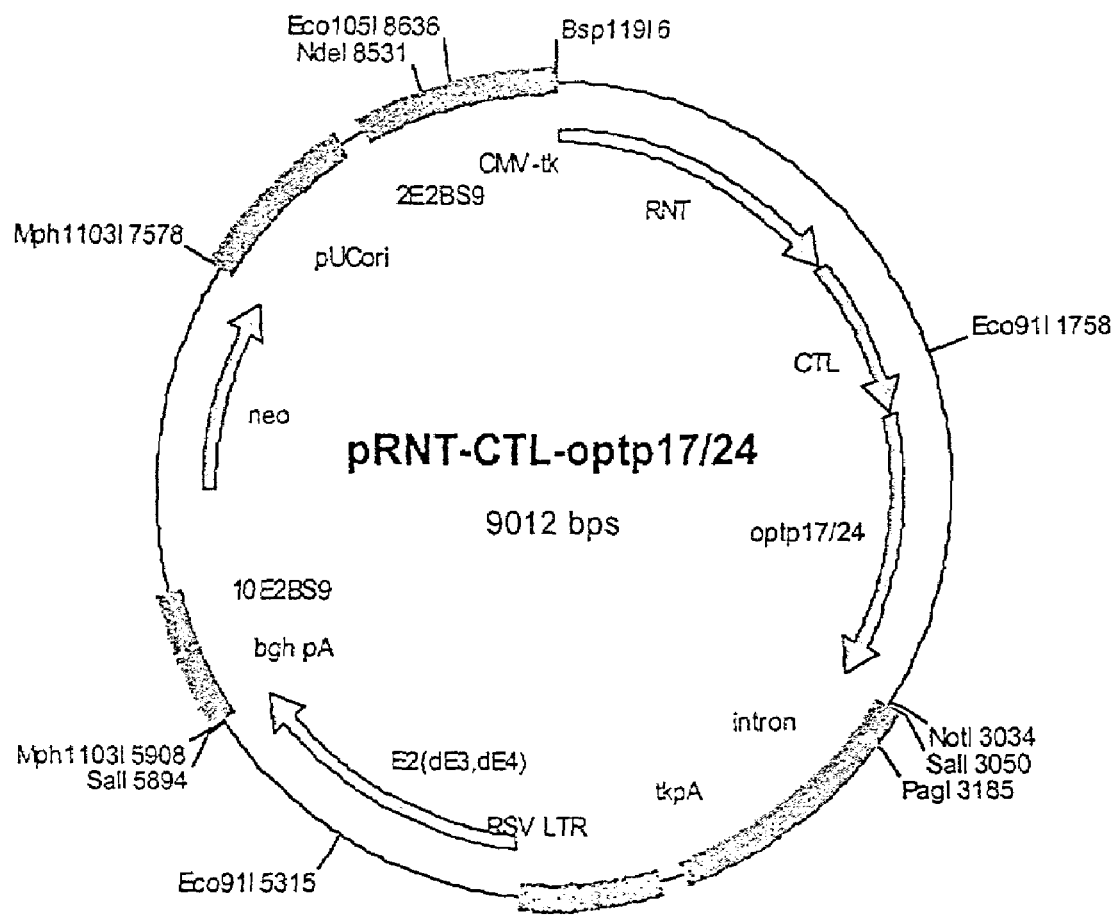
Figure 42K:
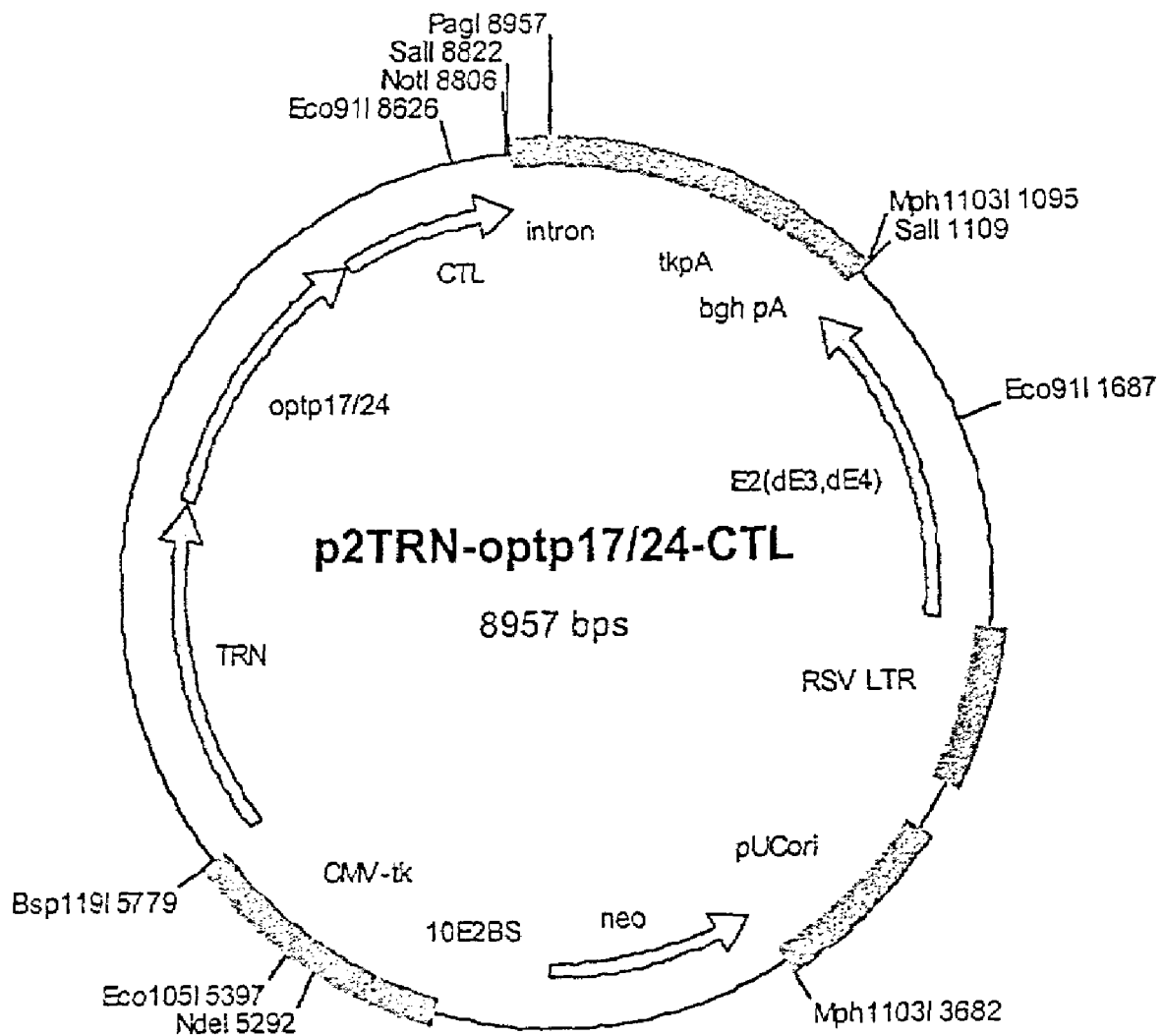
Figure 42L:
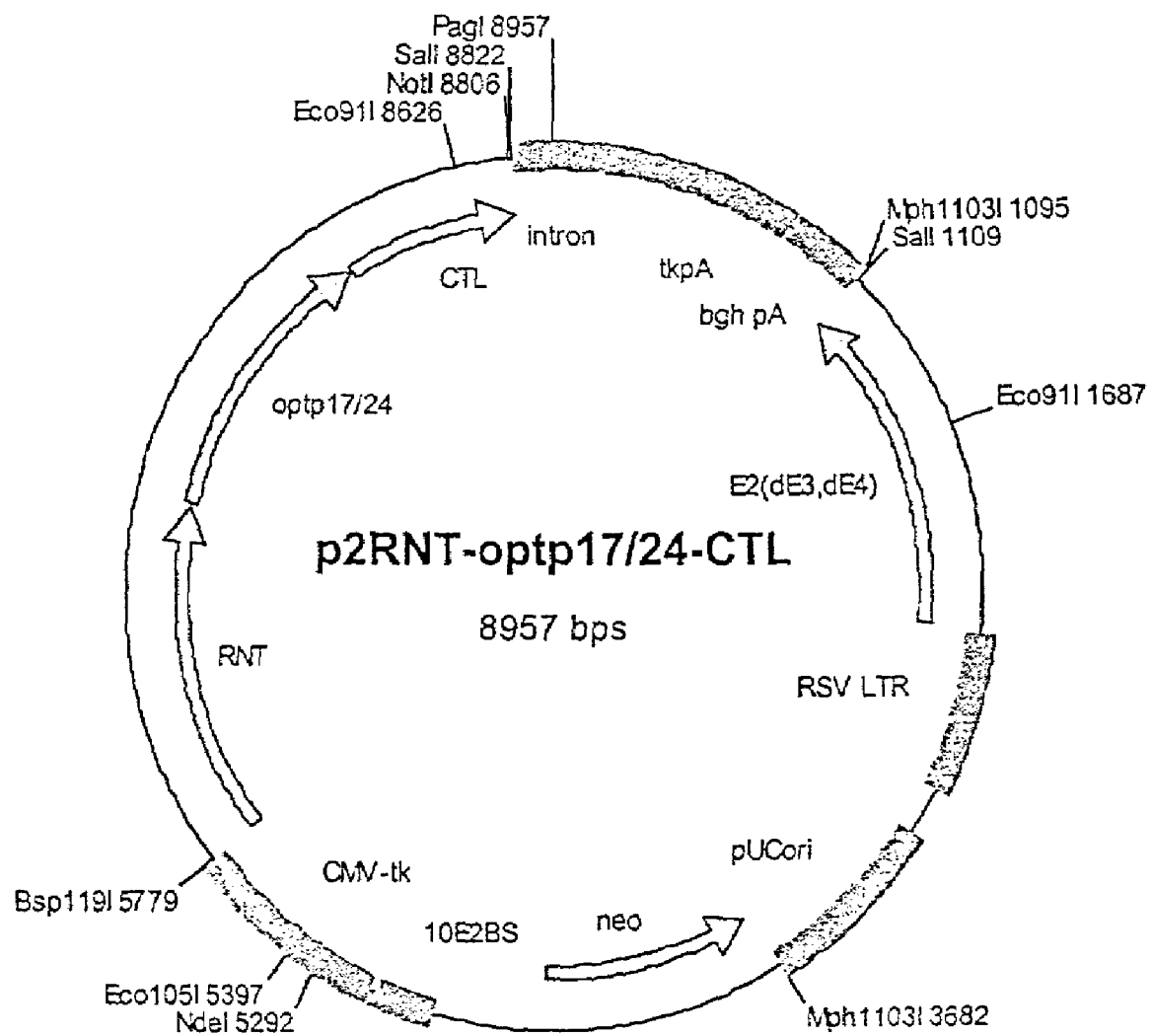
Figure 42M:
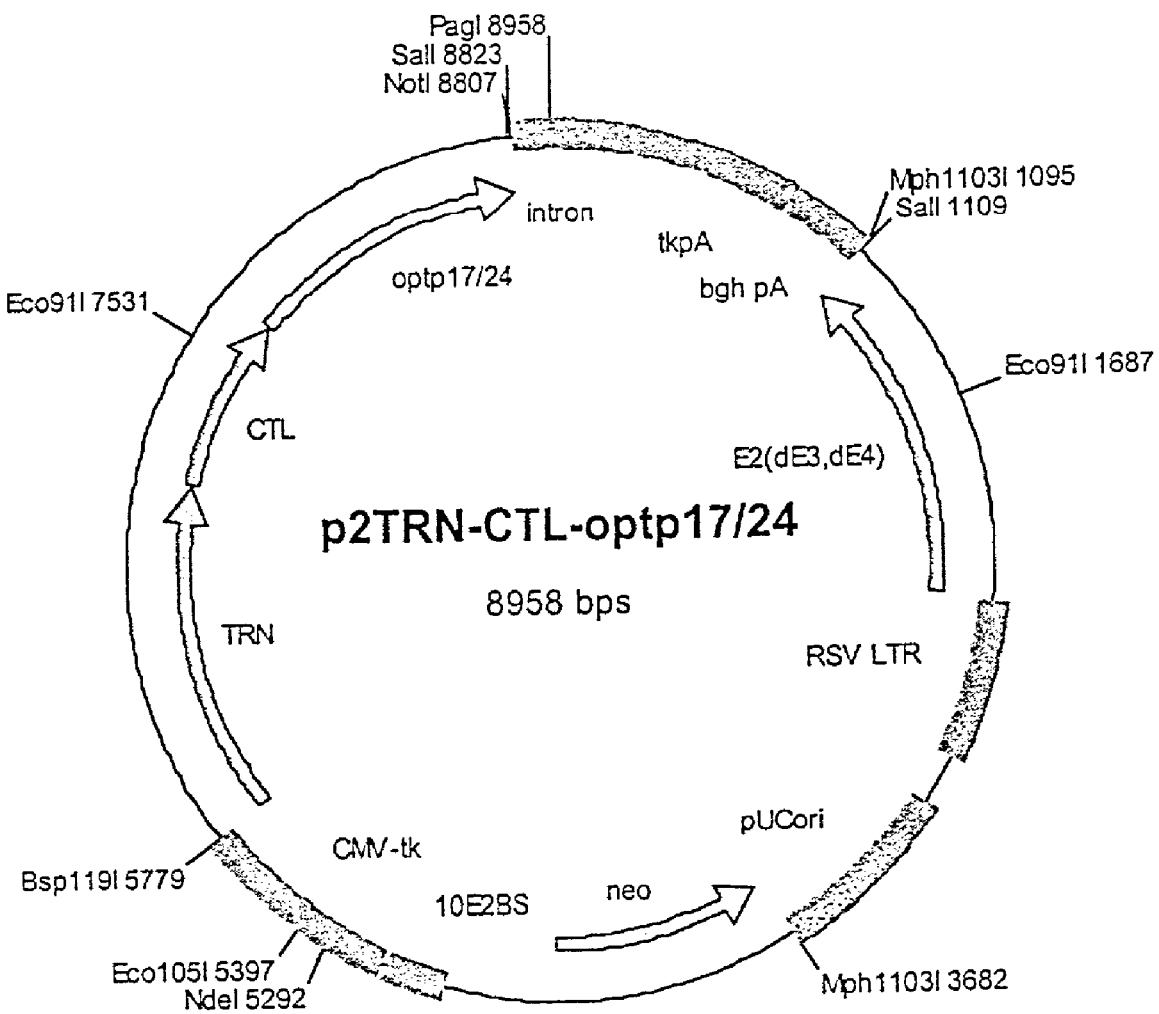
Figure 42N:
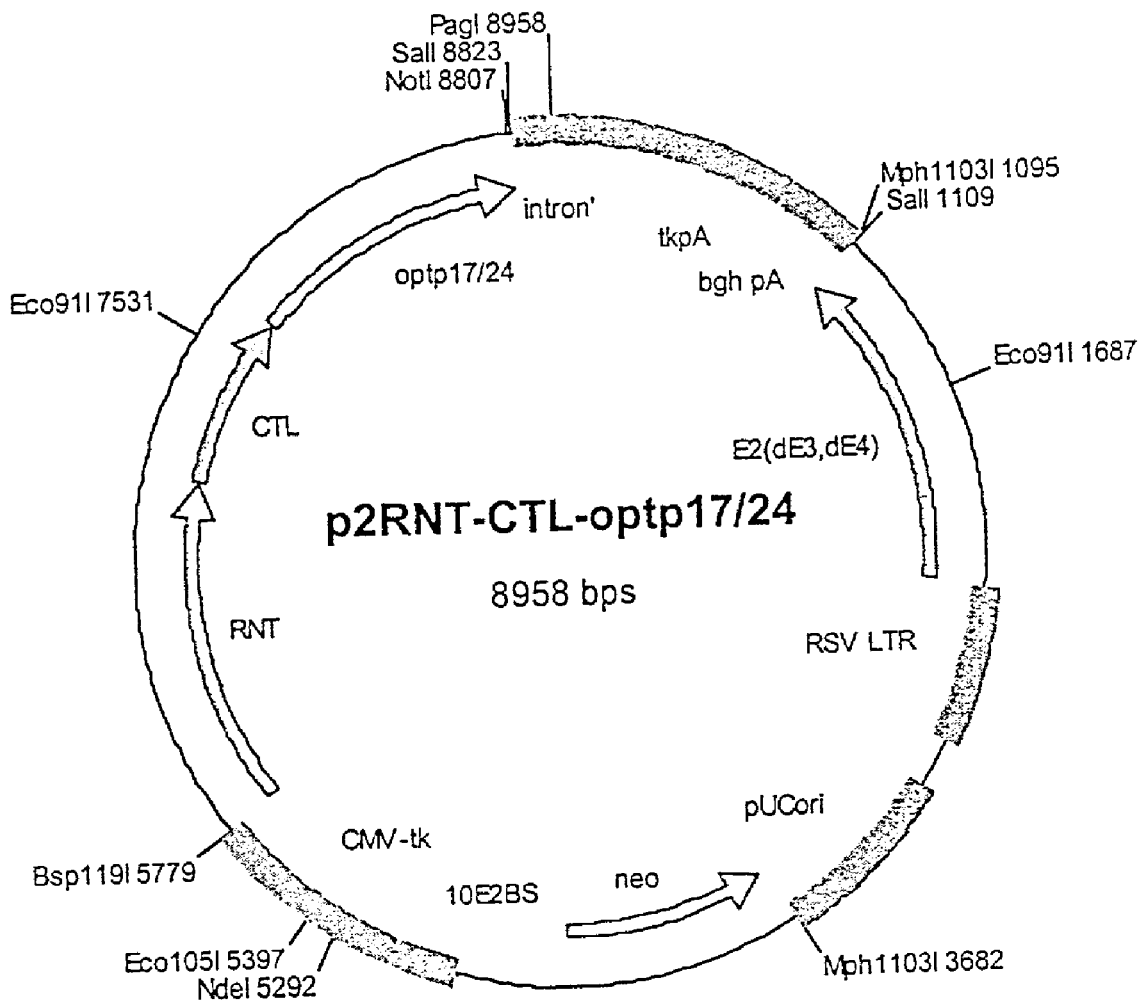
Figure 42:
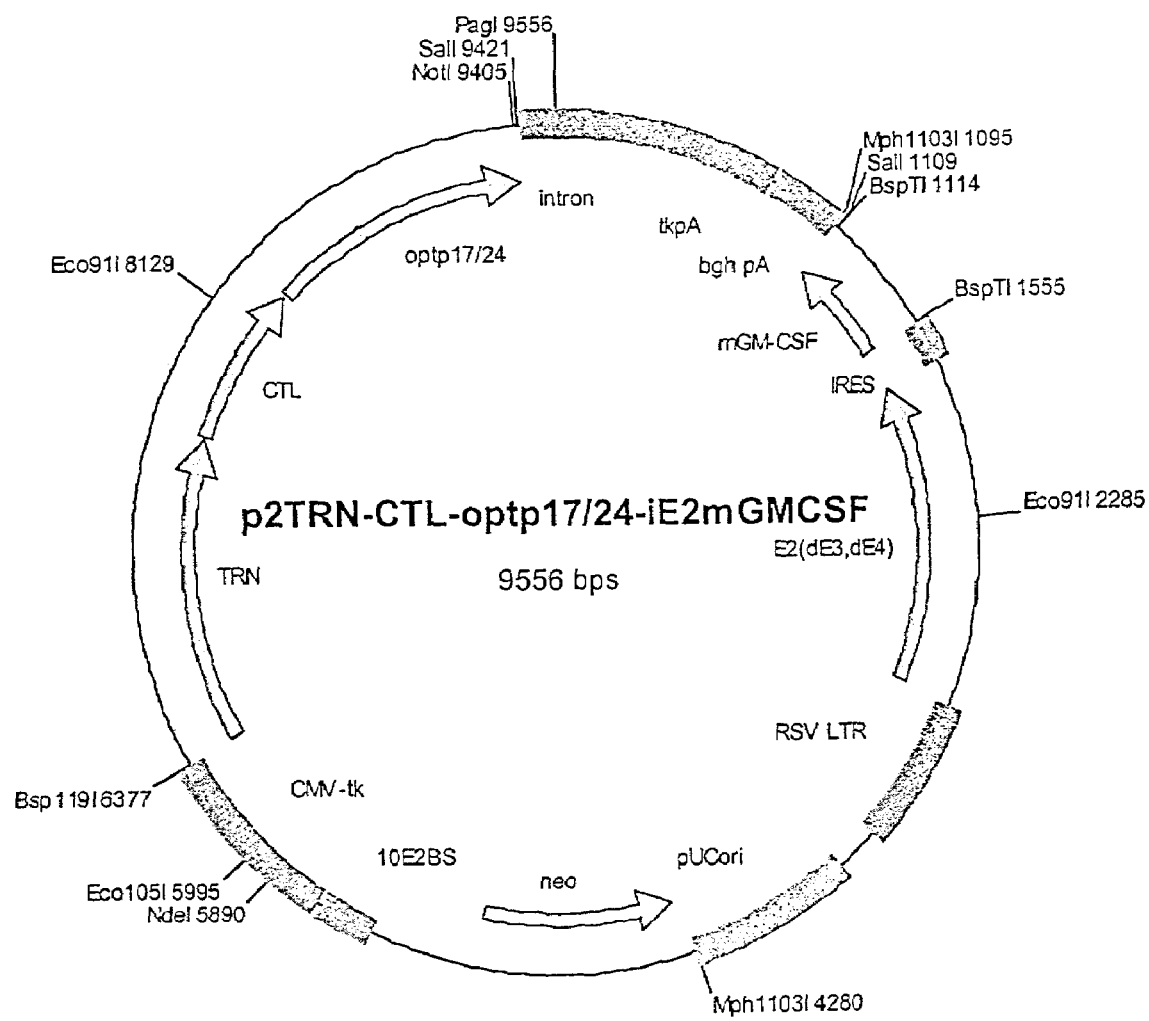
Figure 42P:
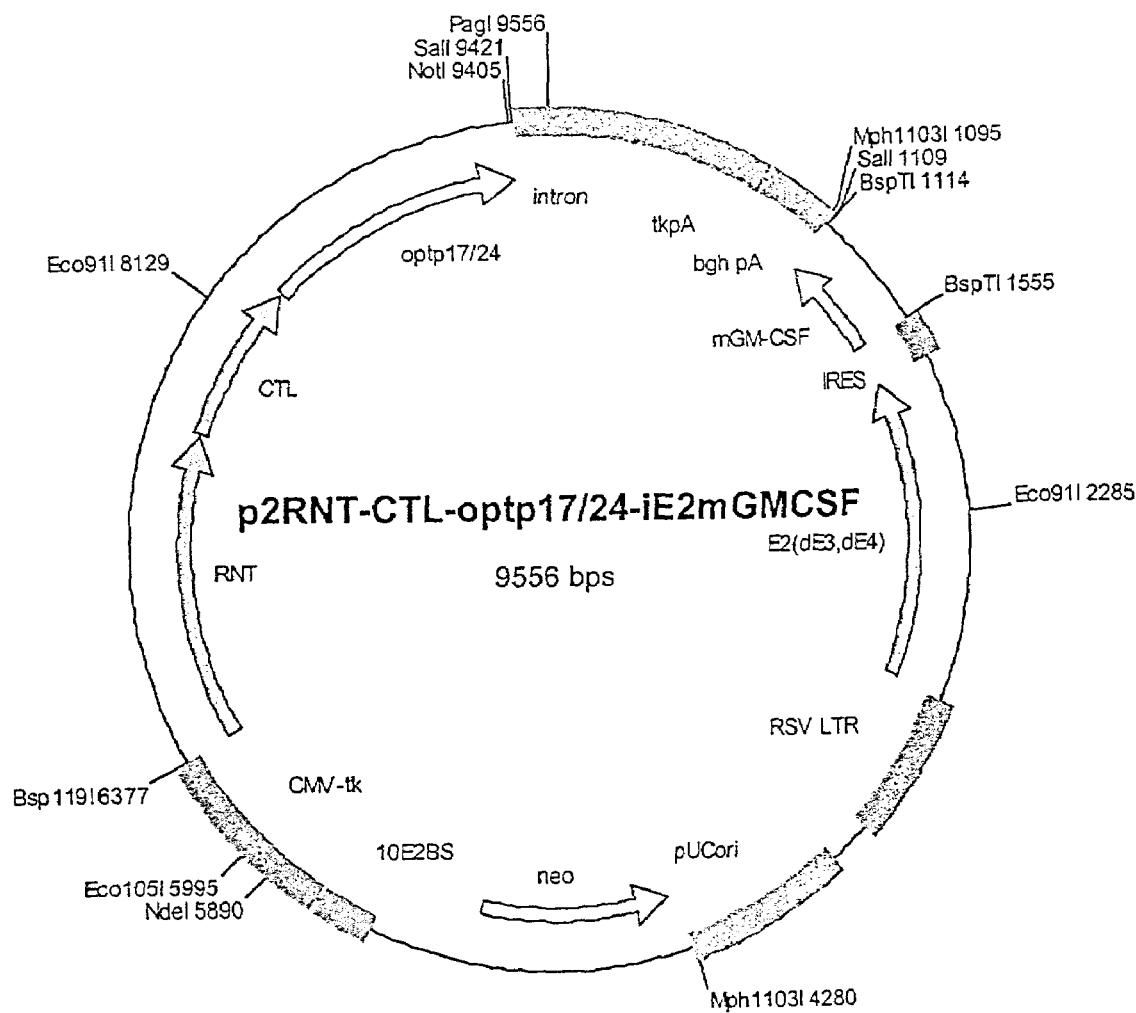
Figure 42Q:
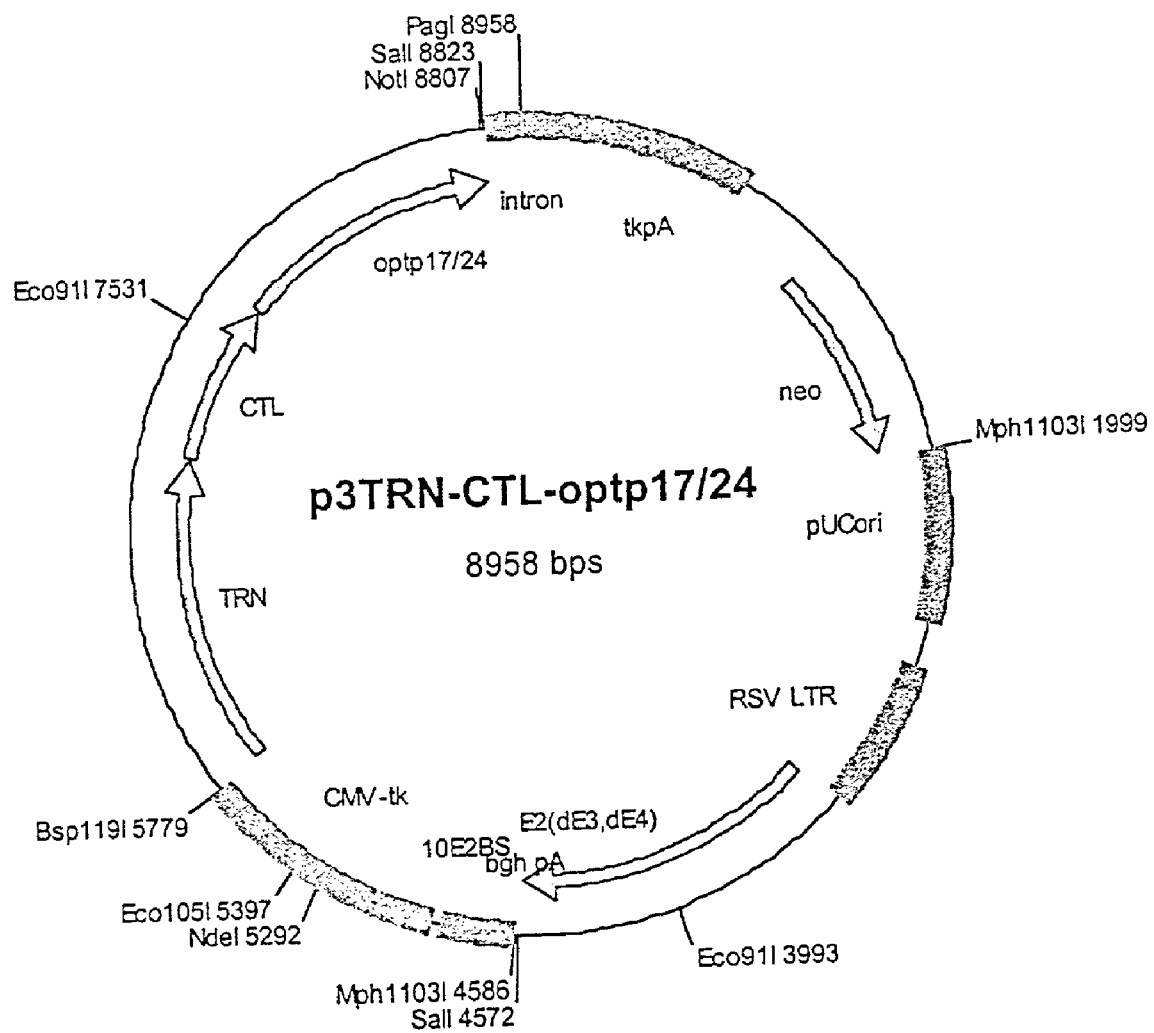
Figure 42R:
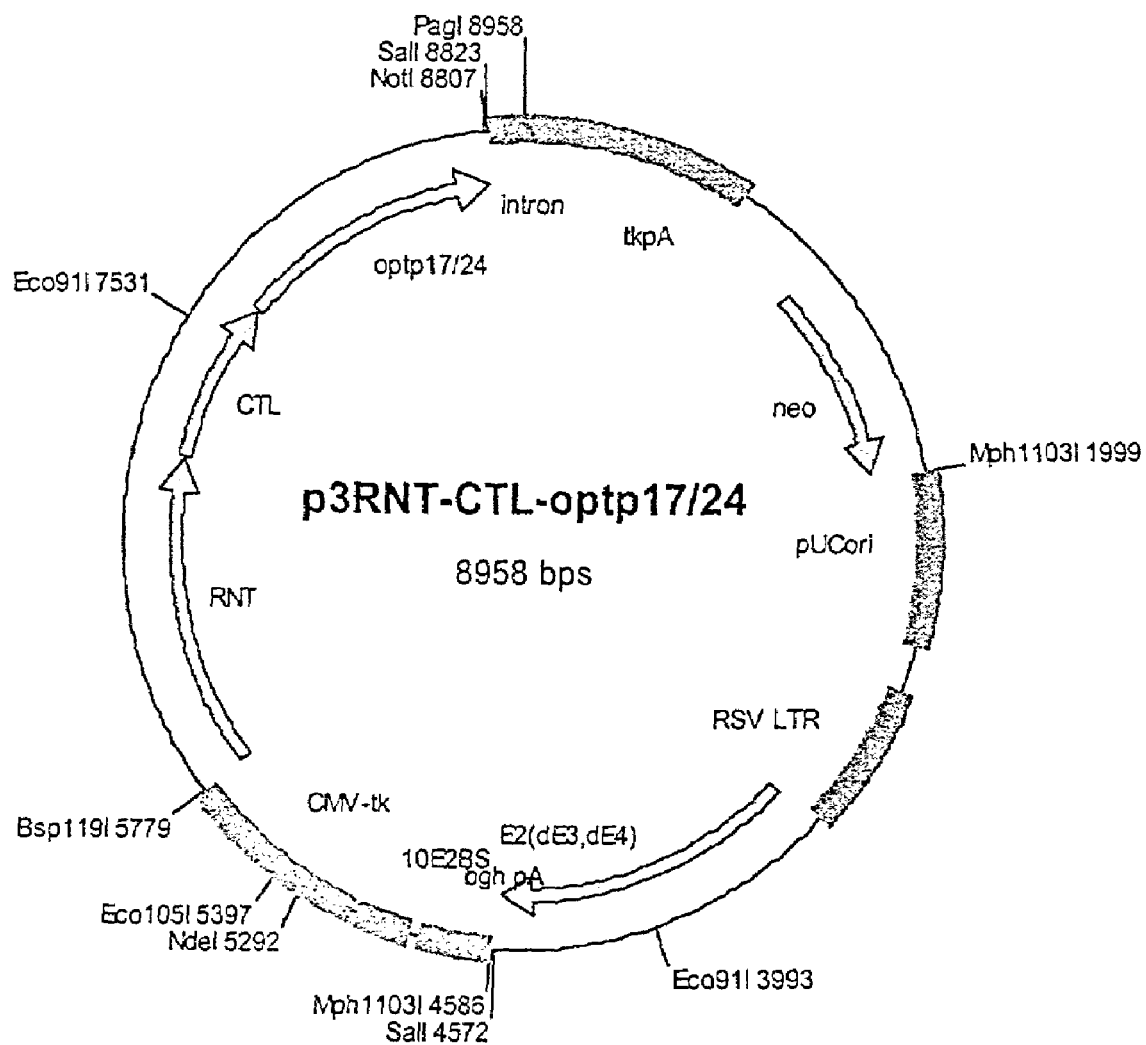
Figure 42S:
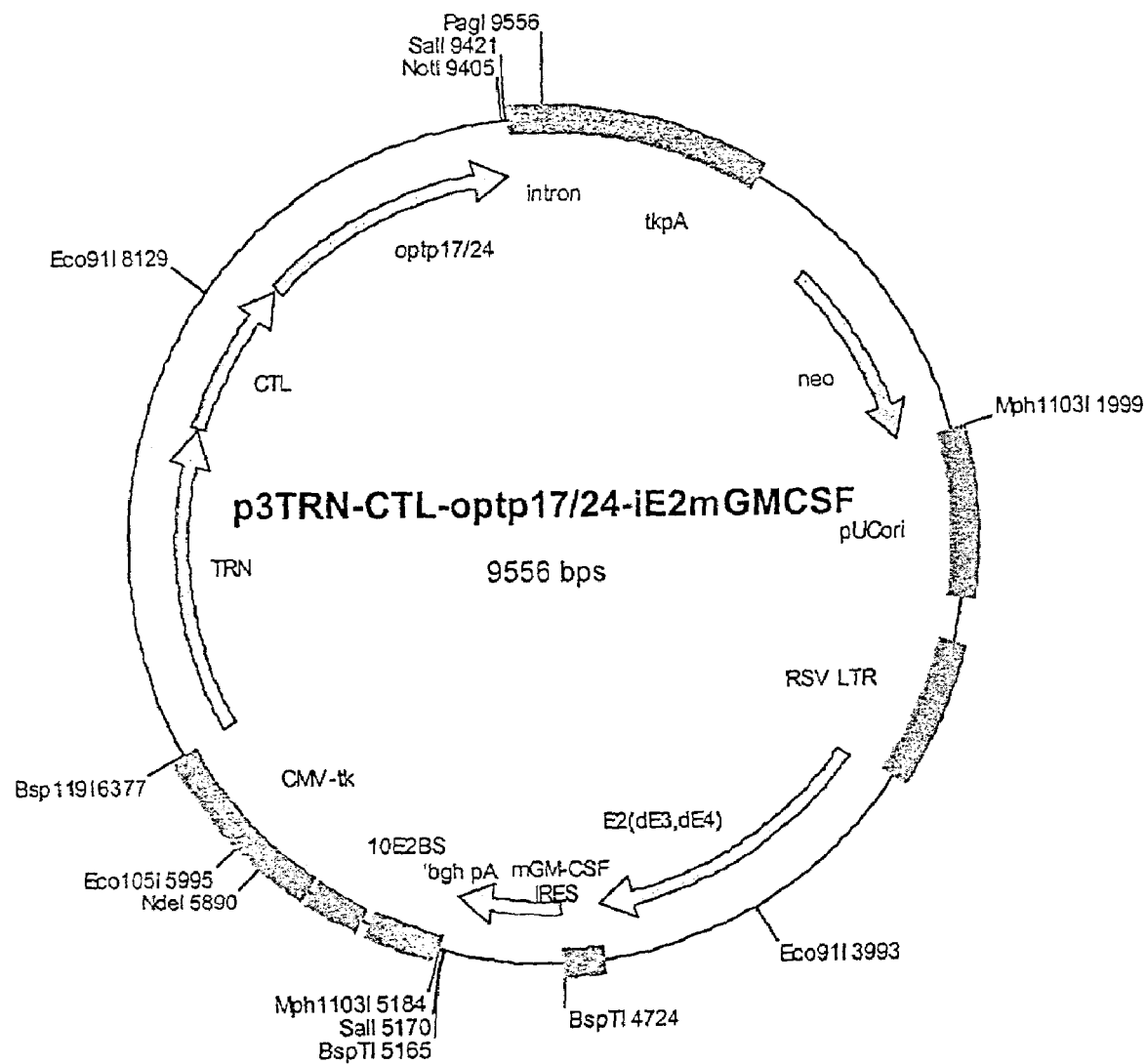
Figure 42T:
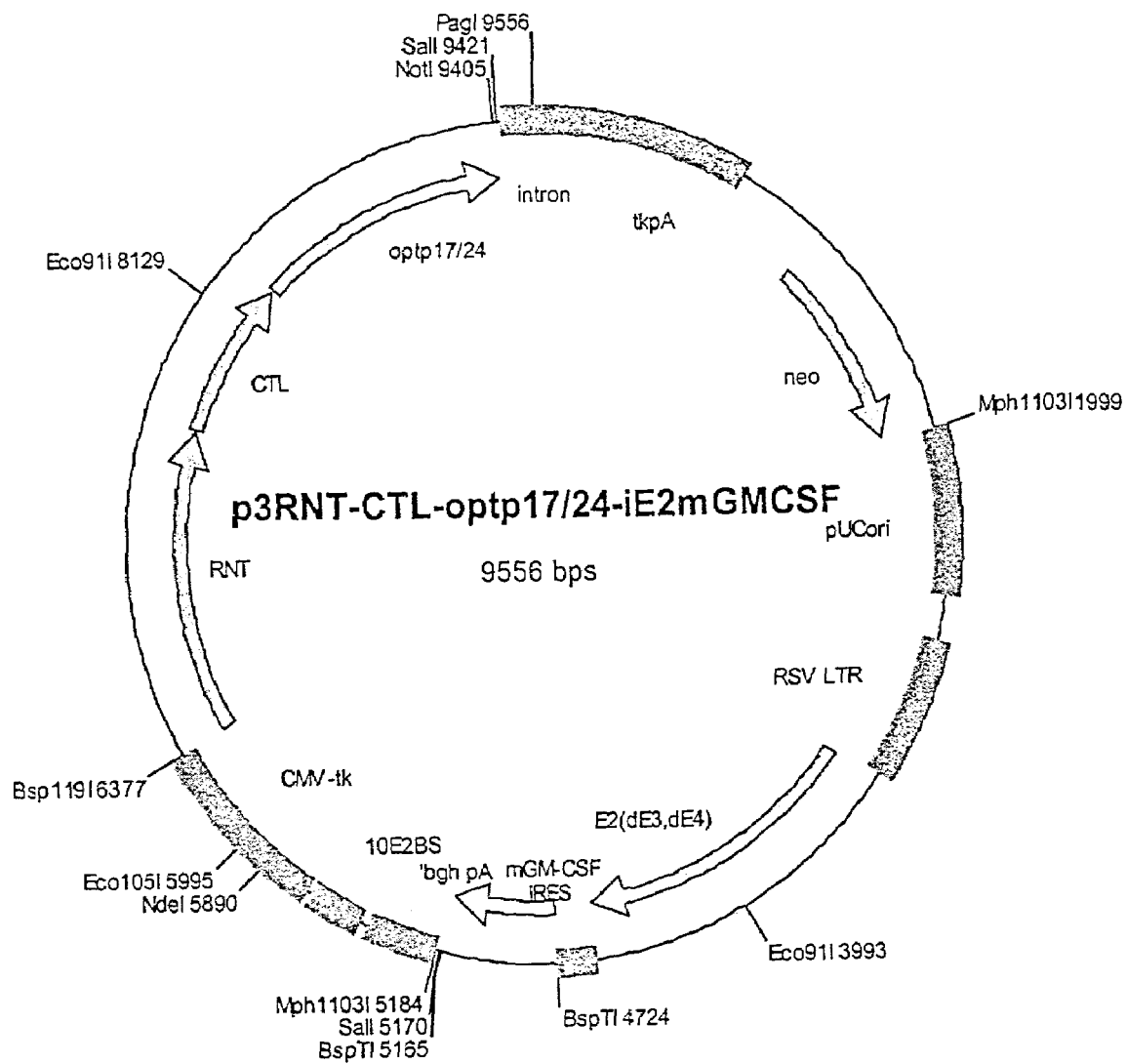
Figure 42U:
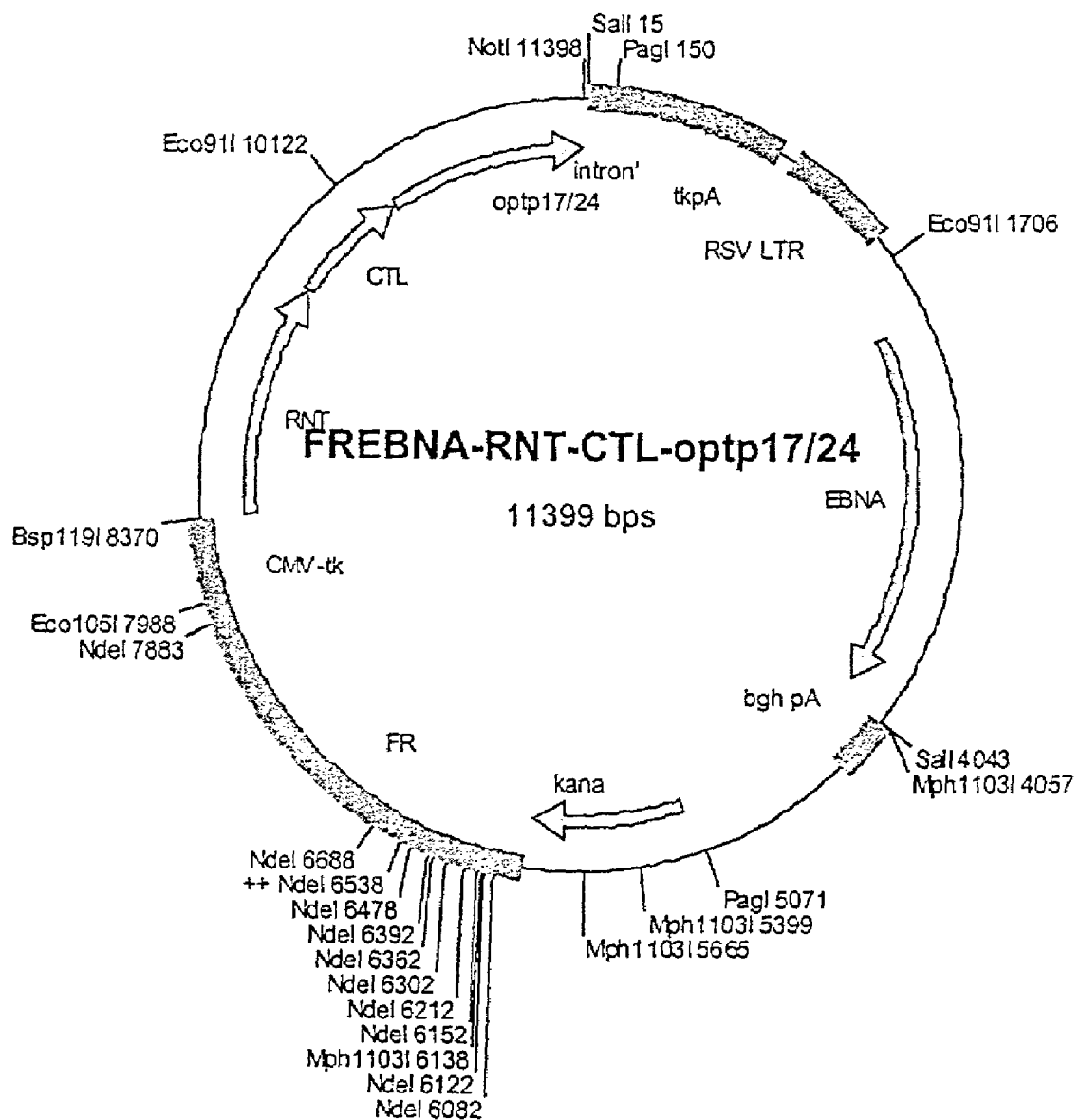
Figure 42V:
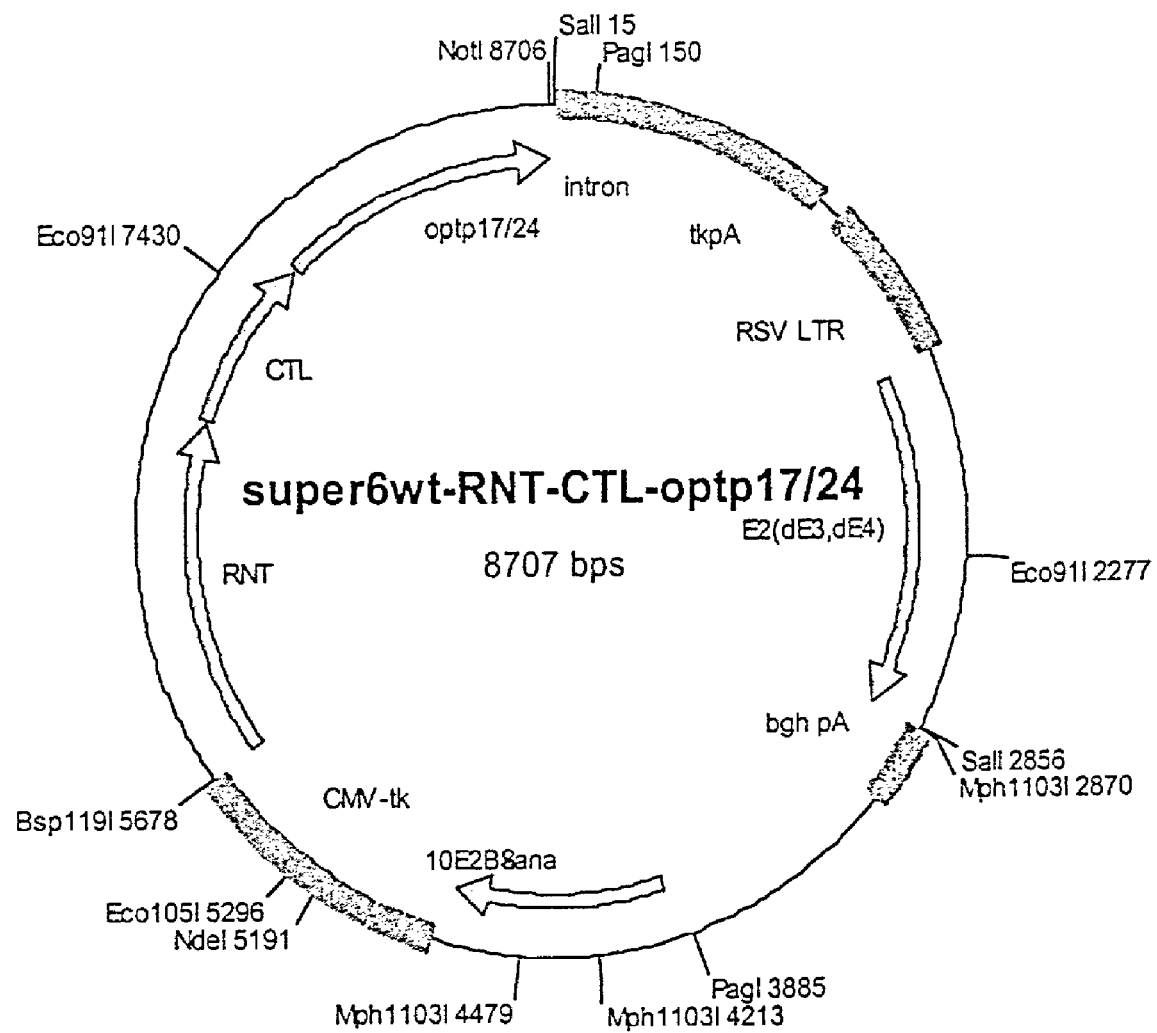
Figure 42W:
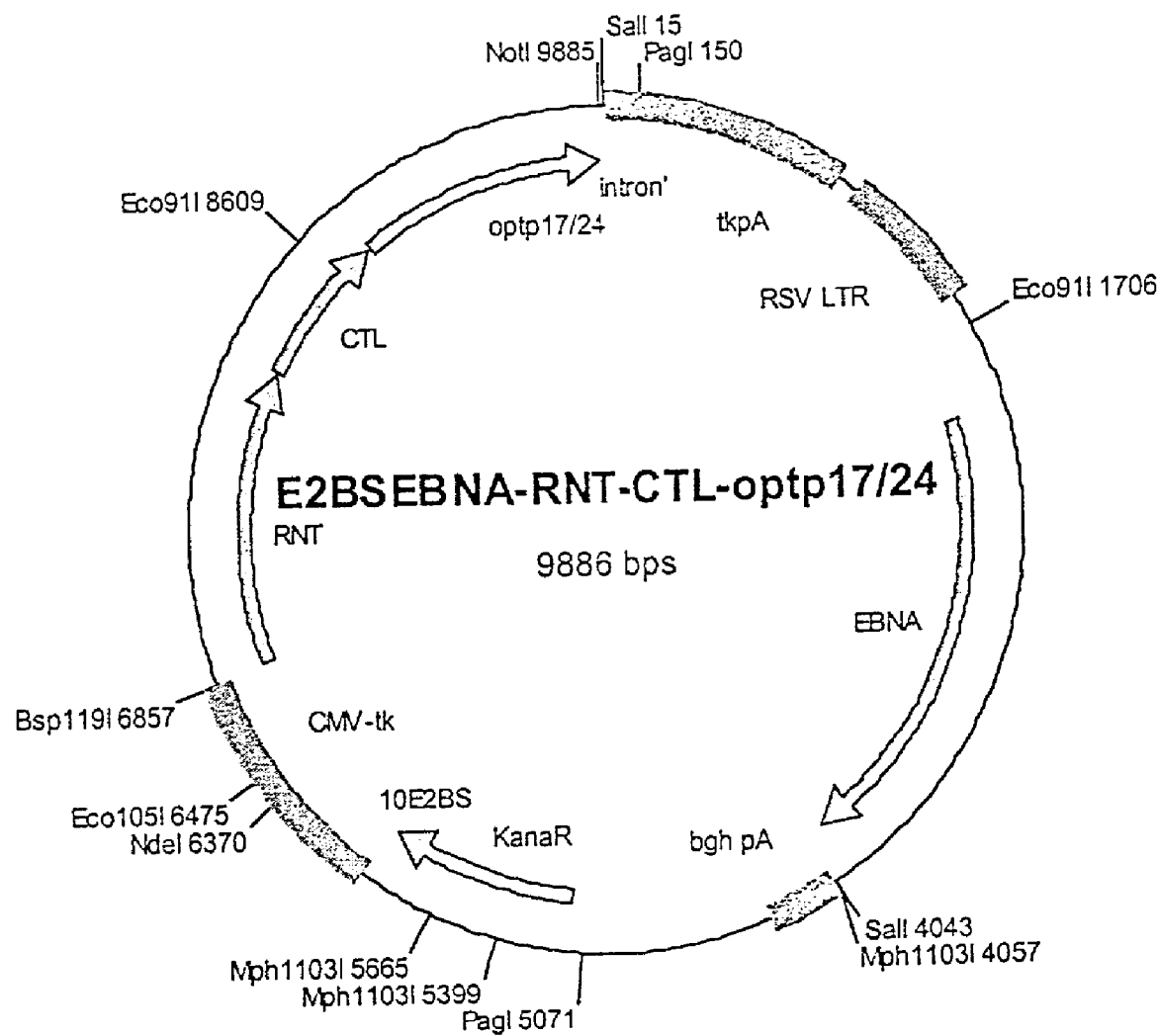
Figure 42X:
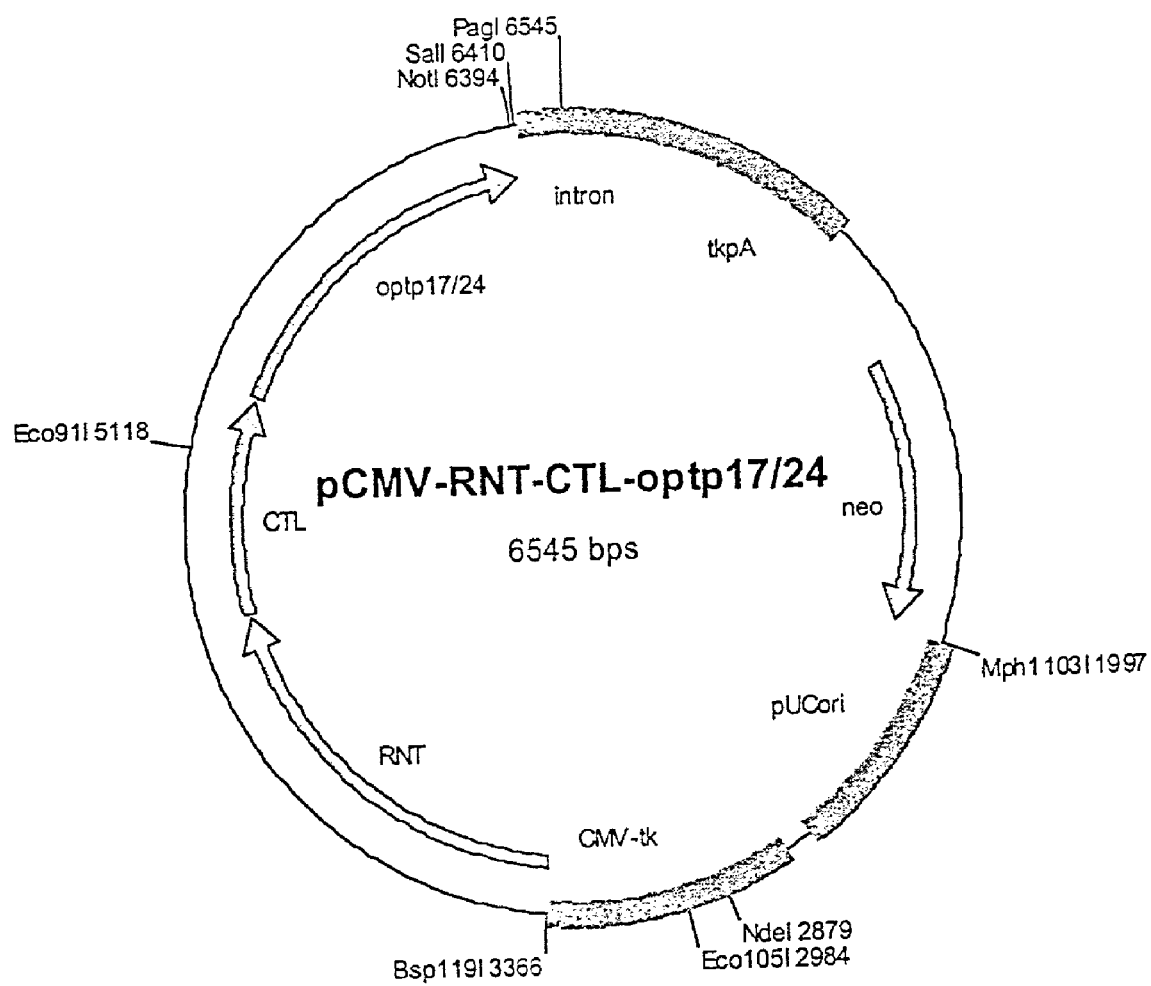

FIG. 42. (A) pTRN-CTL; (B) pRNT-CTL; (C) pTRN-dgag; (D) pTRN-CTL-dgag; (E) pRNT-CTL-dgag; (F) pTRN-dgag-CTL; (G) pRNT-dgag-CTL; (H) pTRN-optp17/24-CTL; (I) pTRN-CTL-optp17/24; (J) pRNT-CTL-optp17/24; (K) p2TRN-optp17/24-CTL; (L) p2RNT-optp17/24-CTL; (M) p2TRN-CTL-optp17/24; (N) p2RNT-CTL-optp17/24; (O) p2TRN-CTL-optp17/24-iE2-mGMCSF; (P) p2RNT-CTL-optp17/24-iE2-mGMCSF; (Q) p3TRN-CTL-optp17/24; (R) p3RNT-CTL-optp17/24; (S) p3TRN-CTL-optp17/24-iE2-mGMCSF; (T) p3RNT-CTL-optp17/24-iE2-mGMCSF; (U) FREBNA-RNT-CTL-optp17/24; (V) super6 wt-RNT-CTL-optp17/24; (W) E2BSEBNA-RNT-CTL-optp17/24; (X) pCMV-RNT-CTL-optp17/24

Figure 43:
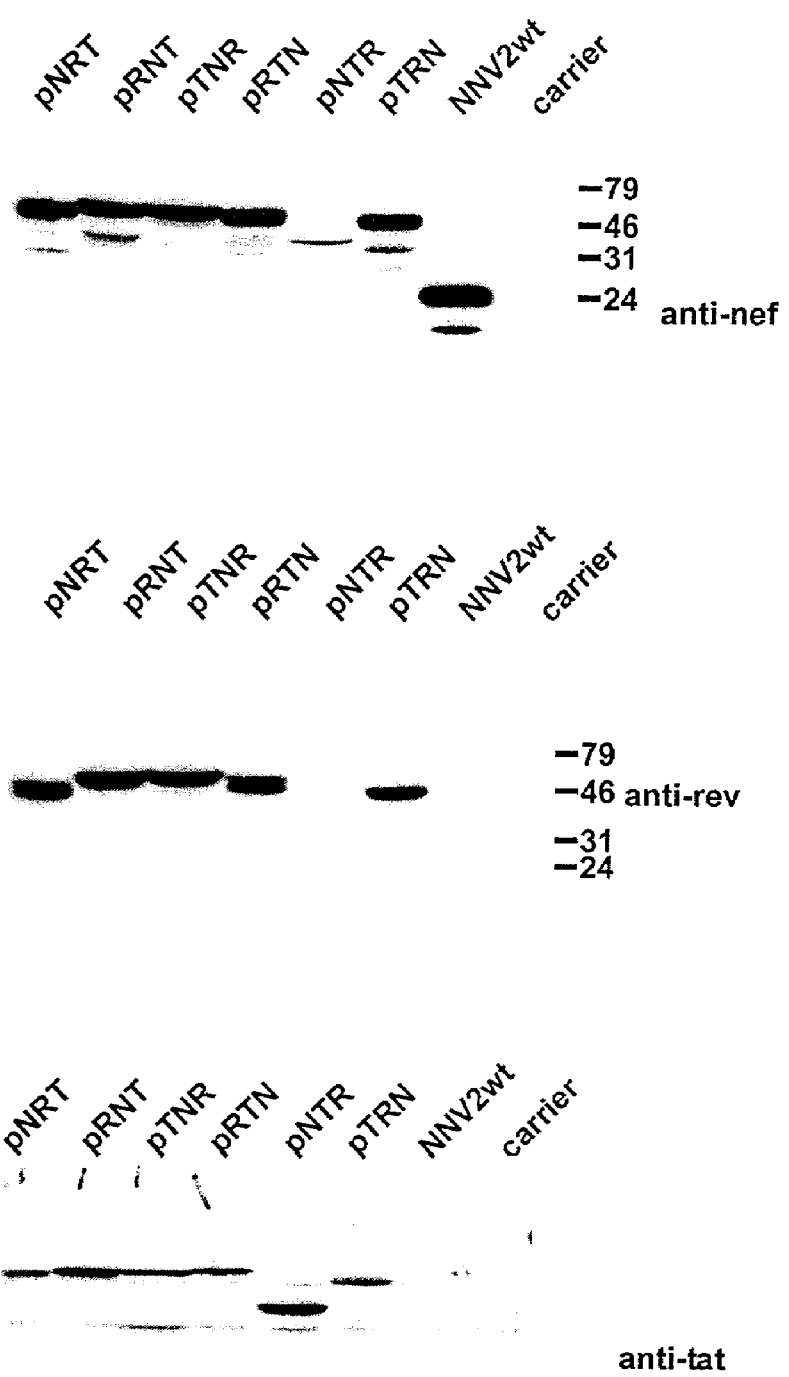

FIG. 43. Analysis of expression of the multireg antigenes. One microgram of each multireg antigene vector (as indicated on the top of each blot) was transfected by electroporation to the Jurkat cells. The cells were lyzed at 44 h post-transfection followed Western blot analysis with anti-Nef, anti-Rev and anti-Tat monoclonal antibodies. Nef expressing vector NNV-2 wt and only carrier DNA transfection were used as positive and negative controls, respectively. Molecular weight marker (kD) are indicated on the blots (with Nef and Rev antibodies).

Figure 44:
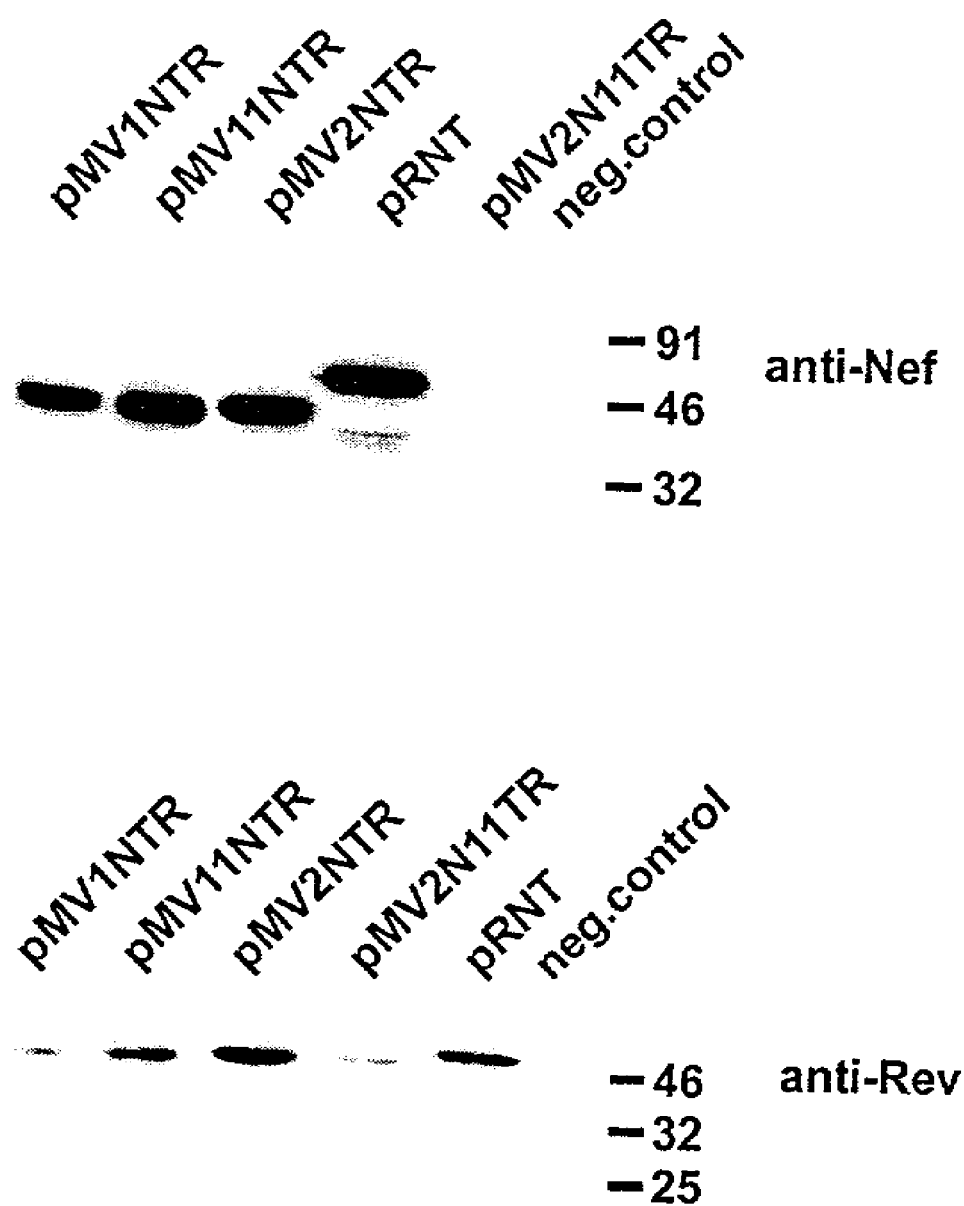

FIG. 44. Analysis of expression of the MultiREG antigenes comprised of immunodominant parts of the proteins. One microgram of each multireg antigene vector was transfected by electroporation to the RD cells. The cells were lyzed two days post-transfection followed Western blot analysis with anti-Nef and anti-Rev monoclonal antibodies. Previously characterized multireg vector pRNT and non-relevant antigene expressing vector were used as positive and negative controls, respectively. Molecular weight marker (kD) are indicated on the blots.

Figure 45:
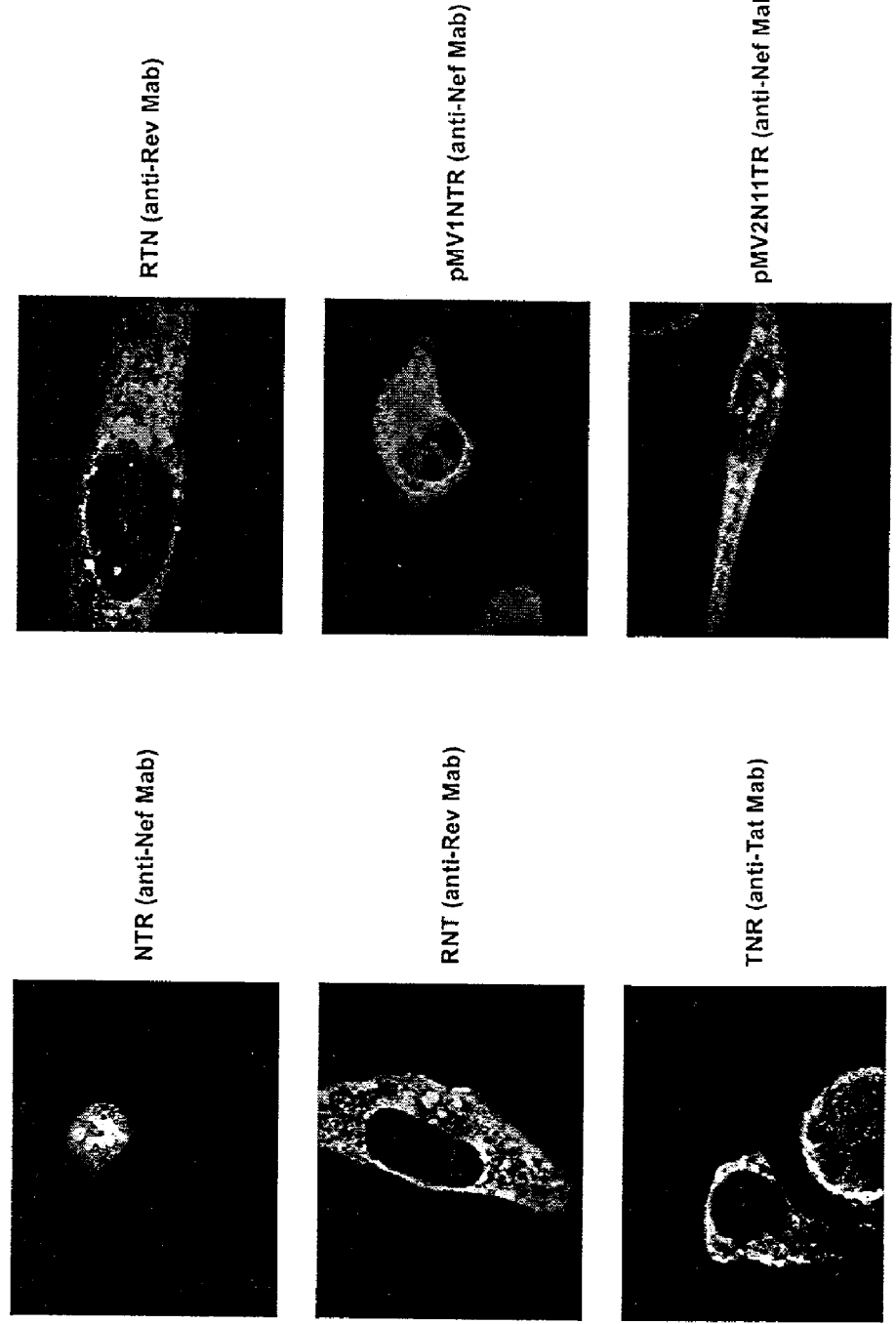

FIG. 45. Analysis of intracellular localization of multireg antigenes by immunofluorescence.

Figure 46:
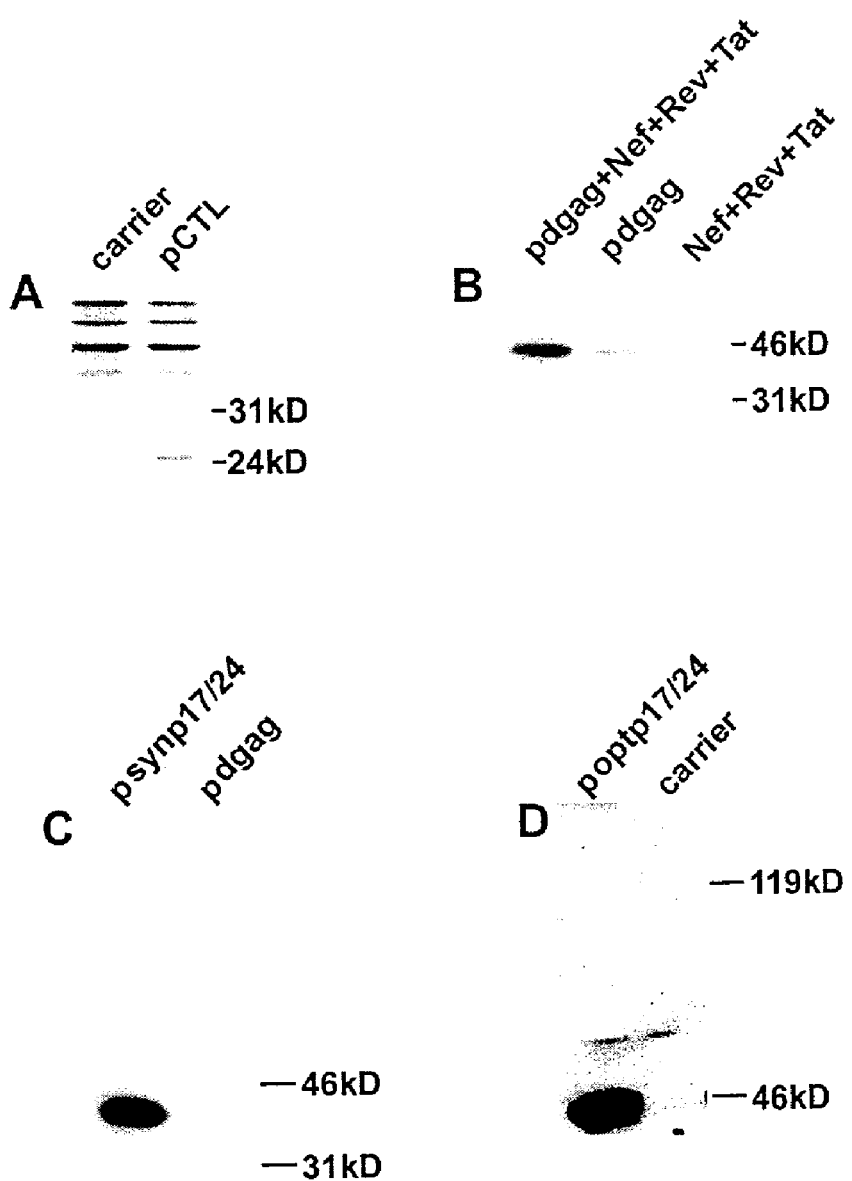

FIG. 46. Analysis of expression of the gag coded structural proteins and the CTL multi-epitope. (A) Cos-7 cells were transfected with 2 micrograms of the pCTL vector or with carrier only. The expression of the protein was detected two days after transfection using anti-CD43 Mab as primary antibody. (B) Two micrograms of pdgag plasmid was transfected to the Cos-7 cells with or without 0.5 micrograms of the CMV promoter driven constructs for Nef, Rev and Tat proteins. The transfection of the Nef, Rev and Tat expression vectors without pdgag was used as a negative control. (C) Analysis of expression of the structural antigenes in Jurkat cells transfected with 1 microgram psynp 17/24 or pdgag vector. (D) Analysis of expression of the p17/24 protein in Jurkat cells transfected with 1 microgram poptp17/24 or with carrier only as a negative control. In cases of blots represented on (B), (C), and (D), the anti p24 Mab was used as primary antibody.

Figure 47:
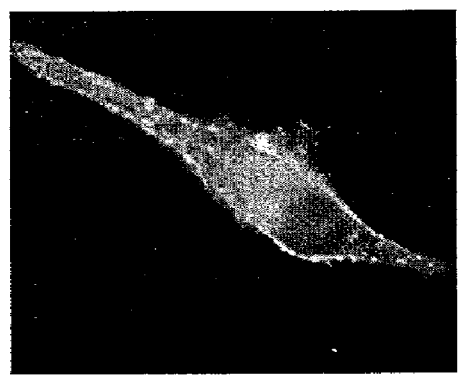

FIG. 47. The p17/24 protein localization in membranes of RD cells.

Figure 48:
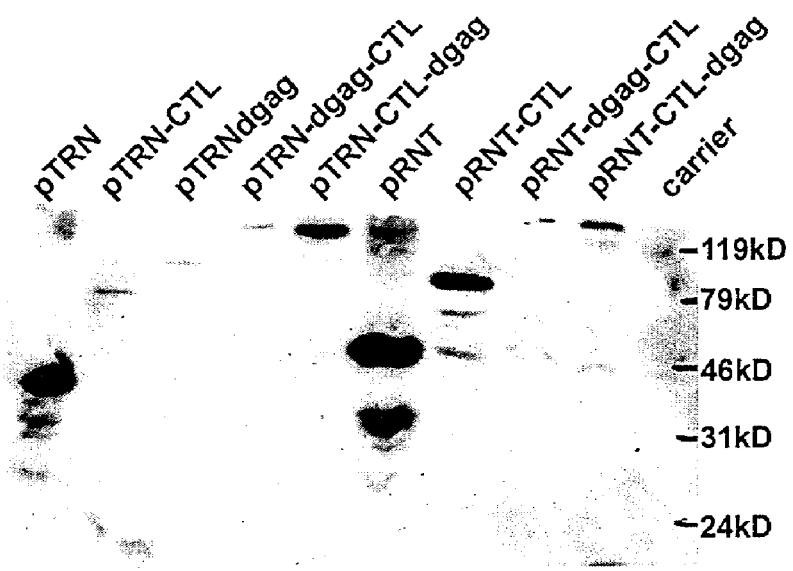

FIG. 48. Analysis expression of the dgag and CTL containing multigenes in Cos-7 cells. The cells were transfected with equimolar amounts (2 micrograms of the multireg+dgag+CTL) of the GTU-1 plasmids indicated on the top of the blot. The cells were lyzed two days post-transfection and analyzed using Mab against Nef protein. Molecular weight marker is also indicated on the blot.

Figure 49:
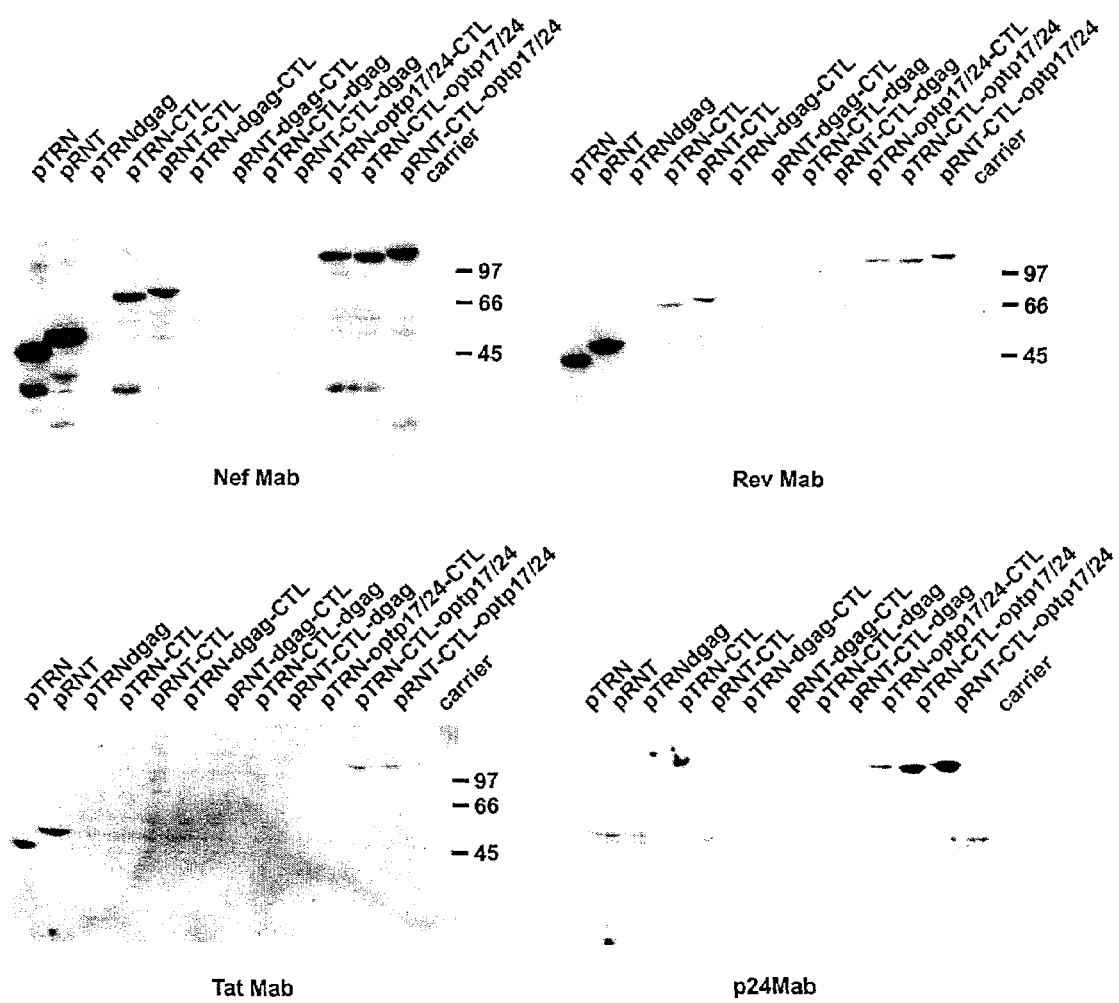

FIG. 49. Western blot analyses of multiHIV antibodies expressed in Jurkat cells transfected with equimolar amounts of GTU-1 vectors (2 micrograms of the biggest plasmids multireg+dgag+CTL) as indicated on the top of each blot. The cells were lyzed at 40 h post-transfection and monoclonal antibodies against Nef, Rev, Tat and p24 proteins were used as indicated on the figure.

Figure 50:
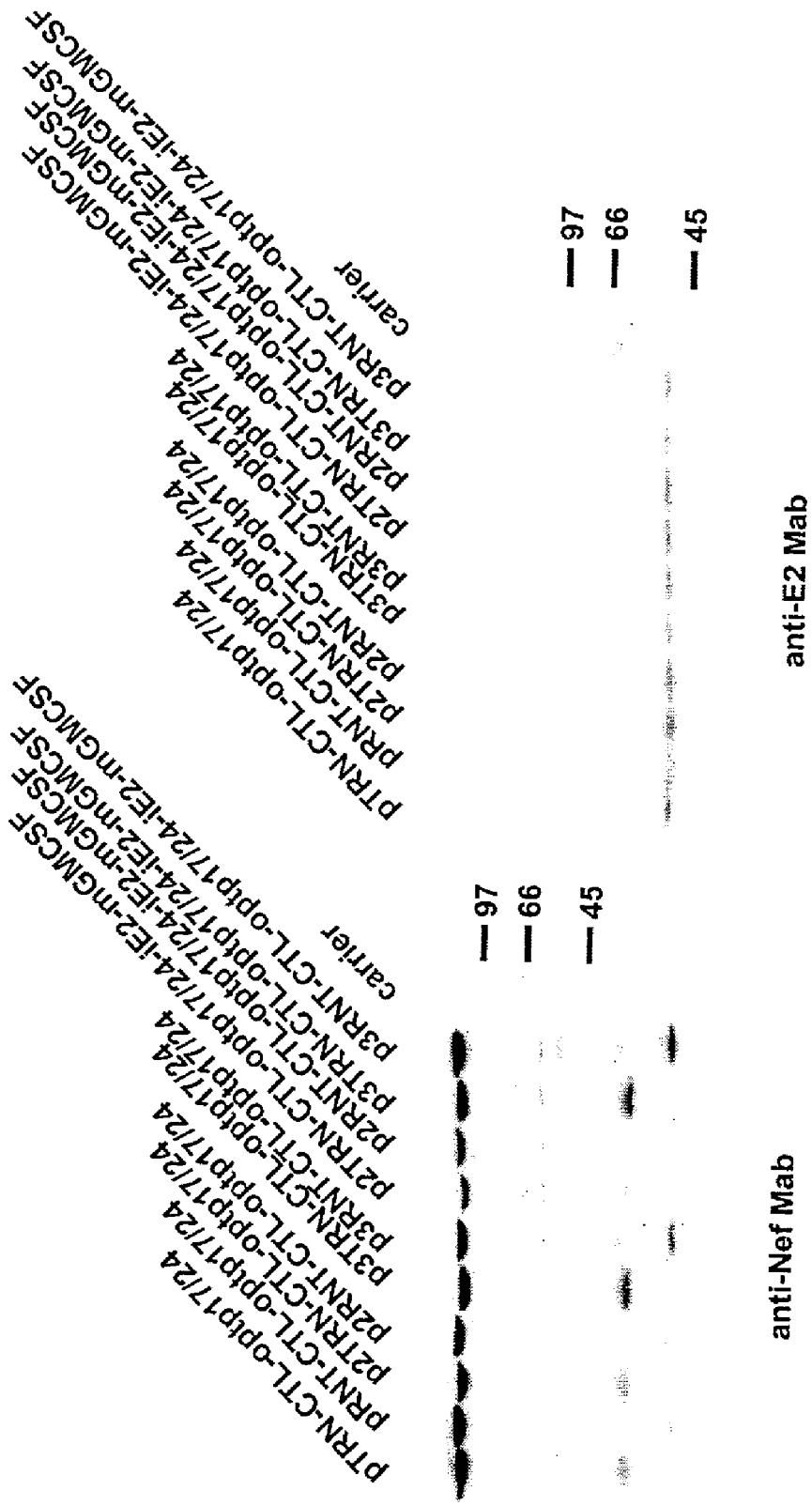

FIG. 50. Analysis of the expression of the TRN-CTL-optp17/24 and RNT-CTL-optp17/24 antigenes as well E2 protein from the GTU-1, GTU-2 and GTU-3 vector. One microgram of each vector were transfected to the Jurkat cells and the cells were lyzed at 38 hours post-transfection. Molecular weigh marker s are indicated on the both blots.

Figure 51:
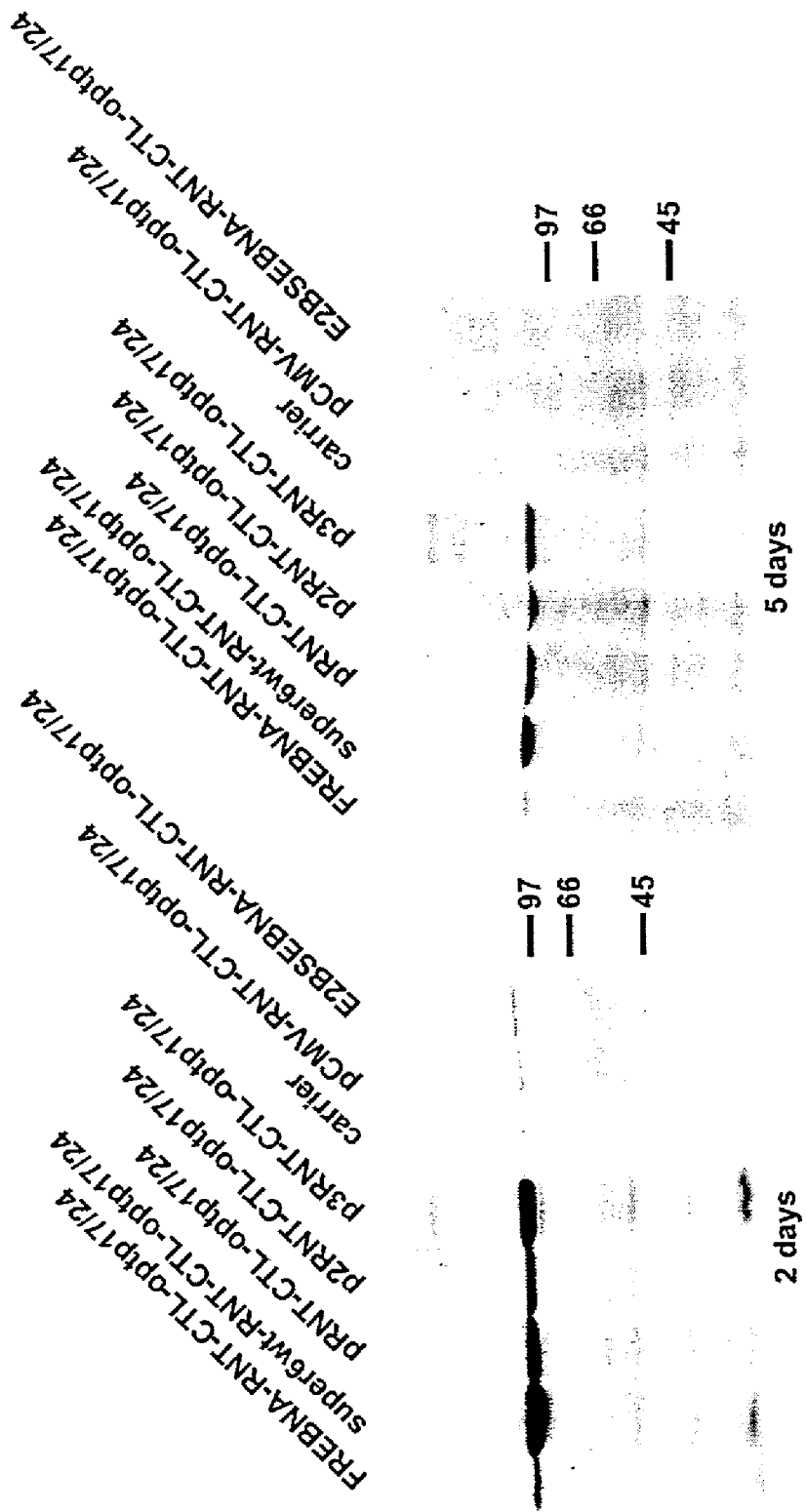

FIG. 51. The maintenance of the multiHIV antigene expression from different vectors. Jurkat cells were transfected with equimolar amounts of the plasmids and antigene expression was studied at 2 and 5 days post-transfection using anti-Nef Mab. Transfection with carrier DNA only was used as a negative control. Molecular weight markers are indicated on the both blots.

Figure 52:
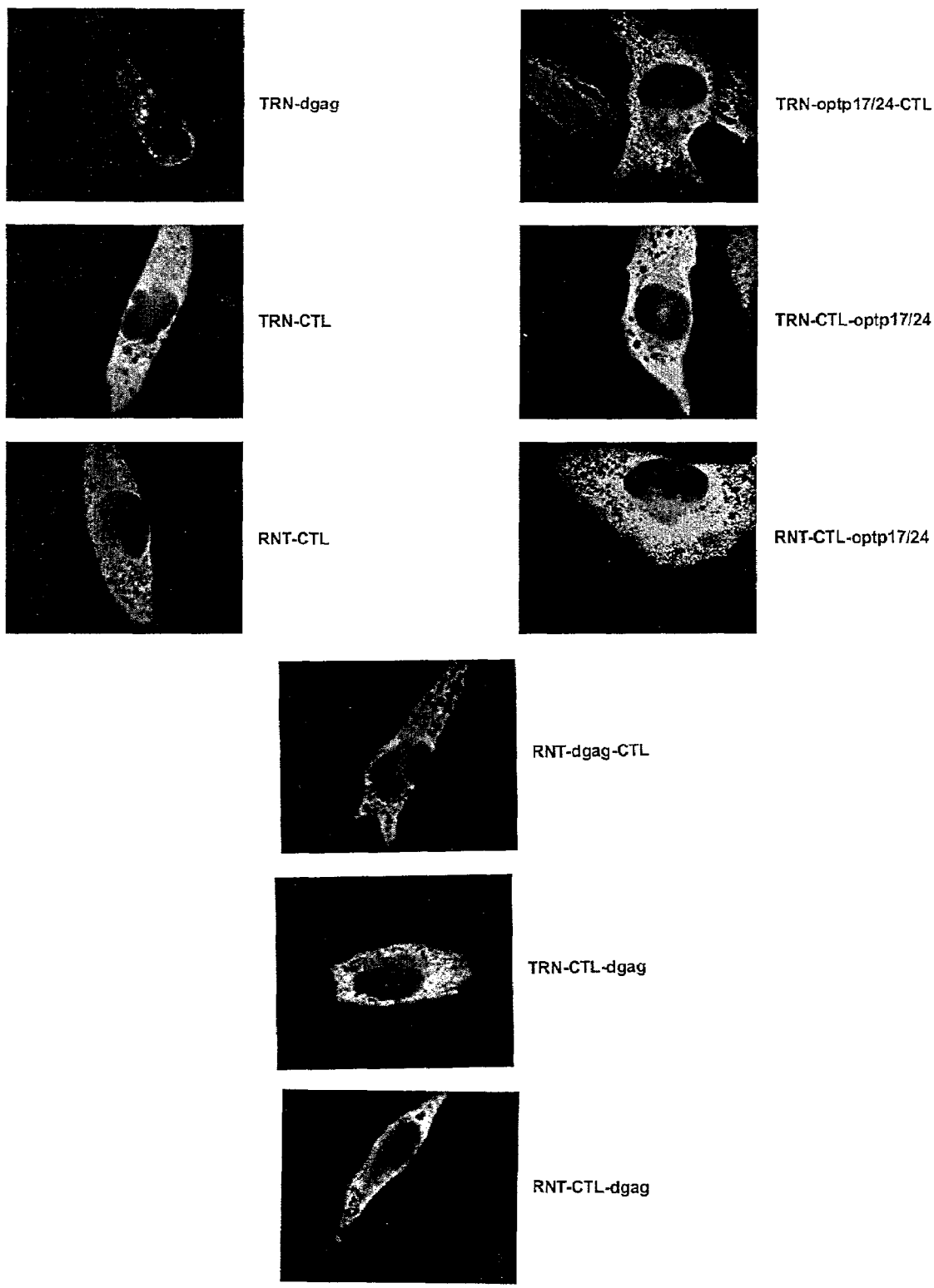

FIG. 52. Intracellular localization of the multiHIV antigenes in RD cells.

5. DETAILED DESCRIPTION OF THE INVENTION

5.1 Vectors of the Invention

The present invention is based on the unexpected finding that expression vectors, which carry (A) an expression cassette of a gene of a nuclear-anchoring protein that binds both to (i) a specific DNA sequence and (ii) to a suitable nuclear component and (B) a multimerized DNA binding sequence for said nuclear-anchoring protein are capable of spreading in a proliferating cell population. Such nuclear-anchoring proteins include, but are not limited to, chromatin-anchoring proteins, such as the Bovine Papilloma Virus type 1 E2 protein (BPV1 E2; SEQ ID NO: 50). The DNA binding sequences can be, but are not limited to, multimerized E2 binding sites. On the basis of prior art, it could not be expected that a segregation/partitioning function of, for instance, the papilloma viruses could be expressed separately and that an addition of such segregation/partitioning function to the vaccine vectors would assure the distribution of the vector in the proliferating cell population. Additionally, on the basis of the prior art, it could not have been expected that functional vectors acting independently of the replication origin can be constructed.

The term "nuclear-anchoring protein" as used in the present invention refers to a protein, which binds to a specific DNA sequence and capable of providing a nuclear compartmentalization function to the vector, i.e., to a protein, which is capable of anchoring or attaching the vector to a specific nuclear compartment. In certain embodiments of the invention, the nuclear-anchoring protein is a natural protein. Examples of such nuclear compartments are the mitotic chromatin or mitotic chromosomes, the nuclear matrix, nuclear domains like ND10 and POD etc. Examples of nuclear-anchoring proteins are the Bovine Papilloma Virus type 1 (BPV1) E2 protein, EBNA1 (Epstein-Barr Virus Nuclear Antigen 1; SEQ ID NO: 52), and High Mobility Group (HMG) proteins etc. The term "functional equivalent of a nuclear-anchoring protein" as used in the present invention refers to a protein or a polypeptide of natural or non-natural origin having the properties of the nuclear-anchoring protein.

In certain other embodiments of the invention, the nuclear-anchoring protein of the invention is a recombinant protein. In certain specific embodiments of the invention, the nuclear-anchoring protein is a fusion protein, a chimeric protein, or a protein obtained by molecular modeling. A fusion protein, or a protein obtained by molecular modeling in connection with the present invention is characterized by its ability to bind to a nuclear component and by its ability to bind sequence-specifically to DNA. In a preferred embodiment of the invention, such a fusion protein is encoded by a vector of the invention which also contains the specific DNA sequence to which the fusion/chimeric protein binds. Nuclear components include, but are not limited to chromatin, the nuclear matrix, the ND10 domain and POD. In order to reduce the risk of interference with the expression of genes endogenous to the host cell, the DNA binding domain and the corresponding DNA sequence is preferably non-endogenous to the host cell/host organism. Such domains include, but are not limited to, the DNA binding domain of the Bovine Papilloma Virus type 1 (BPV1) E2 protein (SEQ ID NO: 50), Epstein-Barr Virus Nuclear Antigen 1 (EBNA1; SEQ ID NO: 52), and High Mobility Group (HMG) proteins (HMG box).

The vector of the invention can further comprise a "DNA sequence of interest", that encodes a protein (including a peptide or polypeptide), e.g., that is an immunogen or a therapeutic. In certain embodiments of the invention, the DNA sequence of interest encodes a biologically active RNA molecule, such as an antisense RNA molecule or a ribozyme.

The expression vectors of the invention carrying an expression cassette for a gene of a nuclear-anchoring protein and multimerized binding sites for said nuclear-anchoring protein spread in a proliferating host cell population. This means that a high copy-number of vectors or plasmids are delivered into the target cells and the use of the segregation/partitioning function of the nuclear-anchoring protein and its multimerized binding sites assures the distribution of the vector to the daughter cells during cell division.

The vector of the invention lacks a papilloma virus origin of replication. Further, in a preferred embodiment, the vector of the invention lacks an origin of replication functional in a mammalian cell. The omission of a papilloma virus origin of replication or a mammalian origin of replication constitutes an improvement over prior art vectors for several reasons. (1) Omission of the origin of replication reduces the size of the vector of the invention compared to prior art vectors. Such a reduction in size increases the stability of the vector and facilitates uptake by the host cell. (2) Omission of the origin of replication reduces the risk for recombination with the host cell's genome, thereby reducing the risk of unwanted side effects. (3) The omission of the origin of replication allows to control the dosage simply by adjusting the amount of vector administered. In contrast, with a functioning origin of replication, replication of the vector has to be taken into consideration when determining the required dosage. (4) If the vector is not administered to a host organism continually, the lack of an origin of replication allows the host organism to clear itself of the vector, thus providing more control over the levels of DNA sequences to be expressed in the host organism. Further, the ability of the organism to clear itself of the vector will be advantageous if the presence of the vector is required only during the course of a therapy but is undesirable in a healthy individual.

The gene of a nuclear-anchoring protein useful in the vectors of the present invention can be any suitable DNA sequence encoding a natural or artificial protein, such as a recombinant protein, a fusion protein or a protein obtained by molecular modeling techniques, having the required properties. Thus the gene of a natural nuclear-anchoring protein, which contains a DNA binding domain capable of binding to a specific DNA sequence and a functional domain capable of binding to a nuclear component, can be that of a viral protein, such as the E2 protein of Bovine Papilloma Virus or the EBNA1 (Epstein-Barr Virus Nuclear Antigen 1) of the Epstein-Barr Virus, a eukaryotic protein such a one of the High Mobility Group (HMG) proteins or a like protein, or a prokaryotic protein. Alternatively, the gene of a nuclear-anchoring protein, which contains a DNA binding domain capable of binding to a specific DNA sequence and a functional domain capable of binding to a nuclear component, can also be comprised of DNA sequences, which encode a domain from a cellular protein having the ability to attach to a suitable nuclear structure, such as to mitotic chromosomes, the nuclear matrix or nuclear domains like ND10 or POD.

Alternatively, the DNA sequence, which encodes a non-natural or artificial protein, such as a recombinant protein or a fusion protein or a protein obtained by molecular modeling, which contains a DNA binding domain capable of binding to a specific DNA sequence of, e.g., a papilloma virus, such as the DNA binding domain of the E2 protein of the BPV1, but in which the N-terminus of the nuclear-anchoring protein, e.g. that of the E2 protein, has been replaced with domains of any suitable protein of similar capacity, for example, with the N-terminal domain of Epstein-Barr Virus Nuclear Antigen 1 sequence, can be used. Similarly, DNA sequences, which encode a recombinant protein or a fusion protein, which contains a functional domain capable of binding to a nuclear component, e.g., the N-terminal functional domain of a papilloma virus, such as the E2 protein of the BPV1, but in which the C-terminal DNA-binding dimerization domain of the nuclear-anchoring protein, e.g., that of the E2 protein, has been replaced with domains of any protein of a sufficient DNA-binding strength, e.g., the DNA binding domain of the BPV-1 E2 protein and the EBNA-1, can be used.

In a preferred embodiment of the invention, the nuclear-anchoring protein is a chromatin-anchoring protein, which contains a DNA binding domain which binds to a specific DNA sequence and a functional domain capable of binding to mitotic chromatin. A preferred example of such a chromatin-anchoring protein and its multimerized binding sites useful in the present invention are the E2 protein of Bovine Papilloma Virus type 1 and E2 protein multimerized binding sites. In the case of E2, the mechanism of the spreading function is due to the dual function of the E2 protein: the capacity of the E2 protein to attach to mitotic chromosomes through the N-terminal domain of the protein and the sequence-specific binding capacity of the C-terminal domain of the E2 protein, which assures the tethering of vectors, which contain a multimerized E2 binding site, to mitotic chromosomes. A segregation/partitioning function is thus provided to the vectors.

In another preferred embodiment of the invention, the expression cassette of a gene of the chromatin-anchoring protein comprises a gene of any suitable protein of cellular, viral or recombinant origin having analogous properties to E2 of the BPV1, i.e., the ability to attach to the mitotic chromatin through one domain and to cooperatively bind DNA through another domain to multimerized binding sites specific for this DNA binding domain.

In a specific embodiment, sequences obtained from BPV1, are used in the vectors of the present invention, they are extensively shortened in size to include just two elements from BPV1. First, they include the E2 protein coding sequence transcribed from a heterologous eukaryotic promoter and polyadenylated at the heterologous polyadenylation site. Second, they include E2 protein multiple binding sites incorporated into the vector as a cluster, where the sites can be as head-to-tail structures or can be included into the vector by spaced positioning. Both of these elements are necessary and, surprisingly, sufficient for the function of the vectors to spread in proliferating cells. Similarly, when DNA sequences based of other suitable sources are used in the vectors of the present invention, the same principles are applied.

According to the present invention, the expression cassette of a gene of a nuclear-anchoring protein, which contains a DNA binding domain capable of binding to a specific DNA sequence and a functional domain capable of binding to a nuclear component, such as an expression cassette of a gene of a chromatin-anchoring protein, like BPV1 E2, comprises a heterologous eukaryotic promoter, the nuclear-anchoring protein coding sequence, such as a chromatin-anchoring protein coding sequence, for instance the BPV1 E2 protein coding sequence, and a poly A site. Different heterologous, eukaryotic promoters which control the expression of the nuclear-anchoring protein can be used. Nucleotide sequences of such heterologous, eukaryotic promoters are well-known in the art and are readily available. Such heterologous eukaryotic promoters are of different strength and tissue-specificity. In a preferred embodiment, the nuclear anchoring protein is expressed at low levels.

The multimerized DNA binding sequences, i.e., DNA sequences containing multimeric binding sites, as defined in the context of the present invention, are the region, to which the DNA binding dimerization domain binds. The multimerized DNA binding sequences of the vectors of the present invention can contain any suitable DNA binding site, provided that it fulfills the above requirements.

In a preferred embodiment, the multimerized DNA binding sequence of a vector of the present invention can contain any one of known 17 different affinity E2 binding sites as a hexamer or a higher oligomer, as a octamer or a higher oligomer, as a decamer or higher oligomer. Oligomers containing different E2 binding sites are also applicable. Specifically preferred E2 binding sites useful in the vectors of the present invention are the BPV1 high affinity sites 9 and 10, affinity site 9 being most preferred. When a higher oligomer is concerned, its size is limited only by the construction circumstances and it may contain from 6 to 30 identical binding sites. Preferred vectors of the invention contain 10 BPV-1 E2 binding sites 9 in tandem. When the multimerized DNA binding sequences are comprised of different E2 binding sites, their size and composition is limited only by the method of construction practice. Thus they may contain two or more different E2 binding sites attached to a series of 6 to 30, most preferably 10, E2 binding sites. The Bovine Papilloma Virus type 1 genome (SEQ ID NO: 49) contains 17 E2 protein binding sites which differ in their affinity to E2. The E2 binding sites are described in Li et al., 1989 (Genes Dev 3(4):510-526), which is incorporated by reference in its entirety herein.

Alternatively, the multimerized DNA binding sequences may be composed of any suitable multimeric specific sequences capable of inducing the cooperative binding of the protein to the plasmid, such as those of the EBNA1 or a suitable HMG protein. 21×30 bp repeats of binding sites for EBNA-1 are localized in the region spanning from nucleotide position 7421 to nucleotide position 8042 of the Epstein-Barr virus genome (SEQ ID NO:51). These EBNA-1 binding sites are described in the following references: Rawlins et al., 1985, Cell 42(3):859-868; Reisman et al., 1985, Mol Cell Biol 5(8):1822-1832; and Lupton and Levine, 1985, Mol Cell Biol 5(10):2533-2542, all three of which are incorporated by reference in their entireties herein.

The position of the multimerized DNA binding sequences relative to the expression cassette for the DNA binding dimerization domain is not critical and can be any position in the plasmid. Thus the multimerized DNA binding sequences can be positioned either downstream or upstream relative to the expression cassette for the gene of interest, a position close to the promoter of the gene of interest being preferred.

The vectors of the invention also contain, where appropriate, a suitable promoter for the transcription of the gene or genes or the DNA sequences of interest, additional regulatory sequences, polyadenylation sequences and introns. Preferably the vectors may also include a bacterial plasmid origin of replication and one or more genes for selectable markers to facilitate the preparation of the vector in a bacterial host and a suitable promoter for the expression the gene for antibiotic selection.

The selectable marker can be any suitable marker allowable in DNA vaccines, such a kanamycin or neomycin, and others. In addition, other positive and negative selection markers can be included in the vectors of the invention, where applicable.

The vectors of the present invention only comprise the DNA sequences, for instance BPV1 DNA sequences, which are necessary and sufficient for long-term maintenance. All superfluous sequences, which may induce adverse reactions, such as oncogenic sequences, have been deleted. Thus in preferred vectors of the invention the E2 coding sequence is modified by mutational analysis so that this expresses only E2 protein and overlapping E3, E4 and E5 sequences have been inactivated by the introduction of mutations, which inactivate the translation from Open Reading Frames for E3, E4 and E5. The vector of the invention does not contain a papilloma virus origin of replication. Preferably, the vector of the invention further does not contain an origin of replication functional in a mammalian cell or a mammal.

Furthermore, the vectors of the present invention are not host specific, since the expression of the nuclear-anchoring protein, such as the E2 protein, is controlled by non-native or heterologous promoters. Depending on the particular promoter chosen, these promoters may be functional in a broad range of mammalian cells or they can be cell or tissue specific. Examples of promoters for the nuclear-anchoring protein, such as for the E2 protein, useful in the vectors of the present invention are thymidine kinase promoters, Human Cytomegalovirus Immediate Early Promoter, Rous Sarcoma Virus LTR and like. For the expression of the gene of interest, preferred promoters are strong promoters assuring high levels of expression of the gene of interest, an example for such a promoter is the Human Cytomegalovirus Immediate Early Promoter.

5.2 The Vectors of the Invention as Vehicles for Expression of a DNA Sequence of Interest A gene, genes or a DNA sequence or DNA sequences to be expressed via a vector of the invention can be any DNA sequence of interest, whose expression is desired. Thus the vectors may contain a gene or genes or a DNA sequence or DNA sequences from infectious microbial pathogens, such as viruses, against which live attenuated vaccines or inactivated vaccines cannot be prepared or used. Such DNA sequences of interest include genes or DNA sequences from viruses, such as Human Immunodeficiency Virus (HIV), Herpex Simplex Virus (HSV), Hepatitis C Virus, Influenzae Virus, Enteroviruses etc.; intracellular bacterial, such as Chlamydia trachomatis, Mycobacterium tuberculosis, Mycoplasma pneumonia etc.; extracellular bacteria, such as Salmonella; or fungi, such as *Candida albigans*.

In a preferred embodiment of the invention, the vectors contain a gene encoding early regulatory proteins of HIV, i.e. the nonstructural regulatory proteins Nef, Tat or Rev, preferably Nef. In another preferred embodiment of the invention the vectors of the invention contain genes encoding structural proteins of the HIV. In another preferred embodiment the vectors of the present invention contain two or more genes encoding any combination of early regulatory proteins and/or structural proteins of HIV. Illustrative examples of such combinations are a combination of a gene encoding the Nef protein and a DNA sequence encoding the Tat protein, possibly together with a DNA sequence encoding outer envelope glycoprotein of HIV, gp120/gp160 or a combination of any immunogenic epitopes of the proteins of pathogens incorporated into artificial recombinant protein.

Alternatively, the vectors of the invention may contain genes or DNA sequences for inherited or acquired genetic defects, such as sequences of differentiation antigens for melanoma, like a Tyrosinase A coding sequence or a coding sequence of beta-catenins.

In a preferred embodiment of the invention, the vectors contain a gene encoding proteins relating to cancer or other mutational diseases, preferably diseases related to immune maturation and regulation of immune response towards self and nonself, such as the APECED gene.

In another preferred embodiment of the invention, the vectors contain any DNA sequence coding for a protein that is defective in any hereditary single gene hereditary disease.

In another preferred embodiment of the invention, the vectors contain any DNA sequence coding for a macromolecular drug to be delivered and produced in vivo.

The method of the invention for the preparation of the vectors of the invention comprises the following steps: (A) cultivating a host cell containing a vector of the invention, and (B) recovering the vector. In certain specific embodiments, step (A) is preceded by transforming a host cell with a vector of the invention.

The vectors of the invention are preferably amplified in a suitable bacterial host cell, such as *Escherichia coli*. The vectors of the invention are stable and replicate at high copy numbers in bacterial cells. If a vector of the invention is to be amplified in a bacterial hast cell, the vector of the invention contains a bacterial origin of replication. Nucleotide sequences of bacterial origins of replication are well-known to the skilled artisan and can readily be obtained.

Upon transfection into a mammalian host in high copy number, the vector spreads along with cell divisions and the number of cells carrying the vector increases without the replication of the vector, each cell being capable of expressing the protein of interest.

The vectors of the invention result in high expression of the desired protein. For instance, as demonstrated in Examples 4, 7-10: a high expression of the Nef protein of the HIV, green fluorescent protein (EGFP) and the AIRE protein could be demonstrated in many different cell lines and the data indicate that not only the number of positive cells, but the quantity of the protein encoded by the gene of interest is increasing in time.

The vectors of the invention also induce both humoral and cellular response as demonstrated in Examples 9 and 10. The results indicate that the vectors of the present invention can effectively be used as DNA vaccines.

The vaccines of the present invention contain a vector of the present invention or a mixture of said vectors in a suitable pharmaceutical carrier. The vaccine may for instance contain a mixture of vectors containing genes for the three different regulatory proteins of the HIV and/or structural proteins of the HIV.

The vaccines of the invention are formulated using standard methods of vaccine formulation to produce vaccines to be administered by any conventional route of administration, i.e. intramuscularily, intradermally and like.

The vectors of the invention may contain the ISS stimulatory sequences in order to activate the immune response of the body.

The vaccines of the invention can be used in a conventional preventive manner to protect an individual from infections, Alternatively, the vaccines of the invention can be used as therapeutical vaccines, especially in the case of viral infections, together with a conventional medication.

As mentioned above, the vectors of the present invention carrying the mechanism of spreading in the host cell find numerous applications as vaccines, in gene therapy, in gene transfer and as therapeutic immunogens. The vectors of the invention can be used to deliver a normal gene to a host having a gene defect, thus leading to a cure or therapy of a genetic disease. Furthermore, the vectors can deliver genes of immunogenic proteins of foreign origin, such as those from microbes or autologous tumor antigens, to be used in the development of vaccines against microbes or cancer. Furthermore, the vectors of the invention can deliver suitable genes of marker substances to nucleus, to be used in studies of cellular function or in diagnostics. Finally, the vectors of the invention can be used to specifically deliver a gene of macromolecular drug to the nucleus, thus enabling the development of novel therapeutic principles to treat and cure diseases, where the expression of the drug in the site of action, the cell nucleus, is of importance. These drugs can be chemical macromolecules, such as any proteins or polypeptides with therapeutic or curative effect, which interfere with any of the nuclear mechanisms, such as the replication or transcription or the transport of substances to and from the nucleus.

Specifically, the vectors of the present invention can be used for the expression of the specific cytokines, like interleukines (IL1, IL2, IL4, IL6, IL12 and others) or interferon, with the aim of modulating the specific immune responses of the organism (immunotherapy) against foreign antigens or boosting of the activity of the immune system against the mutated self-antigens. The vectors of the present invention are also useful in complementing malfunctioning of the brain due to the loss of specific dopamine-ergic neurons leading to the irreversible neurodegeneration, which is cause for Parkinson's disease, by expressing genes involved into synthesis of dopamine, like tyrosine hydroxylase, as well as other genes deficiency of which would have the similar effect. The vectors of the present invention are also useful for the expression of proteins and peptides regulating the brain activity, like dopamine receptors, CCK-A and CCK-B receptors, as well as neurotrophic factors, like GDNF, BDNF and other proteins regulating the brain activity. Further, the vectors of the present invention are useful for a long-term expression of factor IX in hepatocytes and alfa1-antitrypsin in muscle cells with the aim of complementing respective deficiencies of the organism.

5.3 Target Diseases and Disorders

In certain embodiments, a vector of the invention is used as a vaccine. In certain embodiments, a vector of the invention contains a DNA sequence of interest that encodes a protein or a peptide. Upon administering of such a vector to a subject, the protein or peptide encoded by the DNA sequence of interest is expressed and stimulates an immune response specific to the protein or peptide encoded by the DNA sequence of interest.

In specific embodiments, the vector of the invention is used to treat and/or prevent an infectious disease and/or a condition caused by an infectious agent. Such diseases and conditions include, but are not limited to, infectious diseases caused by bacteria, viruses, fungi, protozoa, helminths, and the like. In a more specific embodiment of the invention, the infectious disease is Acquired Immunodeficiency Syndrome.

Preferably, where it is desired to treat or prevent viral diseases, DNA sequences encoding molecules comprising epitopes of known viruses are used. For example, such DNA sequences encoding antigenic epitopes may be prepared from viruses including, but not limited to, hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II).

Preferably, where it is desired to treat or prevent bacterial infections, DNA sequences encoding molecules comprising epitopes of known bacteria are used. For example, such DNA sequences encoding antigenic epitopes may be prepared from bacteria including, but not limited to, mycobacteria rickettsia, mycoplasma, neisseria and legionella.

Preferably, where it is desired to treat or prevent protozoal infections, DNA sequences encoding molecules comprising epitopes of known protozoa are used. For example, such DNA sequences encoding antigenic epitopes may be prepared from protozoa including, but not limited to, leishmania, kokzidioa, and trypanosoma.

Preferably, where it is desired to treat or prevent parasitic infections, DNA sequences encoding molecules comprising epitopes of known parasites are used. For example, such DNA sequences encoding antigenic epitopes may be prepared from parasites including, but not limited to, chlamydia and rickettsia.

In other specific embodiments, the vector of the invention is used to treat and/or prevent a neoplastic disease in a subject. In these embodiments, the DNA sequence of interest encodes a protein or peptide that is specific to or associated with the neoplastic disease. By way of non-limiting example, the neoplastic disease can be a fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease, etc.

In certain other embodiments of the invention, the DNA sequence of interest encodes a protein, that is non-functional or malfunctioning due to an inherited disorder or an acquired mutation in the gene encoding the protein. Such genetic diseases include, but are not limited to, metabolic diseases, e.g., Atherosclerosis (affected gene: APOE); cancer, e.g., Familial Adenomatous Polyposis Coli (affected gene: APC gene); auto-immune diseases, e.g. autoimmune polyendocrinopathy-candidosis-ectodermal dysplasia (affected gene: APECED); disorders of the muscle, e.g., Duchenne muscular dystrophyvaccines (affected gene: DMD); diseases of the nervous system, e.g., Alzheimer's Disease (affected genes: PS1 and PS2).

In even other embodiments, the vectors of the invention are used to treat and/or prevent diseases and disorders caused by pathologically high activity of a protein. In these embodiments of the invention, the DNA sequence of interest encodes an antagonist of the overactive protein. Such antagonists include, but are not limited to, antisense RNA molecules, ribozymes, antibodies, and dominant negative proteins. In specific embodiments of the invention, the DNA sequence of interest encodes an inhibitor of an oncogene.

In certain embodiments, the DNA sequence of interest encodes a molecule that antagonizes neoplastic growth. In specific embodiments of the invention, the DNA sequence of interest encodes a tumor suppressor, such as, but not limited to, p53. In other specific embodiments, the DNA sequence of interest encodes an activator of apoptosis, such as but not limited to, a Caspase.

The invention provides methods, whereby a DNA sequence of interest is expressed in a subject. In certain embodiments, a vector containing one or more expression cassettes of a DNA sequence of interest is administered to the subject, wherein the subject does not express the Bovine Papilloma Virus E1 protein.

5.4 Therapeutic Methods for Use with the Invention 5.4.1 Recombinant DNA

In various embodiments of the invention, the vector of the invention comprises one or more expression cassettes comprising a DNA sequence of interest. The DNA sequence of interest can encode a protein and/or a biologically active RNA molecule. In either case, the DNA sequence is inserted into the vector of the invention for expression in recombinant cells or in cells of the host in the case of gene therapy.

An expression cassette, as used herein, refers to a DNA sequence of interest operably linked to one or more regulatory regions or enhancer/promoter sequences which enables expression of the protein of the invention in an appropriate host cell. "Operably-linked" refers to an association in which the regulatory regions and the DNA sequence to be expressed are joined and positioned in such a way as to permit transcription, and in the case of a protein, translation.

The regulatory regions necessary for transcription of the DNA sequence of interest can be provided by the vector of the invention. In a compatible host-construct system, cellular transcriptional factors, such as RNA polymerase, will bind to the regulatory regions of the vector to effect transcription of the DNA sequence of interest in the host organism. The precise nature of the regulatory regions needed for gene expression may vary from host cell to host cell. Generally, a promoter is required which is capable of binding RNA polymerase and promoting the transcription of an operably-associated DNA sequence. Such regulatory regions may include those 5'-non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

Both constitutive and inducible regulatory regions may be used for expression of the DNA sequence of interest. It may be desirable to use inducible promoters when the conditions optimal for growth of the host cells and the conditions for high level expression of the DNA sequence of interest are different. Examples of useful regulatory regions are provided below (section 5.4.4).

In order to attach DNA sequences with regulatory functions, such as promoters, to the DNA sequence of interest or to insert the DNA sequence of interest into the cloning site of a vector, linkers or adapters providing the appropriate compatible restriction sites may be ligated to the ends of the cDNAs by techniques well known in the art (Wu et al., 1987, Methods in Enzymol 152:343-349). Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA by use of PCR with primers containing the desired restriction enzyme site.

The vector comprising a DNA sequence of interest operably linked to a regulatory region (enhancer/promoter sequences) can be directly introduced into appropriate host cells for expression of the DNA sequence of interest without further cloning.

For expression of the DNA sequence of interest in mammalian host cells, a variety of regulatory regions can be used, for example, the SV40 early and late promoters, the cytomegalovirus (CMV) immediate early promoter, and the Rous sarcoma virus long terminal repeat (RSV-LTR) promoter. Inducible promoters that may be useful in mammalian cells include but are not limited to those associated with the metallothionein II gene, mouse mammary tumor virus glucocorticoid responsive long terminal repeats (MMTV-LTR), β-interferon gene, and hsp70 gene (Williams et al., 1989, Cancer Res. 49:2735-42; Taylor et al., 1990, Mol. Cell Biol., 10:165-75). It may be advantageous to use heat shock promoters or stress promoters to drive expression of the DNA sequence of interest in recombinant host cells.

In addition, the expression vector may contain a selectable or screenable marker gene for initially isolating, identifying or tracking host cells that contain the vector. A number of selection systems may be used for mammalian cells, including but not limited to the Herpes simplex virus thymidine kinase (Wigler et al., 1977, Cell 11:223), hypoxanthine-guanine phosphoribosyltransferase (Szybalski and Szybalski, 1962, Proc. Natl. Acad. Sci. USA 48:2026), and adenine phosphoribosyltransferase (Lowy et al., 1980, Cell 22:817) genes can be employed in tk⁻, hgprt⁻ or aprt⁻ cells, respectively. Also, antimetabolite resistance can be used as the basis of selection for dihydrofolate reductase (dhfr), which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neomycin phosphotransferase (neo), which confers resistance to the aminoglycoside G-418 (Colberre-Garapin et al., 1981, J. Mol. Biol. 150:1); and hygromycin phosphotransferase (hyg), which confers resistance to hygromycin (Santerre et al., 1984, Gene 30:147). Other selectable markers, such as but not limited to histidinol and Zeocin™ can also be used.

5.4.2 Expression Systems and Host Cells

For use with the methods of the invention, the host cell and/or the host organism preferably does not express the Bovine Papilloma Virus E1 protein. Furthermore, preferably the vector of the invention does not encode the Bovine Papilloma Virus E1 protein.

Preferred mammalian host cells include but are not limited to those derived from humans, monkeys and rodents, (see, for example, Kriegler M. in "Gene Transfer and Expression: A Laboratory Manual", New York, Freeman & Co. 1990), such as monkey kidney cell line transformed by SV40 (COS-7, ATCC CRL 1651); human embryonic kidney line (293, 293-EBNA, or 293 cells subcloned for growth in suspension culture, Graham et al., J. Gen. Virol., 36:59, 1977; baby hamster kidney cells (BHK, ATCC CCL 10); chinese hamster ovary-cells-DHFR (CHO, Urlaub and Chasin. Proc. Natl. Acad. Sci. 77; 4216, 1980); mouse sertoli cells (Mather, Biol. Reprod. 23:243-251, 1980); mouse fibroblast cells (NIH-3T3), monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); and mouse mammary tumor cells (MMT 060562, ATCC CCL51).

The vectors of the invention may be synthesized and assembled from known DNA sequences by well-known techniques in the art. The regulatory regions and enhancer elements can be of a variety of origins, both natural and synthetic. Some host cells may be obtained commercially.

The vectors of the invention containing a DNA sequence of interest can be introduced into the host cell by a variety of techniques known in the art, including but not limited to, for prokaryotic cells, bacterial transformation (Hanahan, 1985, in DNA Cloning, A Practical Approach, 1:109-136), and for eukaryotic cells, calcium phosphate mediated transfection (Wigler et al., 1977, Cell 11:223-232), liposome-mediated transfection (Schaefer-Ridder et al., 1982, Science 215:166-168), electroporation (Wolff et al., 1987, Proc Natl Acad Sci 84:3344), and microinjection (Cappechi, 1980, Cell 22:479-488).

In a specific embodiment, cell lines that express the DNA sequence of the invention may be engineered by using a vector that contains a selectable marker. By way of example but not limitation, following the introduction of the vector, engineered cells may be allowed to grow for 1-2 days in an enriched media, and then are switched to a selective media. The selectable marker in the vector confers resistance to the selection and optimally allows only cells that contain the vector with the selectable marker to grow in culture.

5.4.3 Vaccine Approaches

In certain embodiments, a vector of the invention comprising an expression cassette of a DNA sequence of interest is administered to a subject to induce an immune response. Specifically, the DNA sequence of interest encodes a protein (for example, a peptide or polypeptide), which induces a specific immune response upon its expression. Examples of such proteins are discussed in section 5.3.

For the delivery of a vector of the invention for use as a vaccine, methods may be selected from among those known in the art and/or described in section 5.4.6.

5.4.4 Gene Therapy Approaches

In a specific embodiment, a vector of the invention comprising an expression cassette comprising DNA sequences of interest is administered to treat, or prevent various diseases. The DNA sequence of interest may encode a protein and/or a biologically active RNA molecule. Gene therapy refers to therapy performed by the administration to a subject of an expressed or expressible DNA sequence. In this embodiment of the invention, the DNA sequences produce their encoded protein or RNA molecule that mediates a therapeutic effect.

Any of the methods for gene therapy available in the art can be used according to the present invention. Exemplary methods are described below.

For general reviews of the method of gene therapy, see, Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; Morgan and Anderson, 1993, Ann. Rev. Biochem. 62:191-217; May, 1993, TIBTECH 1, 1(5):155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

The following animal regulatory regions, which exhibit tissue specificity and have been utilized in transgenic animals, can be used for expression of the DNA sequence of interest in a particular tissue type: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315: 115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in the liver (Pinkert et al., 1987, Genes and Devel. 1:268-276), alpha-fetoprotein gene control region which is active in the liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

Methods of delivery fro gene therapy approaches are well-known in the art and/or described in section 5.4.6.

5.4.5 Inhibitory Antisense and Ribozyme

In certain embodiments of the invention a vector of the invention contains a DNA sequence of interest that encodes an antisense or ribozyme RNA molecule. Techniques for the production and use of such molecules are well known to those of skill in the art.

Antisense RNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

A sequence "complementary" to a portion of an RNA, as referred to herein, means a sequence having sufficient complementarity to be able to hybridize with at least the non-polyA portion of an RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides. In other embodiments of the invention, the antisense nucleic acids are at least 100, at least 250, at least 500, and at least 1000 nucleotides in length.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense DNA sequence are compared with those obtained using a control DNA sequence. It is preferred that the control DNA sequence is of approximately the same length as the test oligonucleotide and that the DNA sequence of the oligonucleotide differs from the antisense sequence no more than is necessary to prevent specific hybridization to the target sequence.

While antisense DNA sequences complementary to the target gene coding region sequence could be used, those complementary to the transcribed, untranslated region are most preferred.

For expression of the biologically active RNA, e.g., an antisense RNA molecule, from the vector of the invention the DNA sequence encoding the biologically active RNA molecule is operatively linked to a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector of the invention can be introduced, e.g., such that it is taken up by a cell and directs the transcription of an antisense RNA. Such vectors can be constructed by recombinant DNA technology methods standard in the art. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290, 304-310), the promoter contained in the 3 long terminal repeat of Rous sarcoma virus (Yamamoto, et al., 1980, Cell 22, 787-797), the herpes thymidine kinase promoter (Wagner, et al., 1981, Proc. Natl. Acad. Sci. U.S.A. 78, 1441-1445), the regulatory sequences of the metallothionein gene (Brinster, et al., 1982, Nature 296, 39-42), etc.

In certain embodiments of the invention, a vector of the invention contains a DNA sequence which encodes a ribozyme. Ribozyme molecules designed to catalytically cleave target gene mRNA transcripts can also be used to prevent translation of a target gene mRNA and, therefore, expression of a target gene product (see, e.g., PCT International Publication WO90/11364, published Oct. 4, 1990; Sarver, et al., 1990, Science 247, 1222-1225).

Ribozymes are enzymatic RNA molecules capable of catalyzing the specific cleavage of RNA. (For a review, see Rossi, 1994, Current Biology 4, 469-471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, Molecular Biology and Biotechnology: A Comprehensive Desk Reference, VCH Publishers, New York, (see especially FIG. 4, page 833) and in Haseloff & Gerlach, 1988, Nature, 334, 585-591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in Tetrahymena thermophila (known as the IVS, or L-19 IVS RNA) and that has been extensively described by Thomas Cech and collaborators (Zaug, et al., 1984, Science, 224, 574-578; Zaug and Cech, 1986, Science, 231, 470-475; Zaug, et al., 1986, Nature, 324, 429-433; published International patent application No. WO 88/04300 by University Patents Inc.; Been & Cech, 1986, Cell, 47, 207-216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

Expression of a ribozyme can be under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

In instances wherein the antisense and/or ribozyme molecules described herein are utilized to inhibit mutant gene expression, it is possible that the technique may so efficiently reduce or inhibit the translation of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.4.4 that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Methods of administering the ribozyme and antisense RNA molecules are well-known in the art and/or described in section 5.4.6.

5.4.6 Pharmaceutical Formulations and Modes of Administration

In a preferred aspect, a pharmaceutical of the invention comprises a substantially purified vector of the invention (e.g., substantially free from substances that limit its effect or produce undesired side-effects). The subject to whom the pharmaceutical is administered in the methods of the invention is preferably an animal, including but not limited to animals such as cows, pigs, horses, chickens, cats, dogs, etc., and is preferably a mammal, and most preferably a human.

In certain embodiments, the vector of the invention is directly administered in vivo, where the DNA sequence of interest is expressed to produce the encoded product. This can be accomplished by any of numerous methods known in the art. The vectors of the invention can be administered so that the nucleic acid sequences become intracellular. The vectors of the invention can be administered by direct injection of naked DNA; use of microparticle bombardment (e.g., a gene gun; Biolistic, Dupont); coating with lipids or cell-surface receptors or transfecting agents; encapsulation in microparticles or microcapsules; administration in linkage to a peptide which is known to enter the nucleus; administration in linkage to a ligand subject to receptor-mediated endocytosis (see, e.g., Wu and Wu, 1987, J. Biol. Chem. 262:4429-4432) (which can be used to target cell types specifically expressing the receptors); etc. In a specific embodiment, the compound or composition can be delivered in a vesicle, in particular a liposome (see Langer, 1990, Science 249:1527-1533; Treat et al., 1989, in Liposomes in the Therapy of Infectious Disease and Cancer, Lopez-Berestein and Fidler (eds.), Liss, New York, pp. 353-365; Lopez-Berestein, ibid., pp. 317-327)

In certain embodiments, the vector of the invention is coated with lipids or cell-surface receptors or transfecting agents, or linked to a homeobox-like peptide which is known to enter the nucleus (see e.g., Joliot et al., 1991, Proc. Natl. Acad. Sci. USA 88:1864-1868), etc.

In certain other embodiments, nucleic acid-ligand complexes can be formed in which the ligand comprises a fusogenic viral peptide to disrupt endosomes, allowing the nucleic acid to avoid lysosomal degradation.

In yet other embodiments, the vector of the invention can be targeted in vivo for cell specific uptake and expression, by targeting a specific receptor (see, e.g., PCT Publications WO 92/06180; WO 92/22635; WO92/20316; WO93/14188, and WO 93/20221).

Methods for use with the invention include, but are not limited to, intradermal, intramuscular, intraperitoneal, intravenous, subcutaneous, intranasal, epidural, and oral routes. Methods for use with the invention further include administration by any convenient route, for example by infusion or bolus injection, by absorption through epithelial or mucocutaneous linings (e.g., oral mucosa, rectal and intestinal mucosa, etc.). In a specific embodiment, it may be desirable to administer a vector of the invention by injection, by means of a catheter, by means of a suppository, or by means of an implant, said implant being of a porous, non-porous, or gelatinous material, including a membrane, such as a sialastic membrane, or a fiber. Care must be taken to use materials to which the vector does not absorb. Administration can be systemic or local.

In certain embodiments, a vector of the invention is administered together with other biologically active agents such as chemotherapeutic agents or agents that augment the immune system.

In yet another embodiment, methods for use with the invention include delivery via a controlled release system. In one embodiment, a pump may be used (see Langer, supra; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, 1974, Langer and Wise (eds.), CRC Pres., Boca Raton, Fla.; Controlled Drug Bioavailability, Drug Product Design and Performance, 1984, Smolen and Ball (eds.), Wiley, New York; Ranger and Peppas, 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105).

Other controlled release systems are discussed in the review by Langer, 1990, Science 249:1527-1533.

Pharmaceutical compositions of the invention comprise a therapeutically effective amount of a vector of the invention, and a suitable pharmaceutical vehicle. In a specific embodiment, the term "suitable pharmaceutical vehicle" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or vehicle with which the therapeutic is administered. Such suitable pharmaceutical vehicles can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the nucleic acid or protein of the invention, preferably in purified form, together with a suitable amount of carrier so as to provide the form for proper administration to the patient. The formulation should suit the mode of administration.

In a specific embodiment, the pharmaceutical of the invention is formulated in accordance with routine procedures as a pharmaceutical composition adapted for intravenous administration to human beings. Typically, compositions for intravenous administration are solutions in sterile isotonic aqueous buffer. Where necessary, the pharmaceutical of the invention may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical of the invention is to be administered by infusion, it can be dispensed with an infusion bottle containing sterile pharmaceutical grade water or saline. Where the pharmaceutical of the invention is administered by injection, an ampoule of sterile water for injection or saline can be provided so that the ingredients may be mixed prior to administration.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The amount of a vector of the invention which will be effective in the treatment or prevention of the indicated disease can be determined by standard clinical techniques. In addition, in vitro assays may optionally be employed to help identify optimal dosage ranges. The precise dose to be employed in the formulation will also depend on the route of administration, and the stage of indicated disease, and should be decided according to the judgment of the practitioner and each patient's circumstances. Effective doses may be extrapolated from dose-response curves derived from in vitro or animal model test systems.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

6. EXAMPLES

6.1 Nomenclature and Cloning

Nucleotide sequences for the multigene inserts are included as SEQ ID NOS: 1-24. Amino acid sequences of the expressed multigene inserts are included as SEQ ID NOS: 25-48, respectively.

For the production of HIV multi-gene vectors, GTU-1 vector with a multi-cloning site was used as a backbone. Intact Nef, Rev and Tat coding sequences were amplified by the polymerase chain reaction (PCR) and attached to each other in various orders to multi-regulatory (multireg) antigen coding reading frames (Nef-Tat-Rev, Tat-Rev-Nef, Rev-Tat-Nef, Tat-Nef-Rev and Rev-Nef-Tat; SEQ ID NOS: 1 to 5, respectively). These sequences were cloned to the Bsp119I and NotI sites of the GTU-1 vector.

6.1.1

GTU-1 vector with multicloning site and Nef protein expressing GTU-2 and GTU-3 vectors were used as backbones for making HIV multigene vectors. Also, destabilized enhanced green fluorescent protein (d1EGFP) expressing previous generation GTU vector super6 wt and plasmid utilizing the EBNA-1 protein and its binding sites as Gene Transfer Unit (GTU) platform were used. For making control "non-GTU" vectors Rev expressing regular CMV vector NNVRev and EBNA-1 and E2BS containing d1EGFP plasmid E2BSEBNAd1EGFP were used as backbone (FIG. 38):

GTU-1
GTU-2Nef
GTU-3Nef
super6 wtd1EGFP
FREBNAd1EGFP
E2BSEBNAd1EGFP
NNV-Rev 6.1.2

Intact Nef, Rev and Tat coding sequence (cds) was amplified by PCR and joined for the making multiregulatory) antigene coding reading frame in context of the GTU-1 vector (Cloned to the Bsp1191 I and NotI sites). For making GTU-2 and GTU-3 vectors (labelled as p2 . . . and p3 . . . , respectively) the Nef gene in vectors GTU-2Nef and GTU-3Nef was substituted by multireg antigene using NdeI and Pag I sites. The sequence of the letters N(ef), R(ev) and T(at) in the name shows the position of respective cds of the protein in the multigene. There is also two vectors that contain the IRES element placed into the SalI sites followed either to the multi-antigene or E2 cds. The latter controlling the translation of the mouse GM-CSF coding sequence cloned into the single BspTI site introduced with IRES. See FIG. 39.

pNRT
pTRN
pRTN
pTNR
pRNT
p2TRN
p2RNT
p3RNT
pTRN-iE2-GMCSF
pTRN-iMG-GMCSF 6.1.3

Set of the vectors in which only immunodominant parts of the regulatory proteins were used for building up the polyproteins cloned into the Bsp119I and NotI sites of the GTU-1. In case of the pMV2 constructs, linkers that could be digested by intracellular proteases separate the regions of the multi-antigene derived from different regulatory proteins. See FIG. 40.

pMV1NTR
pMV2NTR
pMV1N11TR
pMV2N11TR 6.1.4

GTU-1 (marked as p . . . , GTU-2 (p2 . . . ) and GTU-3 (p3 . . . ) vectors were made that express the structural proteins coded by the gag gene or artificial polyprotein composed by previously described CTL epitopes. The cds are cloned as Bsp119I and Not I digested PCR fragments into the GTU-1 vector and tranfered in Nde I-Pac I fragment to the GTU-2 (p2 . . . ) and GTU-3 (p3 . . . ). See FIG. 41.

The coding segment named as CTL contains fragments from pol and env regions involving many previously identified CTL epitopes. The codon usage is optimized so that only codons used frequently in human cells are involved. This cds also contains well-characterized mouse CTL epitope used in potency assay and epitope for recognition by anti-mouse CD43 antibody. Also, a dominant SIV p27 epitope was included which can be used in potency studies in macaques.

The dgag contains truncated p17 (start at 13 aa)+p24+p2+p7 (p1 and p6 are excluded) of gag region of the Han2 isolate.

The synp17/24 codes the p17+p24 polypeptide of the Han2 HIV-1. The codon usage is modified to be optimal in human cells. Also, previously identified AU rich RNA instability elements were removed by this way.

The optp17/24 coding region is very similar to the synp17/24 except the two synonymous mutations made do not change the protein composition but removes potential splicing donor site. See FIG. 41.

pCTL
pdgag
psynp17/24
poptp17/24
p2mCTL
p2optp17/24
p3mCTL
p3optp17/24

6.1.5

A set of the multi-HIV vectors that contains both multireg-antigen and structural antigenes as single polyprotein. For cloning, as first step the STOP codon was removed in the regulatory multi-antigene cds. Then the structural antigene cds were added by cloning into the NotI site at the end of the frame so that NotI site was reconstituted. If both CTL and gag was added, the first antigen coding sequence was without STOP codon. Generally, the clonings were made in context of GTU-1 and for making the respective GTU-2 (p2 . . . ) and GTU-3 (p3 . . . ) vectors the Nef gene in the plasmids GTU-2Nef and GTU-2Nef was replaced using sites for NdeI and Pag I. See FIG. 42.

However, the RNT-optp17/24-CTL antigene was built up directly in GTU-2 vector. Similarly, the HIV multi-antigene was cloned to the vectors super6 wtd1EGFP and FREBNAd1EGFP instead of the d1EGFP using sites for Eco105I and NotI. If indicated, the IRES and mouse mGM-CSF were cloned into the GTU-2 and GTU-3 vectors behind the E2 cds into the sites Mph1103I and Eco91I from pTRN-iE2-mGMCSF (cut out using same restrictases).

"Non-GTU" control vector E2BSEBNA-RNT-CTL-optp17/24 for the EBNA-1 utilizing system (contains EBNA-1 expression cassette with E2 binding sites) were also made by similar way to the FREBNA-RNT-CTL-optp17/24. Also, the regular CMV vector pCMV-RNT-CTL-optp17/24 expressing the multi HIV antigene was made by cloning the multi-HIV coding fragment from respective GTU-1 vector using sites for NdeI and Pag I (see FIG. 42):

pTRN-CTL
pRNT-CTL
pTRN-dgag
pTRN-CTL-dgag
pRNT-CTL-dgag
pTRN-dgag-CTL
pRNT-dgag-CTL
pTRN-optp17/24-CTL
pTRN-CTL-optp17/24
pRNT-CTL-optp17/24
p2TRN-optp17/24-CTL
p2RNT-optp17/24-CTL
p2TRN-CTL-optp17/24
p2RNT-CTL-optp17/24
p2TRN-CTL-optp17/24-iE2-mGMCSF
p2RNT-CTL-optp17/24-iE2-mGMCSF
p3TRN-CTL-optp17/24
p3RNT-CTL-optp17/24
p3TRN-CTL-optp17/24-iE2-mGMCSF
p3RNT-CTL-optp17/24-iE2-mGMCSF
FREBNA-RNT-CTL-optp17/24
super6 wt-RNT-CTL-optp17/24
E2BSEBNA-RNT-CTL-optp17/24
pCMV-RNT-CTL-optp17/24

6.2. Example 1

Figure 1:
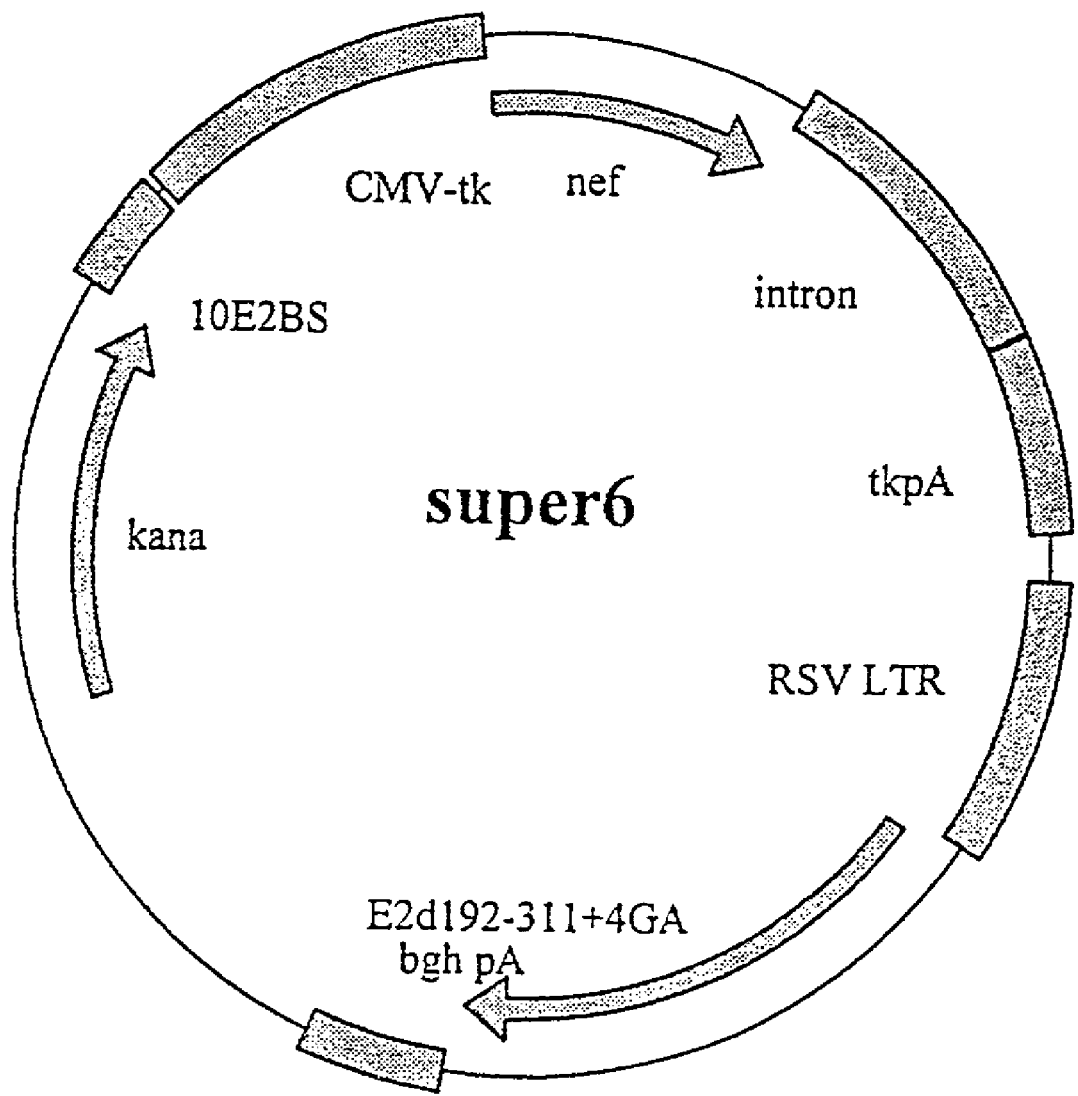
FIG. 1 shows the schematic map of plasmid super6.
Figure 2:
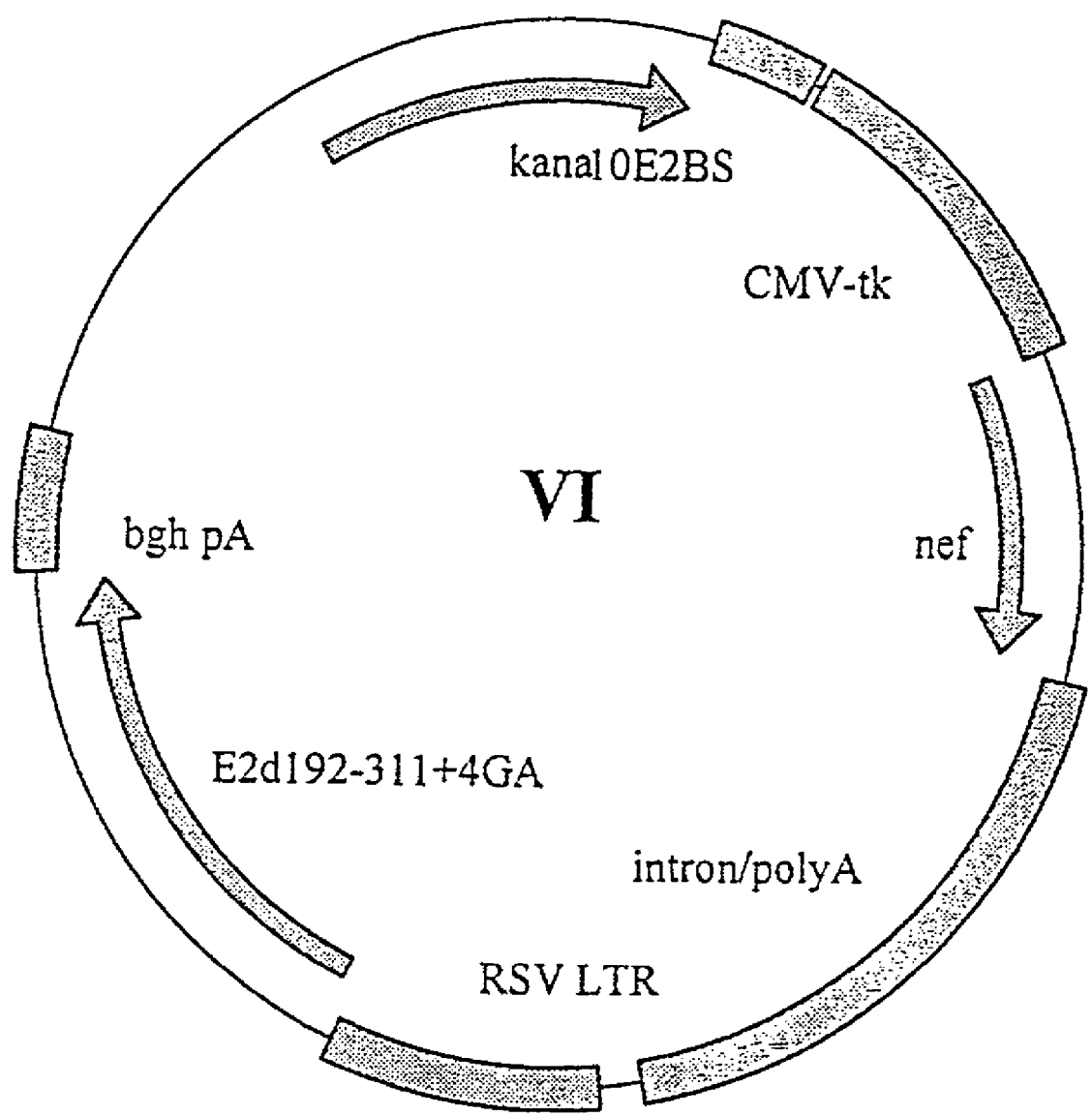
FIG. 2 shows the schematic map of plasmid VI.

Cloning and analysis of the expression properties of the vectors super6 and super6 wt The vector plasmids super6 (FIG. 1) and super6 wt were prepared from previous generation based gene vaccination vectors VI (FIG. 2) and VIwt, respectively. Vectors VI and VIwt are principally synthetic bacterial plasmids that contain a transposon Tn903 derived kanamycin resistance marker gene [Oka, A., et al., J Mol Biol 147 (1981) 217-226] and a modified form of pMB1 replicon [Yanisch-Perron, C., et al., Gene 33 (1985) 103-119] needed for the propagation in *Escherichia coli* cells. Vectors VI and VIwt also contain a Cytomegalovirus Immediately Early Promoter combined with a HSV1 TK leader sequence and rabbit β-globin gene sequences, which both are derived from plasmid pCG [Tanaka, M., et al., 60 (1990) Cell 375-386]. The latter elements are needed for expressing from the nef coding sequence derived from a HAN2 isolate of the HIV-1 strain [Sauermann, U., et al., AIDS Research. Hum. Retrov. 6 (1990) 813-823]. The expression vectors for the Nef carry clustered ten high affinity E2 binding sites (derived from plasmid pUC1910BS, unpublished) just upstream of the CMV promoter.

The parent vector VI contains a modified E2 coding sequence: the hinge region of E2 (amino acids 192-311) is replaced with four glycine-alanine repeats from EBNA1 protein of Epstein-Barr Virus [Baer, R. J., et al., Nature 310 (1984) 207-211]. The protein encoded by this sequence was named as E2d192-311+4G. The parent vector VIwt contains an expression cassette for wild type E2 protein of the bovine papilloma virus type 1 with point mutations introduced for the elimination E3 and E4 open reading frame (ORF) coding capacity by two stop codons into both these ORFs. In the vectors the E2 coding sequences are cloned between a Rous sarcoma virus proviral 5' LTR [Long, E. O., et al., Hum. Immunol. 31 (1991) 229-235] and bovine growth hormone polyadenylation region [Chesnut, J. D., et al., J Immunol Methods 193 (1996) 17-27].

Plasmid vectors super6 and super6 wt were constructed by deleting from the respective parent vectors VI and VIwt all beta-globin sequences downstream of the nef gene except the second intron of the rabbit beta-globin gene. The beta-globin sequences (especially the fragment of the exon) show some homology with sequences in the human beta-globin gene, whereas the intron lacks any significant homology to human genomic sequences. The intron was amplified by PCR from the plasmid pCG [Tanaka, M. et al., Cell 60 (1990) 375-386] using oligonucleotides with some mismatches for modifying the sequences of splicing donor and acceptor sites of the intron to the perfect match to consensus motifs. The Herpes Simplex Virus type 1 thymidine kinase gene polyadenylation region from pHook [Chesnut, J. D., et al., J Immunol Methods 193 (1996) 17-27] was then cloned just next to the 3'-end of the intron, because in parent plasmids the rabbit bb-globin polyadenylation signal were used.

Figure 3:
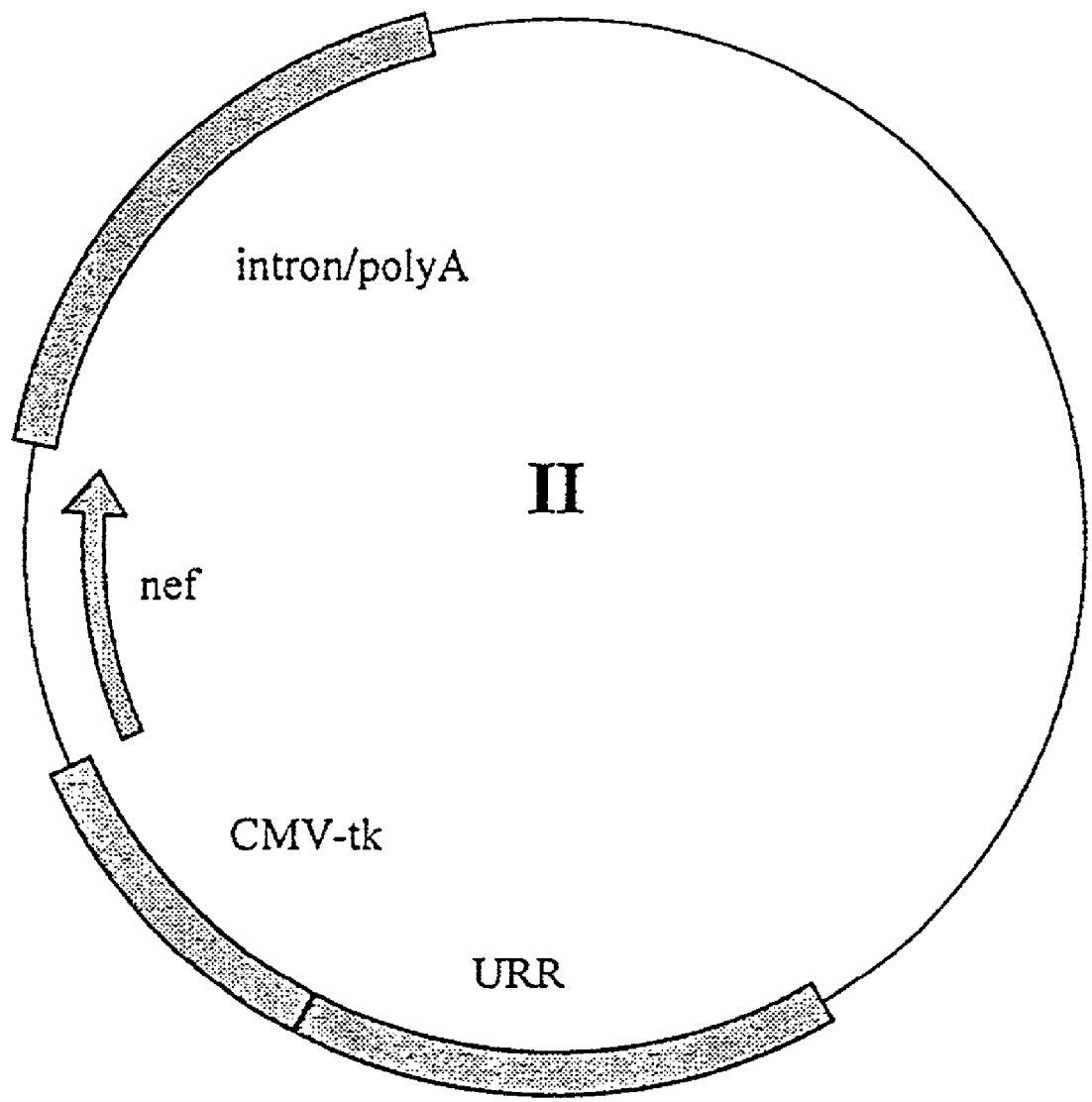
FIG. 3 shows the schematic map of plasmid II.

The expression properties of the Nef and E2 proteins expressed by the plasmid vectors super6 and super6 wt were analyzed and compared with the expression properties of the Nef and E2 proteins expressed by VI and VIwt by Western blotting [Towbin et al., Proc Natl Acad Sci USA 76 (1979) 4350-4354] with monoclonal antibodies against Nef and E2. First, Jurkat cells (a human T-cell lymphoblast cell line) were transfected by electroporation [Ustav et al. EMBO J 2 (1991) 449-457]. with 1 µg of super6, super6WT or equimolar amounts of the plasmids VI, VIwt. As a control an equimolar amount of vector II (FIG. 3), which contains an identical Nef cassette but no E2 coding sequence, was used. Carrier DNA was used as a negative control. Briefly, the plasmid and carrier DNA were mixed with the cell suspension in a 0.4 cm electroporation cuvette (BioRad Laboratories, Hercules, USA) followed an electric pulse (200V; 1 mF) using Gene Pulser IITM with capacitance extender (BioRad Laboratories, Hercules, USA).

Forty-nine hours post-transfection the cells were lysed by treating with a sample buffer containing 50 mM Tris-HCl pH 6.8; 2% SDS, 0.1% bromophenol blue, 100 mM dithiothreitol, and 10% (v/v) glycerol. The lysates were run on a 10% or 12.5% SDS-polyacrylamide gel and subsequently transferred onto a 0.45 µm PVDF nitrocellulose membrane (Millipore). The membrane was first blocked overnight with a blocking solution containing 5% dry milk (fat-free), 0.1% Tween 20 in 50 mM Tris-HCl pH 7.5; 150 mM NaCl and thereafter incubated for 1 h with diluted monoclonal anti-Nef antisera (1:100) or anti-E2-antisera (1:1000) in the blocking solution. After each incubation step, unbound proteins were removed by washing strips three times with TBS-0.1% Tween-20. The binding of primary immunoglobulins was detected by incubating the strips with horse raddish peroxidase conjugate anti-mouse IgG (Labas, Estonia) followed by visualization using a chemoluminesence detection system (Amersham Pharmacia Biotech, United Kingdom).

Figure 4:
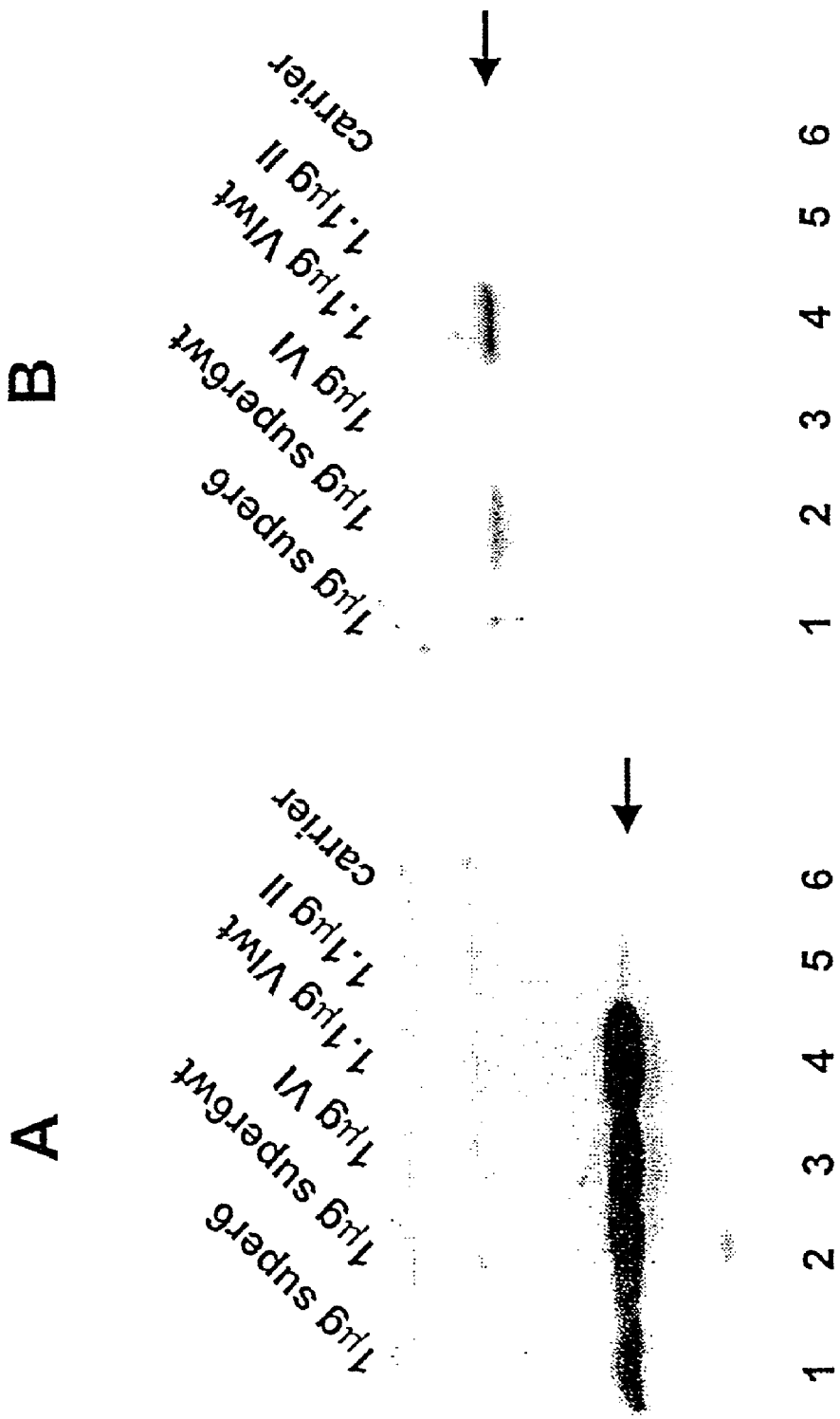
FIG. 4 shows the expression of the Nef and E2 proteins from the vectors super6, super6 wt, VI, VIwt, and II in Jurkat cells.

The results are shown in FIG. 4. The expression of the Nef protein is shown on panel A and the expression of E2 protein on panel B. The arrows indicate the right molecular sizes of the Nef and E2 proteins. The expression level of the E2d192-311+4GA is very low and for this reason cannot be seen on the blot presented in FIG. 4.

The amounts of Nef expressed from the plasmids super6, super6 wt, VI and VIwt (lanes 1-4 in FIG. 4A) are quite similar (FIG. 4, panel A, lanes 1 to 4). Much less protein is produced from plasmid II (lane 5). The expression levels of the Nef protein are higher from vectors containing wtE2 (cf. lane 1 compared with lane 2 and lane 3 compared with lane 4). This is in accordance with the expression levels of E2 and E2d192-311+4GA proteins from these plasmids (FIG. 4, panel B).

6.3. Example 2

Cloning and analysis of the expression properties of plasmids in series product1 and NNV.

Figure 5:
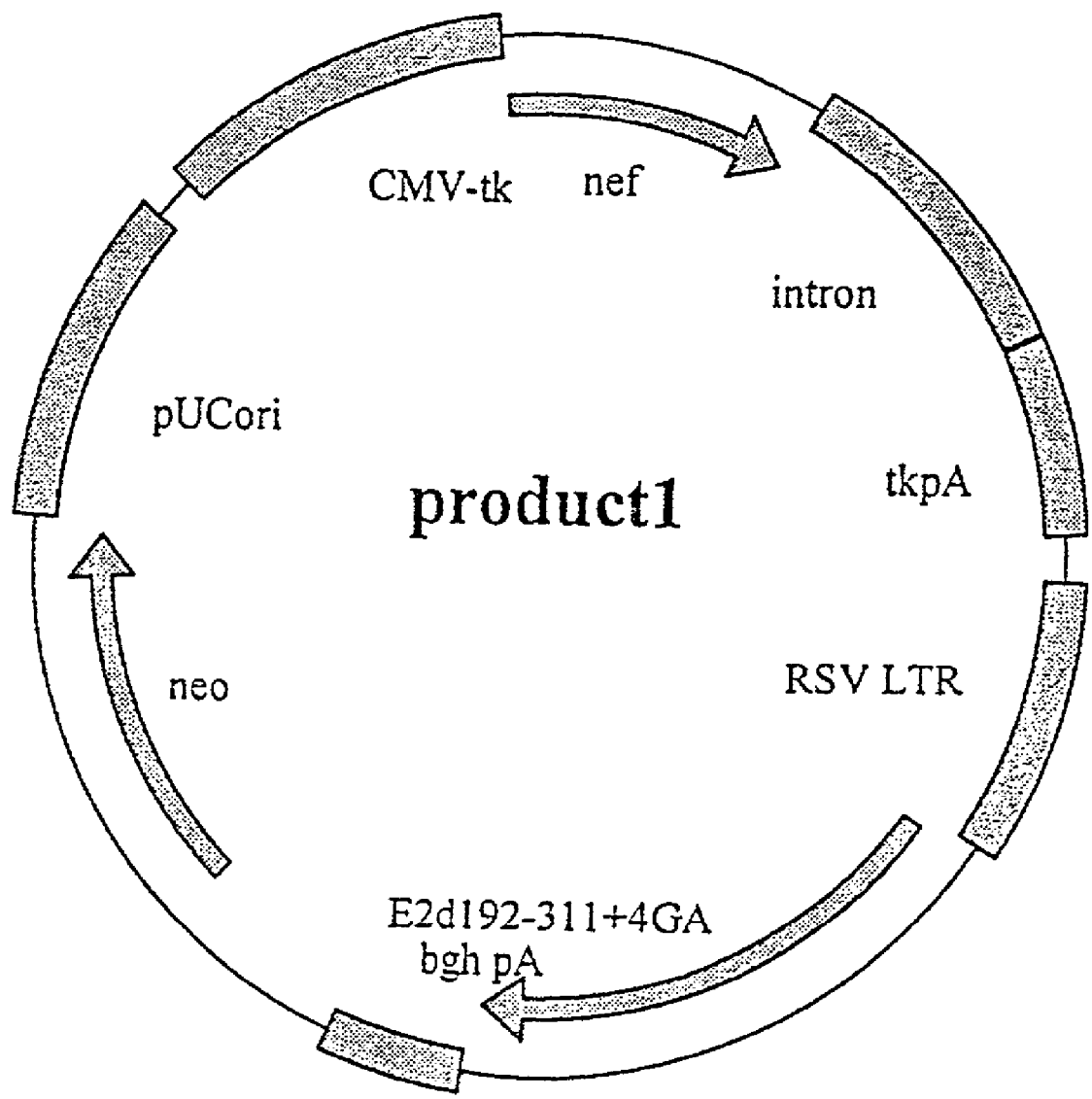
FIG. 5 shows the schematic map of plasmid product1.

To increase the copy number of the vectors super 6 and super6 wt in *Escherichia coli* further modifications were made in these vectors. The Tn903 kanamycin resistance gene, pMB1 replicon and ten E2 binding sites were removed by HindIII/NheI digestion followed by replacing with the Hind III/NheI fragment from retroviral vector pBabe Neo [Morgenstern, J. P. and Land, H., Nucleic Acids Research 18 (1990) 3587-3596]. This fragment contains a modified pMB1 replicon and the Tn5 kanamycin resistance gene that allow relaxed high copy-number replication of the plasmids in bacteria. The new plasmids were named as the product1 (FIG. 5), and product1 wt respectively. An unsuccessful attempt to reinsert the ten E2 binding sites back into the blunted NheI site upstream of the CMV promoter of the product1 resulted in vector New Vector NNV, respectively, with only two binding sites integrated in the plasmid.

Figure 6A:
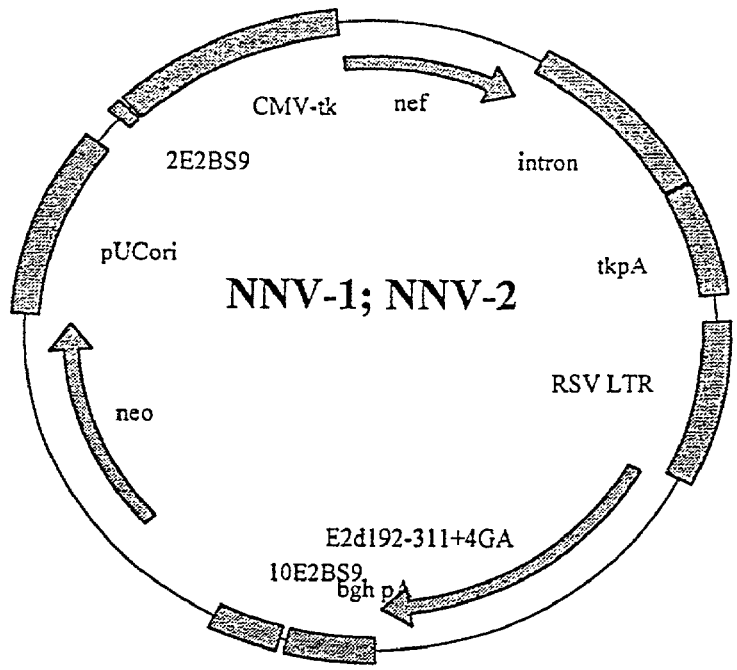
FIG. 6A shows the schematic map of the plasmids NNV-1 and NNV-2 and FIG. 6B shows the schematic map of plasmid and NNV-2 wt.
Figure 6B:
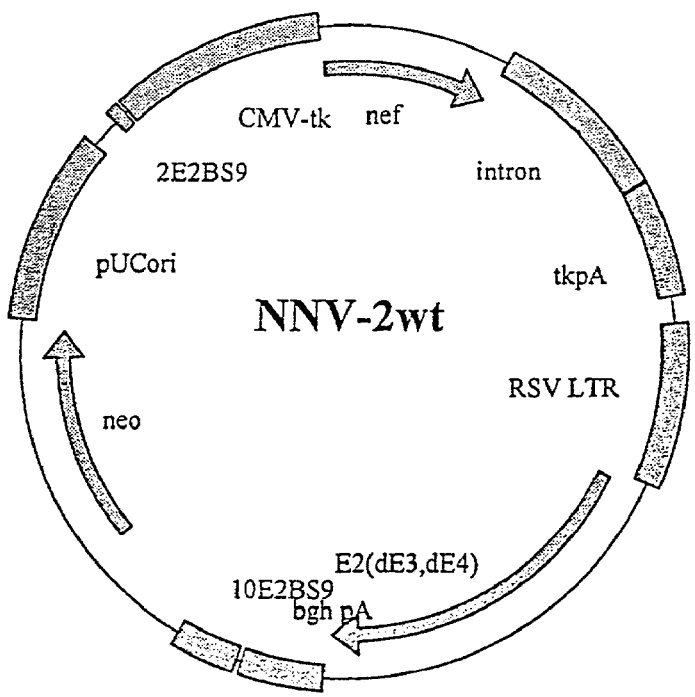

Additional ten E2 binding sites were inserted from plasmid pUC1910BS into the New Vector in just downstream the E2 expression cassette. These new vectors were named NNV-1 and NNV-2 (FIG. 6A). For replacing the E2d192-311+4GA with wt E2 (with deleted E3 and E4 ORFs), the E2d192-311+4GA coding sequence containing Bsp120I fragment was replaced with wt E2 containing an analogous Bsp120I fragment from the super6 wt. Generated plasmids were named NNV-1 wt and NNV-2 wt (FIG. 6B), respectively. The numbers 1 or 2 in vectors of the NNV series mark the orientation of the 10 E2 binding sites region relative to the E2 expression cassette.

Figure 7:
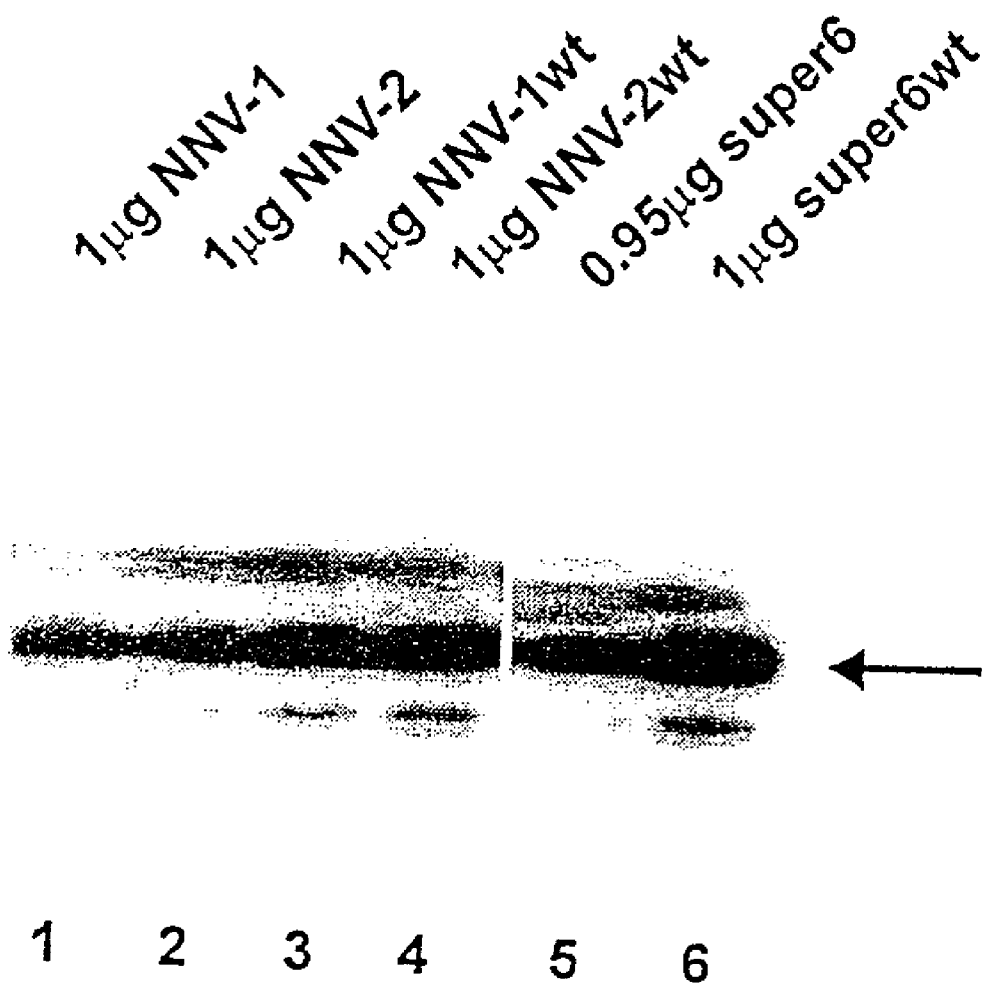
FIG. 7 shows the expression of the Nef protein from the plasmids NNV-1, NNV-2, NNV-1 wt, NNV-2-wt, super6, and super6 wt in Jurkat cells.

The expression properties of the Nef protein from the NNV plasmids, i.e. NNV-1, NNV-2, NNVwt and NNV-2 wt, after the transfection of Jurkat cells by electroporation at a concentration of 1 ìg of the plasmid were analyzed and compared with the expression properties of the Nef proteins from super6 and super6 wt by Western blotting essentially as described in Example 1. The amounts of super6 and super6 wt used for the transfection were 0,95 and 1 ìg, respectively. The results are shown in FIG. 7.

Figure 8:
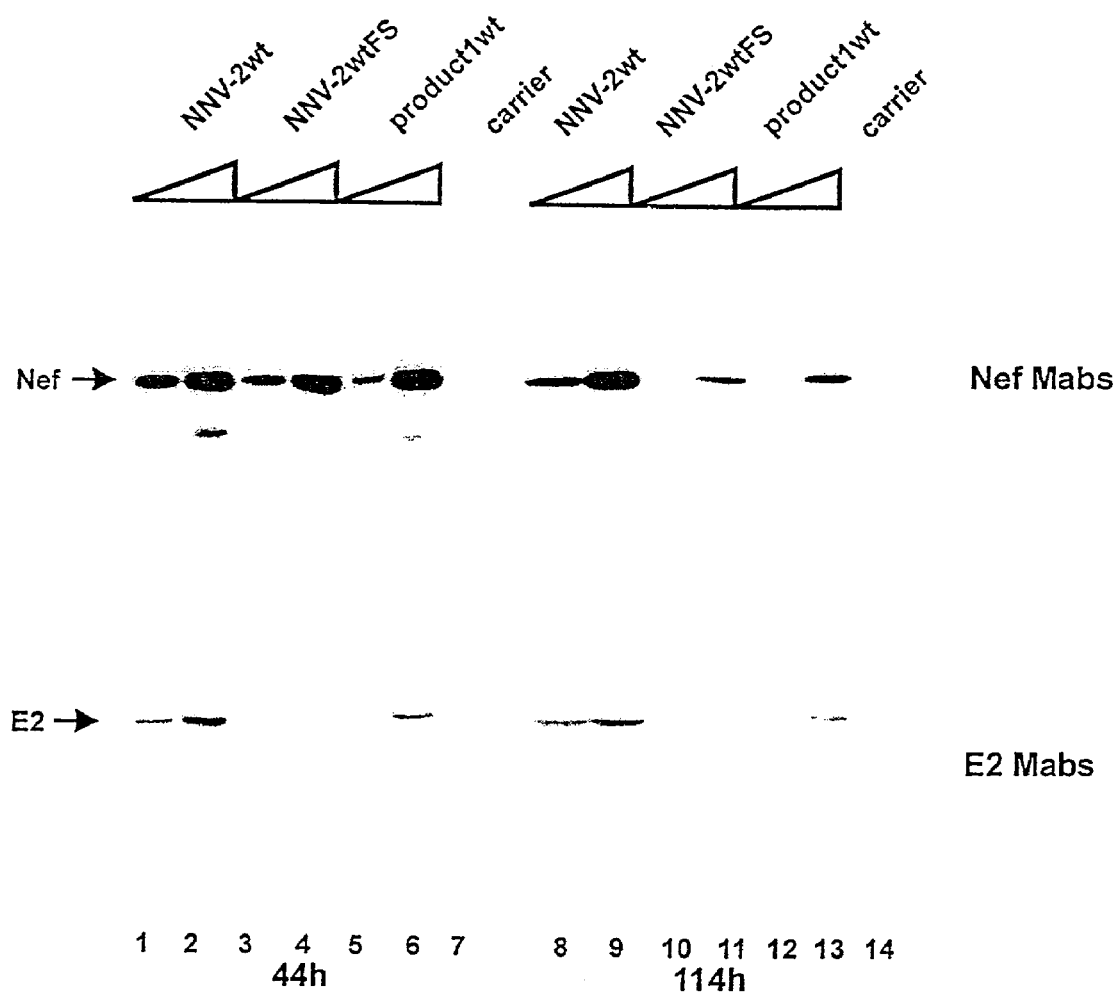
FIG. 8 shows the expression of the Nef and E2 proteins from the plasmids NNV-2-wt, NNV-2-wtFS, and product I in Jurkat cells.

NNV-1 and NNV-2 vectors have expression potential similar to plasmid super6 as evident from the comparison of lanes 1 and 2 on FIG. 8 with lane 5. The same applies to vectors NNV-1 wt, NNV-2 wt and super6 wt (compare lanes 3 and 4 with lane 6 on FIG. 7). In accordance with the previous results the plasmids expressing wt E2 produce more Nef protein than E2d192-311+4GA vectors do (compare lane 1 with lane 3 and lane 2 with lane 4 in FIG. 7). In view of this and since the Nef expression from NNV-2 wt was slightly higher than that from NNV-1 wt, vector NNV-2 wt was selected for further tests.

6.4 Example 3

Analysis of the expression properties of NNV-2 wt.

To analyse the expression properties of NNV-2 wt, four different cell lines, i.e. the Jurkat (human T-cell lymphoblasts), P815 (mouse mastocytoma cells), CHO (Chinese Hamster Ovary cells) lines and RD (human embryo rhabdomyosarcoma cells), were transfected by electroporation and analyzed for their expression of Nef of and E2. To reveal the transcription activation and maintenance properties mediated by E2 protein and E2 oligomerized binding sites product1 wt, which lacks the E2 binding sites (FIG. 5), was used as a control. An additional control plasmid was plasmid NNV-2 wtFS, which differs from NNV-2 wt by containing a frameshift introduced into E2 coding sequence, whereby it does not express functional E2 protein.

Each cell line was transfected with different amounts of the vector DNA by electroporation essentially as described in Example 1. Time-points were taken approximately two and five days after transfection. The results of analyses are presented in FIGS. 8 to 10.

The Jurkat cells were transfected with 0.5 μg or 2 μg of the NNV-2 wt (lanes 1, 2, 8, and 9 in FIG. 8) and equal amounts of the plasmids NNV-2 wtFS (lanes 3, 4, 10, and 11 in FIG. 8) and product1 wt (lanes 5, 6, 12, and 13 in FIG. 8) or carrier only (lanes 7 and 14 in FIG. 8). Time-points were taken 44 hours (lanes 1-7) and 114 hours (lanes 8-14) after transfection: The expression of the Nef and E2 proteins was analyzed by Western blotting essentially as described in Example 1.

Figure 9:
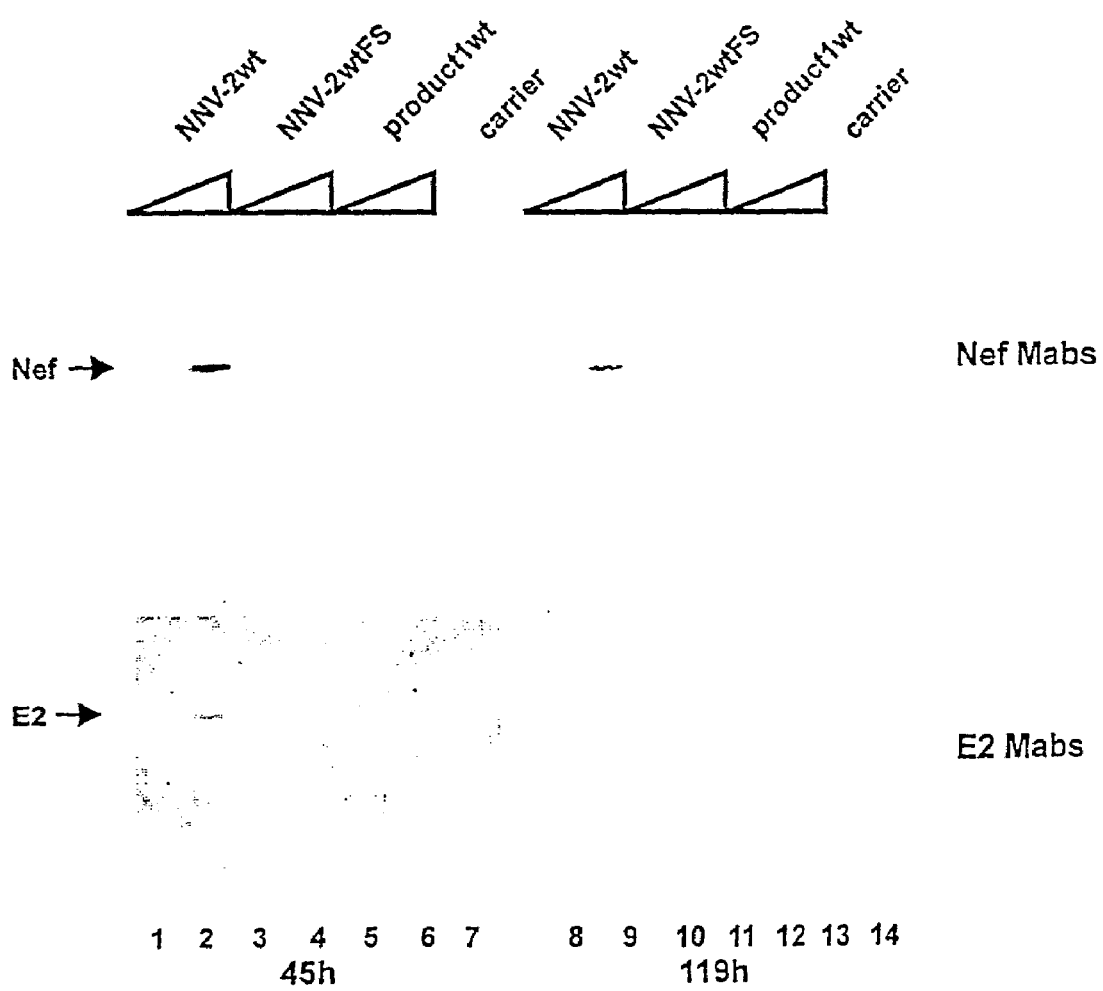
FIG. 9 shows the expression of the Nef and E2 proteins from the plasmids NNV-2-wt, NNV-2-wtFS, and product I in P815 cells.

The P815 cells were transfected with 0.5 mmg or 2 mmg of the NNV-2 wt (lanes 1,2, 8, and 9 in FIG. 9) and equal amounts of the plasmids NNV-2 wtFS (lanes 3, 4, 10, and 11 in FIG. 9) and product1wt (lanes 5, 6, 12, and 13 in FIG. 9) or carrier only (lanes 7 and 14 in FIG. 9). Time-points were taken 45 hours (lanes 1-7) and 119 hours (lanes 8-14) after transfection: The expression of the Nef proteins was analyzed by Western blotting essentially as described in Example 1. The blot with anti-E2 antibodies 119 h post-transfection is not shown, because no special signal could be detected. Generally, the expression level of the Nef protein correlated with the expression level of E2 protein in these cells, which confirms the fact that the function of the E2 protein is to activate the transcription and to help the plasmid to be maintained for a longer time in the proliferating cells.

Figure 10:
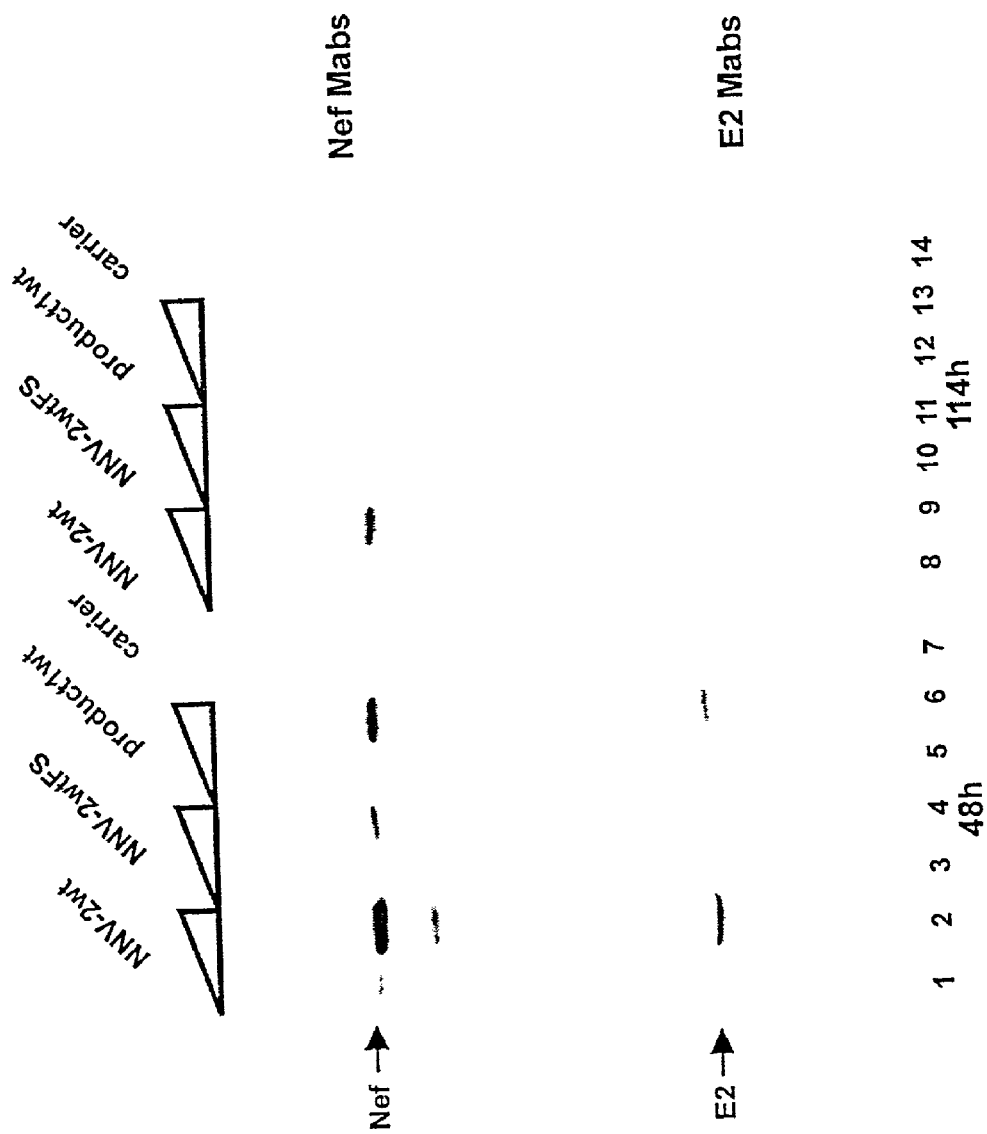
FIG. 10 shows the expression of the Nef and E2 proteins from the plasmids NNV-2-wt, NNV-2-wtFS, and product I in CHO cells.

The CHO cells were transfected with 0.5 mmg or 2 mmg of the NNV-2 wt (lanes 1, 2, 8, and 9 in FIG. 10) and equal amounts of the plasmids NNV-2 wtFS (lanes 3, 4, 10, and 11 in FIG. 10) and product1 wt (lanes 5, 6, 12, and 13 in FIG. 10) or carrier only (lanes 7 and 14 in FIG. 10). Time-points were taken 48 hours (lanes 1-7) and 114 hours (lanes 8-14) after transfection. The expression of the Nef and E2 proteins was analyzed by Western blotting essentially as described in Example 1.

Figure 11:
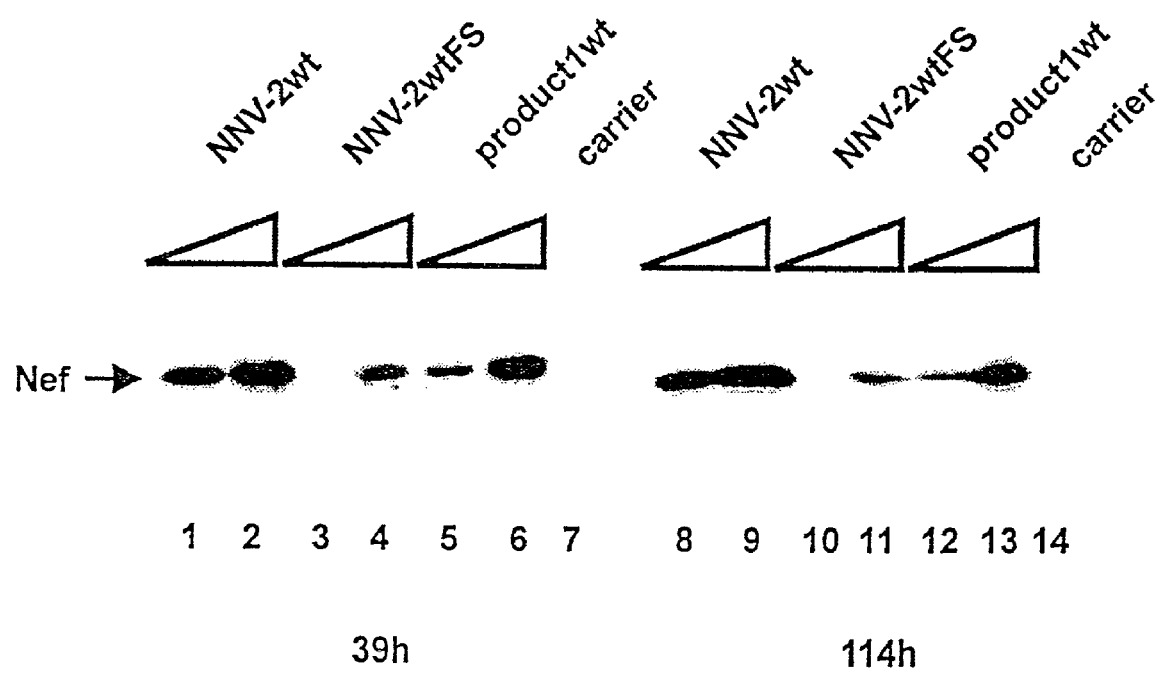
FIG. 11 shows the expression of the Nef protein from the plasmids NNV-2-wt, NNV-2-wtFS, and product I in RD cells.
Figure 12:
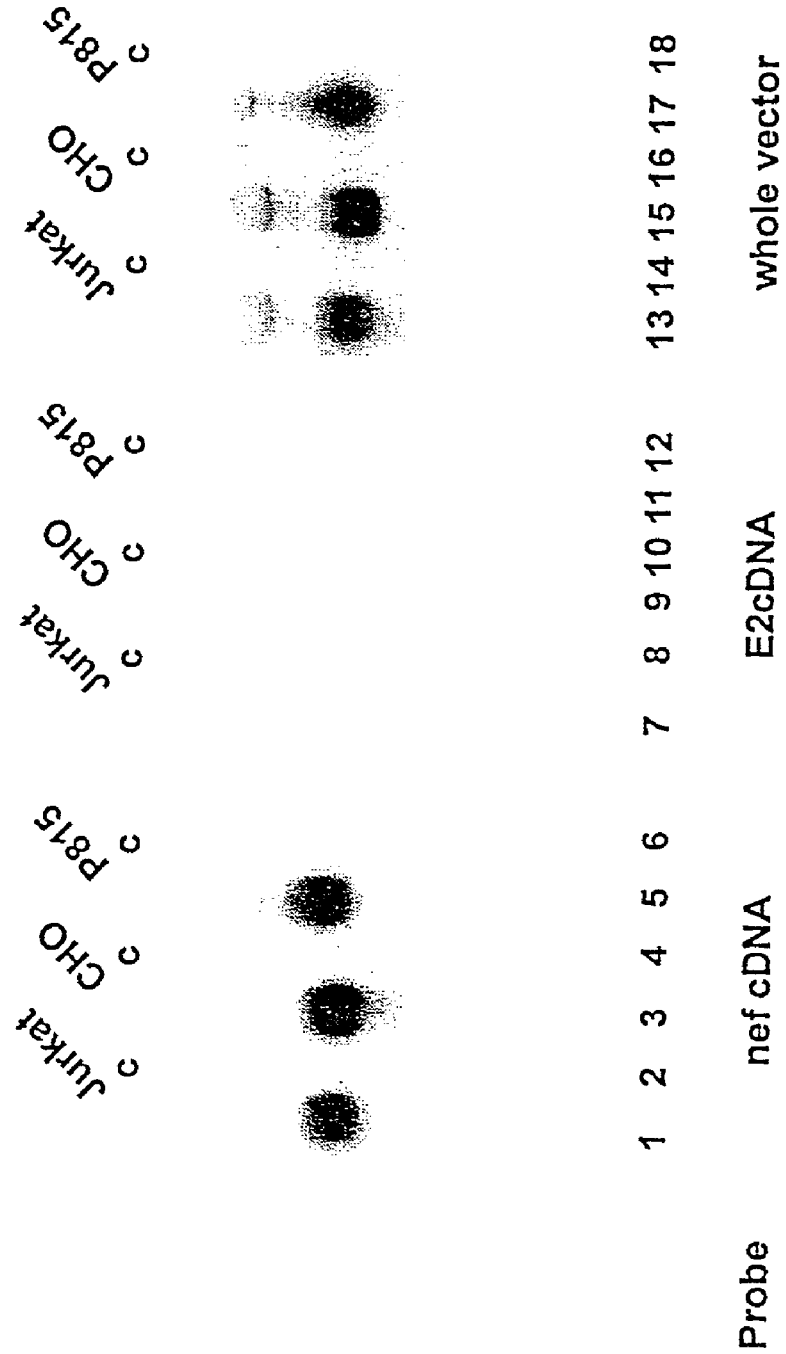
FIG. 12 shows the expression of the RNA molecules NNV-2 wt in CHO, Jurkat cells, and P815 cells.

The RD cells were transfected with 0.5 mmg or 2 mmg of the NNV-2 wt (lanes 1, 2, 8, and 9 in FIG. 11) and equal amounts of the plasmids NNV-2 wtFS (lanes 3, 4, 10, and 11 in FIG. 11) and product1 wt (lanes 5, 6, 12, and 13 in FIG. 11) or carrier only (lanes 7 and 14 in FIG. 11). Time-points were taken 39 hours (lanes 1-7) and 110 hours (lanes 8-14) after transfection. The expression of the Nef protein was analyzed by Western blotting essentially as described in Example 1.

In all four cell lines the expression level of the Nef protein, taken at earlier time points (lanes 1-7 in FIGS. 8-11) and at later time points (laines 8-14 in FIGS. 8-11) hours, from the NNV-2 wt was higher than from control vectors. The superiority of the NNV-2 wt was more obvious at later time-points as evident from the comparision of lane 8 with lanes 10 and 12 in FIG. 8, and also from the comparision of lane 9 with lanes 11 and 13 in FIGS. 8, 9 and 10.

The expression pattern of RNA from these plasmids was also analyzed using the Northern analysis [Alwine, J. C, et al., Proc Natl Acad Sci USA 74 (1977) 5350-5354] for the NNV-2 wt vector. For this purpose, Jurkat and CHO cells were transfected with 2 μg of the NNV-2 wt. For the transfection of P815 cells 10 μg of NNV-2 wt were used. The transfections were made essentially as described in Example 1. Forty-eight hours post-transfection total RNA was extracted using RNAeasy kit (Qiagen) and samples containing 21 mmg (P815), 15 mmg (CHO) or 10 mmg (Jurkat) of the RNA were analysed by electrophoresis under the denaturing conditions (1.3% agarose gel containing 20 mM MOPS pH 7.0; 2 mM NaOAc; 1 mM EDTA pH 8.0; 2.2M formaldehyde). The running buffer contained the same components except formaldehyde. The samples were loaded in a buffer containing formamide and formaldehyde. After the electrophoresis the separated RNAs were blotted onto the HybondN+ membrane (Amersham Pharmacia Biotech, United Kingtom) and hybridization with a radio-labeled nef coding sequence, E2 coding sequence or whole vector probes was carried out. The RNA from cells transfected with the carrier was used as a control. The results of the Northern blot analyses are shown in FIG. 12.

The results indicate that no other RNA species than complementary mRNAs for E2 and nef are expressed from the vector, since no additional signals can be detected with the whole vector probe compared with nef and E2 specific hybridizations (compare lanes 1-12 with lanes 13-18 in FIG. 12).

6.5 Example 4

Analysis of the attachment of the NNV-2 wt to mitotic chromosomes.

The attachment of the NNV-2 wt to mitotic chromosomes in CHO cells was analyzed by fluoresence in situ hybridisation (FISH) [Tucker J. D., et al., In: J. E. Celis (ed.), Cell Biology: A Laboratory Handbook, vol 2, p. 450-458. Academic Press, Inc. New York, N.Y. 1994.].

Thirty-six hours post-transfection the CHO cells by electroporation with 1 ìg of NNV-2 wt or with equimolar amounts of the control plasmids NNV-2 wtFS and product1 wt (performed essentially as described in Example 1) the cultures were treated with colchicin (Gibco) for arresting the cells in metaphase of the mitosis. Briefly, cells were exposed to colchicine added to medium at final concentration of 0.1 mmg/ml for 1-4 h to block the cell cycle at mitosis. Blocked cells were harvested by a trypsin treatment and suspended in a 0.075M KCl solution, incubated at room temperature for 15 min, and fixed in ice-cold methanol-glacial acetic acid (3:1, vol/vol). The spread-out chromosomes at metaphase and nuclei at interphase for fluorescence in situ hybridization analysis were prepared by dropping the cell suspension on wet slides. Several slides from one culture were prepared.

Hybridization probes were generated by nick-translation, using biotin-16-dUTP as a label and plasmid Product1 wt as template. A typical nick-translation reaction mixture contained a nick-translation buffer, unlabeled dNTPs, biotin-16-dUTP, and *E.coli* DNA polymerase.

Chromosome preparations were denatured at 70° C. in 70% formamide (pH 7.0-7.3) for 5 min, then immediately dehydrated in a series of washes (70%, 80%, and 96% ice-cold ethanol washes for 3 min each), and air dried. The hybridization mixture (18 mml per slide) was composed of 50% formamide in 2×SSC (1×SSC is 0.15 M NaCl plus 0.015 M sodium citrate), 10% dextran sulfate, 150 ng of biotinylated plasmid probe DNA and 10 mmg of herring sperm carrier DNA. After 5 min of denaturation at 70° C., probe DNA was applied to each slide, sealed under a coverslip, and hybridized for overnight at 37° C. in a moist chamber. The slides were washed with three changes of 2×SSC, and 2×SSC containing 0.1% IGEPAL CA-630 (Sigma Chemical Co.) at 45 °° C. Prior to the immunofluorescence detection, slides were preincubated for 5 min in PNM a buffer [PN buffer (25.2 g $Na_2HPO_4.7H_2O$, 083 g $NaH_2PO_4.xx\ H_2O$ and 0.6 ml of IGEPAL CA-630 in 1 liter of $H_2O$] with 5% nonfat dried milk and 0.02% sodium azide).

Subsequently, the probe was detected with fluorescein isothiocyanate (FITC)-conjugated extravidin. The signal was amplified with biotinylated antiavidin antibody and a second round of extravidin-FITC tretment. Between each of the steps, the slides were washed in PN buffer containing 0.05% IGEPAL CA-630 at room temperature for 2×5 min. Chromosomes were counterstained with propidium iodide and mounted in p-phenylenediamine antifade mounting medium.

Slides were analyzed with a Olympus VANOX-S fluorescence microscope equipped with appropriate filter set.

The results are shown in Table 1.

TABLE 1

Chromosomal attachment of the NNV-2wt.

| Culture | Metaphases with episomal signal on chromosomes | Analyzed metaphases | % |
|---|---|---|---|
| 0.5 μg NNV-2wt | 11 | 158 | 7 |
| 0.5 μg NNV-2wtFS | 0 | 100 | 0 |
| 0.48 μg product1wt | 0 | 100 | 0 |
| carrier | 0 | 100 | 0 |

The data indicate clearly that the E2 protein and its binding sites are needed for the chromosomal attachment because only the NNV-2 wt but not two other vectors have this ability.

6.6 Example 5

Stability of NNV-2 wt During Propagation in Bacterial Cells

The stability of NNV-2 wt during propagation in bacterial cells was tested. The plasmid NNV-2 wt was mixed with competent *Escherichia coli* cells of the DH5alpha strain [prepared as described in Inoue, H., et al., Gene 96 (1990) 23-28] and incubated on ice for 30 minutes. Subsequently, the cell suspension was subjected to a heat-shock for 3 minutes at 37° C. followed by a rapid cooling on ice. One milliliter of LB medium was added to the sample and the mixture was incubated for 45 minutes at 37° C. with vigorous shaking. Finally, a portion of the cells was plated onto dishes containing LB medium with 50 µg/ml of kanamycin. On the next day, the cells from a single colony were transferred onto the new dishes containing the same medium. This procedure was repeated until four generations of bacteria had been grown, and the plasmid DNA from the colonies of each generation was analyzed.

One colony from each generation was used for an inoculation of 2 ml LB medium containing 50 µg/ml of kanamycin followed by an overnight incubation at 37° C. with vigorous shaking. The cells were harvested and the plasmid DNA was extracted from the cell using classical lysis by boiling. [Sambrook, S., et al., Molecular Cloning A Laboratory Manual. Second ed. Cold Spring Harbor Laboratory Press, Cold Spring Harbor, N.Y.]. The samples were digested with restriction endonuclease XbaI (Fermentas, Lithuania) and analyzed by agarose gel electrophoresis in comparison with the original DNA used for transformation. The results are shown in FIG. 13.

Figure 13:
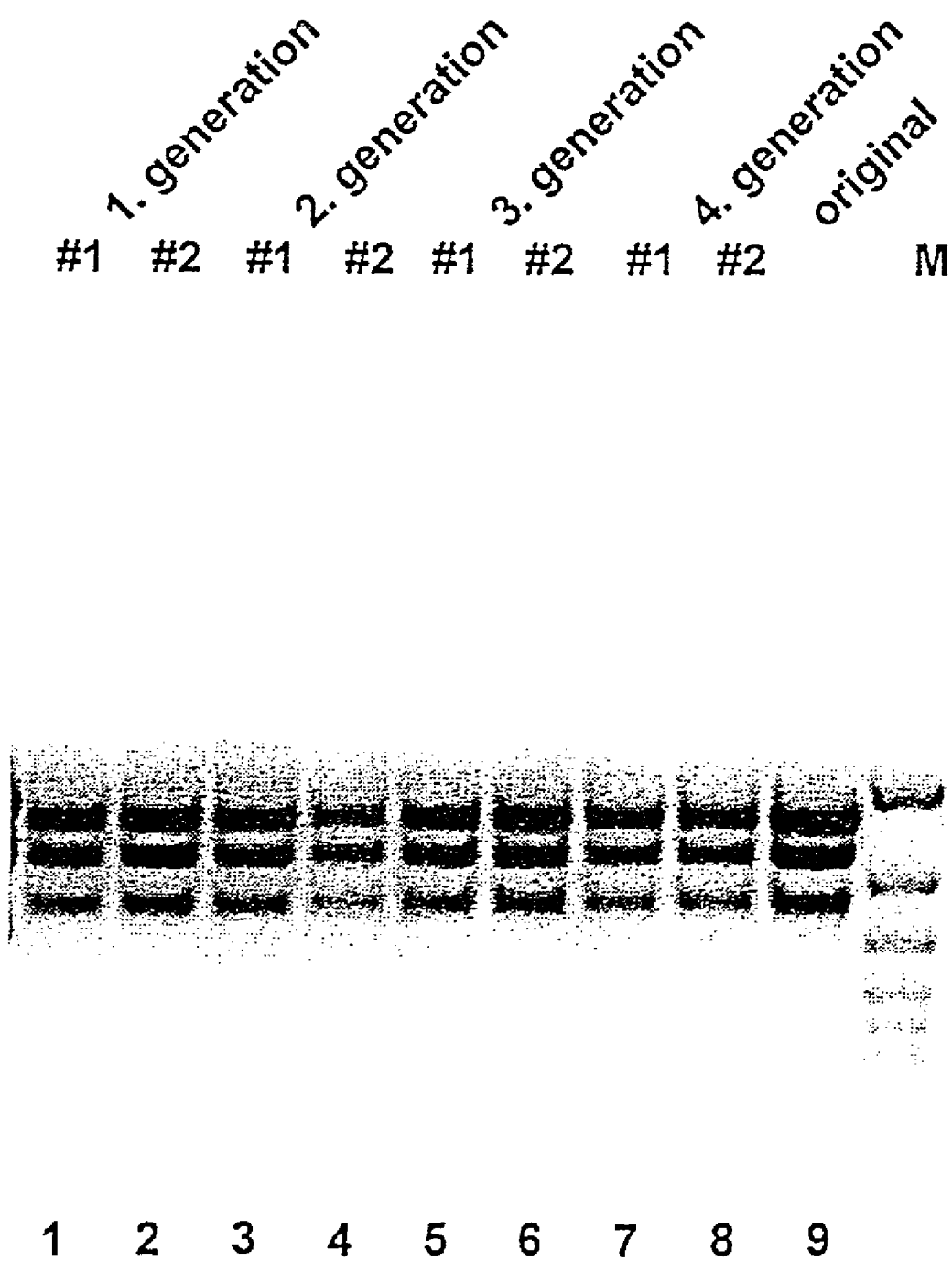
FIG. 13 shows the stability of NNV-2 wt in bacterial cells.

As can be seen in FIG. 13, the vector is stable during the passage in *Escherichia coli* cells: no colonies with re-arrangements were observed when compared with the DNA used for transformation (lane 9).

6.7 Example 6

Stability of NNV-2 wt in Eukaryotic Cells

Figure 14:
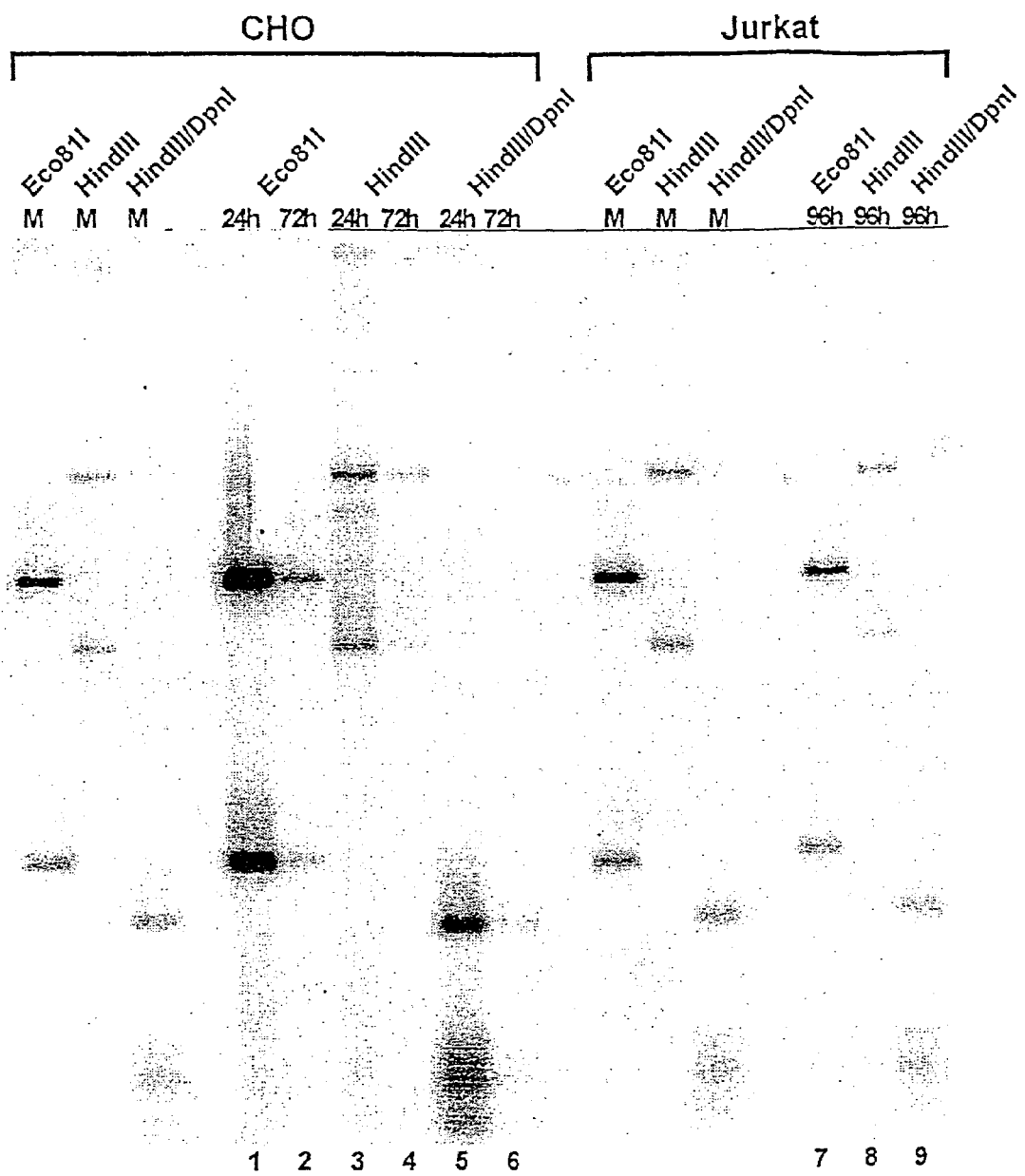
FIG. 14 shows the Southern blot analysis of stability of the NNV-2 wt as non-replicating episomal element in CHO and Jurkat cell lines.

The stability of the plasmid NNV-2 wt as a non-replicating episomal element was also analyzed in eukaryotic cells. For this purpose the CHO and Jurkat cells were transfected with 2 µg of NNV-2 wt. Total DNAs of the cells were extracted at 24, 72 or 96 hours post-transfection. Briefly, the cells were lyzed in 20 mM Tris-HCl pH 8.0; 10 mM EDTA pH 8.0; 100 mM NaCl; 0.2% SDS; in presence of 200 µg/ml of proteinase K (Fermentas, Lithuania). Next, the samples were extracted sequentially with phenol and with chloroform and precipitated with ethanol. The nucleic acids were resuspended in 10 mM Tris-HCl pH 8.0; 1 mM EDTA pH 8.0; 20 µg/ml of RNase A (Fermentas, Lithuania) and incubated for 1 hour at 37° C. Finally the DNA was re-precipitated with ammonium acetate and ethanol, washed with 70% ethanol and resuspended in 10 mM Tris-HCl pH 8.0; 1 mM EDTA pH 8.0. The samples were digested with different restriction endonucleases: with Eco81I (Fermentas, Lithuania) that has two recognition sites on the plasmid, with HindIII (Fennentas, Lithuania) that does not cut the NNV-2 wt DNA and with DpnI (New England Biolabs, USA) that digest only DNA synthesized in *Escherichia coli* cells. Restricted DNAs were separated on TAE agarose electrophoresis and analyzed by Southern blotting [Southern, E. M. J. Mol. Biol. 98 (1975) 503-517] with a vector specific radiolabeled probe. The results are illustrated on FIG. 14. As obvious from comparison of the fragment sizes of Eco81I digestion (lanes 1, 2 and 7 in FIG. 14) with respective marker lanes no arrangements of the vector were detected in the assay. Neither were signals observed at a position different from the marker lanes in cases of the Hind III (lanes 3, 4 and 8 in FIG. 14) or HindIII/DpnI (lanes 5, 6 and 9 in FIG. 14) digestion indicating that integration and/or replication events were not observed.

6.8 Example 7

Analysis of replication of the NNV-2 wt in the presence of human papillomaviral replication factors.

Figure 15:
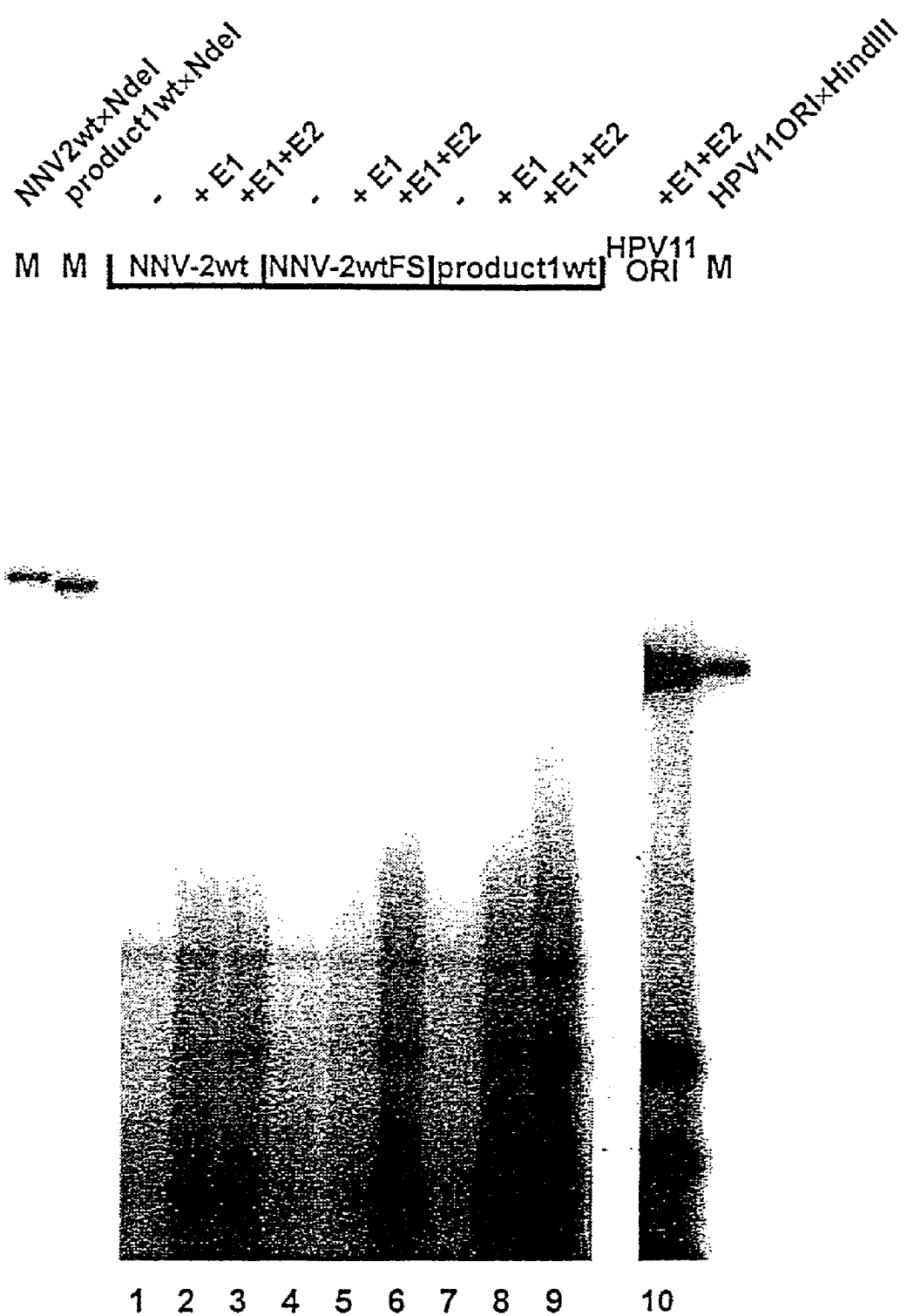
FIG. 15 shows that the vectors NNV2 wt, NNV2 wtFS and product1 are unable to HPV-11 replication factor-dependent replication.

It has been demonstrated previously that papillomaviral proteins are able to initiate the replication of heterologous ori-containing plasmids from many other human and animal papillomaviruses [Chiang, C. M., et al., Proc Natl Acad Sci USA 89 (1992) 5799-5803]. Although NNV-2 wt does not contain an intact viral origin of replication, it was tested how the replication is initiated in the presence of human papillomavirus type 1 E1 and E2 proteins. CHO cells were transfected with one microgram of either plasmids NNV-2 wt, NNV-2 wtFS or product 1 alone or with 4.5 mmg of the HPV-11 E1 expression vector pMT/E1 HPV11 or with same amount of pMT/E1 HPV11 and 4.5 mmg HPV-11 E2 protein expression vector pMT/E2 HPV 11 as indicated on the top of the FIG. 15. Transfections were done essentially as described in Example 1. E1 and E2 expression vectors are described previously (Chiang, C. M. et al., supra). An equimolar amount of HPV-11 replication origin containing plasmid HPV11ORI was transfected with the same expression vectors as a positive control.

Low-molecular weight DNA was extracted by modified Hirt lysis [Ustav, et al., EMBO J 2 (1991) 449-457] at 67 hours post-transfection. Briefly, the cells washed with PBS were lyzed on ice at 5 minutes by adding alkaline lysis solutions I (50 mM glucose; 25 mM Tris-HCl, pH 8.0; 10 mM EDTA, pH 8.0) and II (0.2M NaOH; 1% SDS) in a ratio of 1:2 onto the dishes. The lysates were neutralized by 0.5 vol solution III (a mixture of potassium acetate and acetic acid, 3M with respect to potassium and 5M with respect to acetate). After centrifugation the supernatant was precipitated with isopropanol, resuspended and incubated at 55° C. in 20 mM Tris-HCl pH 8.0; 10 mM EDTA pH 8.0; 100 mM NaCl; 0.2% SDS; in presence of 200 µg/ml of proteinase K (Fermentas, Lithuania). Next, the samples were extracted sequentially with phenol and with chloroform followed by precipitation with ethanol. The nucleic acids were resuspended in 10 mM Tris-HCl pH 8.0; 1 mM EDTA pH 8.0; 20 µg/ml RNase A (Fermentas, Lithuania) and incubated for 30 min at 65° C. The samples were digested with linearizing endonuclease (NdeI; Fermentas, Lithuania) in case of the vectors or HindIII (Fermentas, Lithuania) in case of the HPV11ORI) and DpnI (New England Biolabs, USA) (breaks non-replicated DNA), followed by Southern blotting performed essentially as described earlier using a vector specific radiolabeled probe. For positive control of hybridization appropriate markers of the linearized vectors and HPV11ORI were used (lanes marked as M on FIG. 15). As seen from the results set forth in FIG. 15, no replication signal was detected in case of any vector plasmids.

6.9 Example 8

Analysis of the E2 and its binding sites dependent segregation function of the vectors in dividing cells.

As has been described previously, bovine papillomavirus type 1 E2 protein in trans and its multiple binding sites in cis are both necessary and sufficient for the chromatin attachment of the episomal genetic elements. The phenomenon is suggested to provide a mechanism for partitioning viral genome during viral infection in the dividing cells [Ilves, I., et al., J Virol. 73 (1999) 4404-4412]. Because both functional elements are also included into our vector system, the aim of this study was analyze the importance of the E2 protein and oligomerized binding sites for maintenance of the transcriptionally active vector element in population of dividing cells.

For this purpose the Nef coding sequence of the vectors NNV-2 wt and super6 wt was replaced with coding sequence of the destabilized form of green fluorescent protein (d1EGFP) derived from vector pd1EGFP-N1 (Clontech Laboratories). Because the half-life of this protein is as short as 1 hour, it does not accumulate in the cells and the d1EGFP expression detected by flow cytometer correlates with the presence of transcriptionally active vector in these cells.

Figure 16:
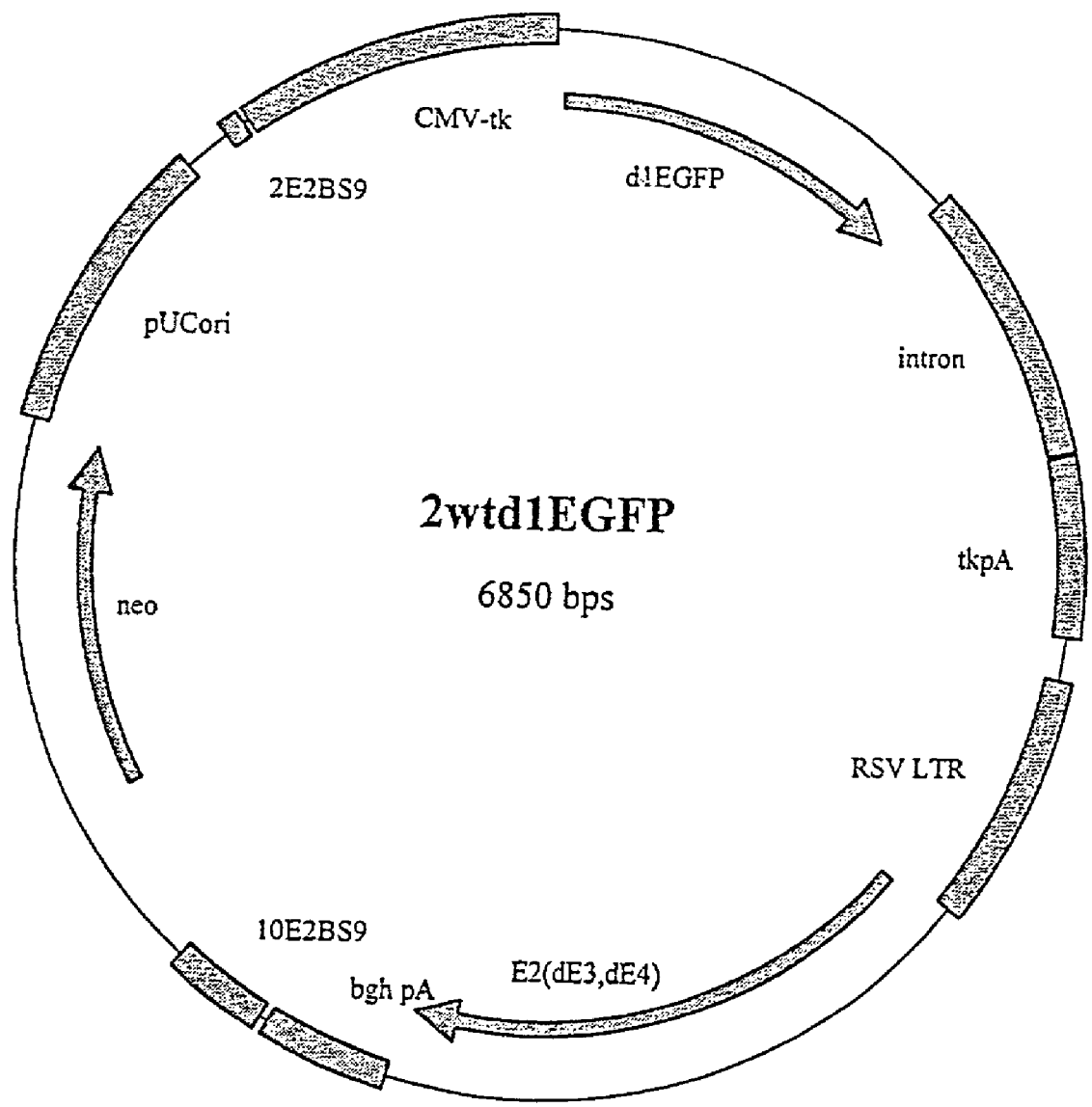
FIG. 16 shows the schematic map of the plasmid 2 wtd1EGFP.
Figure 17:
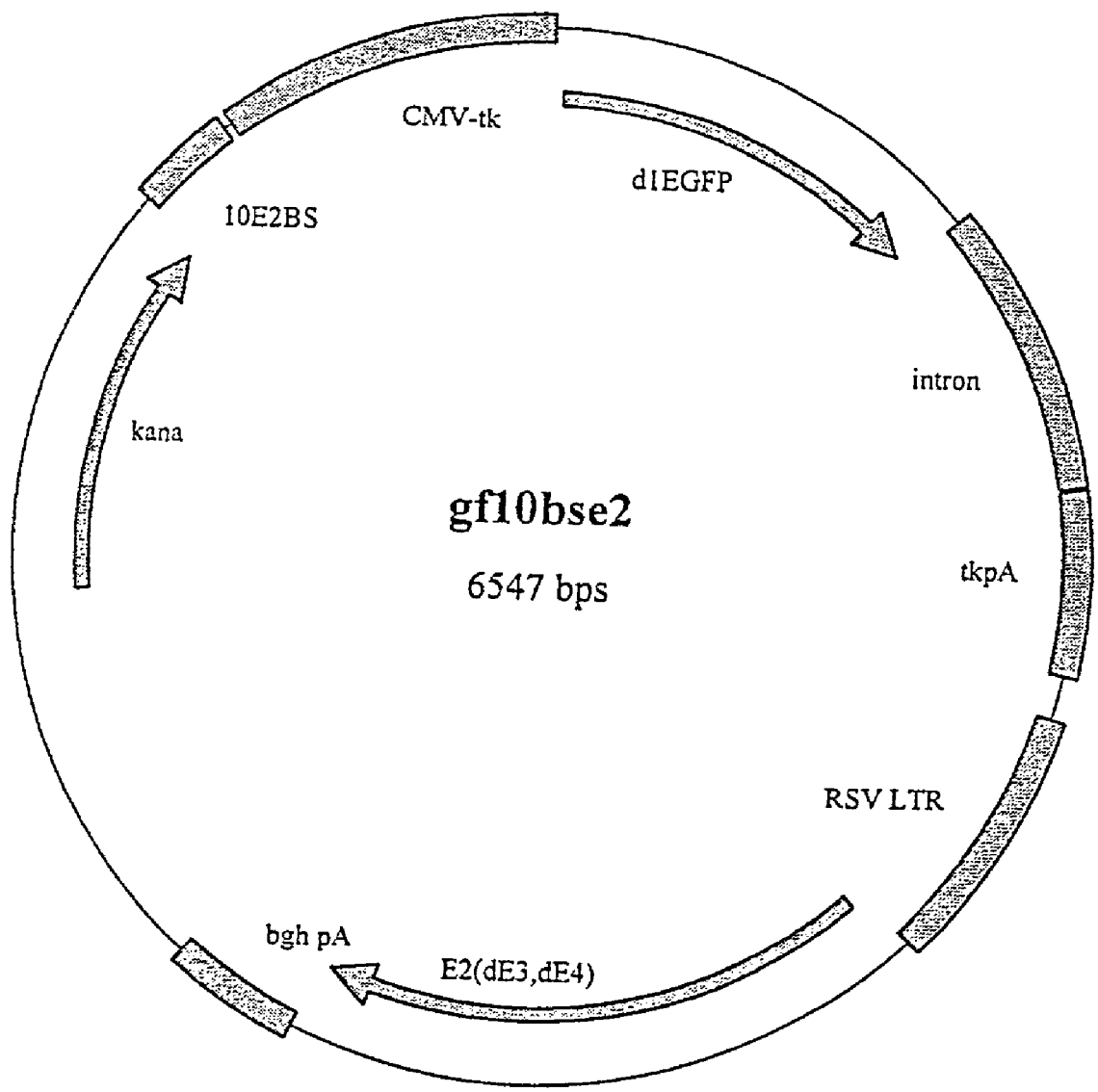
FIG. 17 shows the schematic map of the plasmid gf10bse2

From NNV-2 wt the nef coding sequence was removed and SmaI-NotI fragment from the pd1EGFP-N1 was inserted instead of it. New vector was named as 2 wtd1EGFP (FIG. 16). Similar replacement was made in case of super6 wt for generation gf10bse2 (FIG. 17), respectively. The recognition sequence for restrictional endonuclease SpeI was introduced into the EcoRI site in the super6 wt just upstream the ten E2BS. The vector gf10bse2 is derived from this plasmid by replacing the Nef coding sequence containing NdeI-Bst1107I fragment with d1EGFP coding sequence containing fragment from 2 wtd1EGFP, cut out with same enzymes.

Figure 18:
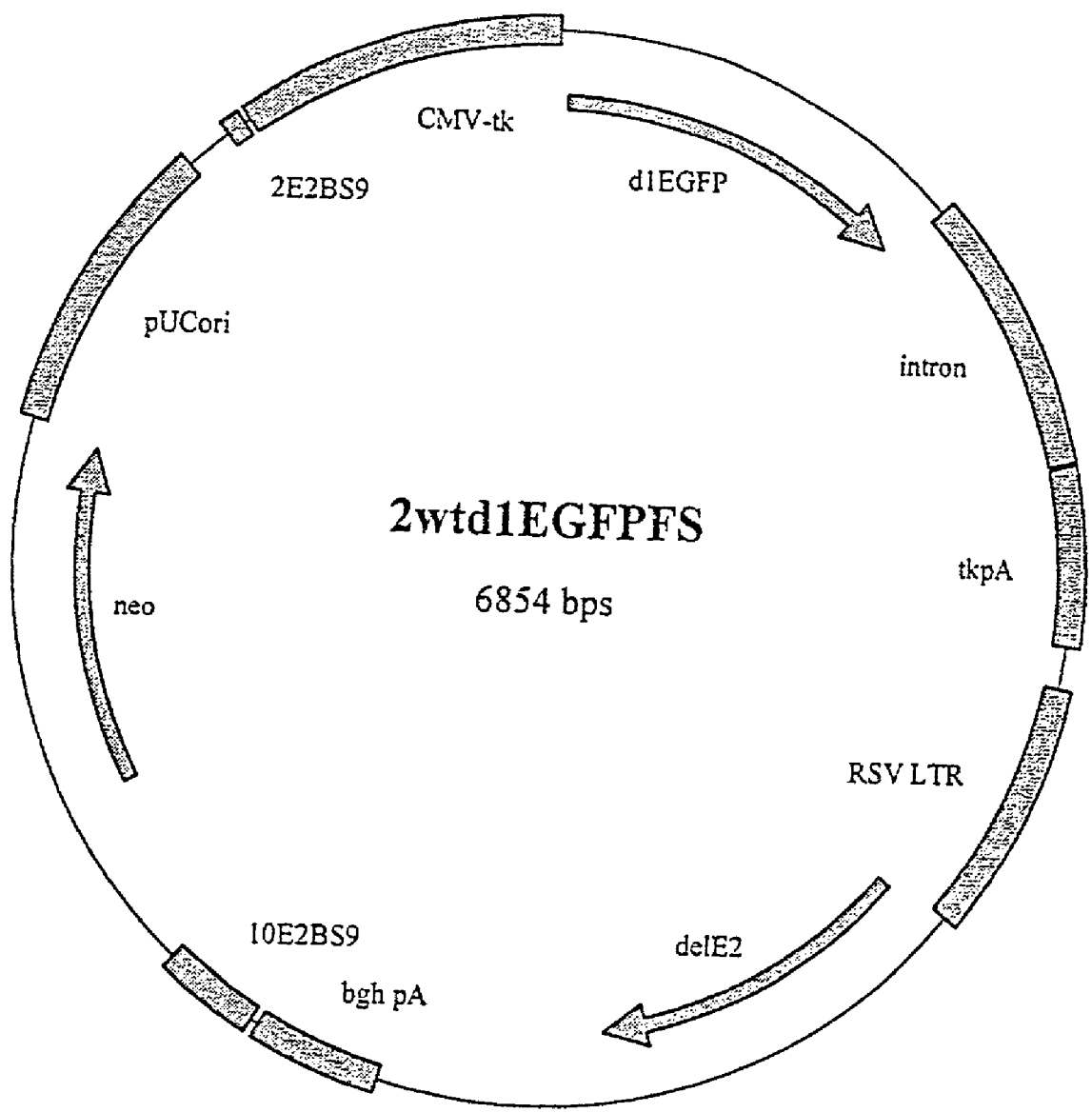
FIG. 18 shows the schematic map of the plasmid 2 wtd1EGFPFS.
Figure 19:
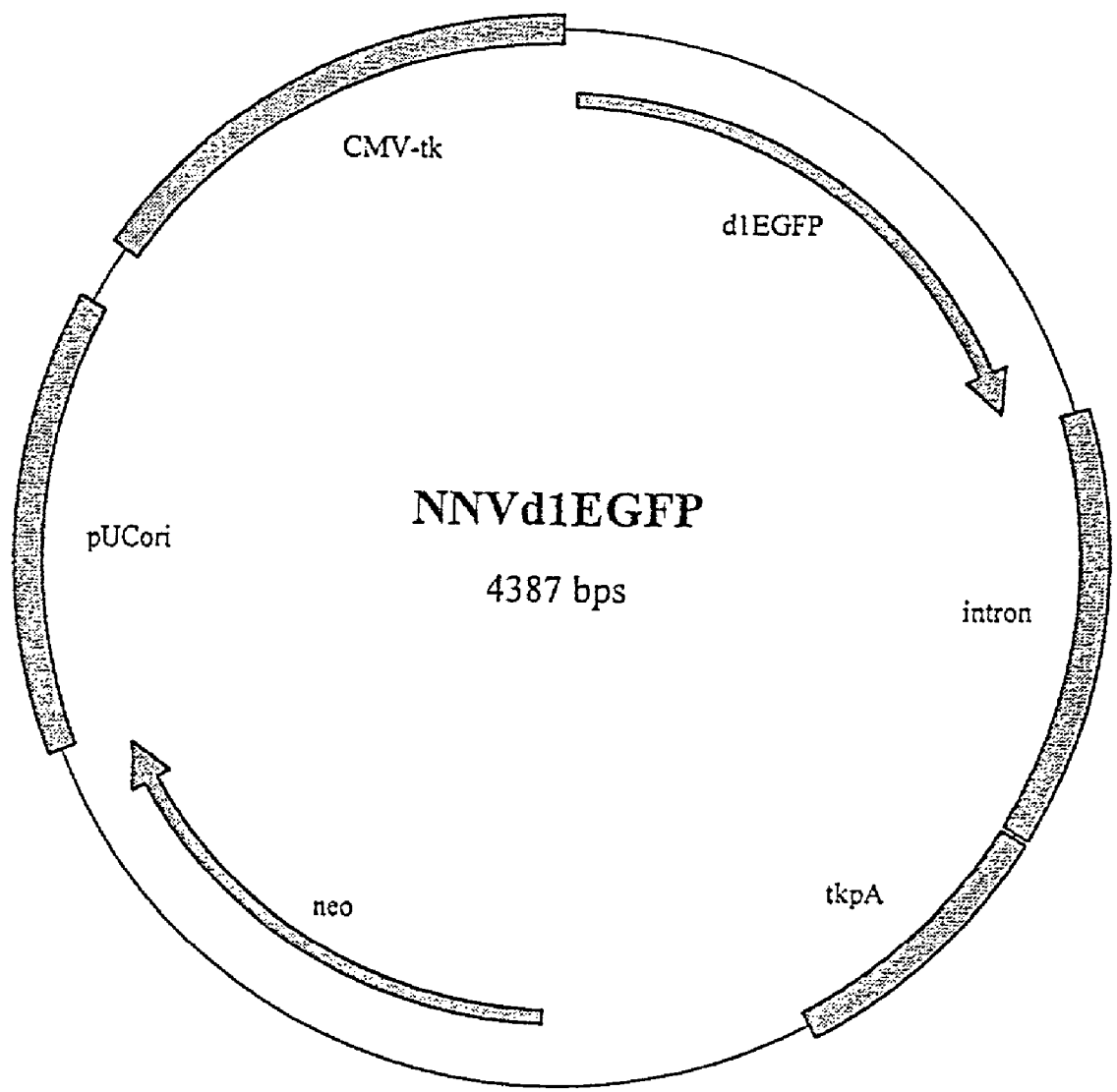
FIG. 19 shows the schematic map of the plasmid NNVd1EGFP.

Negative control plasmids lacking either functional E2 coding sequence or its binding sites were also made: The frameshift was introduced into the E2 coding sequence in context of the 2 wtd1EGFP by replacing E2 coding sequence containing Bsp120I-Bsp120I with similar fragment from plasmid NNV-2 wtFS. The resulting vector was named as 2 wtd1EGFPFS (FIG. 18). For the construction the control plasmid NNVd1EGFP (FIG. 19) the whole E2 expression cartridge (as well bacterial replicon) from the 2 wtd1EGFP was removed by Bst1107 and NheI digestion. The replicon was reconstituted from plasmid productl as HindIII (filled in)-NheI fragment.

Jurkat cells were transfected by electroporation with 1 ig of the vector 2 wtd1EGFP or with equimolar amounts of the plasmids 2 wtd1EGFPFS, NNVd1EGFP, gf10bse2 or with carrier DNA only as described in Example 1. At different time-points post-transfection the equal aliquots of the cell suspension were collected for analysis and the samples were diluted thereafter with the fresh medium. At every time-point total number of the cells as well the number of the d1EGFP expressing cells were counted by flow cytometer (Becton-Dickinson FACSCalibur System). With these data, the percentages of d1EGFP expressing cells, alterations of total numbers of cells and numbers of d1EGFP expressing cells in samples were calculated using the carrier-only transfected cells as a negative control for background fluorescence. The calculations of cell numbers were done in consideration of the dilutions made. Finally, the error values were calculated based on technical data of the cytometer about fluctuations of speed of the flow.

Two independent experiments were done. First, the maintenance of d1EGFP expressed from the plasmids 2 wtd1EGFP, 2 wtd1EGFPFS and NNVd1EGFP were analyzed during the eight days post-transfection. In the second experiment the maintenance of d1EGFP expressed from the plasmids 2 wtd1EGFP, 2 wtd1EGFPFS and gf10bse2 were analyzed during the thirteen days post-transfection.

Figure 20:
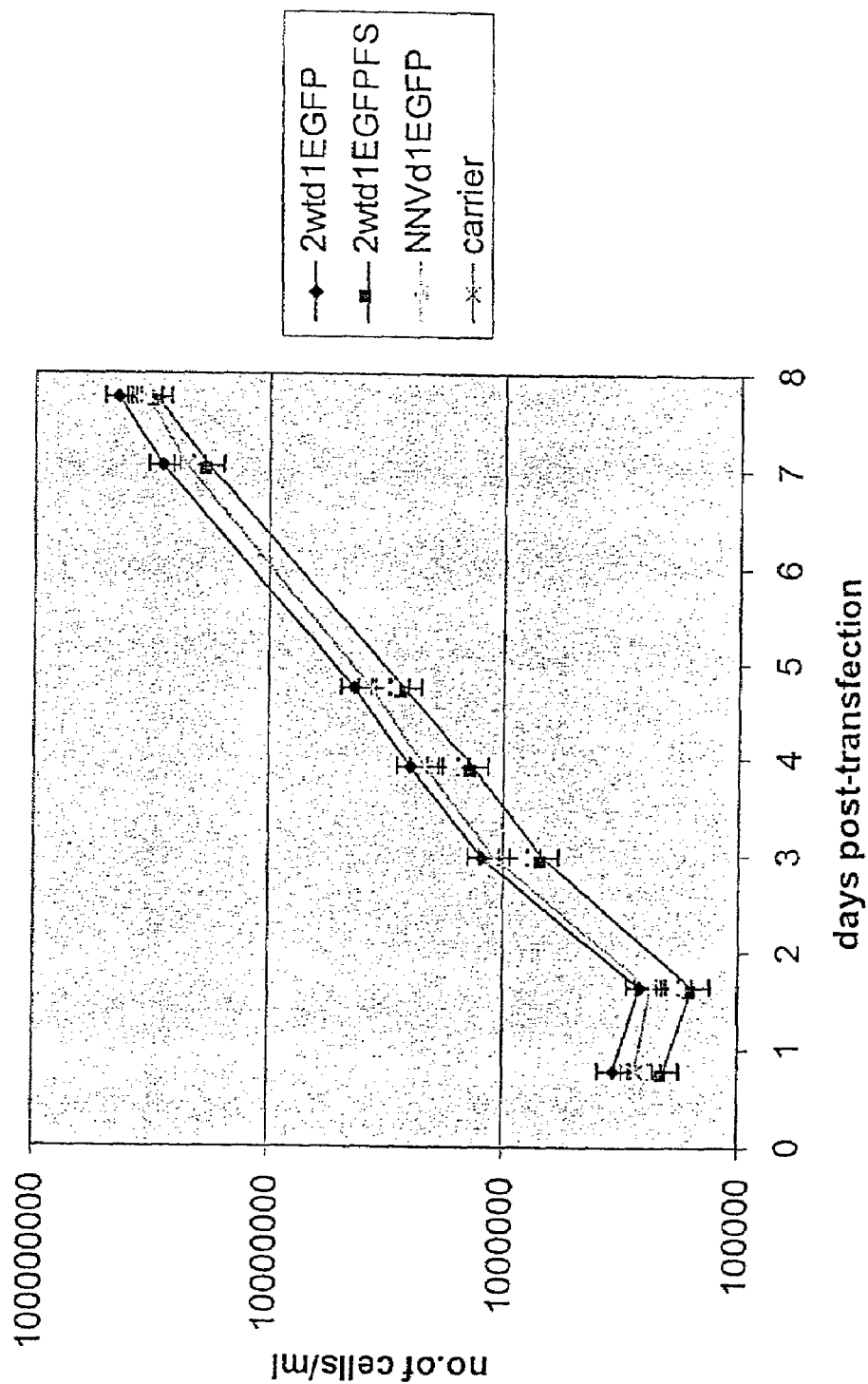
FIG. 20 shows the growth curves of the Jurkat cells transfected with the plasmids 2 wtd1EGFP, 2 wtd1EGFPFS, NNVd1EGFP or with carrier DNA only.
Figure 21:
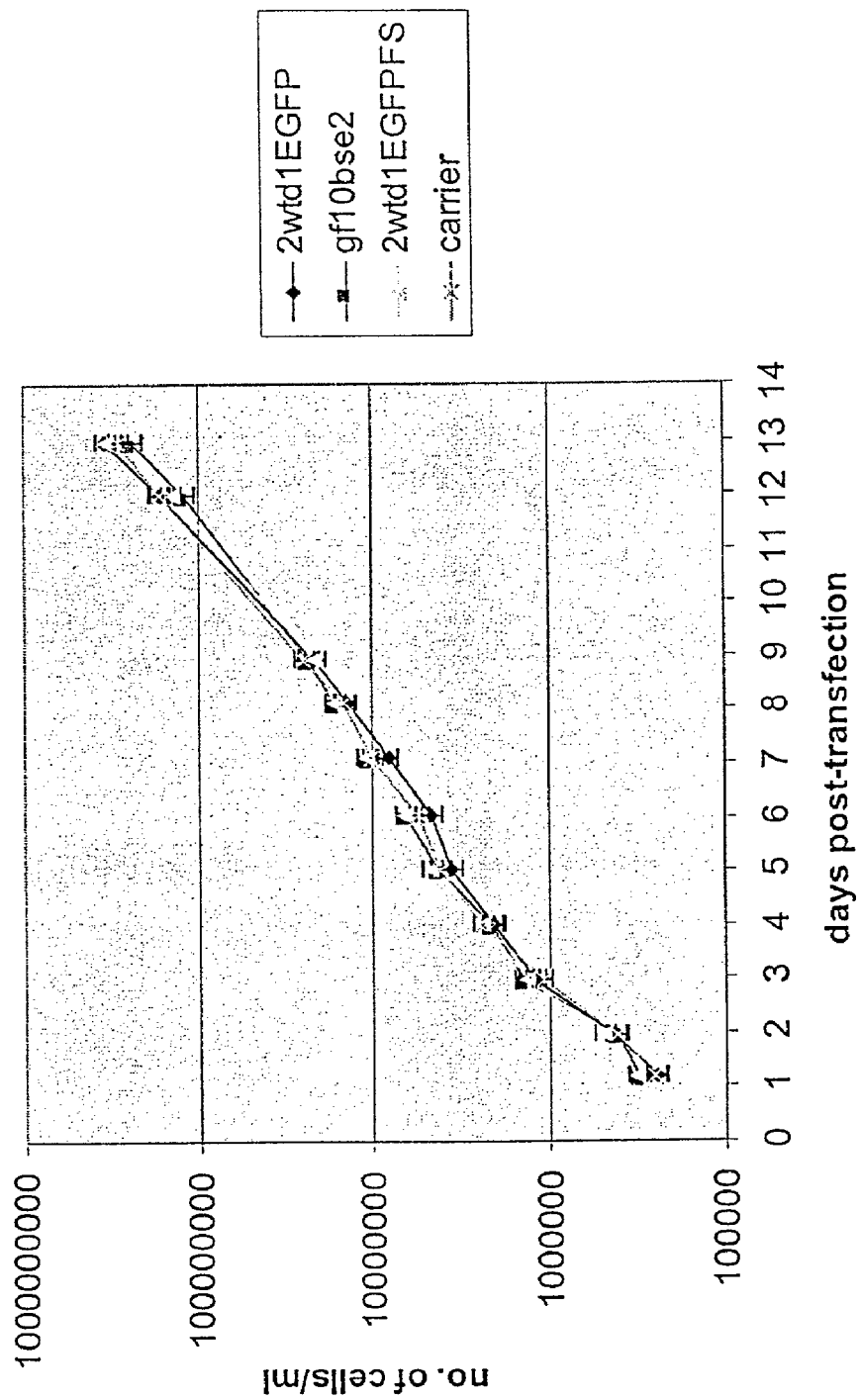
FIG. 21 shows the growth curves of the Jurkat cells transfected with the plasmids 2 wtd1EGFP, 2 wtd1EGFPFS, gf10bse2 or with carrier DNA only.

As is obvious from FIGS. 20 and 21, there was no difference of the growth speed of the cells transfected with any vector or carrier only. It means that differences in the d1EGFP expression maintenance are not caused by influences of transfected vectors themselves on the dividing of the cells. Also, during the assay the logarithmic growth of the cells were detected, except the period until second time-point in the experiment represented in FIG. 20. This lag period of the growth is probably caused by the electroporation shock of the cells, because the first time-point was taken already 19 hours after the transfection.

Figure 22:
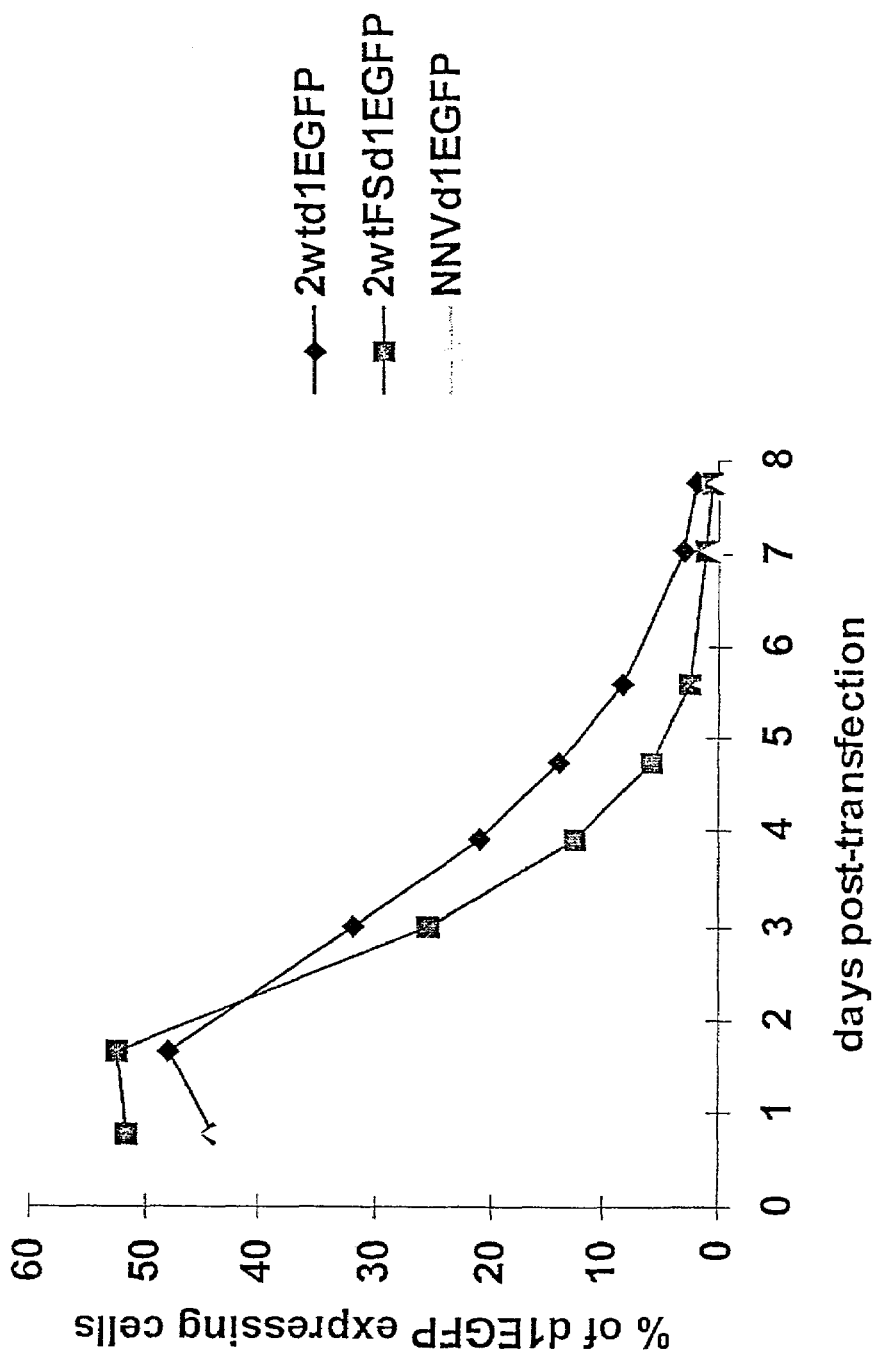
FIG. 22 shows the change in the percentage of d1EGFP positive cells in a population of Jurkat cells transfected with the vectors 2 wtd1EGFP, 2 wtd1EGFPFS or NNVd1EGFP.
Figure 23:
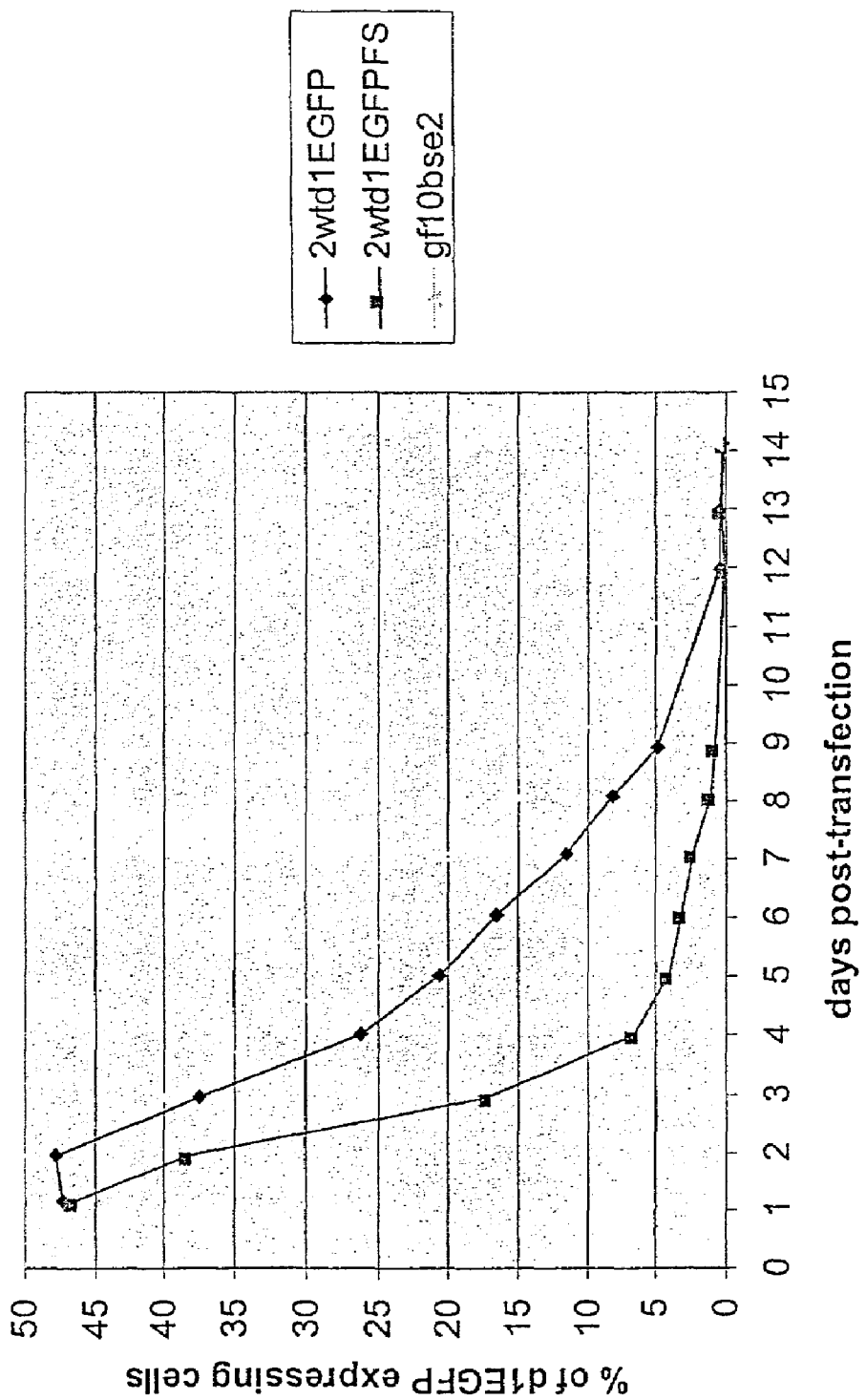
FIG. 23 shows the change in percentage of the d1EGFP positive cells in a population of Jurkat cells transfected with the vectors 2 wtd1EGFP, 2 wtd1EGFPFS or gf10bse2.

As illustrated in FIGS. 22 and 23, the percentages of green fluorescent protein expressing cells decrease in all populations transfected with either plasmid, because the vectors do not replicate in the cells. However, as is seen on the charts, the fraction of positive cells declines more rapidly in cases of control vectors, if compared with the 2 wtd1EGFP or gf10bse2. If compared with each other, the gf10bse2 have clear benefit to 2 wtd1EGFP (FIG. 23.). There is also a notable difference of maintenance between control plasmids 2 wtFSd1EGFP and NNVd1EGFP (FIG. 22).

Figure 24:
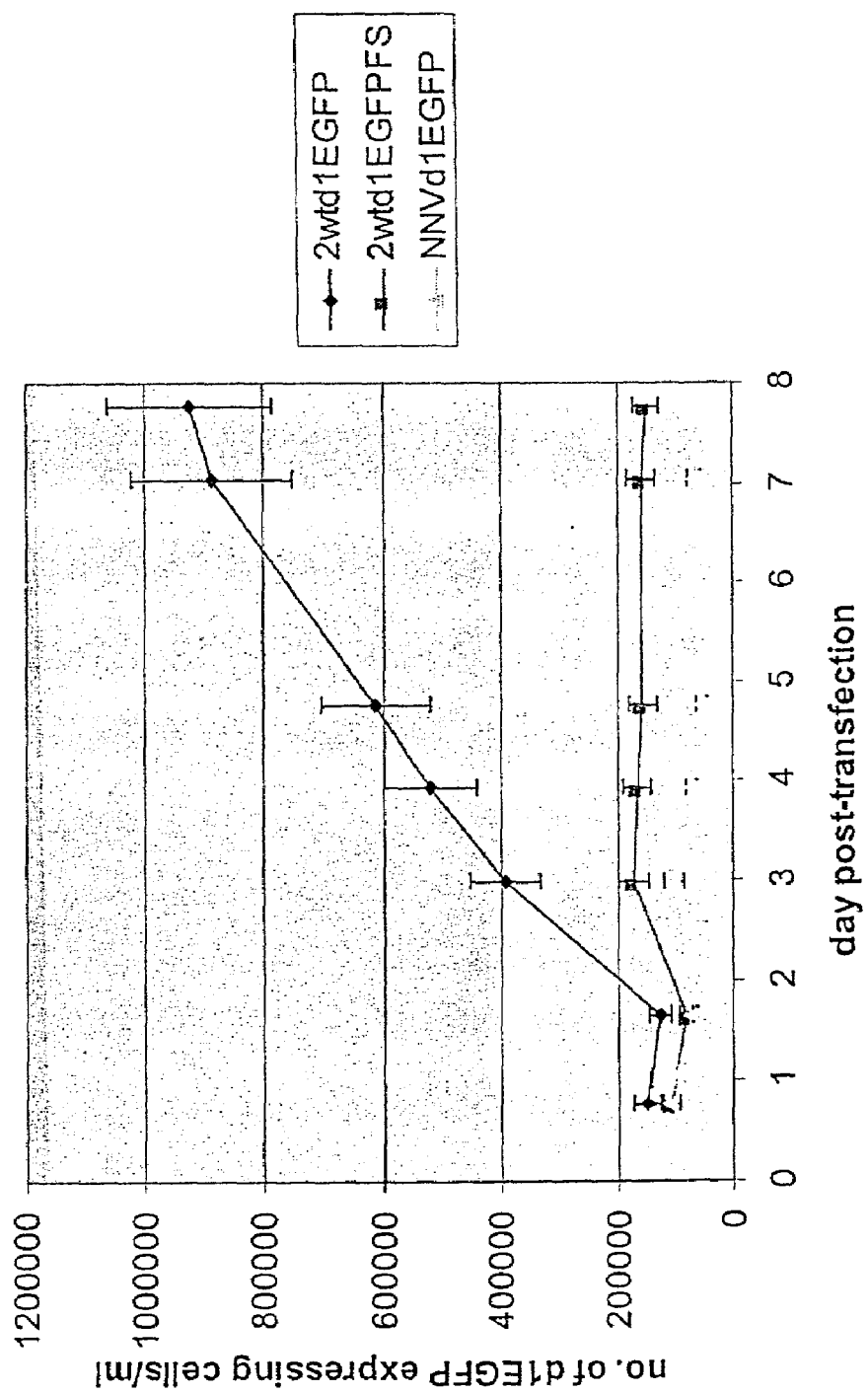
FIG. 24 shows the change in the number of d1EGFP expressing cells in a population of Jurkat cells transfected with the vectors 2 wtd1EGFP, 2 wtd1EGFPFS or NNVd1EGFP.
Figure 25:
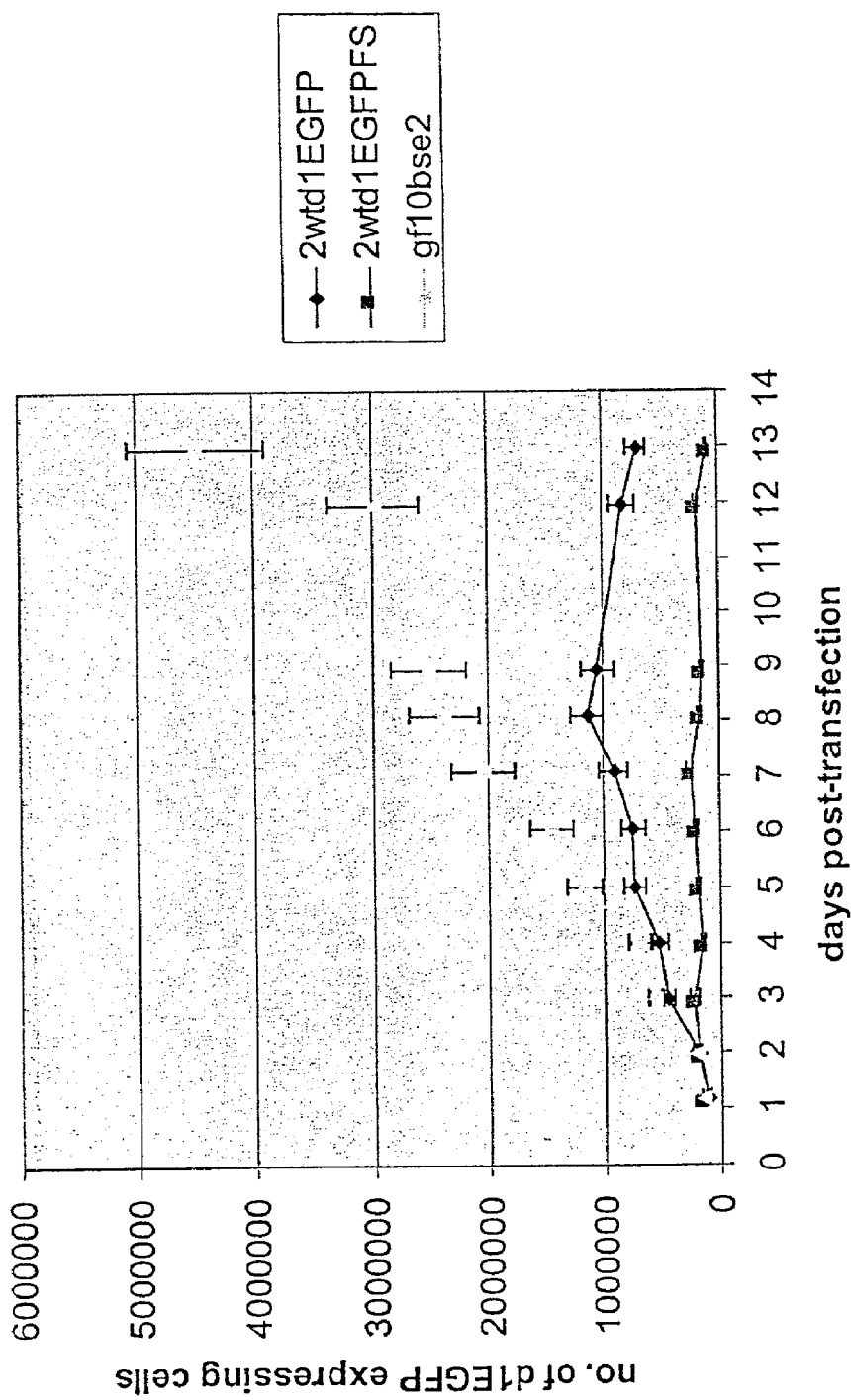
FIG. 25 shows the change in the number of d1EGFP expressing cells in a population of Jurkat cells transfected with the vectors 2 wtd1EGFP, 2 wtd1EGFPFS or gf10bse2.

These differences between the vectors become much more obvious, if the data are represented as alterations of the numbers of the d1EGFP expressing cells in the populations (FIGS. 24 and 25). The numbers of the positive cells in cases of the control plasmids are not notable changed during the assay. In contrast, in case of the 2 wtd1EGFP the number of d1EGFP expressing cells increases during the first week after the transfection becoming approximately five to ten times higher than in control samples (FIG. 24). After this time-point the number start to decrease (FIG. 25). The difference of maintenance is strongest in the case of the gf10bse2 vector. The number of positive cells increases continuously during the analyses period. After two weeks it is 6 times higher than in the sample transfected with 2 wtd1EGFP and 45 times higher than in the population transfected with frameshift mutant (FIG. 25).

The data demonstrate clearly that the vector system of the present invention has active mechanism of segregation based on a nuclear-anchoring protein, i.e. bovine papillomavirus type 1 E2 protein and its binding sites that promotes its maintenance in a population of proliferating cells as a transcriptionally active element.

6.10 Example 9

Cloning of the AIRE Gene into Super6 wt and Expression in an Epithelial Cell Line The AIRE gene coding for the AIRE protein (AIRE=autoimmune regulator) is mutated in an autosomally heredited syndrome APECED (Autoimmune polyendocrinopathy candidiasis ectodermal dystrophy). AIRE is expressed in rare epithelial cells in the medulla of thymus and in the dendritic cells in peripheral blood and in peripheral lymphoid organs. APECED could thus be treated by transferring the non-mutated AIRE gene ex vivo to peripheral blood dendritic cells, followed by the introduction of the corrected dendritic cells back to the patient. To test this possibility human AIRE gene and the homologous murine AIRE gene were transferred to COS-1 cells.

For cloning of the AIRE gene into Super6 wt a maxi-preparation of the vector was prepared. First a transfection with Super6 wt was done to TOP10-cells (chemically competent *Escherichia coli* by Invitrogen) according to manufacturer's protocol. Briefly, the cells were incubated on ice for 30 minutes, after which a heat shock was performed in a water bath at +42°° C. for 30 seconds. The cells were then transferred directly on ice for 2 minutes and grown in 250 mml of SOC-medium (2% tryptone, 0.5% yeast extract, 10 mM NaCl, 2.5 mM KCl, 10 mM MgCl2, 10 mM MgSO4, 20 mM glucose) at +37°° C. with shaking for 1 hour.

Plating was done on LB-plates using kanamycin (50 mmg/ml) for selection. For maxiprep, colonies were transferred to 150 ml of LB-solution containing kanamycin (50 mmg/ml) and grown overnight at +37°° C. with shaking. Preparation of maxiprep was done using Qiagen's Plasmid Maxi Kit according to manufacturer's protocol.

A digestion with BamHI and SalI restriction enzymes was used to check the vector. The reaction mixture contained 500 ng of Super6w, 5 U of BamHI, 5 U of SalI, 2 mml of 2XTANGO buffer (both the restriction enzymes and buffer from Fermentas) and sterile water in total volume of 10 mml. The digestion was carried out at +37° C. for one hour.

The digested vector was checked with 1% agarose gel containing ethidium bromide 1 µg/mml in 1×TAE-buffer.

For cloning of the PCR amplified AIRE gene and Aire fragments into the Super6 wt, 4 mmg of Super6 wt was digested with 10 U NotI restriction enzyme (MBI Fermentas, in 2 mml enzyme buffer and sterile water added to a final volume of 20 µl. The digestion was carried at +37°° C. for 1.5 hours, after which 1U of ZIP-enzyme (alkaline phosphatase) was added to the reaction mixture and incubated further for 30 minutes. The ZIP-enzyme treatment was done to facilitate the insertion of the AIRE gene into the vector by preventing the self-ligation of the vector back to a circular mode. After the digestion the vector was purified using GFXTM PCR DNA and Gel Band Purification Kit (Amersham Pharmacia Biotech) and dissolved in to a concentration of 0.2 micrograms/microliter.

Human and mouse AIRE-gene PCR-products were also digested with NotI restriction enzyme. To the digestion, 26 mml of PCR product, 3 µl of an appropriate enzyme buffer and 10U of NotI restriction enzyme (the buffer and enzyme from MBI Fermentas) was used. The digestion was carried out at +37° C. for 2 hours, after which digested PCR-products were purified and dissolved in sterile water to a volume of 10 µl.

The PCR amplified and digested human and mouse AIRE genes were ligated to Super6 wt by a T4 DNA ligase (MBI Fermentas). The digested insert DNA was taken (a total volume of 10 mml), 1.5 µl of ligase buffer (MBI Fermentas), 5U of T4 DNA ligase and sterile water was added to a final concentration of 15 µl. The ligation was carried out at +17° C. overnight.

After the ligation 10 µl of ligation reaction mixture was taken for transfection into TOP10 cells according to manufacturer's protocol. The cells were incubated on ice for 30 minutes, after which a heat shock was performed in a water bath at +42° C. for 30 seconds. The cells were then transferred directly on ice for 2 minutes and grown in 250 µl of SOC-medium (2% tryptone, 0.5% yeast extract, 10 mM NaCl, 2.5 mM KCl, 10 mM $MgCl_2$, 10 mM $MgSO_4$, 20 mM glucose) at +37° C. with shaking for 1 hour.

The transfected bacterial cells were plated onto LB-kanamycin plates and colonies were picked on the following day to 2 ml of LB-medium (1% tryptone, 0.5% yeast extract, 170 mM NaCl) with kanamycin and grown overnight at +37° C.

Miniprep DNA preparations from selected colonies were purified using Qiagen's Plasmid Midi Kit and dissolved to a volume of 50 µl of sterile water. The presence and size of the insert was checked with NotI and BamHI digestion. 10 µl of miniprep DNA was taken for digestion, 5U of NotI and 5U of BamHI enzymes, 2 ml of R+ enzyme buffer and sterile water was added to a final volume of 20 µl. The digestion was carried out at +37° C. for 1 hour.

The orientation of the insert was analysed with BamHI restriction enzyme. Ten µl of minprep DNA was taken, 5 U of BamHI, 2 µl of BamHI buffer (MBI Fermentas) and sterile water was added to a final volume of 20 µl. The digestion was carried out for 1 hour at +37°° C. and the products were checked on a1% agarose gel with EtBr in 1×TAE.

On the basis on these results, a plasmid containing a mouse AIRE-gene and a plasmid containing a human AIRE-gene were picked and maxipreps were prepared. Briefly, 0.5 ml of *E. coli* cell suspension containing the plasmid of interest or a miniprep culture was added to a 150 ml LB-medium containing kanamycin (50 µg/ml) and grown overnight at +37° C. Maxiprep DNAs were prepared using Qiagen's Plasmid Maxi Kit.

The plasmid containing the mouse AIRE-gene was designated as pS6 wtmAIRE and plasmid containing the human AIRE-gene as pS6 wthAIRE.

The generated vectors were sequenced for approximately 500 bp from both ends to verify the orientation and correctedness of the insert. The sequencing was performed using the dideoxy method with PE Biosystem's Big Dye Terminator RR-mix, which contains the four different terminating dideoxynucletide triphosphates labeled with different fluorescent labels.

Plasmids containing the AIRE gene and AIRE gene fragments were inserted into selected cell lines to check the expression of the protein with Western blot after the transfection.

Cos-1 cells were harvested with trypsin-EDTA (Bio Whittaker Europe) solution and suspended 10×106 cells/ml into Dulbecco's MEM (Life Technologies) medium and 250 mml of cell suspension was taken for transfection. The transfection of Cos-1 cells was performed using electroporation with 2.5× 106 cells, 50 mmg of salmon sperm DNA as a carrier and 5 mmg of appropriate vector. The transfections were made with pS6 wthAIRE, pS6 wtmAIRE, Super6 wt, pCAIRE, psiAIRE and pCAIRE S1-4. pCAIRE and psiAIRE are positive human AIRE controls, pCAIRE S1-4 is a positive mouse AIRE control and Super6 wt is a negative control.

The electroporation was done using Biorad's Gene Pulser with capacitance 960 mmFd, 240 V and 1 pulse. After the pulse the cells were kept at room temperature for 10 minutes and 400 mml of medium was added. The cells were transferred to 5 ml of medium and centrifuged for 5 minutes with 1000 rpm. Cells were plated and grown for 3 days at +37° C., 5% CO2.

The cells were harvested with trypsin-EDTA and centrifuged. Then Cells were then washed once with 500 mml of 1×PBS (0.14 mM NaCl, 2.7 mM KCl, 7.9 mmM $Na_2HPO_4$, 1.5 mmM $KH_2PO_4$). 50 mml of PBS and 100 mml of SDS loading buffer (5% mercaptoethanol, 16 mmM Bromphenol-blue, 20 mmM Xylene Cyanol, 1.6 mM Ficoll 400) was added and cells were heated at +95° C. for 10 minutes.

For the western blot analysis SDS-PAGE was prepared with 10% separation and 5% stacking gels in a SDS running buffer (25 mM Tris, 250 mM glysin, 0.1% SDS). Cell samples and biotinylated molecular weigh marker were loaded on the gel and electrophoresis was performed with 150 V for 1 h 50 minutes. The transfer of proteins to a nitrocellulose membrane was performed at 100 V for 1.5 hours at room temperature with a cooler in transfer buffer.

The membrane was blocked in 5% milk in TBS (0.05 M Tris-Cl, 0.15 M NaCl, pH 7.5) for 30 minutes at room temperature. A primary antibody mixture, anti-AIRE6.1 (human) and anti-AIRE8.1 (mouse) antibodies at a dilution of 1:100 in 5% milk in TBS, was added onto membrane and incubated overnight at +4° C. The membrane was washed two times with 0.1% Tween in TBS for 5 minutes and once with TBS for 5 minutes. The secondary antibody, biotinylated anti-mouse IgG at a dilution of 1:500 in 5% milk in TBS was incubated for 1 hour at room temperature. The membrane was washed and horseradish peroxidase avidin D at a dilution of 1:1000 in 5% milk in TBS was added. The membrane was incubated at room temperature for 1 hour and washed. A substrate for the peroxidase was prepared of 5 ml chloronaphtol, 20 ml TBS and 10 mml hydrogen peroxide and added onto membrane. After the development of the color the membrane was washed with TBS and dried.

The antibody detecting with human AIRE (anti-AIRE6.1) detected the AIRE protein expression in the preparates transfected with pS6 wthAIRE, pCAIRE and psiAIRE The antibody detecting murine AIRE detected likewise the murine AIRE in cells transfected with pS6 wtmAIRE and pCAIRE S1-4. The negative control (Super6 wt) showed no AIRE/aire proteins.

6.11 Example 10

Detection of Cellular and Humoral Immune Response Toward HIV.1 NEF in Mice Immunized with the NNV-NEF Construct DNA Immunizations To further study the induction of humoral immunity by the vectors of the inventions, 5-8 weeks old both male and female BALB/c (H-2d) mice were used. For the DNA immunizations, the mice were anaesthetized with 1,2 mg of pentobarbital (i.p) and DNA was inoculated on shaved abdominal skin using plasmid DNA coated gold particles. The inoculation was made with Helios Gene Gun (Bio-Rad) using the pressure of 300 psi. The gold particles were 1 ìm in diameter, ~1 µg of DNA/cartridge. The mice were immunized twice (on day 0 and day 7) with a total amount of DNA of 0,4 or 8 µg/mouse. The control mice were immunized with 8 µg of the plain vector without the nef-gene, i.e. NNV-deltanef.

A blood sample was taken from the tail of the mice two weeks after the last immunization. The mice were sacrificed four weeks after the last immunization and blood samples (100 µl) were collected to Eppendorf tubes containing 10 µl of 0,5 M blotting (++vs. +) and in ELISA (higher OD, more mice in higher-dose above cut-off EDTA. The absolute number of leukocytes/ml of blood was calculated from these samples for each mouse. The sera were collected for antibody assays and stored at −20° C. The spleens were removed aseptically, weighted and then homogenized to single cell suspensions for use in T, B and NK cell assays and staining.

Detection of the Humoral Immunogenicity of the Vectors of the Invention

For the detection of Nef-specific antibodies by Western blotting, serum samples from mice immunized with the vector constructs of the invention were diluted 1:100 to 5% milk in TBS and applied on nitrocellulose strips made with recombinant HIV-1 Nef protein. For the preparation of the nitrocellulose strips, the purified recombinant protein was boiled in a sample buffer containing 1% SDS and 1% 2-mercaptoethanol, then run on a 10 or 12.5% polyacrylamide gel and subsequently transferred onto a 0.45 ìm nitrocellulose paper. The strips were first blocked with 2% BSA in 5% defatted milk-TBS and thereafter incubated with diluted sera (1:100) overnight. After incubation, unbound proteins were removed by washing the strips three times with TBS—0.05% Tween-20 and twice with water. After washings, the strips were probed with a 1:500 dilution of biotinylated anti-mouse IgG (Vector Laboratories, USA) for 2 hour. After further washings, horseradish peroxidase-avidin in a dilution of 1:1000 (Vector Laboratories, USA) was added for 1 h, the strips were washed again and the bound antibodies were detected with a hydrogen peroxidase substrate, 4-chloro-1-naphtol (Sigma, USA).

The sera were also tested in ELISA to determine the exact antibody titers induced by each construct. Nef antibody ELISA was performed as previously described (Tähtinen et al., 2001). Briefly, Nunc Maxi Sorp plates were coated with 50 ng of Nef (isolate HAN), blocked with 2% BSA in phosphate buffered saline (PBS), and the sera in a dilution of 1:100 to 1:25000 were added in duplicate wells for an overnight incubation. After extensive washings, the secondary antibody, peroxidase conjugated anti-mouse IgG or IgM (DAKO), was added, and the plates were incubated for two hours and then washed. Color intensity produced from the substrate (2,2'-azino-bis(3-ethylbenzthiazoline-6-sulfonic acid, ABTS, Sigma) in a phosphate-citrate buffer was measured at 405 nm using a Labsystems Multiscan Plus ELISA-plate reader. The optical density cut-off value for positive antibody reactions was determined as follows:

cut-off=$OD$($xI$ control mice sera)+3 $SD$.

Detection of the Cellular Immunogenicity of the Vectors of the Invention

To analyze the capacity of the vectors of the invention to induce cellular immunity, T-cell and B-cell assays as well as cell surface staining were performed.

T cell proliferation assay. The spleen cells were suspended to a final concentration of 1×106/ml RPMI-1640 (Gibco-BRL) supplemented with 10% FCS (GibcoBRL), 1% penicillin-streptomycin (GibcoBRL) and 50 µM beta-mercaptoethanol (Sigma). Cells were incubated in microtitre plates at 200 ìl/well with media only or with different stimuli. The final concentrations of stimuli were: Con A 5 µg/ml, HIV-Nef-protein at a concentration of 1 and 10 ìg/ml, and a negative control antigen HIV-gag at a concentration of 1 and 10 ìg/ml. All reactions were made in quadruplicates. On the sixth day of the incubation 100 µl of supernatant from each well was collected and stored at −80° C. for cytokine assays. Six hours before harvesting 1 µCi of 3H-thymidine (Amersham Pharmacia Biotech) was added to each well. The cells were harvested and radioactivity incorporated (cpm) was measured in a scintillation counter. The stimulation indexes (SI) were calculated as follows SI=mean experimental cpm/mean media cpm.

Lymphocyte activation. T and B cell activation was detected by double surface staining of fresh splenocytes with anti-CD3-FITC plus anti-CD69-PE (early activation marker) and anti-CD19-FITC plus anti-CD69-PE antibodies (all from Pharmingen). Stainings were analyzed with flow cytometer (FACScan, Becton Dickinson).

CTL assays. Mouse splenocytes were co-cultured with fixed antigen presenting cells (P-815 cells infected with MVA-HIV-nef or control MVA-F6) for five days after which they were tested in a standard 4 hour 51 chromium release assay [Hiserodt, J., et al., J Immunol 135 (1995) 53-59; Lagranderie, M., et al., J Virol 71 (1997) 2303-2309) against MVA-HIV-nef infected or control target cells. In CTL assays the specific lysis of 10% or more was considered positive.

Cytokine assay. IFN-gamma and IL-10 were measured from antigen-stimulated cell culture supernatants in order to analyze, whether immunized mice develop a Th1 type or Th2 response. The supernatants were collected from antigen-stimulated cells as described above. Pro-inflammatory cytokines TNF-alfa and IL-10 were measured in the sera of the immunized mice. All cytokines were measured with commercial ELISA kits (Quantikine, R&D Systems).

Spontaneous proliferation. Spontaneous splenocyte proliferation was detected by 3H-thymidine uptake of the cells cultured in the medium only for 6 days.

Anti-double strand (ds) DNA antibodies. dsDNA antibodies were measured in the sera of immunized mice, positive control mice (mrl/lpr, a generous gift from Dr. Gene Shearer, NIH, USA) and normal mice. The antibodies were assayed with ELISA on poly-L-Lysine bounded lambda phage dsDNA.

The results are shown in Tables 2 and 3.

Table 2 shows complete immunological results of the mice immunized with HIV-Nef plasmid DNA. Although HIV-1 Nef recombinant protein, which was used for in vitro T cell stimulation, induced some non-HIV-specific proliferation of the cells in each immunized group, there was a significant increase in the mean SI of mice immunized with 0,4 ìg of the plasmid (mean SI=72,2) compared to others. Furthermore, negative control protein HIV-gag did not induce any T cell response. Only the T cells of the mice in the group that had nef-specific proliferation also produced nef-specific IFN-gamma. None of the immunized mice had cells producing IL-10, which shows that the T cell response in the immunized mice was of Th1 type and not of Th2 type. In contrast to the T cell response, mice immunized with the higher concentration of nef plasmid DNA (8 μg) had a stronger B cell response compared to mice immunized with 0,4 μg: the humoral response in mice immunized with the higher dose was detectable already three weeks after the last immunization and the response detected was stronger both in Western-). The antibodies detected belonged to IgG-class, no IgM response was detected. None of the mice developed E2 specific antibody.

The mice immunized with 0,4 μg of HIV-nef plasmid DNA had an increased number of leukocytes (6,38×106/ml) in the peripheral blood compared to other groups of immunized mice and normal mice (3,8×106/ml) (Table 3). The same mice had twice as much activated T cells (21%, CD3+CD69+) compared to other mice (9% and 10%). This finding is in correlation with the positive T cell response to HIV-Nef (Table 2), since the mice with a positive T cell response to Nef also had an increased number of activated T cells in their spleens. The results of Table 3 also show that none of the immunized mice developed anti-dsDNA antibodies as compared to positive control sera (OD=1,208) indicating that there is no adverse effect of the immunization.

TABLE 2

| Mice | HIV-1 nef SI' | HIV-1 gag SI | IFN-g Th1 | IL-10 Th2 | HIV-1 nef Ab | E2 Ab |
|---|---|---|---|---|---|---|
| NNV-Nef 8 | | | | | | |
| 1 | 6 | 1 | – | – | ++ | – |
| 2 | 8 | 1 | – | – | ++ | – |
| 3 | 13 | 2 | – | – | ++ | – |
| 4 | 15 | 1 | – | – | ++ | – |
| 5 | 7 | 1 | – | – | ++ | – |
| Mean | 9.8 | 1.2 | | | | |
| NNV-NEF 0.4 | | | | | | |
| 1 | 24 | 1 | + | – | + | – |
| 2 | 112 | 1 | + | – | + | – |
| 3 | 83 | 1 | + | – | + | – |
| 4 | 73 | 1 | + | – | + | – |
| 5 | 69 | 1 | + | – | + | – |
| Mean | 72.2 | 1 | | | | |
| NNV-▲Nef 8 | | | | | | |
| 1 | 6 | – | – | – | – | – |
| 2 | nt | – | – | – | – | – |
| 3 | 11 | – | – | – | – | – |
| 4 | 23 | – | – | – | – | – |
| 5 | 12 | – | – | – | – | – |
| Mean | 13 | | | | | |

SI = Stimulation index
NT = not tested
– =' negative
+' = positive
+'+', strong positive

TABLE 3

| Mice | WBC ×10$^6$/ml | CD3 % spleen | CD3 + CD69 + % spleen | CD19 % spleen | CD19 + CD69 + spleen | Anti-dsDNA ab OD (1:10 dil) |
|---|---|---|---|---|---|---|
| NM | | | | | | |
| 1 | | | | | | 0.355 |
| 2 | | | | | | 0.255 |
| 3 | | | | | | 0.231 |
| Mean | | | | | | 0.280 |
| NNV-Nef 8 | | | | | | |
| 1 | 5. | nt | nt | nt | nt | 0.387 |
| 2 | 4.3 | 50 | 4 | 11 | 3 | 0.457 |
| 3 | 4.9 | 57 | 4 | 15 | 4 | 0.514 |
| 4 | 4.3 | 55 | 6 | 15 | 4 | 0.367 |
| 5 | 5.1 | 54 | 5 | 7 | 0 | 0.478 |
| mean | 4.72 | 54 | 4.75 | 12 | 2.75 | 0.441 |
| NNV-Nef 0.4 | | | | | | |
| 1 | 3.9 | nt | nt | nt | nt | 0.418 |
| 2 | 8 | 41 | 9 | 18 | 5 | 0.263 |
| 3 | 7.5 | 39 | 8 | 25 | 9 | 0.375 |
| 4 | 5 | 46 | 9 | 16 | 6 | 0.285 |
| 5 | 7.5 | 43 | 10 | 13 | 7 | 0.396 |
| mean | 6.38 | 42.25 | 9 (21%) | 18 | 6.75 | 0347 |
| NNV - Δ Nef 8 | | | | | | |
| 1 | 4.5 | 61 | 4 | 9 | 2 | 0.413 |
| 2 | 4.6 | 59 | 4 | 15 | 1 | 0.353 |
| 3 | 3.8 | 50 | 6 | 17 | 5 | 0.382 |
| 4 | 3.1 | 46 | 7 | 25 | 8 | 0.448 |
| 5 | 3.5 | nt | nt | nt | nt | 0.501 |
| mean | 3.9 | 54 | 5.25 (10%) | 16.5 | 4 | 0.419 |

Normal mouse mean WBC=3,8×10$^6$/ml.
nt, not tested
a-dsDNA positive control sera OD was 1,208 (1:10 dil)

6.12 Example 11

Safety and Immunogenicity of a Prototype HIV Vaccine GTU-Nef in HIV Infected Patients Materials and Methods The GTU-Nef plasmid: The generation of the GTU-Nef plasmid is described in example 2.

Production of the CTU-Nef vaccine: The investigational vaccine GTU-Nef (other laboratory codes used: NNV-2) was manufactured in FIT Biotech's Manufacturing Facility (Manufacturing License no. LLDnro 756/30/2000 issued by the Finnish National Agency for Medicines on 21.12.2000). The manufacturing processes performed fulfil the current Good Manufacturing Practices (cGMP) requirements and provides plasmid DNA preparations suitable for use in clinical phase I and II studies.

The manufacturing process consists of 4 steps:
a) Establishment of Master Cell Banks and Working Cell Banks
b) Fermentation
c) Purification
d) Aseptic Filling of the vaccine The detailed description of each manufacturing step is described below:

a) Establishment of Master Cell Banks and Working Cell Banks

FIT Biotech produced GTU-Nef in *E. coli* bacteria. The Master Cell Banks (MCBs) and Working Cell Banks (WCBs) are established in accordance with the specific Standard Operating Procedure from pure cultured and released Research Cell Banks (containing *E. coli* DH5 alpha T1 phage resistant cell strain)

The schematic diagram of establishing the cell banks system is illustrated below:
  Thawing of one vial of Research Cell Bank (*E. coli* DH5 alpha T1 phage resistant cell strain [Gibco RBL] transformed with the GTU-Nef plasmid)
  Inoculation of the culture on modified Luria Bertani medium plate (containing kanamycin 25 mg/ml)
  Overnight incubation (14-16h) at 37° C.
  Selection of single colony from plate and inoculation into 50 ml media (containing kanamycin 25 µg/ml)
  Overnight incubation (14-16h) at 37° C.
  Optical density measurement of the bacterial culture ($OD_{600}$=2.0–6.0)
  Addition of glycerol to bacterial culture
  Dividing of the culture-glycerol mix to aliquots
  Labelling and storage of the Master Cell Banks The same procedure applies also for the establishment of the Working Cell Bank, with the difference that the starting material in this case is one vial of Master Cell Bank, instead of Research Cell Bank.

The routine tests performed on the MCB and WCB were: microbiological characterization, absence of contamination, assessment of the plasmid stability by replica plating and the plasmid identity (restriction enzyme digestion and sequencing).

b) The fermentation steps are described below:
  Preculture on plate
  Preculture on liquid
  Fermentation
  Harvesting of cells The DH5 alpha T1 phage resistant *E.coli* strain (Gibco RBL, UK) transformed with the plasmid of interest (WCB) was first cultured on plate. From the plate a single colony was inoculated to a 100 ml liquid pre-culture before actual fermentation in the reactor. Fermentation was carried out in a 5 l fermentor (B. Braun Medical) on a fed-batch system basis, after which cells were harvested Culture medium, reagents used within the fermentation:
Culture medium composition for (1 1): 7 g yeast extract, 8 g peptone from soymeal, 10 g NaCl, 800 ml WFI; 1N NaOH; pH 7.0
Kanamycin 50 mg/ml (Sigma)
Antifoam agent: Silicon anti-foaming agent (Merck)
1M $K_2PO_4$ (BioWhittaker)
Buffers used within the purification: Resuspension buffer (50 mM Tris-Cl, pH 8.0)
+RNase A (50 mg)
Lysis buffer (200 mM NaOH)
Neutralization buffer (3M potassium acetate, pH 5.5)
Endotoxin removal buffer (750 mM NaCl, 10% Triton X-100; 50 mM MOPS, pH 7.0)
Equilibration buffer (750 mM NaCl, 50 mM MOPS, pH 7.0)
Wash Buffer (1M NaCl, 50 mM MOPS, pH 7.0, 15% isopropanol)
Elution buffer (1.6 M NaCl, 50 mM MOPS, pH 7.0, 15% isopropanol)

The pre-culture is an overnight culture prepared from a single bacterial colony (colony picked from an agar-plate and transferred to 100 ml of culture medium). In the beginning of the fermentation run, a 1 ml sample was taken through the harvesting tube to determine the initial cell density ($OD_{600}$).

During the fermentation, fresh culture-medium and potassium phosphate buffer (pH 6.-7.3, 1 M) were fed to the reactor with the pumps. Addition of the medium allows replenishment of essential nutrients before they run out and phosphate buffer maintains the pH constant. During the fermentation process (when the process has continued for approximately 5 hours) another 1 ml sample was taken similarly and the cell density was measured.

At the end of the fermentation run (after approximately 10 hours of fermentation) third 1 ml sample was taken similarly to measure the cell density.

The bacterial pellet weight at the end of the fermentation varied between 50-60 g.

c) The Methodology Used to Purify DNA is Based on the QIAGEN Process Scale Technology (Qiagen Plasmid Purification Handbook 11/98)

The purification method used for GTU-Nef is schematically described below and comprises the following steps:
  Bacterial pellet resuspension with resuspension buffer (100-150 ml, RT)
  Lysis with lysis buffer (100-150 ml, 5 minutes, RT)
  Neutralization with neutralization buffers (100-150 ml, +4° C.)
  Incubation (30 minutes, +4° C.)
  Centrifugation (10000 rpm, 30 minutes, +4° C.)
  Supernatant filtration (0.22 micrometers)
  Removal of endotoxins with Endotoxin removal buffer (60-90 ml)
  Ultrapure column equilibration with Equilibration buffer (350 ml, flow rate 10 ml/min)
  Loading of lysate to the column (flow rate 4-6 ml/min)
  Column wash with Wash buffer (31, overnight, flow rate 4-6 ml/min)
  Plasmid DNA elution with Elution buffer (400 ml, flow rate 3.1 ml/min)
  Eluate filtration (0.22 micrometer)
  DNA precipitation (with isopropanol)

Centrifugation (20000 g, 30 minutes, 4° C.))
Purified plasmid DNA

Buffers used within the purification were as follows. The resuspension buffer contained 50 mM Tris-Cl, pH 8.0, plus RNase A (50 mg); the lysis buffer was 200 mM NaOH; the neutralization buffer was 3M potassium acetate, pH 5.5; the endotoxin removal buffer contained 750 mM NaCl, 10% Triton X-100; 50 mM MOPS, pH 7.0; the equilibration buffer contained 750 mM NaCl, 50 mM MOPS, pH 7.0; the wash buffer contained 1 M NaCl, 50 mM MOPS, pH 7.0, 15% isopropanol; and elution buffer contained 1.6 M NaCl, 50 mM MOPS, pH 7.0, 15% isopropanol.

Comments for the Ultrapure Column:

The Ultrapure column is made of glass, the anion exchange material is packed inside the glass tube. Maximum flow rate for the column is 25 ml/min. The buffers are loaded on to the column by using a peristaltic pump with loading pseeds varying from 3-20 ml/min.

The maximum bacterial pellet wet weight to be loaded on to the Ultrapure column is 60 g.

The maximum capacity of the column is to produce 100 mg of plasmid DNA.

d) Aseptic Filling

The purified DNA representing the final bulk was dissolved in 0.9% sterile physiological saline to a final concentration of 1 mg/ml and sterile filtered (0.22 micrometer) during the same day.

The purified bulk was filled manually (filling volume 0.5 ml) in Schott Type 1 plus glass vials using a steam sterilized Finnpipette and sterile endotoxinfree tips. The vials filled with the investigational vaccine GTUTM-Nef were stoppered immediately and labelled and packed in accordance to the specific Standard Operating Procedure (SOP).

Administration of the test vaccine to the patients: Fifteen HIV-1 infected patients undergoing Highly Active Anti-Retroviral therapy (HAART) were immunized with the experimental DNA vaccine GTU-Nef, expressing the HIV-1 Nef gene (Clade B). For immunizations, two intramuscular injections in the gluteal muscle were given two weeks apart. The doses were 1, 20 and 400 micrograms/injection Blood samples are drawn at −4, 0, 1, 2, 4, 8 and 12 weeks.

Samples were analyzed for humoral (ELISA, western blot) and cell mediated immune response (T-cell subsets, T-cell proliferation, ELISPOT, cytokine expression, intracellular cytokines).

Clinical examinations: Clinical examination included patient interview (anamnesis) and weight determination. Cardiac and pulmonar functions were checked by auscultation and percussion, the blood pressure and heart rate were recorded. Enlargement of lymph nodes, liver and thyroid gland were determined by palpation.

Safety laboratory: Laboratory tests to evaluate the safety of the vaccine were performed at each visit. These tests include:
Hematology: red blood cell count, haemoglobin, total and differential WBC, platelet count, prothrombin time and activated partial thromboplastin time at baseline; mean erythrocyte corpuscular volume and hemoglobin content has been calculated.
Immunology: nuclear and ds-DNA antibodies.
Serum chemistries: total bilirubin, alkaline phosphatase, SGOT/SLT or SGPT/ALT, serum creatinine, protein electrophoresis, total serum cholesterol, triglycerides, glucose (at baseline), sodium, potassium, calcium.
Urinanalysis: dip stick protein, glucose, ketones, occult blood, bile pigments, pH. Specific gravity and microscopic examination of urinary sediment (RBC, WBC, epithelial cells, bacteria, casts) when dip stick determination shows one or more abnormal values.
Viral load: Increases of more than one log 10 should be followed by a confirmatory viral load estimate after two weeks.
Immunological Studies Lymphocyte proliferation assay (LPA): Peripheral blood mononuclear cells (PBMC) were isolated from heparinized venous blood by Ficoll-Hypaque density-gradient centrifugation and resuspended at $1 \times 10^6$ cells/ml in RPMI 1640 medium supplemented with 5% pooled, heat-inactivated AB$^+$ serum, antibiotics (penicillin and streptomycin) and L-glutamine (complete medium, CM). Quadruplicate cultures were then set up in flat-bottomed microtiter plates ($1 \times 10^5$ PBMC/well) and the cells were incubated for 6 days in the presence or absence of the following stimuli: rNef (0.2, 1 and 5 µg/ml), GST (0.2, 1 and 5 µg/ml), purified protein derivative of tuberculin (PPD, 12.5 µg/ml), Candida albicans antigen (20 µg/ml) and Phytohaemagglutinin (PHA; 5 µg/ml). For the last 6 h of the incubation period $^3$H-thymidine (1 µCi/well) was added to the cultures and the cells were harvested onto glass fibre filters and incorporated radioactivity was measured in a b-counter. Results are expressed as delta cpm (cpm in the presence of antigen—cpm without antigen) or as stimulation index (cpm in the presence of antigen/cpm without antigen).

IFN-γ assays: The type of immune response (Th1/Th2) induced by the vaccine was evaluated by measuring interferon-gamma (IFN-g) released in 6 days old culture supernatant after antigen (rNef, rGST, PPD) or mitogen (PHA) stimulation of PBMC. For determinations, commercial ELISA kits (R&D Quantikine) were used. The assday employ the quantitative sandwich enzyme immunoassay technique where a monoclonal antibody specific for IFN-γ has been coated onto a microplate. Standards and samples are pipetted into the wells and any IFN-γ present is bound by the immobilized antibody. After washing away any unbound substances, an enzyme-linked polyclonal antibody specific for IFN-γ is added to the wells. Following a wash to remove any unbound antibody-enzyme reagent, a substrate solution is added to the wells and color develops in proportion to the amount of the cytokine bound in the initial step. The color development is stopped and the intensity of the color is measured.

Results

Safety

None of the patients experienced subjective or objective adverse reactions to the vaccination. No adverse laboratory abnormalities were observed in the panel of clinical chemistry tests (see material and methods for details) performed repeatedly during the vaccination period.

Immunogenicity

T-Cell Proliferation

The results are shown in FIGS. 26 and 27. None of the vaccinees showed significant T-cell proliferative response to the test antigen, HIV-1 Nef before the vaccination. In contrast, 2 out of 5 vaccinees in the group that had received 1 microgram dose (FIG. 26) of the test vaccine (patients 1 and 3) and 2 out of 5 in the group receiving 20 micrograms (FIG. 27) of the test vaccine (patients 9 and 10) showed a strong T-cell proliferative response after the first vaccination. After the second vaccination, one (patient 2) vaccinee responded in the 1 microgram group.

IFN-Gamma Response

IFN-gamma response data is presently available only from patient #1. As can be seen from FIG. 28, the vaccinee responded to the rNef antigen by marked IFN-γ response correlated with the T-cell proliferation, indicating that the response seen in the vaccinee is in fact of the Th1 type.

Conclusions

HIV-1 infection is characterized by low or totally lacking cell mediated immune response towards all HIV proteins. The results show that it is possible to induce a robust CMI in such patients with exceptionally low doses of the DNA vaccine GTU-Nef. The doses used were minimal to what has generally been required with DNA vaccines. Thus, for instance, Merch announced recently good results with their experimental HIV vaccine but the doses required were from 1000 to 5000 micrograms (IAVI report, 2002).

6.13 Example 12

Construction of the Plasmid Expressing Epstein-Barr Virus (EBV) EBNA-1 Protein and Containing 20 Binding Sites for EBNA-1 (FR Element)

6.13.1 Substitution of BPV-1 E2 Binding Sites with EBV EBNA-1 Binding Sites (oriP Without DS Element)

Plasmid FRE2d1EGFP (FIG. 29) was constructed by isolating the XmiI(AccI)/Eco32I(EcoRV) DNA fragment (blunt-ended with Klenow enzyme) of pEBO LPP plasmid (fragment contains 20 binding sites for EBNA-1) and inserting it by blunt end ligation into the SpeI/NheI site of s6E2d1EGFP (blunt-ended with Klenow enzyme). The constructed plasmid FRE2d1EGFP was used as a negative control in further experiments (contains binding sites for EBNA-1 protein instead of the BPV1 E2 10 binding sites, expressing E2, but not EBNA-1)

Substitution of Sequence Encoding BPV-1 E2 Protein in FRE2D1EGFP Plasmid with Sequence Encoding EBV EBNA-1 Protein.

The XmiI(AccI)/EcoRI fragment of pEBO LPP plasmid was isolated and blunt-ended with Klenow enzyme and inserted into the XbaI/XbaI site of FRE2d1EGFP plasmid (blunted with Klenow enzyme). The vector FRE2d1EGFP was previously grown in DH5alpha Dam⁻ strain because one XbaI site is sensitive for methylation. The constructed plasmid FREBNAd1EGFP (FIG. 30) expresses EBNA-1 protein and contains 20 binding sites for EBNA-1.

Cell cultures: Jurkat, 293 and 3T6 cells were maintained in Iscove's modified Dulbecco's medium (IMDM) supplemented with 10% fetal calf serum.

Transfection: We used human T cell line Jurkat, human embryonic kidney cell line 293 and mouse fibroblast cell line 3T6. Four million cells (Jurkat), 75% confluent dishes (293) or ¼ of 75% confluent dishes (3T6) were used for each transfection. Carried out by electroporation. Cells were harvested with centrifugation (1000 rpm 5 min. 20° C. Jouan CR 422), and resuspend in complete medium containing 5 mM Na-BES buffer (pH 7.5). 250 µl cell suspension was mixed with 50 µg of carrier DNA (salmon sperm DNA) and 1 µg (in case of Jurkat and 3T6) or 5 µg (in case of 293) of plasmid DNA and electroporated at 200 V and 1000 µF for Jurkat cells, 170 V and 950 µF for 293 cells and 230 V and 975 µF for 3T6 cells. The transfected Jurkat cells were plated in 6-cm dishes with 5 ml of medium; ⅓ of transfected 293 and 3T6 cells were plated in a 6-cm dishes with 5 ml of medium and ⅔ of the cells were plated in a 10-cm dishes with 10 ml of medium.

Analysis of the transfected cells: All of the constructed plasmids expressed d1EGFP protein (modified enhanced green fluorescent protein) that can be detected by measuring its' fluorescence using flow cytometer. Because the short half-life of the d1EGFP protein, it does not accumulate and expression of this protein reflects the presence of transcriptionally active plasmids in the cells. In this experiment Becton-Dickinson FACSCalibur system was used. The volume of the Jurkat cell suspension was measured before each time-point (approximately after every 24 hour) and when it was less than 5 ml, the missing volume of medium was added. Depending on the cell suspension density the appropriate volume was taken for measuring (1 or 2 ml) and replaced with the same amount of medium. This was later taken into consideration when the dilution was calculated. For the first time-point, 293 cells from the 6-cm dish were suspended in 5 ml of medium for measuring. In every next time-point half of the cells were taken from the 10-cm dish, suspended in 5 ml of medium and then measured. Appropriate volume was added to the rest of the cell suspension. For the first time-point, 3T6 cells from the 6-cm dish were suspended in 1 ml of trypsine which was then inactivated with 100 µl of Fetal Calf Serum. In every next time-point cells from the 10-cm dish were suspended in 2 ml of trypsin. 1 ml of this suspension was treated as described previously and taken for measuring. 9 ml of medium was added to the rest of the suspension. The analysed cells were taken out of the incubator right before measuring. The appropriate flow speed (500-1000 cells/sec) was determined before each time-point using cells transfected only with carrier DNA as a control. Three different parameters were used to measure size, surface structure and fluorescence of the cells. The data was presented as graphs. Cells transfected only with carrier DNA were used to measure the auto-fluorescence of the cell-line. 1% of this auto-fluorescence was considered as a background fluorescence and was subtracted later from the d1EGFP fluorescence. The recieved data was analysed with Microsoft Excel program.

Results (A) The Vectors Did not Interfere with the Cell Proliferation

Jurkat cells were transfected with 1 µg of the vector FRE2d1EGFP and equimolar amount of the plasmid FREBNAd1EGFP or with carrier DNA only. At different time-points post transfection the equal aliquots from the each sample were collected for analysis and replaced with same volume of fresh medium. The numbers of the cells were calculated in consideration of dilutions made and represented as number of the cells per one milliliter in FIG. 31.

(B) Vectors Were Maintained in the Cells with Different Kinetcs

Percentages of the d1EGFP expressing cells were calculated using the carrier-only transfected cells as a negative control for background fluorescence (FIG. 32).

(C) Change of the Number of d1EGFP Expressing Cells in Time in Transfected Total Population of Cells.

The number of the d1EGFP expressing cells was calculated in consideration of dilutions made using the carrier-only transfected cells as a negative control for background fluorescence (FIG. 33).

Figure 34A:
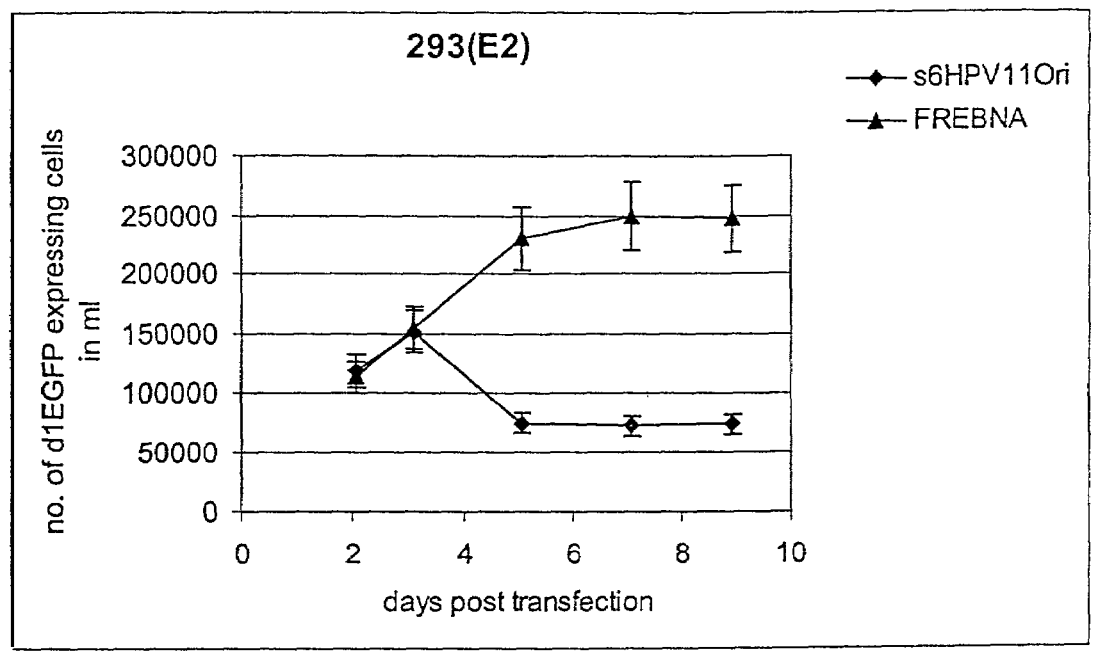
Figure 34B:
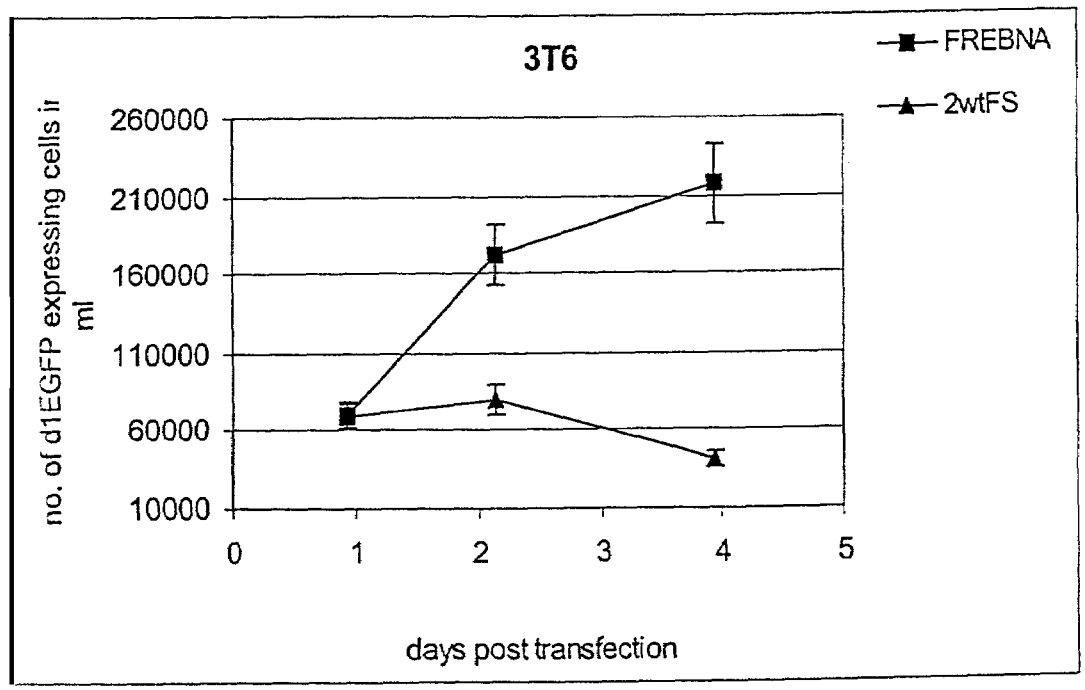

As seen from FIG. 33, the plasmids expressing EBNA-1 and carrying EBNA-1 specific multimeric binding sites is maintained very efficiently in the transfected cells. At the first day after transfection approximately 80000 cells were expressing EGFP. After 8 days in the case of maintenance vectors (FREBNAd1EGFP) the number of the plasmid positive d1EGFP expressing cells has increased ten times to 800000. The plasmids lacking EBNA-1 expression (FRE2d1EGFP) or having no EBNA-1 binding sites are retaining the number of plasmid positive cells or in many cases the number of plasmid positive cells is actually decreasing. This fact confirms once again that in the case of another episomally maintained virus, Epstein-Barr Virus, the same mechanism for segregation/partitioning is used. The only difference comes from the fact that this function is carried out by EBNA-1 and respective cis-sequences are EBNA-1 binding sites (D) The Identical Results Were Obtained Also in Human Embryonic Cell Line 293 and Mouse Cell Line 3T6 (FIG. 34)

As a control for the maintenance for 293 cells was s6HPV11 and for 3T6 2 wtFS were used.

6.14 Example 13

The Immunogenicity of GTU-Multigene Vectors

6.14.1 Introduction

In order to induce a broad immune response against several HIV proteins, several multigene vaccine constructs have been developed by Prof. Ustav's group in Tartu. The constructs contain HIV-1 (isolate HAN) rev, nef and tat (RNT) or tat, rev, nef (TRN) genes either alone, conjugated to codon-modified, partial gag-gene or to oligonucleotides coding selected CTL epitopes of HIV. The immunogenicity of six different construct, e.g. pRNT, pTRN, pRNT-CTL, pTRN-CTL, pTRN-optgag-CTL, pTRN-CTL-optgag vectors was tested in mice.

6.14.2 Test Article

The plasmids were transformed into TOP10 or DH5alpha cells, and the MegaPreps were prepared using Qiagen columns. Endotoxins were removed by Pierce Endotoxin Removal Gel.

6.14.3 Test Article Formulation

The test articles were coated on 1 mm gold particles according to the instructions given by the manufacturer (Bio-Rad) with a few in-house made modifications.

6.14.4 Test Article Administration

Balb/c mice were immunized with a Helios Gene Gun using a pressure of 400 psi and 0.5 mg gold/cartridge. Mice were immunized three times at weeks 0, 1, 3. Mice were sacrified two weeks after the last immunization.

Mice were divided into six test groups (5 mice/group) which received 3×1 µg DNA as follows:
Group 1. GTU-1-RNT
Group 2. GTU-1-TRN
Group 3. GTU-1-RNT-CTL
Group 4. GTU_1-TRN-CTL
Group 5. GTU-1-TRN-optgag-CTL
Group 6. GTU-1-TRN-CTL-optgag
Group 7. Control mice immunized with empty goldparticles not loaded with DNA.

6.14.5 Methods

Serum Collection

The outcome of humoral response was followed by taking tail-blood samples from each mouse. First pre-immunization sample was taken from anesthesized mice before the first immunization was given. Second sample was taken from anesthesized mice before the third immunization At sacrifice, whole blood sample was used for white blood cell counting, and serum was collected for humoral immunity tests.

Antibody Assay

The blood samples were tested in ELISA. Nunc Maxi Sorp plates were coated with 100 ng of Nef, Rev, Tat, Gag, CTL or E2 proteins, blocked and sera diluted 1:100 were added in duplicate wells for an overnight incubation. After washings, plates were incubated 2 h with diluted (1:500) secondary antibody, peroxidase conjugated anti-mouse IgG (DAKO). Colour intensity produced from the substrate (2,2'-azino-bis (3-ethylbenzthiazoline-6-sulfonic acid) (ABTS) in phosphate-citrate buffer was measured at 405 nm using Labsystems ELISA-plate reader.

6.14.6 Results

All plasmids induced Nef antibodies in all mice, none of the mice showed E2 or Rev antibodies (FIGS. 35, 36 and 37, and Table 4). Some of the mice immunized with GTU-1-RNT or GTU-1-RNT-CTL also developed Tat antibodies (FIG. 36 and Table 4) and some of the mice immunized with GTU-1-optgag-CTL developed Gag antibodies (FIG. 37). The antibody assays shown below were done from the sera collected when mice were sacrificed.

6.14.7 Conclusion

The results show that a multigene construct, expressing several HIV genes as a fusion protein, can in deed induce an immune response to most of the gene products. The orientation and order of the genes in the multigene and corresponding proteins in the fusion proteins affects the results, however, dramatically. Thus, a response against Tat was seen only when the Tat gene was placed inside the fusion protein (vectors with RNT motif) and not when Tat was the 5-terminal protein (vectors with the TRN motif). Response towards the Gag proteins were seen only with the vector were Gag was placed before the CTL containing a stretch of Th and CTL epitopes. Basen on these results, and one optimal multiHIV construct should have the genes in the order RNT-optgag-CTL. Other combinations are naturally also possible.

TABLE 4

Immuno III A mice ELISA results (OD mean of five mice)

| Immunogen | Group number | Nef (own prot) | Tat | Rev | Gag | CTL |
|---|---|---|---|---|---|---|
| GTU-1-RNT | 1 | 2.194 | 1.391 | 0.31 | 0.155 | 0.36 |
| GTU-1-TRN | 2 | 1.849 | 0.197 | 0.252 | 0.302 | 0.38 |
| GTU-1-RNT-CTL | 3 | 1.922 | 0.555 | 0.295 | 0.154 | 0.439 |
| GTU-1-TRN-CTL | 4 | 1.677 | 0.211 | 0.298 | 0.14 | 0.425 |
| GTU-1-TRN-optgag-CTL | 5 | 1.722 | 0.182 | 0.24 | 0.667 | 0.381 |
| GTU-1-TRN-CTL-optgag | 6 | 0.547 | 0.225 | 0.322 | 0.228 | 0.43 |
| Controls | 7 | 0.316 | 0.226 | 0.282 | 0.16 | 0.405 |

| Immunogen | Group | Percent of Nef response | Tat response | Rev response | Gag response | CTL response |
|---|---|---|---|---|---|---|
| GTU-1-RNT | 1 | 100 | 80 | 0 | 0 | 0 |
| GTU-1-TRN | 2 | 100 | 0 | 0 | 20 | 0 |
| GTU-1-RNT-CTL | 3 | 100 | 40 | 0 | 0 | 0 |
| GTU-1-TRN-CTL | 4 | 100 | 0 | 0 | 0 | 0 |

TABLE 4-continued

Immuno III A mice ELISA results (OD mean of five mice)

| | | | | | | |
|---|---|---|---|---|---|---|
| GTU-1-TRN-optgag-CTL | 5 | 80 | 0 | 0 | 60 | 0 |
| GTU-1-TRN-CTL-optgag | 6 | 100 | 0 | 0 | 20 | 0 |
| Controls | 7 | 0 | 0 | 0 | 0 | 0 |

Conclusion:

Epstein-Barr Virus Nuclear antigen EBNA-1 is capable of providing segregation/partitioning function to the plasmids in case if EBNA-1 binding sites are present in multimeric form in different cells, including mouse and human cells.

6.15 Example 14

Expression of Hybrid Protein Expressing Nef, Rev and Tat in Different Combinations (Multireg)

Expression properties of the different multiREG antigenes built up by fusion of coding sequences for intact regulatory proteins and cloned into the GTU-1 vector, were initially analyzed in Jurkat cells by Western blotting. The results are presented on FIG. 43. As seen, all tested MultiREG vectors produced the hybrid proteins that could be detected: 1) by anti-Nef, 2) anti-Rev, and 3) anti-Tat antibodies. Only exception was plasmid pNTR that expressed protein with significantly lower molecular weight that cannot be detected with anti-Rev antibody. The sequence analysis showed that this plasmid contained frameshift mutation just upstream the Rev cds. In cases of plasmids pTNR and pRNT, most of the signal was found at predicted position of full-lenght MultiREG protein (48 kD) when compared to the molecular weight marker. In cases of the pRTN, pTRN and pNRT, major signal migrated slightly faster indicating processing events of the full-length proteins or different conformation of the fusion protein, which moves in the gel differently than others. In addition to abundant full size signals, additional bands are visible in all lanes, demonstrate probably post-translational processing events.

6.15.1 Expression Properties of the Multireg Antigens Carrying Only Immunodominant Regions of the Regulatory Proteins.

Using bioinformatic analysis the immunodominant regions of the regulatory HIV1 proteins NEF, REV and TAT were identified and used for construction of MultiREG antigens. The expression properties of these antigens carried only immunodominant regions of the proteins (predicted size 44 kD) were characterized the similar way as described in the previous section. The results are presented on FIG. 44. All proteins moved on the gel at position of predicted molecular weight. No visible digestion products were observed in case of protease sites additionally included to facilitate processing of the hybrid antigens (pMV2 vectors). There is very faint signal at lane loaded material from the pMV2N11TR transfected cells.

6.15.2. Intracellular Localization of the Multireg Antigens

In cases of all MultiREG antigenes, the intracellular localization was studied by in situ immunofluorescence in RD cells using monoclonal antibodies against Nef, Rev and Tat proteins. The results are summarized in table 5 and illustrated on FIG. 45. All antigenes that are comprised of intact Nef, Rev and Tat proteins showed exclusive localization in cytoplasm. Aberrant protein initially designed as N(ef)T(at)R(ev), that does have frameshift before Rev sequence showed only the nuclear localization. MultiREG antigenes carrying truncated sequences of the regulatory proteins were localized in cytoplasm. In this cases distinct structures like "inclusion bodies" were frequently observed. The same was true about antigenes that carried the protease sites expressed from pMV2 vectors. However in these cases the proteins in nucleus were also detected (FIG. 45).

TABLE 5

Intracellular localization in multireg antigenes

| Construct | anti-Nef | anti-Rev | anti-Tat |
|---|---|---|---|
| empty GTU-1 | negative | negative | negative |
| pTRN | strong staining in cytoplasm | good staining in cytoplasm | positive staining in cytoplasm |
| pNTR | strong staining in nucleus, nucleolus | negative | positive staining in nucleus |
| pRNT | strong staining in cytoplasm | good staining in cytoplasm | good staining in cytoplasm |
| pNRT | strong, cytoplasmic | good staining in cytoplasm | good staining in cytoplasm |
| pRTN | strong, cytoplasmic | good staining in cytoplasm | positive staining in cytoplasm |
| pTNR | strong, cytoplasmic | good staining in cytoplasm | good staining in cytoplasm |
| pMV1NTR | strong, cytoplasmic | cytoplasmic + inclusions | cytoplasmic + inclusions |
| pMV1N11TR | strong cytoplasmic + inclusions | cytoplasmic + inclusions | cytoplasmic + inclusions |
| pMV2NTR | inclusions in nuclei and in cytoplasm | inclusions in nuclei and cytoplasm | inclusions in nuclei and cytoplasm |
| pMV2N11TR | only inclusions, in nuclei and in cytoplasm | only inclusions in nuclei and in cytoplasm | only inclusions in nuclei and in cytoplasm |

6.16 Example 15

Analysis of Vectors Encoding Recombinant GAG Antigens and Cytotoxic T-Cell Epitopes (CTL) from POL 6.16.1. Expression Analysis of expression of the vectors expressing CTL cds or proteins from the gag region were performed by western blot. As seen on FIGS. 46A and 46B, the CTL and dgag expression was clearly demonstrated in Cos-7 cells as predicted size proteins (25 kD and 47 kD, respectively). The co-transfection of the Nef, Rev and Tat significantly enhanced the expression of the dgag protein. We interpret this as a result of REV protein action on the GAG mRNA expression We also tried to express the dgag protein from GTU-1 vector in Jurkat cells, but we failed to detect any signal (FIG. 46C). The analysis of the codon usage showed that wt GAG sequence had not optimal codon usage for human cells. When the codon usage was optimized (constructs psynp17/24 and poptp17/24), strong p17+p24 (40 kD) protein expression was detected in Jurkat cells (FIGS. 46C and 46D).

6.16.2. Intracellular Localization

For dgag and p17+p24 proteins, the intracellular localization was also analyzed in RD cells by immunofluorescence with anti p24 Mab. Similar to the western blot results in Jurkat cells, the dgag could not be detected. The p17/24 protein showed localization in plasma membranes (FIG. 47). The localization of CTL protein was not analyzed caused by lacking of suitable antibody

6.17 Example 16

Multireg+Structural Proteins as MultiHIV Antigen Expression

As next step, the expression of the MultiHIV antigenes consisting of both, regular multigene together with ga encoded protein and/or CTL multiepitope as single polypeptide was analysed. On FIG. 48, the Western blot shows the expression of several multiHIV-antigenes expressing vectors transfected to the Cos-7 cells. It is clearly seen that the expression levels of all regulatory+structural multi-antigenes are significantly lower than of the RNT or TRN proteins. All tested MultiHIV antigenes migrate in the gel as distinct bands near the position of predicted size (73 kD for multireg+CTL; 95 kD for multireg+dgag and 120 kD for multireg+CTL+dgag). Similar to the RNT and TRN, the RNT-CTL migrates more slowly than TRN-CTL. Also, in cases of both TRN and RNT constructs, the MultiREG-CTL-dgag combination showed higher expression level than MultiREG-dgag-CTL.

More detailed analysis of the multiHIV antigenes was performed in Jurkat cells. For this reason, most of the constructed MultiHIV antigenes (multireg+structural), included the MultiREG+CTL+optp17/24 (with predicted size 113 kD) were analyzed by Western blotting using antibodies against different parts of the antigene. The results are presented on FIG. 49 are principially similar to those were reported in previous section in case of Cos-7 cells. As it was seen in the previous experiments, the dgag containing multi-antigenes express very low levels of the hybrid protein in Jurkat cells. The expression from the vector pTRNdgag was undetectable on all blots. In lanes loaded material from cells transfected with other dgag containing antigene expression vectors, very faint signals only on the Nef Mab hybridized blot were detected at positions of predicted sizes. In contrast, if the dgag part is replaced with the codon optimized p17/24, the expression level increase was observed.

Because the TRN-CTL-optp17/24 and RNT-optp17/24 were initially chosen for further analysis, the expression of the antigenes was analyzed from all GTU vectors containing these expression cassettes. Also, the E2 protein expression from these plasmids was analyzed. The results are illustrated on FIG. 50. There are no big differences between the vectors in expression levels of both multi-antigene and the E2 protein. The E2 expression level is not significantly influenced by presence of IRES element followed mouse GM-CSF gene in the plasmid, translated from the same mRNA as the E2.

6.17.1. Maintenance of Expression of Antigen

The GTU concept as active segregation function for maintaining the plasmid in population of dividing cells is proved using green fluorescent protein and Nef protein as markers. We also tested the maintenance of expression of the RNT-CTL-optp17/24 antigene produced from different GTU or non-GTU vectors. Exactly, GTU-1 (p RNT-CTL-optp17/24), GTU-2 (p2 RNT-CTL-optp17/24), GTU-3 (p3 RNT-CTL-optp17/24), super6 wt (super6 wt-RNT-CTL-optp17/24) vectors all utilize the E2 protein and its binding sites for plasmid maintenance activity. In this experiment, also EBNA-1 and its binding site utilizing GTU vector FREBNA-RNT-CTL-optp17/24 was included. For negative controls, "non-GTU" plasmid contains mixed pair of the EBNA-1 expression cassette together with E2 binding sites (E2BSEBNA-RNT-CTL-optp17/24) were used. Also, regular CMV expression vector pCMV-RNT-CTL-optp17/24 was used in this experiment. The time points were taken two and five days post-transfection. As it seems on FIG. 51, only from GTU vectors the expression is detectable at second time-point. As expected, the antigen expression from the FREBNA-RNT-CTL-optp17/24 is lower in both time-points because unlike E2 the EBNA-1 does not have transcription activation ability.

6.17.2 Intracellular Localization of the Antigens

The intracellular localization of the multireg+structural polyproteins was studied by in situ immunofluorescence analysis in RD cells. In all cases localization only in cytoplasm was detected using either anti-Nef or anti-p24 Mabs. In accordance with Western blots data, the expression level of optp17/24 containing proteins was much stronger than dgag fragment containing antigenes. The results are also represented on FIG. 52.

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. An expression vector comprising:
   (a) a DNA sequence encoding a E2 protein of Bovine Papilloma Virus type 1 operatively linked to a heterologous promoter, said E2 protein comprising (i) a DNA binding domain of said E2 protein which binds to a specific E2 binding DNA sequence, and (ii) a functional domain of said E2 protein that binds to a nuclear component; and
   (b) a multimerized DNA binding sequence for the E2 protein, wherein said vector lacks an origin of replication functional in mammalian cells.

2. The vector of claim 1, wherein said nuclear component is mitotic chromatin, the nuclear matrix, nuclear domain 10 (ND 10), or nuclear domain PML oncogenic domain (POD).

3. The vector of claim 1, wherein said E2 protein is a chromatin-anchoring protein, and said functional domain binds mitotic chromatin.

4. The vector of claim 1, wherein said E2 protein contains a hinge or linker region.

5. The vector of claim 1, wherein said E2 protein is a natural protein of viral origin.

6. The vector of claim 1, wherein said E2 protein is an artificial protein.

7. The vector of claim 1, wherein said vector further comprises one or more expression cassettes of a DNA sequence of interest.

8. A method for providing a protein to a subject, said method comprising administering to the subject the vector of claim 1, wherein said vector (i) further comprises a second DNA sequence encoding the protein to be provided to the subject, which second DNA sequence is operably linked to a second promoter, and (ii) does not encode Bovine Papilloma Virus protein E1, and wherein said subject does not express Bovine Papilloma Virus protein E1.

9. A method for inducing an immune response to a protein in a subject, said method comprising administering to the subject the vector of claim 1, wherein said vector (i) further comprises a second DNA sequence encoding said protein, which second DNA sequence is operably linked to a second promoter, and (ii) does not encode Bovine Papilloma Virus protein E1, and wherein said subject does not express Bovine Papilloma Virus protein E1.

10. A method for the preparation of a vector of claim 1 comprising: (a) cultivating a host cell containing said vector; and (b) recovering the vector.

11. An isolated host cell comprising the vector of claim 1.

12. A carrier vector containing the vector of claim 1.

13. The vector of claim 6, wherein said E2 protein is a recombinant protein, a fusion protein, or a protein obtained by molecular modeling techniques.

14. The vector of claim 7, wherein said DNA sequence of interest is that of a gene obtained from an infectious pathogen.

15. The vector of claim 7, wherein said DNA sequence of interest is that of a gene obtained from a fungal pathogen.

16. The vector of claim 7, wherein said DNA sequence of interest encodes a structural protein of HIV.

17. The vector of claim 7, wherein a first said expression cassette comprises a DNA sequence of interest which encodes Nef, Tat or Rev, and wherein a second said expression cassette comprises a DNA sequence of interest which encodes Nef, Tat or Rev.

18. The vector of claim 7, wherein a first said expression cassette comprises a DNA sequence of interest which encodes Nef, Tat or Rev, and wherein a second said expression cassette comprises a DNA sequence of interest which encodes a structural protein of HIV.

19. The vector of claim 7, wherein the DNA sequence of interest encodes a protein associated with cancer.

20. The vector of claim 7, wherein the DNA sequence of interest encodes a protein associated with immune maturation, regulation of immune responses, or regulation of autoimmune responses.

21. The vector of claim 7, wherein the DNA sequence of interest is the Aire gene.

22. The vector of claim 7, wherein the DNA sequence of interest encodes a protein that is defective in any hereditary single gene disease.

23. The vector of claim 7, wherein the DNA sequence of interest encodes a macromolecular drug.

24. The vector of claim 7, wherein said DNA sequence or interest encodes a biologically active RNA molecule.

25. A method for treating an infectious disease in a subject in need of said treatment, said method comprising administering to said subject a therapeutically effective amount of the vector of claim 7, wherein said DNA sequence of interest encodes a protein comprising an immunogenic epitope of an infectious agent.

26. A method for treating an inherited or acquired genetic defect in a subject in need of said treatment, said method comprising: administering to said subject a therapeutically effective amount of the vector of claim 7, wherein said DNA sequence of interest encodes a protein which is affected by said inherited or acquired genetic defect.

27. A method for expressing a DNA sequence in a subject, said method comprising administering the vector of claim 7 to said subject.

28. An isolated host cell comprising the vector of claim 7.

29. An immunogenic composition containing the vector of claim 7.

30. A gene therapeutic agent containing the vector of claim 7.

31. A method for the preparation of an immunogenic composition, said method comprising combining the vector of claim 7 with a suitable pharmaceutical vehicle.

32. A method for the preparation of a gene therapy agent, said method comprising combining the vector of claim 7 with a suitable pharmaceutical vehicle.

33. A pharmaceutical composition comprising the vector of claim 7 and a suitable pharmaceutical carrier.

34. The vector of claim 14, wherein said infectious pathogen is a virus.

35. The vector of claim 14, wherein said DNA sequence of interest is that of a gene obtained from a bacterium.

36. An immunogenic composition containing the vector of claim 14.

37. A method for the preparation of an immunogenic composition, said method comprising combining the vector of claim 14 with a suitable pharmaceutical vehicle.

38. The vector of claim 34, wherein said virus is selected from the group consisting of Human Immunodeficiency Virus (HIV), Herpex Simplex Virus (HSV), Hepatitis C Virus, Influenzae Virus, and Enterovirus.

39. An immunogenic composition containing the vector of claim 34.

40. A method for the preparation of an immunogenic composition, said method comprising combining the vector of claim 34 with a suitable pharmaceutical vehicle.

41. The vector of claim 38, wherein said DNA sequence of interest is of HIV origin.

42. The vector of claim 35, wherein said bacterium is selected from the group consisting of Chlamydia trachomatis, Mycobacterium tuberculosis, and Mycoplasma pneumoma.

43. The vector of claim 35, wherein said bacterium is Salmonella.

44. An immunogenic composition containing the vector of claim 35.

45. A method for the preparation of an immunogenic composition, said method comprising combining the vector of claim 35 with a suitable pharmaceutical vehicle.

46. The vector of claim 15, wherein said fungal pathogen is Candida albicans.

47. An immunogenic composition containing the vector of claim 15.

48. A method for the preparation of an immunogenic composition, said method comprising combining the vector of claim 15 with a suitable pharmaceutical vehicle.

49. The vector of claim 41, wherein said DNA sequence of interest encodes a non-structural regulatory protein of HIV.

50. The vector of claim 49, wherein said nonstructural regulatory protein of HIV is Nef, Tat or Rev.

51. The vector of claim 50, wherein said non structural regulatory protein of HIV is Nef.

52. The vector of claim 16, wherein said DNA sequence of interest is the gene encoding HIV gp 120/gp 160.

53. The vector of claim 20, wherein said protein is APECED.

54. The vector of claim 23, wherein the DNA sequence of interest encodes a cytokine.

55. The vector of claim 54, wherein said cytokine is an interleukin selected from the group consisting of IL1, IL2, IL4, IL6 and IL12.

56. The vector of claim 54, wherein the DNA sequence of interest encodes an interferon.

57. The vector of claim 24, wherein said biologically active RNA molecule is selected from the group consisting of inhibitory antisense and ribozyme molecules.

58. The vector of claim 57, wherein said inhibitory antisense or ribozyme molecules inhibit the function of an oncogene.

59. The method of claim 25, 26, or 27, wherein said vector does not encode Bovine Papilloma Virus protein E1, and wherein said subject does not express Bovine Papilloma Virus protein E1.

60. The method of claim 10, further comprising before step (a) a step of transforming said host cell with said vector.

61. The method of claim 10, wherein said host cell is a prokaryotic cell.

62. The method of claim 10, wherein said host cell is an Escherichia coli.

63. The isolated host cell of claim 11, wherein said host cell is a bacterial cell.

64. The isolated host cell of claim 11, wherein said host cell is a mammalian cell.

* * * * *